(12) United States Patent
Bourdeau et al.

(10) Patent No.: US 11,118,210 B2
(45) Date of Patent: Sep. 14, 2021

(54) GENETICALLY ENGINEERED GAS VESICLE GENE CLUSTERS, GENETIC CIRCUITS, VECTORS, PROKARYOTIC CELLS, COMPOSITIONS, METHODS AND SYSTEMS FOR CONTRAST-ENHANCED IMAGING

(71) Applicant: CALIFORNIA INSTITUTE OF TECHNOLOGY, Pasadena, CA (US)

(72) Inventors: Raymond W. Bourdeau, Watertown, MA (US); Anupama Lakshmanan, Pasadena, CA (US); Arash Farhadi, Pasadena, CA (US); Mikhail G. Shapiro, Los Angeles, CA (US); Audrey Lee-Gosselin, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/663,635

(22) Filed: Jul. 28, 2017

(65) Prior Publication Data

US 2018/0030501 A1 Feb. 1, 2018

Related U.S. Application Data

(60) Provisional application No. 62/413,206, filed on Oct. 26, 2016, provisional application No. 62/367,750, filed on Jul. 28, 2016.

(51) Int. Cl.
| | |
|---|---|
| C12Q 1/10 | (2006.01) |
| A61K 49/22 | (2006.01) |
| A61K 49/18 | (2006.01) |
| C12N 15/74 | (2006.01) |
| C07K 14/32 | (2006.01) |
| C12N 15/70 | (2006.01) |
| C07K 14/195 | (2006.01) |

(52) U.S. Cl.
CPC ............ *C12Q 1/10* (2013.01); *A61K 49/1896* (2013.01); *A61K 49/223* (2013.01); *C07K 14/195* (2013.01); *C07K 14/32* (2013.01); *C12N 15/70* (2013.01); *C12N 15/74* (2013.01)

(58) Field of Classification Search
None
See application file for complete search history.

(56) References Cited

U.S. PATENT DOCUMENTS

| | | | |
|---|---|---|---|
| 5,824,309 A | 10/1998 | DasSarma et al. | |
| 7,498,024 B2 | 3/2009 | Fang et al. | |
| 9,107,949 B2 | 8/2015 | Ju | |
| 10,493,172 B2 | 12/2019 | Lakshmanan et al. | |
| 10,955,496 B2 | 3/2021 | Lu et al. | |
| 2003/0157025 A1 | 8/2003 | Unger et al. | |
| 2005/0058605 A1 | 3/2005 | Schneider et al. | |
| 2006/0216810 A1 | 9/2006 | Ju | |
| 2014/0288411 A1 | 9/2014 | Shapiro et al. | |
| 2014/0288421 A1 | 9/2014 | Shapiro et al. | |
| 2016/0220672 A1 | 8/2016 | Chalasani et al. | |
| 2018/0028693 A1 | 2/2018 | Lakshmanan et al. | |
| 2018/0038922 A1 | 2/2018 | Lu et al. | |
| 2020/0164095 A1 | 5/2020 | Lakshmanan et al. | |
| 2020/0237346 A1 | 7/2020 | Sawyer et al. | |
| 2020/0291409 A1 | 9/2020 | Farhadi et al. | |
| 2020/0306564 A1 | 10/2020 | Bar-Zion et al. | |
| 2021/0060185 A1 | 3/2021 | Lakshmanan et al. | |

FOREIGN PATENT DOCUMENTS

| | | |
|---|---|---|
| CN | 105232045 A | 1/2016 |
| WO | 2007/014162 A2 | 2/2007 |
| WO | 2012/038950 A1 | 3/2012 |
| WO | 2018/069788 A1 | 4/2018 |
| WO | 2020/146367 A1 | 7/2020 |
| WO | 2020/146379 A1 | 7/2020 |
| WO | 2020/198728 A1 | 10/2020 |
| WO | 2021/041934 A1 | 3/2021 |

OTHER PUBLICATIONS

Ngamdee, et al. (2015) "Competition between Burkholderia pseudomallei and B. Thailandensis", BMC Microbiology, 15:56, 15 pages. (Year: 2015).*

Caldwell, et al. (1978) "A *Zoogloea* sp. Associated with blooms Anabaena flos-aquae", Canadian Journal of Microbiology, 24(8): 922-31 (Abstract Only). (Year: 1978).*

Watanabe, et al. (1993) "Distribution and identification of proteolytic *Bacillus* spp. in paddy field soil under rice cultivation", Canadian Journal of Microbiology, 39(7): 674-80. (Year: 1993).*

Qin, et al. (2016) "Bacterial abundance and diversity in pond water supplied with different feeds", Nature Scientific Reports: article No. 35232 (13 pages). (Year: 2016).*

Abdul-Rahman, H.S., et al., "Fast and Robust Three-Dimensional Best Path Phase Unwrapping Algorithm." *Applied Optics*, 46(26), 6623-6635, (2007). 13 pages.

(Continued)

*Primary Examiner* — Robert M Kelly

(74) *Attorney, Agent, or Firm* — Steinfl + Bruno LLP

(57) ABSTRACT

Hybrid gas vesicle gene cluster (GVGC) configured for expression in a prokaryotic host are described comprising gas vesicle assembly (GVA) genes native to a GVA prokaryotic species and capable of being expressed in a functional form in the prokaryotic host, and one or more gas vesicle structural (GVS) genes native to one or more GVS prokaryotic species, at least one of the one or more GVS prokaryotic species different from the GVA prokaryotic species, and related gas vesicle reporting (GVR) genetic circuits, genetic, vectors, engineered cells, and related compositions methods and systems to produce GVs, hybrid GVGC and/or image a target site.

30 Claims, 26 Drawing Sheets

Specification includes a Sequence Listing.

(56) References Cited

OTHER PUBLICATIONS

Ahrens, E.T. et al., "Tracking Immune Cells in vivo using Magnetic Resonance Imaging." *Nature Reviews Immunology*, 13(10), 755-763, (2013). 19 pages.

Archer, E.J., et al., "Engineered *E. coli* That Detect and Respond to Gut Inflammation through Nitric Oxide Sensing." *ACS Synthetic Biology*, 1(10), 451-457, (2012). 7 pages.

Atanasijevic, T., et al., "Calcium-Sensitive MRI Contrast Agents Based on Superparamagnetic Iron Oxide Nanoparticles and Calmodulin." *Proceedings of the National Academy of Sciences*, 103(40), 14707-14712, (2006). 6 pages.

Barrett, T., et al., "MRI of Tumor Angiogenesis." *Journal of Magnetic Resonance Imaging* 26, 235-249 (2007). 15 pages.

Blanco, E. H. Shen, and M. Ferrari, "Principles of nanoparticle design for overcoming biological barriers to drug delivery." *Nature Biotechnology* 33(9), 941-951, (2015). 11 pages.

Bourdeau, R.W., et al., "Acoustic Reporter Genes for Non-Invasive Imaging of Microbial Populations in Mammalian Hosts." *Nature* 553, 86-90, (Jan. 2018). 19 pages.

Bowen, C.V., et al., "Application of the Static Dephasing Regime Theory to Superparamagnetic Iron-Oxide Loaded Cells." *Magnetic Resonance in Medicine* 48, 52-61, (2002). 10 pages.

Brock, R., "The uptake of arginine-rich cell-penetrating peptides: putting the puzzle together." *Bioconjugate Chemistry* 25(5), 863-868, (2014). 6 pages.

Brooks, R.A., et al., "On T2-Shortening by Weakly Magnetized Particles: The Chemical Exchange Model." *Magnetic Resonance in Medicine* 45, 1014-1020, (2001). 7 pages.

Buchholz, B.,et al., "The distribution of the outer gas vesicle protein, GvpC, on the *Anabaena* gas vesicle, and its ratio to GvpA." *Microbiology* 139(10), 2353-2363, (1993). 11 pages.

Burns, P.N., "Harmonic imaging with ultrasound contrast agents." *Clinical Radiology* 51, 50-55, (1996). 7 pages.

Caravan, P., et al., "Gadolinium(III) Chelates as MRI Contrast Agents: Structure, Dynamics, and Applications." *Chemical Reviews*, 99(9), 2293-2352, (1999). 60 pages.

Cherin, E., et al., "Acoustic Behavior of *Halobacterium salinarum* Gas Vesicles in the High Frequency Range: Experiments and Modeling." *Ultrasound in Medicine & Biology* 43(5), 1016-1030, (2017). 33 pages.

Choi, J.J., et al., "Noninvasive, Transcranial and Localized Opening of the Blood-Brain Barrier Using Focused Ultrasound in Mice." *Ultrasound in Medicine & Biology*, 33(1), 95-104 (2007). 12 pages.

Cohen, B., et al., "Ferritin as an Endogenous MRI Reporter for Noninvasive Imaging of Gene Expression in C6 Glioma Tumors." *Neoplasia*, 7(2), 109-117, (2005). 9 pages.

Cohen, B., et al., "MRI Detection of Transcriptional Regulation of Gene Expression in Transgenic Mice." *Nature Medicine*, 13(4), 498-503, (2007). 6 pages.

Cosgrove, D., et al., "Clinical Uses of Microbubbles in Diagnosis and Treatment." *Med. Biol. Eng. Comput.* 47, 813-826, (2009), 14 pages.

Cunningham, C.H., et al., "Positive Contrast Magnetic Resonance Imaging of Cells Labeled with Magnetic Nanoparticles." *Magnetic Resonance in Medicine*, 53(5), 999-1005, (2005). 7 pages.

Dassarma, P., et al., "Bioengineering Novel Floating Nanoparticles for Protein and Drug Delivery." *Materials Today: Proceedings: Advances in Functional Materials (Conference 2015)*, 3(2), 206-210, (2016). 8 pages.

Dassarma, S., et al., "An Improved Genetic System for Bioengineering Buoyant Gas Vesicle Nanoparticles from Haloarchaea." *BMC Biotechnology* 13(112), (2013). 10 pages.

Dawson, P.E., et al., "Synthesis of proteins by native chemical ligation." *Science* 266(5186), 776-780, (1994). 5 pages.

Derrien, M. et al. "Fate, Activity, and Impact of Ingested Bacteria within the Human Gut Microbiota." *Trends in Microbiology*, 23(6), 354-366, (2015). 13 pages.

Donaldson, G.P., et al., "Gut Biogeography of the Bacterial Microbiota." *Nature Reviews Microbiology*, 14(1), 20-32, (2016). 13 pages.

Errico, C., et al., "Ultrafast Ultrasound Localization Microscopy for Deep Super-Resolution Vascular Imaging." *Nature*, 527(7579), 499-502, (2015). 9 pages.

Evbuomwan, O.M., et al. "Chapter 10: CEST and PARACEST Agents for Molecular Imaging," in *The Chemistry of Molecular Imaging*. Ed. Nicholas Long and Wing-Tak Wong, 225-243, Wiley & Sons, 2015. 27 pages.

Ferrara, K., et al., "Ultrasound Microbubble Contrast Agents: Fundamentals and Application to Gene and Drug Delivery." *Annu. Rev. Biomed. Eng.* 9, 415-447, (2017). 35 pages.

Fischer, H., et al., "Average Protein Density is a Molecular-Weight-Dependent Function." *Protein Science* 13, 2825-2828 (2004). 4 pages.

Foster, F.S., et al., "Principles and Applications of Ultrasound Backscatter Microscopy." *IEEE Transactions on Ultrasonics, Ferroelectrics and Frequency Control*, 40(5), 608-617, (1993). 10 pages.

Genove, G., et al., "A New Transgene Reporter for in vivo Magnetic Resonance Imaging." *Nature Medicine*, 11(4), 450-454, (2005). 5 pages.

Gilad, A.A. et al. "Developing MR Reporter Genes: Promises and Pitfalls." *NMR in Biomedicine* 20, 275-290, (2007). 16 pages.

Gilad, A.A. et al. "MRI Reporter Genes." *Journal of Nuclear Medicine* 49, 1905-1908 (2008). 5 pages.

Gilad, A.A., et al., "Artificial Reporter Gene Providing MRI Contrast Based on Proton Exchange." *Nature Biotechnology*, 25(2), 217-219, (2007). 3 pages.

Gillis, P. et al. "Transverse Relaxation of Solvent Protons Induced by Magnetized Spheres: Application to Ferritin, Erythrocytes, and Magnetite." *Magnetic Resonance in Medicine* 5, 323-345, (1987). 24 pages.

Gillis, P. et al., "On T2-Shortening by Strongly Magnetized Spheres: A Partial Refocusing Model." *Magnetic Resonance in Medicine* 47, 257-263, (2002). 8 pages.

Gorbach, S.L., "Chapter 95: Microbiology of the Gastrointestinal Tract", *Medical Microbiology, 4th Edition*, Editor: Samuel Baron, University of Texas Medical Branch at Galveston, Galveston, TX (1996). 10 pages.

Haacke, E.M. et al., "Susceptible-Weighted Imaging: Technical Aspects and Clinical Applications, Part 1." *American Journal of Neuroradiology* 30, 19-30, (2009). 12 pages.

Hayes, P. K., et al., "Gas Vesicles are Strengthened by the Outer-Surface Protein, GvpC." *Archives of Microbiology*, 157(3), 229-234, (1992). 2 pages.

Hayes, P., et al., "The gvpA/C Cluster of *Anabaena flos-aquae* has Multiple Copies of a Gene Encoding GvpA." *Archives of Microbiology*, 164(1), 50-57, (1995). 9 pages.

Hayes, P.K., et al., "Complete Amino Acid Sequence of Cyanobacterial Gas-Vesicle Protein Indicates a 70-Residue Molecule that Corresponds in Size to the Crystallographic Unit Cell." *Biochemical Journal* 236, 31-36, (1986). 6 pages.

He, X., et al., "Biophysical Mechanisms of Phase Contrast in Gradient Echo MRI." *Proceedings of the National Academy of Sciences*, 106(32), 13558-13563, (2009). 6 pages.

Hung, A.H., et al., "Magnetic Barcode Imaging for Contrast Agents." *Magnetic Resonance in Medicine*, 77(3), 970-978, (2017). 9 pages.

Jaffer, F.A., et al., "Molecular and Cellular Imaging of Atherosclerosis: Emerging Applications." *Journal of the Americal College of Cardiology*, 47(7), 1328-1338 (2006). 11 pages.

Jensen, J.H., et al., "NMR Relaxation in Tissues with Weak Magnetic Inhomogeneities." *Magnetic Resonance in Medicine* 44, 144-156, (2000). 13 pages.

Jolesz, F.A. "MRI-Guided Focused Ultrasound Surgery." *Annual Review of Medicine* 60, 417-430, (2009). 17 pages.

Karlin, S., et al., "Applications and Statistics for Multiple High-Scoring Segments in Molecular Sequences." *Proceedings of the National Academy of Sciences*, 90(12), 5873-5877, (1993). 5 pages.

Karlin, S., et al., "Methods for Assessing the Statistical Significance of Molecular Sequence Features by Using General Scoring Schemes." *Proceedings of the National Academy of Sciences*, 87(6), 2264-2268, (1990). 5 pages.

(56) References Cited

OTHER PUBLICATIONS

Kaufmann, B.A., et al., "Molecular Imaging with Targeted Contrast Ultrasound." *Current Opinion in Biotechnology* 18(1), 11-16, (2007). 6 pages.

Kinsman, R., et al., "Genes Encoding Proteins Homologous to Halobacterial Gvps N, J, K, F & L are Located Downstream of gvpC in the Cyanobacterium *Anabaena flos-aquae.*" *DNA Sequence*, 7(2), 97-106, (1997). 13 pages.

Kinsman, R., et al., "GvpCs with Reduced Numbers of Repeating Sequence Elements Bind to and Strengthen Cyanobacterial Gas Vesicles." *Molecular Microbiology*, 17(1), 147-154, (1995). 9 pages.

Kislukhin, A.A., et al., "Paramagnetic Fluorinated Nanoemulsions for Sensitive Cellular Fluorine-19 Magnetic Resonance Imaging." *Nature Materials* , 15(6), 662-668, (2016). 19 pages.

Lakshmanan, A., et al., "Molecular Engineering of Acoustic Protein Nanostructures." *ACS Nano*, 10(8), 7314-7322, (2016). 9 pages.

Lecoq, J., et al., "An Infared Flourescent Protein for Deeper Imaging." *Nature Biotechnology*, 29(8), 715-716, (2011). 5 pages.

Lee, J.-H., et al., "Artificially Engineered Magnetic Nanoparticles for Ultra-Sensitive Molecular Imaging." *Nature Medicine*, 13(1), 95-99, (2007). 5 pages.

Li, N. et al., "Gas Vesicle Genes Identified in *Bacillus megaterium* and Functional Expression in *Escherichia coli.*" *Journal of Bacteriology*, 180(9), 2450-2458, (1998). 9 pages.

Li, Z., et al., "Comparison of Reporter Gene and Iron Particle Labeling for Tracking Fate of Human Embryonic Stem Cells and Differentiated Endothelial Cells in Living Subjects." *Stem Cells* 26, 864-873, (2008). 10 pages.

Mani, V., et al., "GRadient echo Acquisition for Superparamagnetic particles with Positive Contrast (GRASP): Sequence Characterization in Membrane and Glass Superparamagnetic Iron Oxide Phantoms at 1.5T and 3T." *Magnetic Resonance in Medicine*, 55(1), 126-135, (2006). 10 pages.

Maresca, D., et al., "Imaging microvasculature with contrast-enhanced ultraharmonic ultrasound." *Ultrasound in Medicine & Biology* 40(6), 1318-1328, (2014). 13 pages.

Maresca, D., et al., "Nonlinear Ultrasound Imaging of Nanoscale Acoustic Biomolecules." *Applied Physics Letters*, 110(7), (2017). 6 pages.

Matsumoto, Y., et al., "T2 Relaxation Inducesd by Clusters of Supermagnetic Nanoparticles: Monte Carlo Simulations." *Magnetic Resonance Imaging* 26, 994-998, (2008). 6 pages.

McMahon, M.T., et al., "New 'Multicolor' Polypeptide Diamagnetic Chemical Exchange Saturation Transfer (DIACEST) Contrast Agents for MRI." *Magnetic Resonance in Medicine*, 60(4), 803-812, (2008). 10 pages.

Meeker, D. Finite Element Method Magnetics. *FEMM*, 4, 32 (2010). 162 pages.

Milo, R., et al., "BioNumbers—the Database of Key Numbers in Molecular and Cell Biology." *Nucleic Acids Research* 38, D750-D753, (2010). 4 pages.

Mowat, A.M., et al., "Regional Specialization within the Intestinal Immune System." *Nature Reviews Immunology*, 14(10), 667-685, (2014). 19 pages.

Myers, E.W. et al., "Optimal Alignments in Linear Space." *Computer Applications in the Blosciences: CABIOS*, 4(1), 11-17, (1988). 8 pages.

Needleman, S.B., et al., "A General Method Applicable to the Search for Similarities in the Amino Acid Sequence of Two Proteins." *Journal of Molecular Biology*, 48(3), 443-453, (1970). 12 pages.

Nilsson, B.L.,et al., "Chemical synthesis of proteins." *Annu. Rev. Biophys. Biomol. Struct.* 34, 91-118, (2005). 38 pages.

Ntziachristos, V., et al., "Looking and Listening to Light: the Evolution of Whole-Body Photonic Imaging." *Nature Biotechnology*, 23(3), 313-320, (2005). 8 pages.

Pearson, W.R., et al., "Improved Tools for Biological Sequence Comparison." *Proceedings of the National Academy of Sciences*, 85(8), 2444-2448, (1988). 5 pages.

Perez, J.M., et al., "Magnetic Relaxation Switches Capable of Sensing Molecular Interactions." *Nature Biotechnology*, 20(8), 816-820, (2002). 5 pages.

Pfeifer, F., "Distribution, Formation and Regulation of Gas Vesicles." *Nature Reviews Microbiology*, 10(10), 705-715, (2012). 11 pages.

Puderbach, M. et al. "MR Imaging of the Chest: A Practical Approach at 1.5 T." *European Journal of Radiology* 64, 345-355, (2007). 13 pages.

Rodriguez, P.L., et al., "Minimal 'Self' peptides that inhibit phagocytic clearance and enhance delivery of nanoparticles." *Science* 339(6122), 971-975, (2013). 11 pages.

Round, J.L., et al., "The Gut Microbiota Shapes Intestinal Immune Responses During Health and Disease." *Nature Reviews Immunology*, 9(5), 313-323, (2009). 12 pages.

Ruoslahti, E., "RGD and other recognition sequences for integrins." *Annual Review of Cell and Developmental Biology* 12(1), 697-715, (1996). 21 pages.

Schindelin, J., et al., "Fiji: an Open-Source Platform for Biological-Image Analysis." *Nature Methods*, 9(7), 676-682, (2012). 15 pages.

Schweser, F., et al., "Quantitative Imaging of Intrinsic Magnetic Tissue Properties Using MRI Signal Phase: An Approach to in vivo Brain Iron Metabolism?" *NeuroImage*, 54(4), 2789-2807, (2011). 19 pages.

Shaner, N.C., et al., "A Bright Monomeric Green Fluorescent Protein Derived from *Branchiostoma lanceolatum.*" *Nature Methods*, 10(5), 407-409, (2013). 8 pages.

Shapiro, M.G., et al., "Biogenic Gas Nanostructures as Ultrasonic Molecular Reporters." *Nature Nanotechnology*, 9(4), 311-316, (2014). 16 pages.

Shapiro, M.G., et al., "Directed Evolution of a Magnetic Resonance Imaging Contrast Agent for Noninvasive Imaging of Dopamine." *Nature Biotechnology*, 28(3), 264-270, (2010). 15 pages.

Shapiro, M.G., et al., "Genetically Encoded Reporters for Hyperpolarized Xenon Magnetic Resonance Imaging." *Nature Chemistry*, 6(7), 629-634, (2014). 6 pages.

Shapiro, M.G., et al., "Protein Nanoparticles Engineered to Sense Kinase Activity in MRI." *Journal of the American Chemical Society*, 131(7), 2484-2486, (2009). 8 pages.

Simon, R.D. "Morphology and Protein Composition of Gas Vesicles from Wild Type and Gas Vacuole Defective Strains of *Halobacetium salinarium* Strain 5." *Journal of General Microbiology* 125, 103-111 (1981). 9 pages.

Sremac, M., et al., "Recombinant Gas Vesicles from *Halobacterium* sp. Displaying SIV Peptides Demonstrate Biotechnology Potential as a Pathogen Peptide Delivery Vehicle", *BMC Biotechnology* 8(9), (2008). 14 pages.

Srivastava, A.K., et al., "Advances in using MRI Probes and Sensors for in vivo Cell Tracking as Applied to Regenerative Medicine." *Disease Models and Mechanisms*, 8(4), 323-336, (2015). 14 pages.

Stuber, M., et al., "Positive Contrast Visualization of Iron Oxide-Labeled Stem Cells using Inversion-Recovery With ON-Resonant Water Suppression (IRON)." *Magnetic Resonance in Medicine*, 58(5), 1072-1077, (2007). 6 pages.

Tang, J., et al., "Chapter 25: SWIM: Susceptibility Mapping as a Means to Visualize Veins and Quantify Oxygen Saturation." in *Susceptibility Weighted Imaging in MRI*. John Wiley & Sons, Inc., 461-485, (2011). 26 pages.

Taratula, O. et al., "Functionalized 129Xe Contrast Agents for Magnetic Resonance Imaging." *Current Opinion in Chemical Biology*, 14(1), 97-104, (2010). 14 pages.

Tashiro, Y., et al., "Molecular genetic and physical analysis of gas vesicles in buoyant enterobacteria." *Environmental Microbiology*, 18(4), 1264-1276 (2016). 13 pages.

Terreno, E., et al., "Challenges for Molecular Magnetic Resonance Imaging." *Chemical Reviews*, 110(5), 3019-3042, (2010). 24 pages.

Walsby, A.E., "Chapter 10: Cyanobacteria: Planktonic Gas-Vacuolate Forms," in *The Prokaryotes, a Handbook on Habitats, Isolation, and Identification of Bacteria*, 224-235, Springer (2013). 13 pages.

Walsby, A.E., "Chapter 28: Gas-Vacuolate Bacteria (Apart from Cyanobacteria)," in *The Prokaryotes*, 441-447, Springer (1981). 8 pages.

(56) References Cited

OTHER PUBLICATIONS

Walsby, A.E., "Gas vesicles." *Microbiological Review*, 58(1), 94-144, (1994). 51 pages.
Walsby, A.E., et al., "Average Thickness of the Gas Vesicle Wall in *Anabaena flos-aquae*." *Journal of Molecular Biology* 129, 279-285, (1979). 7 pages.
Walsby, A.E., et al., "The gas-permeability coefficient of the cyanobacterial gas vesicle wall." *Journal of General Microbiology* 138, 837-845, (1992). 9 pages.
Walsby, A.E., et al., "Gas vesicle proteins." *Biochem. J.* 264, 313-322, (1989). 10 pages.
Wang, Y. et al. "Quantitative Susceptibility Mapping (QSM): Decoding MRI Data for a Tissue Magnetic Biomarker." *Magnetic Resonance in Medicine* 73, 82-101, (2015). 20 pages.
Weissleder, R., et al., "Ultrasmall Superparamagnetic Iron Oxide: Characterization of a New Class of Contrast Agents for MR Imaging." *Radiology*, 175(2), 489-493, (1990). 7 pages.
Woese, C.R., "Bacterial evolution." *Microbiological Reviews*, 51(2), 221-271, (1987). 51 pages.
Yablonskiy, D.A. et al., "Theory of NMR Signal Behavior in Magnetically Inhomogeneous Tissues: The Static Dephasing Regime." *Magnetic Resonance in Medicine* 32, 749-763, (1994). 16 pages.
Yi G. et al., "Identifying Clusters of Functionally Related Genes in Genomes." *Bioinformatics*, 23(9), 1053-1060, (2007). 8 pages.
Zabow, G., et al., "Shape-Changing Magnetic Assemblies as High-Sensitivity NMR-Readable Nanoprobes." *Nature*, 520(7545), 73-77, (2015). 24 pages.
Zakeri, B., et al., "Peptide tag forming a rapid covalent bond to a protein, through engineering a bacterial adhesin." *Proc. Natl. Acad. Sci. U. S. A.* 109(12), E690-E697, (2012). 8 pages.
Zhang, S., et al., "PARACEST Agents: Modulating MRI Contrast via Water Proton Exchange." *Accounts of Chemical Research*, 36(10), 783-790, (2003). 8 pages.
Zordan, R.E., et al., "Avoiding the Ends: Internal Epitope Tagging of Proteins Using Transposon Tn7." *Genetics*, 200(1), 47-58, (2015). 42 pages.
Zurkiya, O., et al., Off-Resonance Saturation as a Means of Generating Contrast with Superparamagnetic Nanoparticles. *Magnetic Resonance in Medicine*, 56(4), 726-732, (2006). 7 pages.
Belkaid, Y., et al., "Role of the Microbiota in Immunity and Inflammation", Cell, 157 (1): pp. 121-141, (2014), 21 pages.
Braat, H., et al., "A phase I Trial with Transgenic Bacteria Expressing Interleukin-10 in Crohn's Disease", Clinical Gastroenterology and Hepatology, 4 (6): pp. 754-759, (2006), 6 pages.
Buchler, N.E., et al., "On Schemes of Combinatorial Transcription Logic", Proceedings of the National Academy of Sciences, 100 (9): pp. 5136-5141, (2003), 6 pages.
Chu, J., et al., "A Bright Cyan-Excitable Orange Fluorescent Protein Facilitates Dual-Emission Microscopy and Enhances Bioluminescence Imaging in Vivo." Nat Biotech, 34 (7): pp. 760-767, (2016), 29 pages.
Claesen, J., et al., "Synthetic Microbes as Drug Delivery Systems" ACS Synthetic Biology, 4 (4): pp. 358-364, (2014), 7 pages.
Courbet, A., et al., "Detection of Pathological Biomarkers in Human Clinical Samples via Amplifying Genetic Switches and Logic Gates", Science Translational Medicine, 7 (289): pp. 289ra83-289ra83, (2015), 49 pages.
Daniel, C., et al., "Bioluminescence Imaging Study of Spatial and Temporal Persistence of *Lactobacillus plantarum* and *Lactococcus lactis* in Living Mice" Applied and Environmental Microbiology, 79 (4): pp. 1086-1094, (2013), 9 pages.
Daniel, C., et al., "Recombinant Lactic Acid Bacteria as Mucosal Biotherapeutic Agents", Trends in Biotechnology, 29 (10): pp. 499-508, (2011), 10 pages.
Danino, T., et al., "In Vivo Gene Expression Dynamics of Tumor-Targeted Bacteria", ACS Synthetic Biology, 1 (10): pp. 465-470, (2012), 6 pages.
Danino, T., et al., "Programmable Probiotics for Detection of Cancer in Urine", Science Translational Medicine, 7 (289): pp. 289ra84-289ra84, (2015), 28 pages.
Derrien, M., et al., "Fate, Activity, and Impact of Ingested Bacteria Within the Human Gut Microbiota", Trends in Microbiology, vol. 23, No. 6, pp. 354-366 (2015), 13 pages.
Din, M.O., et al., "Synchronized Cycles of Bacterial Lysis for in Vivo Delivery", Nature, 536 (7614): pp. 81-85, (2016), 18 pages.
Fischbach, M.A., et al., "Cell-Based Therapeutics: The Next Pillar of Medicine", Science Translational Medicine, 5 (179), pp. 179ps7-179ps7, (2013), 7 pages.
Foster, F.S., et al., "Advances in Ultrasound Biomicroscopy", Ultrasound in Medicine & Biology, 26 (1), pp. 1-27, (2000), 27 pages.
Foucault, M.-L., et al., "In Vivo Bioluminescence Imaging for the Study of Intestinal Colonization by *Escherichia coli* in Mice", Applied and Environmental Microbiology, 76 (1): pp. 264-274, (2010), 11 pages.
Gorbach, S.L., "Chapter 95: Microbiology of the Gastrointestinal Tract", Medical Microbiology, 4$^{th}$ Edition, Editor: Samuel Baron, University of Texas Medical Branch at Galveston, Galveston, TX (1996), 9 pages.
Klumpp, S., et al., "Bacterial Growth: Global Effects on Gene Expression, Growth Feedback and Proteome Partition", Current Opinion in Biotechnology, 28, pp. 96-102, (2014), 7 pages.
Kotula, J.W., et al., "Programmable Bacteria Detect and Record an Environmental Signal in the Mammalian Gut", Proceedings of the National Academy of Sciences, 111 (13): pp. 4838-4843, (2014), 6 pages.
Reits, E.A., et al., "From Fixed to FRAP: Measuring Protein Mobility and Activity in Living Cells", Nature Cell Biology, 3 (6), pp. E145-E147, (2001), 3 pages.
Romero, P.A., et al., "Exploring Protein Fitness Landscapes by Directed Evolution", Nature Reviews Molecular Cell Biology, 10 (12): pp. 866-876, (2009), 25 pages.
Round, J.L., et al., "The Gut Microbiota Shapes Intestinal Immune Responses During Health and Disease", Nature Reviews Immunology, 9 (5): pp. 313-323, (2009), 25 pages.
Shaner, N.C., et al., "Improved Monomeric Red, Orange and Yellow Fluorescent Proteins Derived from *Discosoma* sp. Red Fluorescent Protein", Nature Biotechnology, 22 (12): pp. 1567-1572, (2004), 7 pages.
Shaner, N.C., et al., "Improving the Photostability of Bright Monomeric Orange and Red Fluorescent Proteins", Nature Methods, 5 (6): pp. 545-551, (2008), 25 pages.
Silva-Rocha, et al., "Mining Logic Gates in Prokaryotic Transcriptional Regulation Networks", FEBS Letters, 582 (8): pp. 1237-1244, (2008), 8 pages.
Smith, T.F., et al., "Comparison of Biosequences", Advances in Applied Mathematics, 2 (4): pp. 482-489, (1981), 8 pages.
Smith-Bindman, R., et al., "Use of Diagnostic Imaging Studies and Associated Radiation Exposure for Patients Enrolled in Large Integrated Health Care Systems, 1996-2010" JAMA, 307 (22): pp. 2400-2409, (2012), 10 pages.
Sprinzak. D., et al., "Reconstruction of Genetic Circuits", Nature, 438 (7067), pp. 443-448, (2005), 6 pages.
Steidler, L., et al., "Treatment of Murine Colitis by *Lactococcus lactis* Secreting Interleukin-10", Science, 289 (5483): pp. 1352-1355, (2000), 4 pages.
Van Keulen, G., et al., "Gas Vesicles in Actinomycetes: Old Buoys in Novel Habitats?", Trends in Microbiology, 13 (8): pp. 350-354, (2005), 6 pages.
Wang, Y., et al., "The Role of Microbiome in Central Nervous System Disorders", Brain, Behavior, and Immunity, 38, pp. 1-12, (2014), 28 pages.
Wells, J.M., et al., "Mucosal Delivery of Therapeutic and Prophylactic Molecules Using Lactic Acid Bacteria", Nature Reviews Microbiology, 6 (5), pp. 349-362, (2008), 14 pages.
Yurist-Doutsch, S., et al., "Gastrointestinal Microbiota-Mediated Control of Enteric Pathogens", Annual Review of Genetics, 48, pp. 361-382, (2014), 25 pages.
Griffiths, et al., "The homologies of gas vesicle proteins", Journal of General Microbiology (1992), 138, 1243-1250.
Restriction Requirement for U.S. Appl. No. 15/613,104, filed Jun. 2, 2017 on behalf of California Institute of Technology, dated Feb. 21, 2019. 9 pages.

(56) References Cited

OTHER PUBLICATIONS

Altschul, et al, Gapped BLAST and PSI-BLAST: a new generation of protein database search programs. Nucleic Acids Res., 1997. 25(17): 3389-3402. p. 14.
Bar-Zion, A. et al. Acoustically Detonated Biomolecules for Genetically Encodable Inertial Cavitation. bioRxiv 620567 (2019) 11 pages.
Calvo, et al, Upstream open reading frames cause widespread reduction of protein expression and are polymorphic among humans. Proc Natl Acad Sci U S A, 2009. 106(18): p. 7507-12.
Corrected Notice of Allowability for U.S. Appl. No. 15/613,104, filed Jun. 2, 2017 on behalf of California Institute of Technology dated Sep. 9, 2019 10 pages.
Del Vecchio, D and Muarray, R.M. "Biomolecular Feedback Systems" bfs-pupss. Jun. 13, 2014. 280 pages.
Farhadi, A., et al., Recombinantly Expressed Gas Vesicles as Nanoscale Contrast Agents for Ultrasound and Hyperpolarized MRI. AIChE J, 2018. 64(8): p. 2927-2933.
Farhadi A. et al., "Ultrasound imaging of gene expression in mammalian cells" Science 365, 1469-1475, Sep. 2019, 43 pages.
Huang, H. et al. "A G-Quadruplex-Containing RNA Activates Flourescence in a GFP-Like Flourophore", Nat Chem Biol., Aug. 2014, 10 (8); 686-691. 22 pages.
Koehne G. et al., "Serial in vivo imaging of the targeted migration of human HSV-TK-transduced antigen-specific lymphocytes." *Nature Biotechnology* vol. 21, 405-413 (Apr. 2003).
Lakshmanan, A., et al., Preparation of biogenic gas vesicle nanostructures for use as contrast agents for ultrasound and MRI. Nat Protoc, 2017. 12(10): p. 2050-2080.
Lu, G.J., et al., Acoustically modulated magnetic resonance imaging of gas-filled protein nanostructures. Nat Mater, 2018. 17(5): p. 456-463. 15 pages.
Maresca D, et al ., "Nonlinear X-Wave Ultrasound Imaging of Acoustic Biomolecules" *Phys Rev X* vol. 8,(2018). 041002-1 to 041002-12. 12 pages.
Maresca D, et al., "Biomolecular Ultrasound and Sonogenetics" *Annu Rev Chem Biomol Eng* vol. 9, 229-252(Jun. 2018). 29 pages.
Natarajan, S, "NS3 protease from flavivirus as a target for designing antiviral inhibitors against dengue virus", Genetics and Molecular Biology, 33, 2, 214-219 (2010).
Notice of Allowance for U.S. Appl. No. 15/613,104, filed Jun. 2, 2017 on behalf of California Institute of Technology dated Jul. 18, 2019 15 pages.
Ntziachristos, V. "Going deeper than microscopy: the optical imaging frontier in biology." *Nature Methods* 7, No. 8, 603-614 (2010).
Piraner, D. I. et al. Going Deeper: Biomolecular Tools for Acoustic and Magnetic Imaging and Control of Cellular Function. Biochemistry 56, 5202-5209 (2017).
Purnick, P.E. and R. Weiss, "The second wave of synthetic biology: from modules to systems." *Nat Rev Mol Cell Biol*, 2009. 10(6): p. 410-22.
Ramnarine, et al, "Construction and geometric stability of physiological flow rate wall-less stenosis phantoms." *Ultrasound in medicine & biology* 27, 245-250 (2001).
Ramsay, J.P., et al., "A quorum-sensing molecule acts as a morphogen controlling gas vesicle organelle biogenesis and adaptive flotation in an enterobacterium." *Proc Natl Acad Sci U S A*, 2011. 108(36): p. 14932-7.
Restriction Requirement for U.S. Appl. No. 15/663,600, filed Jul. 28, 2017 on behalf of California Institute of Technology, dated Dec. 27, 2019. 7 pages.
Rose, A.B., Intron-mediated regulation of gene expression. Curr Top Microbiol Immunol, 2008. 326: p. 277-90.
Santos E. B. et al., "Sensitive in vivo imaging of T cells using a membrane-bound Gaussia princeps luciferase", *Nat Med* vol. 15, No. 3, 338-344 (Mar. 2009).
Savage, D. C. "Microbial ecology of the gastrointestinal tract." *Annual review of microbiology* 31, 107-133 (1977).

Schechter, et al, On the active site of proteases. 3. Mapping the active site of papain; specific peptide inhibitors of papain. Biochem Biophys Res Commun., 1968 32(5): p. 898-902.
Schechter, et al, On the size of the active site in proteases. I. Papain. Biochem Biophys Res Commun., 1967. 27(2): p. 157-162.
Simon, G. L. & Gorbach, S. L. Intestinal flora in health and disease. Gastroenterology 86, 174-193 (1984).
Smith TF, et al., Identification of common molecular subsequences. J Mol Biol, 1981. 147(1): 195-197. p. 3.
Szymczak A. L. et al., "Development of 2A peptide-based strategies in the design of multicistronic vectors." *Expert Opin Biol* Th 5 (5), 627-638 (2005).
Tsien R. Y., "Imagining imaging's future" *Nature Reviews Molecular Cell Biology*, Ss16-Ss21 (Sep. 2003).
Tsien, R. Y. The Green Fluorescent Protein. Annual Review of Biochemistry 67, 509-544 (1998).
Aguilera et al., "Systemic in vivo distribution of activatable cell penetrating peptides is superior to cell penetrating peptides." Integr Biol (Camb). 2009. 1 (5-6): p. 371-381. 22 pages.
Baker, T.A. et al., "ClpXP, an ATP-powered unfolding and protein-degradation machine." Biochimica et Biophysica Acta (BBA)— Molecular Cell Research, 2012. 1823 (1): p. 15-28. 33 pages.
Beard, P. "Biomedical photoacoustic imaging." *Interface Focus* 1, 602-631 (2011).
Blum-Oehler, G., et al., "Development of strain-specific PCR reactions for the detection of the probiotic *Escherichia coli* strain Nissle 1917 in fecal samples." Research in Microbiology, 2002. 154 (1): p. 59-66.
Cameron, D.E. and Collins, J.J., "Tunable protein degradation in bacteria." Nature Biotechnology 2014. 32 (12): p. 1276-1281. 19 pages.
Cha-Molstad et al., "Modulation of SQSTM1/p62 activity by N-terminal arginylation of the endoplasmic reticulum chaperone HSPA5/ GRP78/BiP." Autophagy, 2016. 12 (2): p. 426-428.
Chassin H. et al., "A modular degron library for synthetic circuits in mammalian cells." Nature Communications 2019.10: 2013. 11 pages.
Church C. "Frequency, pulse length, and the mechanical index." *Acoustics Research Letters Online*, 6 (3), 162-168, 8 pages (2005).
Coussios, C. et al., "Applications of Acoustics and Cavitation to Noninvasive Therapy and Drug Delivery." *Annu. Rev. Fluid Mech.* (2008) 40, 395-420. 28 pages.
Dang, L. H. et al., "Combination bacteriolytic therapy for the treatment of experimental tumors." *Proc. Natl. Acad. Sci. U. S. A.* 98, 26, 15155-60 (2001).
Datsenko, K.A. et al., "One-step inactivation of chromosomal genes in *Escherichia coli* K12 using PCR products." Proceedings of the National Academy of Sciences, 2000. 97 (12): p. 6640-6645.
Davila, M. L. et al. "Efficacy and Toxicity Management of 19-28z CAR T Cell Therapy in B Cell Acute Lymphoblastic Leukemia". 6(224), *Sci Transl Med* (2014). 23 pages.
Drag, M. et al., "Emerging principles in protease-based drug discovery." Nature Reviews Drug Discovery 9 (9), 690-701, (2010). 27 pages.
Elowitz, M.B. and S. Leibler, A synthetic oscillatory network of transcriptional regulators. Nature, 2000. 403 (6767): p. 335-338.
Fernandez-Rodriguez, J. et al., "Post-translational control of genetic circuits using Potyvirus proteases." Nucleic Acids Research 44, No. 13, 6493-6502 (2016).
Forbes N. S., et al., "Sparse initial entrapment of systemically injected *Salmonella typhimurium* leads to heterogeneous accumulation within tumors." *Cancer Res.* 63, 5188-5193 (2003).
Gao, X.J. et al., "Programmable protein circuits in living cells." Science 361, 1252-1258 (2018). 8 pages.
Gardner, T.S. et al., "Construction of a genetic toggle switch in *Escherichia coli.*" Nature, 2000. 403 (6767): p. 339-342.
Geva-Zatorsky, N., et al., "In vivo imaging and tracking of host-microbiota interactions via metabolic labeling of gut anaerobic bacteria." Nature Medicine, 2015. 21 (9): p. 1091-1100. 27 pages.
Goll, D.E., et al., "The calpain system." Physiological Reviews, 2003. 83 (3): p. 731-801.
Häcker, G. et al., "Activation of the immune system by bacterial CpG-DNA." *Immunology* 105, 245-251 (2002).

(56) References Cited

OTHER PUBLICATIONS

Heim, R. et al., "Engineering green fluorescent protein for improved brightness, longer wavelengths and fluorescence resonance energy transfer." Current Biology 6, 178-182 (1996).
Holland C. et al., "An Improved Theory for the Prediction of Microcavitation Thresholds." *IEEE Transactions on Ultrasonics, Ferroelectrics, and Frequency Control*, vol. 36, No. 2, 204-208 (1989).
International Search Report and Written Opinion for PCT App. No. PCT/US2020/025608 filed on Mar. 29, 2020 on behalf of California Institute of Technology, dated Jul. 17, 2020. 13 pages.
International Search Report for International Application No. PCT/US2020/012557 filed on Jan. 7, 2020 on behalf of California Institute of Technology dated May 1, 2020 5 pages.
International Search Report for International Application No. PCT/US2020/012572 filed on Jan. 7, 2020 on behalf of California Institute of Technology dated May 6, 2020 4 pages.
Jackson, H. J. et al., "Driving CAR T-cells forward." *Nat. Rev. Clin. Oncl.*13 (6), 370-383 (2016). 31 pages.
Jang, M. J. et al., "NeuroCa: integrated framework for systematic analysis of spatiotemporal neuronal activity patterns from large-scale optical recording data." *Neurophotonics* 2 (3), 035003 (2015). 16 pages.
Khalil, A.S. et al., "Synthetic biology: applications come of age." Nature Reviews Genetics, 2010. 11 (5): p. 367-379.
Kunth, M. et al., "Protein Nanostructures Produce Self-Adjusting Hyperpolarized Magnetic Resonance Imaging Contrast through Physical Gas Partitioning." *ACS Nano* (2018). 12, 10939-10948. doi:10.1021/acsnano.8b04222.
Kwan, J. J. et al. "Ultrasound-Propelled Nanocups for Drug Delivery." *Small Journal* 11, No. 39, 5305-5314 (2015).
Lakshmanan A. et al., "Acoustic biosensors for ultrasound imaging of enzyme activity (Supplementary Information)" Nature Chemical Biology, Jul. 2020, 3 pages.
Lakshmanan,A et al., "Acoustic Biosensors for Ultrasound Imaging of Enzyme Activity", Nature Chemical Biology, 16, pp. 988-996 (Jul. 13, 2020), 23 pages.
Lin, M.Z. et al., "Genetically encoded indicators of neuronal activity." Nature Neuroscience 19, No. 9, 1142-1153 (2016).
Lopez-Otin, C. et al., "Proteases: multifunctional enzymes in life and disease." Journal of Biological Chemistry 283, No. 45, 30433-7 (2008).
Machtaler, S., et al., "Assessment of inflammation in an acute on chronic model of inflammatory bowel disease with ultrasound molecular imaging." Theranostics, 2015. 5 (11): p. 1175-1186.
Mark Welch, J.L., et al., "Spatial organization of a model 15-member human gut microbiota established in gnotobiotic mice." Proceedings of the National Academy of Sciences, 2017. 114 (43): p. E9105-E9114.
Milenic D. E. et al., "Antibody-Targeted Radiation Cancer Therapy." *Nature*, (2004). vol. 3, 488-498.
Mitra, R.D. et al., "Fluorescence resonance energy transfer between blue emitting and red-shifted excitation derivatives of the green fluorescent protein." Gene 173, 13-17 (1996).
Miyawaki, A. et al., "Molecular spies for bioimaging-fluorescent protein-based probes." Molecular Cell 58, 632-643 (2015).
Muradali, D. et al., "US of gastrointestinal tract disease." Radiographics, 2015. 35 (1): p. 50-68.
Non-Final Office Action for U.S. Appl. No. 15/663,600, filed Jul. 28, 2017 on behalf of California Institute of Technology, dated Jun. 23, 2020. 26 pages.
Ong, I.L.H. et al., "Recent developments in protease activity assays and sensors." Analyst 142, 1867-1881 (2017).
Ono, Y. et al., "Calpain research for drug discovery: challenges and potential." Nature Reviews Drug Discovery, 2016. 15 (12): p. 854-876. 34 pages.
Ono, Y. et al., "Calpains—an elaborate proteolytic system." Biochimica et Biophysica Acta (BBA)—Proteins and Proteomics, 2012. 1824 (1): p. 224-236.
Palmer, A.E. et al., "Design and application of genetically encoded biosensors." Trends in Biotechnology 29 (3), 144-152 (2011). 18 pages.
Parks, T.D., et al., "Release of proteins and peptides from fusion proteins using a recombinant plant virus proteinase." Analytical Biochemistry, 1994. 216 (2): p. 413-417.
Phan, J., et al., "Structural basis for the substrate specificity of tobacco etch virus protease." Journal of Biological Chemistry, 2002. 277 (52): p. 50564-50572.
Rodriguez, E.A. et al. "The growing and glowing toolbox of fluorescent and photoactive proteins." Trends in Biochemical Sciences 42 (2), 111-129 (2017). 31 pages.
Ryan, R. M. et al. "Bacterial delivery of a novel cytolysin to hypoxic areas of solid tumors." *Gene Ther*.16, 329-339 (2009).
Sauer, R.T. and Baker, T.A., "AAA+ Proteases: ATP-Fueled Machines of Protein Destruction." Annual Review of Biochemistry, 2011. 80: p. 587-612.
Sauer, R.T., et al., "Sculpting the proteome with AAA+ proteases and disassembly machines." Cell, 2004. 119 (1): p. 9-18. 21 pages.
Schneider, C. et al., "NIH Image to ImageJ: 25 years of image analysis." *Nat. Methods* 9 (7), 671-675 (2012). 12 pages.
Sonnenborn, U. et al., "The non-pathogenic *Escherichia coli* strain Nissle 1917—features of a versatile probiotic." Microbial Ecology in Health and Disease, 2009. 21 (3-4): p. 122-158.
Stein, V. et al. "Protease-based synthetic sensing and signal amplification." Proceedings of the National Academy of Sciences 111, No. 45, 15934-15939 (2014).
St-Pierre, F., et al., "One-step cloning and chromosomal integration of DNA." ACS Synthetic Biology, 2013.2 (9): p. 537-541.
Suzuki, S., et al., "Development of an artificial calcium-dependent transcription factor to detect sustained intracellular calcium elevation." ACS Synthetic Biology, 2014.3 (10): p. 717-722.
Tigges, M., et al., "A tunable synthetic mammalian oscillator. Nature," 2009. 457 (7227): p. 309-312.
Turk, B., et al., "Protease signaling: the cutting edge." The EMBO Journal 31, 1630-1643 (2012).
Walsby, A. E." Gas Vesicles." *Annu. Rev. Plant Physiol.* 26, 427-439 (1975).
Walsby, A. E. "The pressure relationships of gas vacuoles." *Proc. R. Soc. London. Ser. B. Biol. Sci.* 178, 301-326 (1971).
Written Opinion for International Application No. PCT/US2020/012572 filed on Jan. 7, 2020 on behalf of California Institute of Technology dated May 6, 2020 6 pages.
Written Opinion for International Application No. PCT/US2020/012557 filed on Jan. 7, 2020 on behalf of California Institute of Technology dated May 1, 2020 6 pages.
Yin, L. et al., "Quantitatively Visualizing Tumor-Related Protease Activity in Vivo Using a Ratiometric Photoacoustic Probe." J. Am. Chem. Soc., 2019. 141 (7): p. 3265-3273.
Zhang, H. F. et al., "Imaging of hemoglobin oxygen saturation variations in single vessels in vivo using photoacoustic microscopy." *Appl. Phys. Lett.* 90, 5-7, 053901 (2007). 4 pages.
International Search Report and Written Opinion for PCT App. No. PCT/US2020/048572 filed on Aug. 28, 2020, on behalf of California Institute of Technology, dated Dec. 29, 2020. 11 pages.
Notice of Allowance for U.S. Appl. No. 15/663,600, filed Jul. 28, 2017 on behalf of California Institute of Technology, dated Dec. 11, 2020.13 pages.
Non-Final Office Action for U.S. Appl. No. 16/656,417, filed Oct. 17, 2019 on behalf of California Institute of Technology dated Mar. 23, 2021 20 pages.

\* cited by examiner

FIG. 14

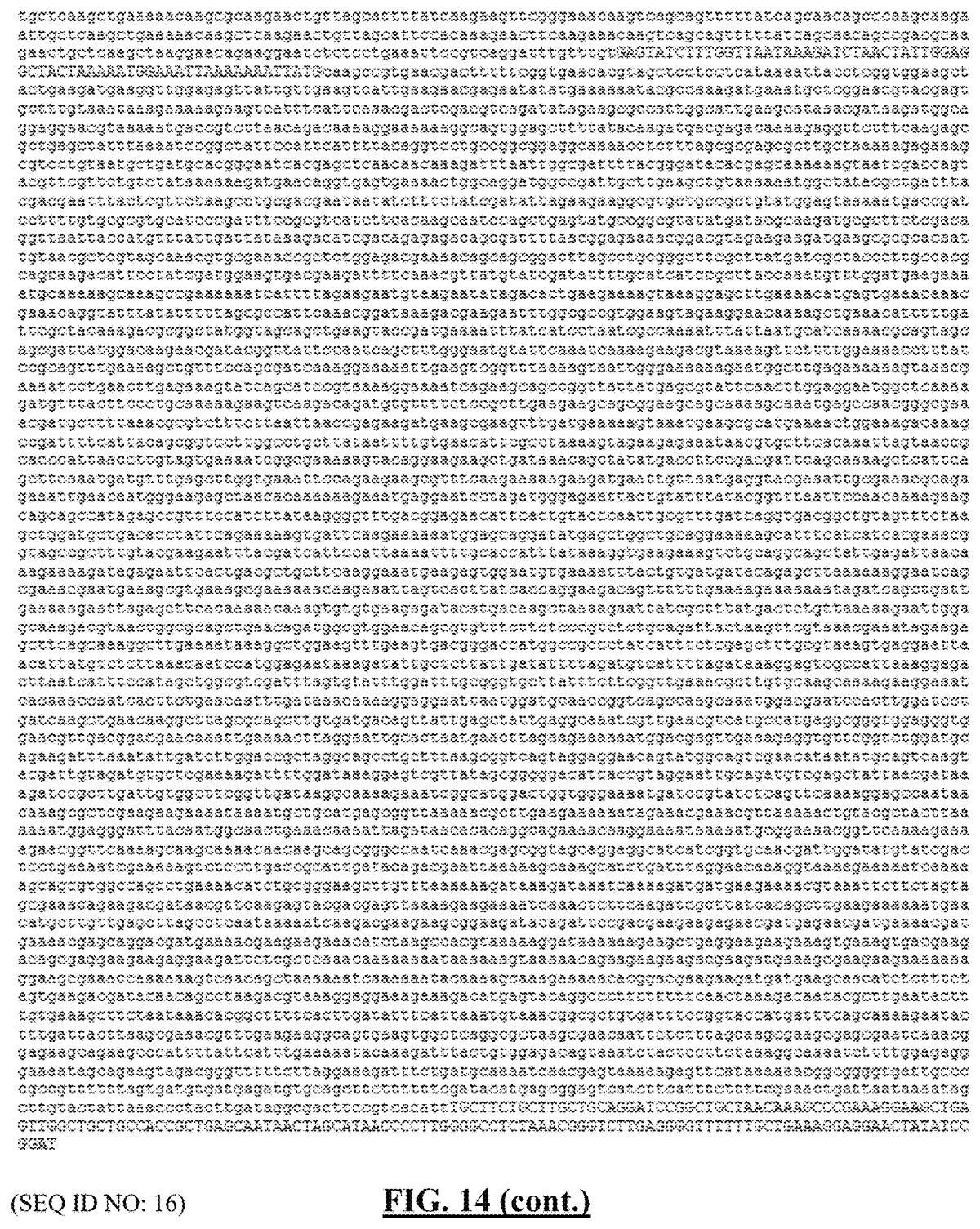

(SEQ ID NO: 16)   FIG. 14 (cont.)

ARG2

FIG. 15

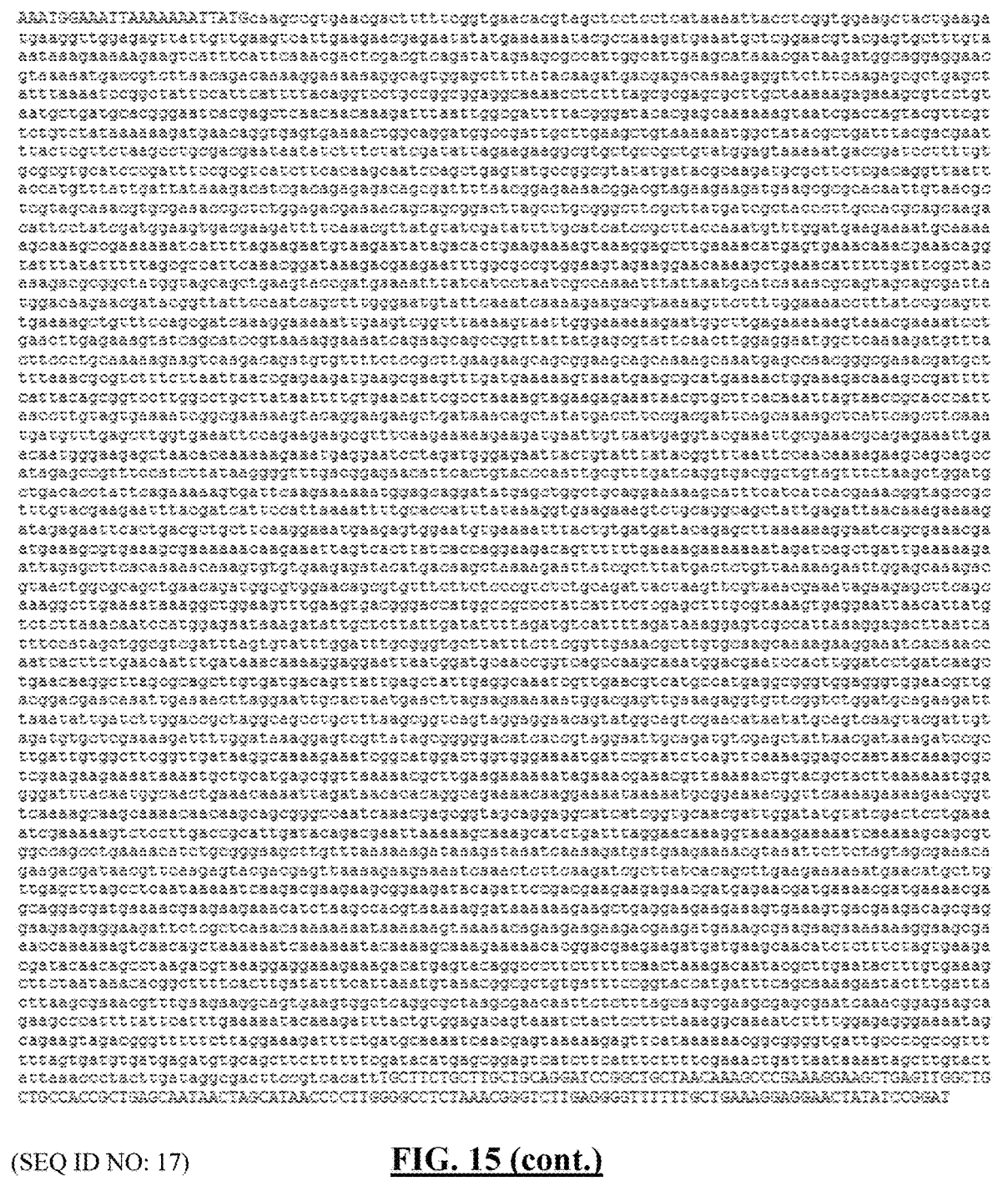

(SEQ ID NO: 17)

Archaea
Halobacterium sp. NRC-1 pNRC200
Halobacterium sp. NRC-1 pNRC100
Halobacterium mediterranei c-vac
Natronobacterium vacuolatum
Methanosarcina barkeri

Cyanobacteria
Anabaena flos-aquae
Nostoc sp. ATCC29413
Pseudoanabaena sp. PCC6901
Microcystis aeruginosa
Trichodesmium erythraeum

Actinomycetes
Streptomyces coelicolor gvp1
Streptomyces coelicolor gvp2
Streptomyces avermitilis gvp1
Streptomyces avermitilis gvp2
Streptomyces avermitilis gvp3
Streptomyces scabies gvp1
Streptomyces scabies gvp2
Streptomyces peucetius gvp1
Streptomyces peucetius gvp2
Streptomyces diversea™ gvp1
Streptomyces diversea™ gvp2
Saccharopolyspora erythraea
Frankia alni
Frankia sp. EAN1pec
Frankia sp. Ccl3
Rhodococcus sp. RHA1 gvp1
Rhodococcus sp. RHA1 gvp2
Rhodococcus equi

Other bacteria
Bacillus megaterium
Rhodobacter sphaeroides
Ancylobacter aquaticus

FIG. 21

SEQUENCE LISTING

<160> NUMBER OF SEQ ID NOS: 108

<210> SEQ ID NO 1
<211> LENGTH: 88
<212> TYPE: PRT
<213> ORGANISM: Bacillus megaterium
<220> FEATURE:
<221> NAME/KEY: MISC_FEATURE
<222> LOCATION: (1)..(88)
<223> OTHER INFORMATION: Gas vesicle structural protein GvpB

<400> SEQUENCE: 1

Met Ser Ile Gln Lys Ser Thr Asn Ser Ser Leu Ala Glu Val Ile
1               5                   10                  15

Asp Arg Ile Leu Asp Lys Gly Ile Val Ile Asp Ala Phe Ala Arg Val
            20                  25                  30

Ser Val Val Gly Ile Glu Ile Leu Thr Ile Glu Ala Arg Val Val Ile
        35                  40                  45

Ala Ser Val Asp Thr Trp Leu Arg Tyr Ala Glu Ala Val Gly Leu Leu
    50                  55                  60

Arg Asp Asp Val Glu Glu Asn Gly Leu Pro Glu Arg Ser Asn Ser Ser
65                  70                  75                  80

Glu Gly Gln Pro Arg Phe Ser Ile
                85

<210> SEQ ID NO 2
<211> LENGTH: 71
<212> TYPE: PRT
<213> ORGANISM: Anabaena flos-aquae
<220> FEATURE:
<221> NAME/KEY: MISC_FEATURE
<222> LOCATION: (1)..(71)
<223> OTHER INFORMATION: Gas vesicle structural protein GvpA

<400> SEQUENCE: 2

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Val Arg Val
            20                  25                  30

Ser Leu Val Gly Ile Glu Leu Leu Ala Ile Glu Ala Arg Ile Val Ile
        35                  40                  45

Ala Ser Val Glu Thr Tyr Leu Lys Tyr Ala Glu Ala Val Gly Leu Thr
    50                  55                  60

Gln Ser Ala Ala Val Pro Ala
65                  70

<210> SEQ ID NO 3
<211> LENGTH: 48
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(48)
<223> OTHER INFORMATION: Consensus sequence of a gvp A/B protein
<220> FEATURE:
<221> NAME/KEY: MISC_FEATURE
<222> LOCATION: (16)..(16)
<223> OTHER INFORMATION: Xaa can be any amino acid

<400> SEQUENCE: 3

Ser Ser Ser Leu Ala Glu Val Leu Asp Arg Ile Leu Asp Lys Gly Xaa
1               5                   10                  15

Val Ile Asp Ala Trp Ala Arg Val Ser Leu Val Gly Ile Glu Ile Leu
            20                  25                  30

Thr Ile Glu Ala Arg Val Val Ile Ala Ser Val Asp Thr Tyr Leu Arg
        35                  40                  45

<210> SEQ ID NO 4
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(6)
<223> OTHER INFORMATION: Portion of the gvp A/B consensus sequence of
      SEQ ID NO: 3 having an alpha-helical structure in prokaryotes

<400> SEQUENCE: 4

Leu Asp Arg Ile Leu Asp
1               5

<210> SEQ ID NO 5
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(16)
<223> OTHER INFORMATION: Portion of the gvp A/B consensus sequence of
      SEQ ID NO: 3 having a beta strand beta strand structure in
      prokaryotes
<220> FEATURE:
<221> NAME/KEY: MISC_FEATURE
<222> LOCATION: (7)..(7)
<223> OTHER INFORMATION: Xaa can be any amino acid

<400> SEQUENCE: 5

Arg Ile Leu Asp Lys Gly Xaa Val Ile Asp Ala Trp Ala Arg Val Ser
1               5                   10                  15

<210> SEQ ID NO 6
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(5)
<223> OTHER INFORMATION: Portion of the gvp A/B consensus sequence SEQ
      ID NO: 3 having an alpha-helical structure in prokaryotes

<400> SEQUENCE: 6

Asp Thr Tyr Leu Arg
1               5

<210> SEQ ID NO 7
<211> LENGTH: 8
<212> TYPE: PRT
<213> ORGANISM: Anabaena flos-aquae
<220> FEATURE:
<221> NAME/KEY: MISC_FEATURE
<222> LOCATION: (1)..(8)
<223> OTHER INFORMATION: Exemplary consensus sequence in GvpC repeats

<400> SEQUENCE: 7

Gln Ala Gln Glu Leu Leu Ala Phe

```
<210> SEQ ID NO 8
<211> LENGTH: 4
<212> TYPE: PRT
<213> ORGANISM: Microchaete diplosiphon
<220> FEATURE:
<221> NAME/KEY: MISC_FEATURE
<222> LOCATION: (1)..(4)
<223> OTHER INFORMATION: Exemplary consensus sequence in GvpC repeats

<400> SEQUENCE: 8

Leu His Gln Phe
1

<210> SEQ ID NO 9
<211> LENGTH: 4
<212> TYPE: PRT
<213> ORGANISM: Microcystis aeruginosa
<220> FEATURE:
<221> NAME/KEY: MISC_FEATURE
<222> LOCATION: (1)..(4)
<223> OTHER INFORMATION: Exemplary consensus sequence in GvpC repeats

<400> SEQUENCE: 9

Leu Ser Gln Phe
1

<210> SEQ ID NO 10
<211> LENGTH: 3
<212> TYPE: PRT
<213> ORGANISM: Halobacterium salinarum
<220> FEATURE:
<221> NAME/KEY: MISC_FEATURE
<222> LOCATION: (1)..(3)
<223> OTHER INFORMATION: Exemplary consensus sequence in GvpC repeats

<400> SEQUENCE: 10

Asp Ala Phe
1

<210> SEQ ID NO 11
<211> LENGTH: 308
<212> TYPE: PRT
<213> ORGANISM: Bacillus megaterium
<220> FEATURE:
<221> NAME/KEY: MISC_FEATURE
<222> LOCATION: (1)..(308)
<223> OTHER INFORMATION: gvpN

<400> SEQUENCE: 11

Met Thr Val Leu Thr Asp Lys Arg Lys Lys Gly Ser Gly Ala Phe Ile
1               5                   10                  15

Gln Asp Asp Glu Thr Lys Glu Val Leu Ser Arg Ala Leu Ser Tyr Leu
            20                  25                  30

Lys Ser Gly Tyr Ser Ile His Phe Thr Gly Pro Ala Gly Gly Gly Lys
        35                  40                  45

Thr Ser Leu Ala Arg Ala Leu Ala Lys Lys Arg Lys Arg Pro Val Met
    50                  55                  60

Leu Met His Gly Asn His Glu Leu Asn Asn Lys Asp Leu Ile Gly Asp
65                  70                  75                  80

Phe Thr Gly Tyr Thr Ser Lys Lys Val Ile Asp Gln Tyr Val Arg Ser
                85                  90                  95

Val Tyr Lys Lys Asp Glu Gln Val Ser Glu Asn Trp Gln Asp Gly Arg
            100                 105                 110
```

```
Leu Leu Glu Ala Val Lys Asn Gly Tyr Thr Leu Ile Tyr Asp Glu Phe
            115                 120                 125

Thr Arg Ser Lys Pro Ala Thr Asn Asn Ile Phe Leu Ser Ile Leu Glu
130                 135                 140

Glu Gly Val Leu Pro Leu Tyr Gly Val Lys Met Thr Asp Pro Phe Val
145                 150                 155                 160

Arg Val His Pro Asp Phe Arg Val Ile Phe Thr Ser Asn Pro Ala Glu
            165                 170                 175

Tyr Ala Gly Val Tyr Asp Thr Gln Asp Ala Leu Leu Asp Arg Leu Ile
            180                 185                 190

Thr Met Phe Ile Asp Tyr Lys Asp Ile Asp Arg Glu Thr Ala Ile Leu
            195                 200                 205

Thr Glu Lys Thr Asp Val Glu Glu Asp Glu Ala Arg Thr Ile Val Thr
            210                 215                 220

Leu Val Ala Asn Val Arg Asn Arg Ser Gly Asp Glu Asn Ser Ser Gly
225                 230                 235                 240

Leu Ser Leu Arg Ala Ser Leu Met Ile Ala Thr Leu Ala Thr Gln Gln
            245                 250                 255

Asp Ile Pro Ile Asp Gly Ser Asp Glu Asp Phe Gln Thr Leu Cys Ile
            260                 265                 270

Asp Ile Leu His His Pro Leu Thr Lys Cys Leu Asp Glu Glu Asn Ala
            275                 280                 285

Lys Ser Lys Ala Glu Lys Ile Ile Leu Glu Glu Cys Lys Asn Ile Asp
            290                 295                 300

Thr Glu Glu Lys
305

<210> SEQ ID NO 12
<211> LENGTH: 255
<212> TYPE: PRT
<213> ORGANISM: Bacillus megaterium
<220> FEATURE:
<221> NAME/KEY: MISC_FEATURE
<222> LOCATION: (1)..(255)
<223> OTHER INFORMATION: gvpF

<400> SEQUENCE: 12

Met Ser Glu Thr Asn Glu Thr Gly Ile Tyr Ile Phe Ser Ala Ile Gln
1               5                   10                  15

Thr Asp Lys Asp Glu Glu Phe Gly Ala Val Glu Val Glu Gly Thr Lys
            20                  25                  30

Ala Glu Thr Phe Leu Ile Arg Tyr Lys Asp Ala Ala Met Val Ala Ala
            35                  40                  45

Glu Val Pro Met Lys Ile Tyr His Pro Asn Arg Gln Asn Leu Leu Met
50                  55                  60

His Gln Asn Ala Val Ala Ala Ile Met Asp Lys Asn Asp Thr Val Ile
65                  70                  75                  80

Pro Ile Ser Phe Gly Asn Val Phe Lys Ser Lys Glu Asp Val Lys Val
            85                  90                  95

Leu Leu Glu Asn Leu Tyr Pro Gln Phe Glu Lys Leu Phe Pro Ala Ile
            100                 105                 110

Lys Gly Lys Ile Glu Val Gly Leu Lys Val Ile Gly Lys Lys Glu Trp
            115                 120                 125

Leu Glu Lys Lys Val Asn Glu Asn Pro Glu Leu Glu Lys Val Ser Ala
            130                 135                 140
```

```
Ser Val Lys Gly Lys Ser Glu Ala Ala Gly Tyr Tyr Glu Arg Ile Gln
145                 150                 155                 160

Leu Gly Gly Met Ala Gln Lys Met Phe Thr Ser Leu Gln Lys Glu Val
            165                 170                 175

Lys Thr Asp Val Phe Ser Pro Leu Glu Glu Ala Ala Gly Ala Ala Lys
            180                 185                 190

Ala Asn Glu Pro Thr Gly Glu Thr Met Leu Leu Asn Ala Ser Phe Leu
            195                 200                 205

Ile Asn Arg Glu Asp Glu Ala Lys Phe Asp Glu Lys Val Asn Glu Ala
            210                 215                 220

His Glu Asn Trp Lys Asp Lys Ala Asp Phe His Tyr Ser Gly Pro Trp
225                 230                 235                 240

Pro Ala Tyr Asn Phe Val Asn Ile Arg Leu Lys Val Glu Glu Lys
            245                 250                 255

<210> SEQ ID NO 13
<211> LENGTH: 4
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: TATA Box

<400> SEQUENCE: 13 tata                                                                    4

<210> SEQ ID NO 14
<211> LENGTH: 6
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: Pribnow box

<400> SEQUENCE: 14 tataat                                                                  6

<210> SEQ ID NO 15
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: -35 position, also referred to as the -35
      element

<400> SEQUENCE: 15 ttgaca                                                                  6

<210> SEQ ID NO 16
<211> LENGTH: 12129
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
```

<222> LOCATION: (1)..(12129)
<223> OTHER INFORMATION: Plasmid sequence of exemplary hybrid GV
      clusters encoding acoustic reporter gene 1 ARG1 construct

<400> SEQUENCE: 16

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tcccttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | ccccatttg | tttattttt | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatcctttt | ttctgcgcgt | aatctgctgc | ttgcaaacaa | aaaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |
| cagcggtcgg | gctgaacggg | gggttcgtgc | acacagccca | gcttggagcg | aacgacctac | 1860 |
| accgaactga | gatacctaca | gcgtgagcta | tgagaaagcg | ccacgcttcc | cgaagggaga | 1920 |
| aaggcggaca | ggtatccggt | aagcggcagg | gtcggaacag | gagagcgcac | gagggagctt | 1980 |
| ccagggggaa | acgcctggta | tctttatagt | cctgtcgggt | ttcgccacct | ctgacttgag | 2040 |
| cgtcgatttt | tgtgatgctc | gtcaggggg | cggagcctat | ggaaaaacgc | cagcaacgcg | 2100 |
| gcctttttac | ggttcctggc | cttttgctgg | ccttttgctc | acatgttctt | tcctgcgtta | 2160 |
| tcccctgatt | ctgtggataa | ccgtattacc | gcctttgagt | gagctgatac | cgctcgccgc | 2220 |

```
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aaggggattc tgttcatgg gggtaatga taccgatgaa    2760 acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat tgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
```

```
catactctgc gacatcgtat aacgttactg gtttcacatt caccacCctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattccaag cttcgccagg    5040
gttttcccag tcgagctcat gactcatatt tatagttatt ctcctcattt cccaagtttc    5100
cgacaacaaa taacaaggaa ttaaaaaaat ggcagttgaa aaaaccaatt cttcctccag    5160
cttggcagaa gttattgata gaatcctcga caaaggtatc gtaattgacg cttgggttcg    5220
tgtttcctta gttggtatcg aactactagc aattgaagct cggatcgtta tcgcttccgt    5280
tgaaacctac ttgaagtatg ctgaagcagt tggtttgacc caatcagcag cagtacctgc    5340
ttaatttaat taagcaagtt accaagtagg agaataacca tgactcatat ttatagttat    5400
tctcctcatt tcccaagttt ccgacaacaa ataacaagga attaaaaaaa tggcagttga    5460
aaaaaccaat tcttcctcca gcttggcaga agttattgat agaatcctcg acaaaggtat    5520
cgtaattgac gcttgggttc gtgtttcctt agttggtatc gaactactag caattgaagc    5580
tcggatcgtt atcgcttccg ttgaaaccta cttgaagtat gctgaagcag ttggtttgac    5640
ccaatcagca gcagtacctg cttaatttaa ttaagctcca taatatcagg attaattaat    5700
cctgatattg gttctgcttt ttttaattat ctagatattt ggaaatcaac gcttctcaaa    5760
ggatattaca aaaaagtacg aatccttata atgtagtacc tggagaagca atttctgtta    5820
ggtctgggag ctcccatggg atcgttatcc cgcggccaag cttgctagcg ctaatttact    5880
atttttggga gaacttcatg attctcttaa tggcaaaaat ccggcaagaa catcagtcaa    5940
tagcagagaa agtggctgaa ctatctcttg agaccagaga attcttgtcc gtcacgacag    6000
cgaaaagaca agagcaagct gaaaaacaag ctcaagaact gcaagcattc tacaaggatc    6060
ttcaggaaac aagtcagcag tttttatcag aaacagccca agccagaatt gctcaagctg    6120
aaaaacaagc tcaagaactg ttagcattcc acaaagaact tcaagaaaca agtcagcagt    6180
ttttatcagc aacagcccaa gccagaattg ctcaagctga aaaacaagcg caagaactgt    6240
tagcatttta tcaagaagtt cgggaaacaa gtcagcagtt tttatcagca acagcccaag    6300
caagaattgc tcaagctgaa aaacaagctc aagaactgtt agcattccac aaagaacttc    6360
aagaaacaag tcagcagttt ttatcagcaa cagccgacgc aagaactgct caagctaagg    6420
aacagaagga atctctcctg aaattccgtc aggatttgtt tgtgagtatc tttggttaat    6480
aaagatctaa ctattggagg ctactaaaaa tggaaattaa aaaaattatg caagccgtga    6540
acgacttttt cggtgaacac gtagctcctc ctcataaaat tacctcggtg aagctactg    6600 aagatgaagg ttggagagtt attgttgaag tcattgaaga acgagaatat atgaaaaaat    6660
acgccaaaga tgaaatgctc ggaacgtacg agtgctttgt aaataagaa aagaagtca    6720 tttcattcaa acgactcgac gtcagatata gaagcgccat tggcattgaa gcataaacga    6780
taagatggca ggaggaacgt aaaaatgacc gtcttaacag acaaaggaa aaaggcagt    6840 ggagctttta tacaagatga cgagacaaaa gaggttcttt caagagcgct gagctattta    6900
aaatccggct attccattca ttttacaggt cctgccggcg gaggcaaaac ctctttagcg    6960
```

```
cgagcgcttg ctaaaaagag aaagcgtcct gtaatgctga tgcacgggaa tcacgagctc    7020
aacaacaaag atttaattgg cgattttacg ggatacacga gcaaaaaagt aatcgaccag    7080
tacgttcgtt ctgtctataa aaagatgaa caggtgagtg aaaactggca ggatggccga     7140
ttgcttgaag ctgtaaaaaa tggctatacg ctgatttacg acgaatttac tcgttctaag    7200
cctgcgacga ataatatctt tctatcgata ttagaagaag gcgtgctgcc gctgtatgga    7260
gtaaaaatga ccgatccttt tgtgcgcgtg catcccgatt tccgcgtcat cttcacaagc    7320
aatccagctg agtatgccgg cgtatatgat acgcaagatg cgcttctcga caggttaatt    7380
accatgttta ttgattataa agacatcgac agagagacag cgattttaac ggagaaaacg    7440
gacgtagaag aagatgaagc gcgcacaatt gtaacgctcg tagcaaacgt gcgaaaccgc    7500
tctggagacg aaaacagcag cggacttagc ctgcgggctt cgcttatgat cgctacccct    7560
gccacgcagc aagacattcc tatcgatgga agtgacgaag attttcaaac gttatgtatc    7620
gatattttgc atcatccgct taccaaatgt ttggatgaag aaaatgcaaa aagcaaagcc    7680
gaaaaaatca ttttagaaga atgtaagaat atagacactg aagaaaagta aaggagcttg    7740
aaaacatgag tgaaacaaac gaaacaggta tttatatttt tagcgccatt caaacggata    7800
aagacgaaga atttggcgcc gtggaagtag aaggaacaaa agctgaaaca ttttttgattc   7860 gctacaaaga cgcggctatg gtagcagctg aagtaccgat gaaaatttat catcctaatc    7920
gccaaaattt attaatgcat caaaacgcag tagcagcgat tatggacaag aacgatacgg    7980
ttattccaat cagctttggg aatgtattca aatcaaaaga agacgtaaaa gttcttttgg    8040
aaaaccttta tccgcagttt gaaaagctgt ttccagcgat caaaggaaaa attgaagtcg    8100
gtttaaaagt aattgggaaa aaagaatggc ttgagaaaaa agtaaacgaa atcctgaac    8160 ttgagaaagt atcagcatcc gtaaaggaa atcagaagc agccggttat tatgagcgta    8220
ttcaacttgg aggaatggct caaaagatgt ttacttccct gcaaaaagaa gtcaagacag    8280
atgtgttttc tccgcttgaa gaagcagcgg aagcagcaaa agcaaatgag ccaacgggcg    8340
aaacgatgct tttaaacgcg tcttttcttaa ttaaccgaga agatgaagcg aagtttgatg    8400
aaaaagtaaa tgaagcgcat gaaaactgga agacaaagc cgattttcat tacagcggtc    8460
cttggcctgc ttataatttt gtgaacattc gcctaaaagt agaagagaaa taacgtgctt    8520
cacaaattag taaccgcacc cattaacctt gtagtgaaaa tcggcgaaaa agtacaggaa    8580
gaagctgata acagctata tgaccttccg acgattcagc aaaagctcat tcagcttcaa    8640
atgatgtttg agcttggtga aattccagaa gaagcgtttc aagaaaaaga agatgaattg    8700
ttaatgaggt acgaaattgc gaaacgcaga gaaattgaac aatgggaaga gctaacacaa    8760
aaaagaaatg aggaatccta gatgggagaa ttactgtatt tatacggttt aattccaaca    8820
aaagaagcag cagccataga gccgtttcca tcttataagg ggtttgacgg agaacattca    8880
ctgtacccaa ttgcgtttga tcaggtgacg gctgtagttt ctaagctgga tgctgacacc    8940
tattcagaaa aagtgattca agaaaaaatg gagcaggata tgagctggct gcaggaaaaa    9000
gcatttcatc atcacgaaac ggtagccgct ttgtacgaag aatttacgat cattccatta    9060
aaattttgca ccatttataa aggtgaagaa agtctgcagg cagctattga gattaacaaa    9120
gaaaagatag agaattcact gacgctgctt caaggaaatg aagagtggaa tgtgaaaatt    9180
tactgtgatg atacagagct taaaaaagga atcagcgaaa cgaatgaaag cgtgaaagcg    9240
aaaaaacaag aaattagtca cttatcacca ggaagacagt ttttttgaaaa gaaaaaaata    9300
```

```
gatcagctga ttgaaaaaga attagagctt cacaaaaaca aagtgtgtga agagatacat    9360
gacaagctaa aagaattatc gctttatgac tctgttaaaa agaattggag caaagacgta    9420
actggcgcag ctgaacagat ggcgtggaac agcgtgtttc ttctcccgtc tctgcagatt    9480
actaagttcg taaacgaaat agaagagctt cagcaaaggc ttgaaaataa aggctggaag    9540
tttgaagtga cgggaccatg gccgccctat catttctcga gctttgcgta aagtgaggaa    9600
ttaacattat gtctcttaaa caatccatgg agaataaaga tattgctctt attgatattt    9660
tagatgtcat tttagataaa ggagtcgcca ttaaggagac ttaatcatt tccatagctg     9720
gcgtcgattt agtgtatttg gatttgcggg tgcttatttc ttcggttgaa acgcttgtgc    9780
aagcaaaaga aggaaatcac aaaccaatca cttctgaaca atttgataaa caaaaggagg    9840
aattaatgga tgcaaccggt cagccaagca aatggacgaa tccacttgga tcctgatcaa    9900
gctgaacaag gcttagcgca gcttgtgatg acagttattg agctattgag gcaaatcgtt    9960
gaacgtcatg ccatgaggcg ggtggagggt ggaacgttga cggacgaaca aattgaaaac   10020
ttaggaattg cactaatgaa cttagaagaa aaatgaacg agttgaaaga ggtgttcggt    10080
ctggatgcag aagatttaaa tattgatctt ggaccgctag gcagcctgct ttaagcggtc   10140
agtaggagga acagtatggc agtcgaacat aatatgcagt caagtacgat tgtagatgtg   10200
ctcgaaaaga ttttggataa aggagtcgtt atagcggggg acatcaccgt aggaattgca   10260
gatgtcgagc tattaacgat aaagatccgc ttgattgtgg cttcggttga taaggcaaaa   10320
gaaatcggca tggactggtg ggaaaatgat ccgtatctca gttcaaaagg agccaataac   10380
aaagcgctcg aagaagaaaa taaatgctg catgagcggt taaaaacgct tgaagaaaaa    10440
atagaaacga acgttaaaa actgtacgct acttaaaaaa tggagggatt tacaatggca    10500
actgaaacaa aattagataa cacacaggca gaaaacaagg aaaataaaaa tgcggaaaac   10560
ggttcaaaag aaaagaacgg ttcaaaagca agcaaaacaa caagcagcgg gccaatcaaa   10620
cgagcggtag caggaggcat catccggtgca acgattggat atgtatcgac tcctgaaaat   10680
cgaaaagtc tccttgaccg cattgataca gacgaattaa aaagcaaagc atctgattta    10740
ggaacaaagg taaagaaaa atcaaaaagc agcgtggcca gcctgaaaac atctgcggga   10800
agcttgttta aaaagataa agataaatca aaagatgatg aagaaaacgt aaattcttct   10860
agtagcgaaa cagaagacga taacgttcaa gagtacgacg agttaaaaga gaaaatcaa   10920
actcttcaag atcgcttatc acagcttgaa gaaaaaatga acatgcttgt tgagcttagc   10980
ctcaataaaa atcaagacga agaagcggaa gatacagatt ccgacgaaga agagaacgat   11040
gagaacgatg aaaacgatga aaacgagcag gacgatgaaa acgaagaaga aacatctaag   11100
ccacgtaaaa aggataaaaa agaagctgag gaagaagaaa gtgaaagtga cgaagacagc   11160
gaggaagaag aggaagattc tcgctcaaac aaaaaaaata aaaagtaaa aacagaagaa   11220
gaagacgaag atgaaagcga agaagaaaaa aggaagcga accaaaaaaa gtcaacagct   11280
aaaaatcaa aaaatacaaa agcaaagaaa aacacggacg aagaagatga tgaagcaaca   11340
tctctttcta gtgaagacga tacaacagcc taagacgtaa aggaggaaag aaagacatga   11400
gtacaggccc ttcttttca actaaagaca atacgcttga atactttgtg aaagcttcta   11460
ataaacacgg cttttcactt gatatttcat taaatgtaaa cggcgctgtg atttccggta   11520
ccatgatttc agcaaaagaa tactttgatt acttaagcga aacgtttgaa gaaggcagtg   11580
aagtggctca ggcgctaagc gaacaattct ctttagcaag cgaagcgagc gaatcaaacg   11640
gagaagcaga agcccatttt attcatttga aaaatacaaa gatttactgt ggagacagta   11700
```

-continued

```
aatctactcc ttctaaaggc aaaatctttt ggagagggaa aatagcagaa gtagacgggt    11760
ttttcttagg aaagatttct gatgcaaaat caacgagtaa aaagagttca taaaaaacgg    11820
cggggtgatt gccccgccgt ttttagtga tgtgatgaga tgtgcagctt ctttttcga      11880 tacatgagcg gagtcatctt catttctttt cgaaactgat taataaaata gcttgtacta    11940
ttaaacccta cttgataggc gacttccgtc acatttgctt ctgcttgctg caggatccgg    12000
ctgctaacaa agcccgaaag gaagctgagt tggctgctgc caccgctgag caataactag    12060
cataacccct tggggcctct aaacgggtct tgaggggttt tttgctgaaa ggaggaacta    12120
tatccggat                                                           12129
```

<210> SEQ ID NO 17
<211> LENGTH: 11733
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(11733)
<223> OTHER INFORMATION: Plasmid sequence of exemplary hybrid GV
      clusters encoding acoustic reporter gene 2 ARG2 construct

<400> SEQUENCE: 17

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcggggggc tccctttagg    180
gttccgattt agtgctttac ggcacctcga ccccaaaaaa cttgattagg gtgatggttc    240
acgtagtggg ccatcgccct gatagacggt ttttcgccct tgacgttgg agtccacgtt     300 ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta     540
tccgctcatg aattaattct tagaaaaact catcgagcat caaatgaaac tgcaatttat    600
tcatatcagg attatcaata ccatatttt gaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
```

```
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
```

```
atcccactac cgagatatcc gcaccaacgc gcagcccgga ctcggtaatg gcgcgcattg      3840
cgcccagcgc catctgatcg ttggcaacca gcatcgcagt gggaacgatg ccctcattca      3900
gcatttgcat ggtttgttga aaaccggaca tggcactcca gtcgccttcc cgttccgcta      3960
tcggctgaat ttgattgcga gtgagatatt tatgccagcc agccgacgcg agacgcgccg      4020
agacagaact taatgggccc gctaacagcg cgatttgctg gtgacccaat gcgaccagat      4080
gctccacgcc cagtcgcgta ccgtcttcat gggagaaaat aatactgttg atgggtgtct      4140
ggtcagagac atcaagaaat aacgccggaa cattagtgca ggcagcttcc acagcaatgg      4200
catcctggtc atccagcgga tagttaatga tcagcccact gacgcgttgc gcgagaagat      4260
tgtgcaccgc cgctttacag gcttcgacgc cgcttcgttc taccatcgac accaccacgc      4320
tggcacccag ttgatcggcg cgagatttaa tcgccgcgac aatttgcgac ggcgcgtgca      4380
gggccagact ggaggtggca acgccaatca gcaacgactg tttgcccgcc agttgttgtg      4440
ccacgcggtt gggaatgtaa ttcagctccg ccatcgccgc ttccacttt tcccgcgttt       4500 tcgcagaaac gtggctggcc tggttcacca cgcgggaaac ggtctgataa agacaccgg       4560 catactctgc gacatcgtat aacgttactg gtttcacatt caccaccctg aattgactct      4620
cttccgggcg ctatcatgcc ataccgcgaa aggttttgcg ccattcgatg gtgtccggga      4680
tctcgacgct ctcccttatg cgactcctgc attaggaagc agcccagtag taggttgagg      4740
ccgttgagca ccgccgccgc aaggaatggt gcatgcaagg agatggcgcc caacagtccc      4800
ccggccacgg ggcctgccac catacccacg ccgaaacaag cgctcatgag cccgaagtgg      4860
cgagcccgat cttccccatc ggtgatgtcg gcgatatagg cgccagcaac cgcacctgtg      4920
gcgccggtga tgccggccac gatgcgtccg gcgtagagga tcgagatctc gatcccgcga      4980
aattaatacg actcactata ggggaattgt gagcggataa caattccaag cttcgccagg      5040
gttttcccag tcgagctcat gactcatatt tatagttatt ctcctcattt cccaagtttc      5100
cgacaacaaa taacaaggaa ttaaaaaaat ggcagttgaa aaaaccaatt cttcctccag      5160
cttggcagaa gttattgata gaatcctcga caaaggtatc gtaattgacg cttgggttcg      5220
tgtttcctta gttggtatcg aactactagc aattgaagct cggatcgtta tcgcttccgt      5280
tgaaacctac ttgaagtatg ctgaagcagt tggtttgacc caatcagcag cagtacctgc      5340
ttaatttaat taagcaagtt accaagtagg agaataacca tgactcatat ttatagttat      5400
tctcctcatt tcccaagttt ccgacaacaa ataacaagga attaaaaaaa tggcagttga      5460
aaaaaccaat tcttcctcca gcttggcaga agttattgat agaatcctcg acaaaggtat      5520
cgtaattgac gcttgggttc gtgtttcctt agttggtatc gaactactag caattgaagc      5580
tcggatcgtt atcgcttccg ttgaaaccta cttgaagtat gctgaagcag ttggtttgac      5640
ccaatcagca gcagtacctg cttaatttaa ttaagctcca taatatcagg attaattaat      5700
cctgatattg gttctgcttt ttttaattat ctagatattt ggaaatcaac gcttctcaaa      5760
ggatattaca aaaagtacg aatccttata atgtagtacc tggagaagca atttctgtta       5820
ggtctgggag ctcccatggg atcgttatcc cgcggccaag cttgctagcg ctaatttact      5880
attttttgga gaacttcatg atttcttta tggcaaaaat ccggcaagaa catcagtcaa       5940
tagcagagaa agtggctgaa ctatctcttg agaccagaga attcttgtcc gtcacgacag      6000
cgaaaagaca agagcaagct gaaaaacaag ctcaagaact gcaagcattc cgtcaggatt      6060
tgtttgtgag tatctttggt taataaagat ctaactattg gaggctacta aaaatgaaa       6120 ttaaaaaaat tatgcaagcc gtgaacgact ttttcggtga acacgtagct cctcctcata      6180
```

```
aaattacctc ggtggaagct actgaagatg aaggttggag agttattgtt gaagtcattg   6240
aagaacgaga atatatgaaa aaatacgcca aagatgaaat gctcggaacg tacgagtgct   6300
ttgtaaataa agaaaaagaa gtcatttcat tcaaacgact cgacgtcaga tatagaagcg   6360
ccattggcat tgaagcataa acgataagat ggcaggagga acgtaaaaat gaccgtctta   6420
acagacaaaa ggaaaaaagg cagtggagct tttatacaag atgacgagac aaaagaggtt   6480
ctttcaagag cgctgagcta tttaaaatcc ggctattcca ttcattttac aggtcctgcc   6540
ggcggaggca aaacctcttt agcgcgagcg cttgctaaaa agagaaagcg tcctgtaatg   6600
ctgatgcacg ggaatcacga gctcaacaac aaagatttaa ttggcgattt tacgggatac   6660
acgagcaaaa aagtaatcga ccagtacgtt cgttctgtct ataaaaaga tgaacaggtg   6720 agtgaaaact ggcaggatgg ccgattgctt gaagctgtaa aaaatggcta tacgctgatt   6780
tacgacgaat ttactcgttc taagcctgcg acgaataata tctttctatc gatattagaa   6840
gaaggcgtgc tgccgctgta tggagtaaaa atgaccgatc cttttgtgcg cgtgcatccc   6900
gatttccgcg tcatcttcac aagcaatcca gctgagtatg ccggcgtata tgatacgcaa   6960
gatgcgcttc tcgacaggtt aattaccatg tttattgatt ataaagacat cgacagagag   7020
acagcgattt taacggagaa aacggacgta gaagaagatg aagcgcgcac aattgtaacg   7080
ctcgtagcaa acgtgcgaaa ccgctctgga gacgaaaaca gcagcggact agcctgcgg    7140 gcttcgctta tgatcgctac ccttgccacg cagcaagaca ttcctatcga tggaagtgac   7200
gaagattttc aaacgttatg tatcgatatt ttgcatcatc cgcttaccaa atgtttggat   7260
gaagaaaatg caaaaagcaa agccgaaaaa atcattttag aagaatgtaa gaatatagac   7320
actgaagaaa agtaaaggag cttgaaaaca tgagtgaaac aaacgaaaca ggtatttata   7380
tttttagcgc cattcaaacg gataaagacg aagaatttgg cgccgtggaa gtagaaggaa   7440
caaaagctga acattttttg attcgctaca agacgcgggc tatggtagca gctgaagtac   7500
cgatgaaaat ttatcatcct aatcgccaaa atttattaat gcatcaaaac gcagtagcag   7560
cgattatgga caagaacgat acggttattc caatcagctt tgggaatgta ttcaaatcaa   7620
aagaagacgt aaaagttctt ttggaaaacc tttatccgca gtttgaaaag ctgtttccag   7680
cgatcaaagg aaaaattgaa gtcggtttaa aagtaattgg gaaaaaagaa tggcttgaga   7740
aaaaagtaaa cgaaatcct gaacttgaga agtatcagc atccgtaaaa ggaaaatcag    7800
aagcagccgg ttattatgag cgtattcaac ttggaggaat ggctcaaaag atgtttactt   7860
ccctgcaaaa agaagtcaag acagatgtgt tttctccgct tgaagaagca gcggaagcag   7920
caaaagcaaa tgagccaacg ggcgaaacga tgcttttaaa cgcgtctttc ttaattaacc   7980
gagaagatga agcgaagttt gatgaaaaag taaatgaagc gcatgaaaac tggaaagaca   8040
aagccgattt tcattacagc ggtccttggc ctgcttataa ttttgtgaac attcgcctaa   8100
aagtagaaga gaaataacgt gcttcacaaa ttagtaaccg cacccattaa ccttgtagtg   8160
aaaatcggcg aaaagtaca ggaagaagct gataaacagc tatatgacct tccgacgatt   8220
cagcaaaagc tcattcagct tcaaatgatg tttgagcttg gtgaaattcc agaagaagcg   8280
tttcaagaaa agaagatga attgttaatg aggtacgaaa ttgcgaaacg cagagaaatt   8340
gaacaatggg aagagctaac acaaaaaaga aatgaggaat cctagatggg agaattactg   8400
tatttatacg gtttaattcc aacaaaagaa gcagcagcca tagagccgtt tccatcttat   8460 aagggtttg acggagaaca ttcactgtac ccaattgcgt ttgatcaggt gacggctgta   8520
```

```
gtttctaagc tggatgctga cacctattca gaaaaagtga ttcaagaaaa aatggagcag    8580
gatatgagct ggctgcagga aaaagcattt catcatcacg aaacggtagc cgctttgtac    8640
gaagaattta cgatcattcc attaaaattt tgcaccattt ataaaggtga agaaagtctg    8700
caggcagcta ttgagattaa caagaaaaag atagagaatt cactgacgct gcttcaagga    8760
aatgaagagt ggaatgtgaa aatttactgt gatgatacag agcttaaaaa aggaatcagc    8820
gaaacgaatg aaagcgtgaa agcgaaaaaa caagaaatta gtcacttatc accaggaaga    8880
cagttttttg aaaagaaaaa aatagatcag ctgattgaaa aagaattaga gcttcacaaa    8940
aacaaagtgt gtgaagagat acatgacaag ctaaaagaat tatcgcttta tgactctgtt    9000
aaaaagaatt ggagcaaaga cgtaactggc gcagctgaac agatggcgtg aacagcgtg    9060 tttcttctcc cgtctctgca gattactaag ttcgtaaacg aaatagaaga gcttcagcaa    9120
aggcttgaaa ataaaggctg gaagtttgaa gtgacgggac catggccgcc ctatcatttc    9180
tcgagctttg cgtaaagtga ggaattaaca ttatgtctct taaacaatcc atggagaata    9240
aagatattgc tcttattgat attttagatg tcattttaga taaaggagtc gccattaaag    9300
gagacttaat catttccata gctggcgtcg atttagtgta tttggatttg cgggtgctta    9360
tttcttcggt tgaaacgctt gtgcaagcaa aagaaggaaa tcacaaacca atcacttctg    9420
aacaatttga taaacaaaag gaggaattaa tggatgcaac cggtcagcca agcaaatgga    9480
cgaatccact tggatcctga tcaagctgaa caaggcttag cgcagcttgt gatgacagtt    9540
attgagctat tgaggcaaat cgttgaacgt catgccatga ggcgggtgga gggtggaacg    9600
ttgacggacg aacaaattga aaacttagga attgcactaa tgaacttaga agaaaaaatg    9660
gacgagttga agaggtgtt cggtctggat gcagaagatt taaatattga tcttggaccg    9720
ctaggcagcc tgctttaagc ggtcagtagg aggaacagta tggcagtcga acataatatg    9780
cagtcaagta cgattgtaga tgtgctcgaa aagattttgg ataaaggagt cgttatagcg    9840
ggggacatca ccgtaggaat tgcagatgtc gagctattaa cgataaagat ccgcttgatt    9900
gtggcttcgg ttgataaggc aaaagaaatc ggcatggact ggtgggaaaa tgatccgtat    9960
ctcagttcaa aaggagccaa taacaaagcg ctcgaagaag aaaataaaat gctgcatgag   10020
cggttaaaaa cgcttgaaga aaaatagaa acgaaacgtt aaaaactgta cgctacttaa   10080
aaaatggagg gatttacaat ggcaactgaa acaaaattag ataacacaca ggcagaaaac   10140
aaggaaaata aaaatgcgga aaacggttca aagaaaaga acggttcaaa agcaagcaaa   10200
acaacaagca gcgggccaat caaacgagcg gtagcaggag gcatcatcgg tgcaacgatt   10260
ggatatgtat cgactcctga aaatcgaaaa agtctccttg accgcattga tacagacgaa   10320
ttaaaaagca aagcatctga tttaggaaca aaggtaaaag aaaaatcaaa agcagcgtg   10380 gccagcctga aaacatctgc gggaagcttg tttaaaaaag ataaagataa atcaaaagat   10440
gatgaagaaa acgtaaattc ttctagtagc gaaacagaag acgataacgt tcaagagtac   10500
gacgagttaa aagaagaaaa tcaaactctt caagatcgct tatcacagct tgaagaaaaa   10560
atgaacatgc ttgttgagct tagcctcaat aaaaatcaag acgaagaagc ggaagataca   10620
gattccgacg aagaagagaa cgatgagaac gatgaaaacg atgaaaacga gcaggacgat   10680
gaaaacgaag aagaaacatc taagccacgt aaaaaggata aaaagaagc tgaggaagaa   10740 gaaagtgaaa gtgacgaaga cagcgaggaa gaagaggaag attctcgctc aaacaaaaaa   10800 aataaaaag taaaaacaga agaagaagac gaagatgaaa gcgaagaaga aaaaaggaa   10860 gcgaaaccaa aaaagtcaac agctaaaaaa tcaaaaaata caaaagcaaa gaaaaacacg   10920
```

```
gacgaagaag atgatgaagc aacatctctt tctagtgaag acgatacaac agcctaagac   10980
gtaaaggagg aaagaaagac atgagtacag gcccttcttt ttcaactaaa gacaatacgc   11040
ttgaatactt tgtgaaagct tctaataaac acggcttttc acttgatatt tcattaaatg   11100
taaacggcgc tgtgatttcc ggtaccatga tttcagcaaa agaatacttt gattacttaa   11160
gcgaaacgtt tgaagaaggc agtgaagtgg ctcaggcgct aagcgaacaa ttctctttag   11220
caagcgaagc gagcgaatca aacggagaag cagaagccca tttattcat ttgaaaaata   11280 caaagattta ctgtggagac agtaaatcta ctccttctaa aggcaaaatc ttttggagag   11340
ggaaaatagc agaagtagac gggttttct taggaaagat ttctgatgca aaatcaacga   11400
gtaaaaagag ttcataaaaa acggcggggt gattgccccg ccgttttta gtgatgtgat   11460 gagatgtgca gcttcttttt tcgatacatg agcggagtca tcttcatttc ttttcgaaac   11520
tgattaataa aatagcttgt actattaaac cctacttgat aggcgacttc cgtcacattt   11580
gcttctgctt gctgcaggat ccggctgcta acaaagcccg aaaggaagct gagttggctg   11640
ctgccaccgc tgagcaataa ctagcataac cccttggggc ctctaaacgg gtcttgaggg   11700
gttttttgct gaaaggagga actatatccg gat                                11733
```

```
<210> SEQ ID NO 18
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(15)
<223> OTHER INFORMATION: AviTag peptide

<400> SEQUENCE: 18

Gly Leu Asn Asp Ile Phe Glu Ala Gln Lys Ile Glu Trp His Glu
1               5                   10                  15

<210> SEQ ID NO 19
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(26)
<223> OTHER INFORMATION: Calmodulin-tag peptide

<400> SEQUENCE: 19

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 20
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(6)
<223> OTHER INFORMATION: Polyglutamate tag

<400> SEQUENCE: 20
```

```
Glu Glu Glu Glu Glu Glu
1               5

<210> SEQ ID NO 21
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(13)
<223> OTHER INFORMATION: E-tag

<400> SEQUENCE: 21

Gly Ala Pro Val Pro Tyr Pro Asp Pro Leu Glu Pro Arg
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Syntetic construct
<220> FEATURE:
<221> NAME/KEY: MISC_FEATURE
<222> LOCATION: (1)..(8)
<223> OTHER INFORMATION: FLAG-tag

<400> SEQUENCE: 22

Asp Tyr Lys Asp Asp Asp Asp Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(9)
<223> OTHER INFORMATION: HA-tag

<400> SEQUENCE: 23

Tyr Pro Tyr Asp Val Pro Asp Tyr Ala
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(6)
<223> OTHER INFORMATION: His-tag

<400> SEQUENCE: 24

His His His His His His
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic construct
```

```
<220> FEATURE:
<221> NAME/KEY: MISC_FEATURE
<222> LOCATION: (1)..(10)
<223> OTHER INFORMATION: Myc-tag

<400> SEQUENCE: 25

Glu Gln Lys Leu Ile Ser Glu Glu Asp Leu
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(18)
<223> OTHER INFORMATION: NE-tag

<400> SEQUENCE: 26

Thr Lys Glu Asn Pro Arg Ser Asn Gln Glu Glu Ser Tyr Asp Asp Asn
1               5                   10                  15

Glu Ser

<210> SEQ ID NO 27
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(15)
<223> OTHER INFORMATION: S-tag

<400> SEQUENCE: 27

Lys Glu Thr Ala Ala Ala Lys Phe Glu Arg Gln His Met Asp Ser
1               5                   10                  15

<210> SEQ ID NO 28
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(28)
<223> OTHER INFORMATION: SBP-tag

<400> SEQUENCE: 28

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
                20                  25                  30

Gln Gly Gln Arg Glu Pro
                35

<210> SEQ ID NO 29
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(13)
```

```
<223> OTHER INFORMATION: Softag 1

<400> SEQUENCE: 29

Ser Leu Ala Glu Leu Leu Asn Ala Gly Leu Gly Gly Ser
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(8)
<223> OTHER INFORMATION: Softag 3

<400> SEQUENCE: 30

Thr Gln Asp Pro Ser Arg Val Gly
1               5

<210> SEQ ID NO 31
<211> LENGTH: 8
<212> TYPE: PRT
<213> ORGANISM: Artificial Sequence
<220> FEATURE:
<223> OTHER INFORMATION: Syntetic construct
<220> FEATURE:
<221> NAME/KEY: MISC_FEATURE
<222> LOCATION: (1)..(8)
<223> OTHER INFORMATION: Strep-tag

<400> SEQUENCE: 31

Trp Ser His Pro Gln Phe Glu Lys
1               5

<210> SEQ ID NO 32
<211> LENGTH: 6
<212> TYPE: PRT
<213> ORGANISM: Artificial Sequence
<220> FEATURE:
<223> OTHER INFORMATION: Syntetic construct
<220> FEATURE:
<221> NAME/KEY: MISC_FEATURE
<222> LOCATION: (1)..(6)
<223> OTHER INFORMATION: TC tag

<400> SEQUENCE: 32

Cys Cys Pro Gly Cys Cys
1               5

<210> SEQ ID NO 33
<211> LENGTH: 14
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (1)..(14)
<223> OTHER INFORMATION: V5 tag

<400> SEQUENCE: 33

Gly Lys Pro Ile Pro Asn Pro Leu Leu Gly Leu Asp Ser Thr
1               5                   10

<210> SEQ ID NO 34
<211> LENGTH: 11
<212> TYPE: PRT
```

<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(11)
<223> OTHER INFORMATION: VSV-tag

<400> SEQUENCE: 34

Tyr Thr Asp Ile Glu Met Asn Arg Leu Gly Lys
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(8)
<223> OTHER INFORMATION: Xpress tag

<400> SEQUENCE: 35

Asp Leu Tyr Asp Asp Asp Asp Lys
1               5

<210> SEQ ID NO 36
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(16)
<223> OTHER INFORMATION: Isopeptag

<400> SEQUENCE: 36

Thr Asp Lys Asp Met Thr Ile Thr Phe Thr Asn Lys Lys Asp Ala Glu
1               5                   10                  15

<210> SEQ ID NO 37
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(13)
<223> OTHER INFORMATION: SpyTag

<400> SEQUENCE: 37

Ala His Ile Val Met Val Asp Ala Tyr Lys Pro Thr Lys
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(12)
<223> OTHER INFORMATION: SnoopTag

<400> SEQUENCE: 38

Lys Leu Gly Asp Ile Glu Phe Ile Lys Val Asn Lys

-continued

```
<210> SEQ ID NO 39
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(13)
<223> OTHER INFORMATION: Exemplary myristoylation tag from Src Kinase

<400> SEQUENCE: 39

Gly Ser Ser Lys Ser Lys Pro Lys Asp Pro Ser Gln Arg
1               5                   10

<210> SEQ ID NO 40
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(20)
<223> OTHER INFORMATION: Exemplary palmitoylation tag from GAP43

<400> SEQUENCE: 40

Met Leu Cys Cys Met Arg Arg Thr Lys Gln Val Glu Lys Asn Asp Glu
1               5                   10                  15

Asp Gln Lys Ile
            20

<210> SEQ ID NO 41
<211> LENGTH: 71
<212> TYPE: PRT
<213> ORGANISM: Anabaena flos-aquae
<220> FEATURE:
<221> NAME/KEY: MISC_FEATURE
<222> LOCATION: (1)..(71)
<223> OTHER INFORMATION: gvpA

<400> SEQUENCE: 41

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Val Arg Val
            20                  25                  30

Ser Leu Val Gly Ile Glu Leu Leu Ala Ile Glu Ala Arg Ile Val Ile
        35                  40                  45

Ala Ser Val Glu Thr Tyr Leu Lys Tyr Ala Glu Ala Val Gly Leu Thr
    50                  55                  60

Gln Ser Ala Ala Val Pro Ala
65                  70

<210> SEQ ID NO 42
<211> LENGTH: 86
<212> TYPE: PRT
<213> ORGANISM: Bacillus megaterium
<220> FEATURE:
<221> NAME/KEY: MISC_FEATURE
<222> LOCATION: (1)..(86)
<223> OTHER INFORMATION: gvpA

<400> SEQUENCE: 42

Met Ser Ile Gln Lys Ser Thr Asp Ser Ser Ser Leu Ala Glu Val Ile
```

-continued

```
                1               5                   10                  15
Asp Arg Ile Leu Asp Lys Gly Ile Val Ile Asp Ala Phe Ala Arg Val
                20                  25                  30

Ser Leu Val Gly Ile Glu Ile Leu Thr Ile Glu Ala Arg Val Val Ile
            35                  40                  45

Ala Ser Val Asp Thr Trp Leu Arg Tyr Ala Glu Ala Val Gly Leu Leu
        50                  55                  60

Thr Asp Lys Val Glu Glu Gly Leu Pro Gly Arg Thr Glu Arg
65                  70                  75                  80

Gly Ala Gly Leu Ser Phe
                85

<210> SEQ ID NO 43
<211> LENGTH: 88
<212> TYPE: PRT
<213> ORGANISM: Bacillus megaterium
<220> FEATURE:
<221> NAME/KEY: MISC_FEATURE
<222> LOCATION: (1)..(88)
<223> OTHER INFORMATION: gvpB1

<400> SEQUENCE: 43

Met Ser Ile Gln Lys Ser Thr Asn Ser Ser Leu Ala Glu Val Ile
1               5                   10                  15

Asp Arg Ile Leu Asp Lys Gly Ile Val Ile Asp Ala Phe Ala Arg Val
                20                  25                  30

Ser Val Val Gly Ile Glu Ile Leu Thr Ile Glu Ala Arg Val Val Ile
            35                  40                  45

Ala Ser Val Asp Thr Trp Leu Arg Tyr Ala Glu Ala Val Gly Leu Leu
        50                  55                  60

Arg Asp Asp Val Glu Glu Asn Gly Leu Pro Glu Arg Ser Asn Ser Ser
65                  70                  75                  80

Glu Gly Gln Pro Arg Phe Ser Ile
                85

<210> SEQ ID NO 44
<211> LENGTH: 143
<212> TYPE: PRT
<213> ORGANISM: Frankia sp.
<220> FEATURE:
<221> NAME/KEY: MISC_FEATURE
<222> LOCATION: (1)..(143)
<223> OTHER INFORMATION: gvpA

<400> SEQUENCE: 44

Met Thr Val Ser Ser Gln Ser Met Asn Arg Ala Pro Lys Pro Ser Ser
1               5                   10                  15

Leu Ala Asp Val Leu Asp Val Val Leu Asp Arg Gly Ile Val Ile Asp
                20                  25                  30

Ala Tyr Ala Arg Val Ala Leu Val Gly Ile Glu Val Leu Thr Ala Asp
            35                  40                  45

Ala Arg Val Val Ile Ala Thr Val Asp Thr Tyr Leu Arg Phe Ala Glu
        50                  55                  60

Ala Val Asn Arg Leu Asp Leu Ala Pro Lys Gln Val Pro Gly Leu
65                  70                  75                  80

Pro Gly Leu Met His Glu Val Thr Asp Gly Thr Ala Arg Gln Lys Ser
                85                  90                  95

Lys Gly Ala Leu Glu Gly Leu Lys Asp Thr Ala Glu Glu Ala Val Gly
            100                 105                 110
```

```
Ser Leu Arg Gly Gly Ser Ser Glu Glu His Ala Arg Arg Asp Leu Pro
        115                 120                 125

Ala Gly Arg Ser Ala Pro Gly Asp Arg Arg Ser Gly Arg Glu Gly
    130                 135                 140

<210> SEQ ID NO 45
<211> LENGTH: 78
<212> TYPE: PRT
<213> ORGANISM: Haloferax mediterranei
<220> FEATURE:
<221> NAME/KEY: MISC_FEATURE
<222> LOCATION: (1)..(78)
<223> OTHER INFORMATION: gvpA

<400> SEQUENCE: 45

Met Val Gln Pro Asp Ser Ser Leu Ala Glu Val Leu Asp Arg Val
1               5                   10                  15

Leu Asp Lys Gly Val Val Asp Val Trp Ala Arg Ile Ser Leu Val
            20                  25                  30

Gly Ile Glu Ile Leu Thr Val Glu Ala Arg Val Val Ala Ala Ser Val
        35                  40                  45

Asp Thr Phe Leu His Tyr Ala Glu Glu Ile Ala Lys Ile Glu Gln Ala
    50                  55                  60

Glu Leu Thr Ala Gly Ala Glu Ala Ala Pro Thr Pro Glu Ala
65                  70                  75

<210> SEQ ID NO 46
<211> LENGTH: 76
<212> TYPE: PRT
<213> ORGANISM: Halobacterium sp. NRC-1
<220> FEATURE:
<221> NAME/KEY: MISC_FEATURE
<222> LOCATION: (1)..(76)
<223> OTHER INFORMATION: gvpA1

<400> SEQUENCE: 46

Met Ala Gln Pro Asp Ser Ser Gly Leu Ala Glu Val Leu Asp Arg Val
1               5                   10                  15

Leu Asp Lys Gly Val Val Val Asp Val Trp Ala Arg Val Ser Leu Val
            20                  25                  30

Gly Ile Glu Ile Leu Thr Val Glu Ala Arg Val Val Ala Ala Ser Val
        35                  40                  45

Asp Thr Phe Leu His Tyr Ala Glu Glu Ile Ala Lys Ile Glu Gln Ala
    50                  55                  60

Glu Leu Thr Ala Gly Ala Glu Ala Ala Pro Glu Ala
65                  70                  75

<210> SEQ ID NO 47
<211> LENGTH: 79
<212> TYPE: PRT
<213> ORGANISM: Halobacterium sp. NRC-1
<220> FEATURE:
<221> NAME/KEY: MISC_FEATURE
<222> LOCATION: (1)..(79)
<223> OTHER INFORMATION: gvpA2

<400> SEQUENCE: 47

Met Ala Gln Pro Asp Ser Ser Ser Leu Ala Glu Val Leu Asp Arg Val
1               5                   10                  15

Leu Asp Lys Gly Val Val Val Asp Val Trp Ala Arg Ile Ser Leu Val
            20                  25                  30
```

```
Gly Ile Glu Ile Leu Thr Val Glu Ala Arg Val Val Ala Ala Ser Val
            35                  40                  45

Asp Thr Phe Leu His Tyr Ala Glu Glu Ile Ala Lys Ile Glu Gln Ala
        50                  55                  60

Glu Leu Thr Ala Gly Ala Glu Ala Pro Glu Pro Ala Pro Glu Ala
65                  70                  75

<210> SEQ ID NO 48
<211> LENGTH: 78
<212> TYPE: PRT
<213> ORGANISM: Halorubrum vacuolatum
<220> FEATURE:
<221> NAME/KEY: MISC_FEATURE
<222> LOCATION: (1)..(78)
<223> OTHER INFORMATION: gvpA

<400> SEQUENCE: 48

Met Ala Gln Pro Asp Ser Ser Leu Ala Glu Val Leu Asp Arg Val
1               5                   10                  15

Leu Asp Lys Gly Val Val Asp Val Tyr Ala Arg Leu Ser Leu Val
            20                  25                  30

Gly Ile Glu Ile Leu Thr Val Glu Ala Arg Val Val Ala Ala Ser Val
            35                  40                  45

Asp Thr Phe Leu His Tyr Ala Glu Glu Ile Ala Lys Ile Glu Gln Ala
        50                  55                  60

Glu Leu Thr Ala Gly Ala Glu Ala Ala Pro Thr Pro Glu Ala
65                  70                  75

<210> SEQ ID NO 49
<211> LENGTH: 71
<212> TYPE: PRT
<213> ORGANISM: Microcystis aeruginosa NIES-843
<220> FEATURE:
<221> NAME/KEY: MISC_FEATURE
<222> LOCATION: (1)..(71)
<223> OTHER INFORMATION: gvpA

<400> SEQUENCE: 49

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Ala Arg Val
            20                  25                  30

Ser Leu Val Gly Ile Glu Leu Leu Ala Ile Glu Ala Arg Val Val Ile
            35                  40                  45

Ala Ser Val Glu Thr Tyr Leu Lys Tyr Ala Glu Ala Val Gly Leu Thr
        50                  55                  60

Gln Ser Ala Ala Val Pro Ala
65                  70

<210> SEQ ID NO 50
<211> LENGTH: 76
<212> TYPE: PRT
<213> ORGANISM: Methanosarcina barkeri
<220> FEATURE:
<221> NAME/KEY: MISC_FEATURE
<222> LOCATION: (1)..(76)
<223> OTHER INFORMATION: gvpA

<400> SEQUENCE: 50

Met Val Ser Gln Ser Pro Asp Ser Ser Ser Leu Ala Glu Val Leu Asp
1               5                   10                  15

Arg Ile Leu Asp Lys Gly Ile Val Val Asp Thr Trp Ala Arg Val Ser
```

```
                    20                  25                  30

Leu Val Gly Ile Glu Ile Leu Ala Ile Glu Ala Arg Val Val Ala
            35                  40                  45

Ser Val Asp Thr Phe Leu His Tyr Ala Glu Glu Ile Thr Lys Ile Glu
    50                  55                  60

Ile Ala Ala Arg Glu Glu Lys Pro Ala Ile Ala Ala
65                  70                  75

<210> SEQ ID NO 51
<211> LENGTH: 72
<212> TYPE: PRT
<213> ORGANISM: Serratia sp. ATCC 39006
<220> FEATURE:
<221> NAME/KEY: MISC_FEATURE
<222> LOCATION: (1)..(72)
<223> OTHER INFORMATION: gvpA1

<400> SEQUENCE: 51

Met Ala Lys Val Gln Lys Ser Thr Asp Ser Ser Leu Ala Glu Val
1               5                   10                  15

Val Asp Arg Ile Leu Asp Lys Gly Ile Val Ile Asp Ala Trp Val Lys
                20                  25                  30

Val Ser Leu Val Gly Ile Glu Leu Leu Ser Ile Glu Ala Arg Val Val
            35                  40                  45

Ile Ala Ser Val Glu Thr Tyr Leu Lys Tyr Ala Glu Ala Ile Gly Leu
    50                  55                  60

Thr Ala Ser Ala Ala Thr Pro Ala
65                  70

<210> SEQ ID NO 52
<211> LENGTH: 65
<212> TYPE: PRT
<213> ORGANISM: Serratia sp. ATCC 39006
<220> FEATURE:
<221> NAME/KEY: MISC_FEATURE
<222> LOCATION: (1)..(65)
<223> OTHER INFORMATION: gvpA2

<400> SEQUENCE: 52

Met Pro Val Asn Lys Gln Tyr Gln Asp Glu Gln Gln Gln Val Ser Leu
1               5                   10                  15

Cys Glu Ala Leu Asp Arg Val Leu Asn Lys Gly Val Val Ile Val Ala
                20                  25                  30

Asp Ile Thr Ile Ser Val Ala Asn Ile Asp Leu Ile Tyr Leu Ser Leu
            35                  40                  45

Gln Ala Leu Val Ser Ser Val Glu Ala Lys Asn Arg Leu Pro Gly Arg
    50                  55                  60

Glu
65

<210> SEQ ID NO 53
<211> LENGTH: 110
<212> TYPE: PRT
<213> ORGANISM: Serratia sp. ATCC 39006
<220> FEATURE:
<221> NAME/KEY: MISC_FEATURE
<222> LOCATION: (1)..(110)
<223> OTHER INFORMATION: gvpA3

<400> SEQUENCE: 53

Met Ser Gly Asn Lys Lys Leu Thr His Ser Thr Asp Ser Thr Thr Val
1               5                   10                  15
```

Ala Asp Leu Leu Glu Arg Leu Leu Asp Lys Gly Val Val Ile Ser Gly
            20                  25                  30

Asp Ile Arg Ile Arg Leu Val Glu Val Glu Leu Leu Thr Leu Glu Ile
            35                  40                  45

Arg Leu Leu Ile Cys Ser Val Asp Lys Ala Val Glu Met Gly Leu Asp
 50                  55                  60

Trp Trp Ser Gly Asn Pro Ala Phe Asp Ser Arg Ala Arg Val Ser Ser
 65                  70                  75                  80

Ser Ala Pro Ala Pro Glu Leu Glu Arg Leu Gln Arg Leu Glu Ala
                85                  90                  95

Arg Leu Glu Ala Ala Pro Ser Val Ile Glu Glu Thr His Leu
            100                 105                 110

<210> SEQ ID NO 54
<211> LENGTH: 170
<212> TYPE: PRT
<213> ORGANISM: Streptomyces coelicolor
<220> FEATURE:
<221> NAME/KEY: MISC_FEATURE
<222> LOCATION: (1)..(170)
<223> OTHER INFORMATION: gvpA1

<400> SEQUENCE: 54

Met Ile Thr Tyr Asp Asp Glu Val Val Cys Ala Pro Arg Ala Gly Thr
1               5                   10                  15

Leu Tyr Asp Val Leu Glu Leu Ile Leu Asp Arg Gly Met Val Ile Asp
            20                  25                  30

Val Phe Val Arg Val Ser Leu Val Gly Ile Glu Ile Leu Lys Val Asp
            35                  40                  45

Ala Arg Ile Val Val Ala Ser Val Asp Thr Tyr Leu Arg Phe Ala Glu
 50                  55                  60

Ala Cys Asn Arg Leu Asp Leu Glu His Asp Val Arg Ser Lys Thr Val
 65                  70                  75                  80

Pro Glu Met Phe Gly Ser Pro Met Ala Lys Thr Val Gly Arg Ala Gly
                85                  90                  95

Ala Arg Arg Thr Ala Arg Ser Leu Thr Asp Lys Val Arg Asp Val Leu
            100                 105                 110

Thr Pro Glu His Glu His Glu Glu Pro Glu Glu Ala Glu Asp Arg
            115                 120                 125

Pro Arg Ala Gly Ala Glu Arg Gly Arg Ser Thr Gln Arg Pro Arg Ser
            130                 135                 140

Arg Pro Ala Ala Arg Pro Arg Asp Glu Asp Arg Pro Arg Ser Arg
145                 150                 155                 160

Pro Arg Arg Arg Thr Glu Glu Glu Asp Arg
                165                 170

<210> SEQ ID NO 55
<211> LENGTH: 144
<212> TYPE: PRT
<213> ORGANISM: Streptomyces coelicolor
<220> FEATURE:
<221> NAME/KEY: MISC_FEATURE
<222> LOCATION: (1)..(144)
<223> OTHER INFORMATION: gvpA2

<400> SEQUENCE: 55

Met Thr Val Val Pro Ala Gln Gln Thr Gly Gly Gly Gly Ser Ser Gly
1               5                   10                  15

-continued

Leu Tyr Asp Val Leu Glu Leu Val Asp Arg Gly Leu Val Ile Asp
            20                  25                  30

Ala Phe Val Arg Val Ser Leu Val Gly Ile Glu Ile Leu Lys Ile Asp
        35                  40                  45

Val Arg Val Val Ala Ser Val Asp Thr Tyr Leu Arg Phe Ala Glu
    50                  55                  60

Ala Cys Asn Arg Leu Asp Leu Glu Ala Gly Pro Arg Lys Asp Pro Gly
65                  70                  75                  80

Leu Pro Asp Leu Val Gly Glu Met Thr Glu Ser Gly Ala Arg Gly Lys
                85                  90                  95

Ser Lys Gly Ala Leu Ser Gly Ala Ala Glu Thr Ile Ser Asp Ala Phe
            100                 105                 110

Lys Gln Ala Arg Asp Asp Gly Gly Ser Glu Arg Glu Thr Ser Ser Arg
        115                 120                 125

Pro Arg Ala Arg Lys Ala Ala Pro Ser Arg Arg Lys Glu Glu Gln Glu
    130                 135                 140

<210> SEQ ID NO 56
<211> LENGTH: 73
<212> TYPE: PRT
<213> ORGANISM: Bukholderia
<220> FEATURE:
<221> NAME/KEY: MISC_FEATURE
<222> LOCATION: (1)..(73)
<223> OTHER INFORMATION: gvpA1

<400> SEQUENCE: 56

Met Ala Lys Val Gln Lys Ser Thr Asp Ser Ser Leu Ala Glu Val
1               5                   10                  15

Val Asp Arg Ile Leu Asp Lys Gly Ile Val Ile Asp Val Trp Ala Lys
            20                  25                  30

Val Ser Leu Val Gly Ile Glu Leu Leu Ser Ile Glu Ala Arg Val Val
        35                  40                  45

Ile Ala Ser Val Glu Thr Tyr Leu Lys Tyr Ala Glu Ala Ile Gly Leu
    50                  55                  60

Thr Ala Thr Ala Ala Ala Pro Thr Ala
65                  70

<210> SEQ ID NO 57
<211> LENGTH: 89
<212> TYPE: PRT
<213> ORGANISM: Bukholderia
<220> FEATURE:
<221> NAME/KEY: MISC_FEATURE
<222> LOCATION: (1)..(89)
<223> OTHER INFORMATION: gvpA2

<400> SEQUENCE: 57

Met Ala Asp Leu Leu Glu Arg Val Leu Asp Lys Gly Val Val Ile Thr
1               5                   10                  15

Gly Asp Ile Arg Ile Asn Leu Val Asp Val Glu Leu Leu Thr Ile Arg
            20                  25                  30

Ile Arg Leu Leu Val Cys Ser Val Asp Lys Ala Lys Glu Leu Gly Ile
        35                  40                  45

Asp Trp Trp Asn Ala Asp Thr Phe Phe Leu Gly Pro Asp Arg Gly Gln
    50                  55                  60

Ser Ala Leu Pro Gly Arg Ala Ser Ala Val Asp Val Ala Ala Gly Ser
65                  70                  75                  80

Ala Val His Ala Asp Ala Ala His Arg

```
<210> SEQ ID NO 58
<211> LENGTH: 72
<212> TYPE: PRT
<213> ORGANISM: Psychromonas
<220> FEATURE:
<221> NAME/KEY: MISC_FEATURE
<222> LOCATION: (1)..(72)
<223> OTHER INFORMATION: gvpA1

<400> SEQUENCE: 58

Met Ala Asn Val Gln Lys Ser Thr Asp Ser Ser Gly Leu Ala Glu Val
1               5                   10                  15

Val Asp Arg Ile Leu Glu Lys Gly Ile Val Ile Asp Ala Phe Val Lys
            20                  25                  30

Val Ser Leu Val Gly Ile Glu Leu Leu Ser Ile Glu Ala Arg Val Val
        35                  40                  45

Ile Ala Ser Val Glu Thr Tyr Leu Lys Tyr Ala Glu Ala Ile Gly Leu
    50                  55                  60

Thr Ala Ser Ala Ala Thr Pro Ala
65                  70

<210> SEQ ID NO 59
<211> LENGTH: 72
<212> TYPE: PRT
<213> ORGANISM: Psychromonas
<220> FEATURE:
<221> NAME/KEY: MISC_FEATURE
<222> LOCATION: (1)..(72)
<223> OTHER INFORMATION: gvpA2

<400> SEQUENCE: 59

Met Ala Asn Val Gln Lys Thr Thr Asp Ser Ser Gly Leu Ala Glu Val
1               5                   10                  15

Ile Asp Arg Ile Leu Asp Lys Gly Ile Val Ile Asp Ala Phe Val Lys
            20                  25                  30

Val Ser Leu Val Gly Ile Glu Leu Leu Ser Ile Glu Ala Arg Val Val
        35                  40                  45

Ile Ala Ser Val Glu Thr Tyr Leu Lys Tyr Ala Glu Ala Ile Gly Leu
    50                  55                  60

Thr Ala Ser Ala Ala Thr Pro Ala
65                  70

<210> SEQ ID NO 60
<211> LENGTH: 101
<212> TYPE: PRT
<213> ORGANISM: Psychromonas
<220> FEATURE:
<221> NAME/KEY: MISC_FEATURE
<222> LOCATION: (1)..(101)
<223> OTHER INFORMATION: gvpA3

<400> SEQUENCE: 60

Met Ala Thr Gly Lys Pro Gln Ser Met Thr His Ser Val Lys Ser Thr
1               5                   10                  15

Thr Val Ala Asp Leu Leu Glu Arg Ile Leu Asp Lys Gly Ile Val Val
            20                  25                  30

Thr Gly Asp Ile Lys Ile Lys Leu Val Asp Val Glu Leu Leu Thr Val
        35                  40                  45

Glu Leu Arg Leu Val Ile Cys Ser Val Asp Lys Ala Val Glu Met Gly
    50                  55                  60
```

```
Met Asp Trp Trp Asn Asn Pro Ala Phe Ala Pro Gln Ala Pro Ala
 65                  70                  75                  80

Gln Glu Gly Glu Leu Ser Ser Ile Glu Lys Arg Leu Glu Lys Ile Glu
                 85                  90                  95

Lys Ala Leu Val Lys
            100

<210> SEQ ID NO 61
<211> LENGTH: 74
<212> TYPE: PRT
<213> ORGANISM: Psychromonas
<220> FEATURE:
<221> NAME/KEY: MISC_FEATURE
<222> LOCATION: (1)..(74)
<223> OTHER INFORMATION: gvpA4

<400> SEQUENCE: 61

Met Pro Met Ala Asn Val Ser Ile Asn Pro Glu Leu Thr Ala Gln Glu
  1               5                  10                  15

Cys Glu Lys Ile Ser Leu Cys Asp Ala Leu Asp Arg Ile Ile Asn Lys
                 20                  25                  30

Gly Val Val Ile His Gly Glu Ile Thr Ile Ser Val Ala Asn Val Asp
             35                  40                  45

Leu Ile Ser Leu Gly Val Arg Leu Ile Leu Ser Asn Val Glu Thr Arg
         50                  55                  60

Glu Gln Ser Asn Thr Pro Lys Glu Glu Val
 65                  70

<210> SEQ ID NO 62
<211> LENGTH: 193
<212> TYPE: PRT
<213> ORGANISM: Anabaena flos-aquae
<220> FEATURE:
<221> NAME/KEY: MISC_FEATURE
<222> LOCATION: (1)..(193)
<223> OTHER INFORMATION: gvpC

<400> SEQUENCE: 62

Met Ile Ser Leu Met Ala Lys Ile Arg Gln Glu His Gln Ser Ile Ala
  1               5                  10                  15

Glu Lys Val Ala Glu Leu Ser Leu Glu Thr Arg Glu Phe Leu Ser Val
                 20                  25                  30

Thr Thr Ala Lys Arg Gln Glu Gln Ala Glu Lys Gln Ala Gln Glu Leu
             35                  40                  45

Gln Ala Phe Tyr Lys Asp Leu Gln Glu Thr Ser Gln Gln Phe Leu Ser
         50                  55                  60

Glu Thr Ala Gln Ala Arg Ile Ala Gln Ala Glu Lys Gln Ala Gln Glu
 65                  70                  75                  80

Leu Leu Ala Phe His Lys Glu Leu Gln Glu Thr Ser Gln Gln Phe Leu
                 85                  90                  95

Ser Ala Thr Ala Gln Ala Arg Ile Ala Gln Ala Glu Lys Gln Ala Gln
            100                 105                 110

Glu Leu Leu Ala Phe Tyr Gln Glu Val Arg Glu Thr Ser Gln Gln Phe
            115                 120                 125

Leu Ser Ala Thr Ala Gln Ala Arg Ile Ala Gln Ala Glu Lys Gln Ala
        130                 135                 140

Gln Glu Leu Leu Ala Phe His Lys Glu Leu Gln Glu Thr Ser Gln Gln
145                 150                 155                 160
```

-continued

```
Phe Leu Ser Ala Thr Ala Asp Ala Arg Thr Ala Gln Ala Lys Glu Gln
                165                 170                 175

Lys Glu Ser Leu Leu Lys Phe Arg Gln Asp Leu Phe Val Ser Ile Phe
            180                 185                 190

Gly

<210> SEQ ID NO 63
<211> LENGTH: 382
<212> TYPE: PRT
<213> ORGANISM: Halobacterium salinarum
<220> FEATURE:
<221> NAME/KEY: MISC_FEATURE
<222> LOCATION: (1)..(382)
<223> OTHER INFORMATION: gvpC

<400> SEQUENCE: 63

Met Ser Val Thr Asp Lys Arg Asp Glu Met Ser Thr Ala Arg Asp Lys
1               5                   10                  15

Phe Ala Glu Ser Gln Gln Glu Phe Glu Ser Tyr Ala Asp Glu Phe Ala
            20                  25                  30

Ala Asp Ile Thr Ala Lys Gln Asp Val Ser Asp Leu Val Asp Ala
        35                  40                  45

Ile Thr Asp Phe Gln Ala Glu Met Thr Asn Thr Thr Asp Ala Phe His
    50                  55                  60

Thr Tyr Gly Asp Glu Phe Ala Ala Glu Val Asp His Leu Arg Ala Asp
65                  70                  75                  80

Ile Asp Ala Gln Arg Asp Val Ile Arg Glu Met Gln Asp Ala Phe Glu
                85                  90                  95

Ala Tyr Ala Asp Ile Phe Ala Thr Asp Ile Ala Asp Lys Gln Asp Ile
            100                 105                 110

Gly Asn Leu Leu Ala Ala Ile Glu Ala Leu Arg Thr Glu Met Asn Ser
        115                 120                 125

Thr His Gly Ala Phe Glu Ala Tyr Ala Asp Asp Phe Ala Ala Asp Val
    130                 135                 140

Ala Ala Leu Arg Asp Ile Ser Asp Leu Val Ala Ala Ile Asp Asp Phe
145                 150                 155                 160

Gln Glu Glu Phe Ile Ala Val Gln Asp Ala Phe Asp Asn Tyr Ala Gly
                165                 170                 175

Asp Phe Asp Ala Glu Ile Asp Gln Leu His Ala Ile Ala Asp Gln
            180                 185                 190

His Asp Ser Phe Asp Ala Thr Ala Asp Ala Phe Ala Glu Tyr Arg Asp
        195                 200                 205

Glu Phe Tyr Arg Ile Glu Val Glu Ala Leu Leu Glu Ala Ile Asn Asp
    210                 215                 220

Phe Gln Gln Asp Ile Gly Asp Phe Arg Ala Glu Phe Glu Thr Thr Glu
225                 230                 235                 240

Asp Ala Phe Val Ala Phe Ala Arg Asp Phe Tyr Gly His Glu Ile Thr
                245                 250                 255

Ala Glu Glu Gly Ala Ala Glu Ala Glu Ala Glu Pro Val Glu Ala Asp
            260                 265                 270

Ala Asp Val Glu Ala Glu Ala Glu Val Ser Pro Asp Glu Ala Gly Gly
        275                 280                 285

Glu Ser Ala Gly Thr Glu Glu Glu Thr Glu Pro Ala Glu Val Glu
    290                 295                 300

Thr Ala Ala Pro Glu Val Glu Gly Ser Pro Ala Asp Thr Ala Asp Glu
305                 310                 315                 320
```

```
Ala Glu Asp Thr Glu Ala Glu Glu Thr Glu Glu Ala Pro Glu
            325                 330                 335

Asp Met Val Gln Cys Arg Val Cys Gly Glu Tyr Tyr Gln Ala Ile Thr
            340                 345                 350

Glu Pro His Leu Gln Thr His Asp Met Thr Ile Gln Glu Tyr Arg Asp
            355                 360                 365

Glu Tyr Gly Glu Asp Val Pro Leu Arg Pro Asp Asp Lys Thr
            370                 375                 380

<210> SEQ ID NO 64
<211> LENGTH: 381
<212> TYPE: PRT
<213> ORGANISM: Halobacterium mediterranei
<220> FEATURE:
<221> NAME/KEY: MISC_FEATURE
<222> LOCATION: (1)..(381)
<223> OTHER INFORMATION: gvpC

<400> SEQUENCE: 64

Met Ser Val Lys Asp Lys Arg Glu Lys Met Thr Ala Thr Arg Glu Glu
1               5                   10                  15

Phe Ala Glu Val Gln Gln Ala Phe Ala Ala Tyr Ala Asp Glu Phe Ala
            20                  25                  30

Ala Asp Val Asp Lys Arg Asp Val Ser Glu Leu Val Asp Gly Ile
            35                  40                  45

Asp Thr Leu Arg Thr Glu Met Asn Ser Thr Asn Asp Ala Phe Arg Ala
    50                  55                  60

Tyr Ser Glu Glu Phe Ala Ala Asp Val Glu His Phe His Thr Ser Val
65                  70                  75                  80

Ala Asp Arg Arg Asp Ala Phe Asp Ala Tyr Ala Asp Ile Phe Ala Thr
                85                  90                  95

Asp Val Ala Glu Met Gln Asp Val Ser Asp Leu Leu Ala Ala Ile Asp
            100                 105                 110

Asp Leu Arg Ala Glu Met Asp Glu Thr His Glu Ala Phe Asp Ala Tyr
            115                 120                 125

Ala Asp Ala Phe Val Thr Asp Val Ala Thr Leu Arg Asp Val Ser Asp
        130                 135                 140

Leu Leu Thr Ala Ile Ser Glu Leu Gln Ser Glu Phe Val Ser Val Gln
145                 150                 155                 160

Gly Glu Phe Asn Gly Tyr Ala Ser Glu Phe Gly Ala Asp Ile Asp Gln
                165                 170                 175

Phe His Ala Val Val Ala Glu Lys Arg Asp Gly His Lys Asp Val Ala
            180                 185                 190

Asp Ala Phe Leu Gln Tyr Arg Glu Glu Phe His Gly Val Glu Val Gln
        195                 200                 205

Ser Leu Leu Asp Asn Ile Ala Ala Phe Gln Arg Glu Met Gly Asp Tyr
    210                 215                 220

Arg Lys Ala Phe Glu Thr Thr Glu Glu Ala Phe Ala Ser Phe Ala Arg
225                 230                 235                 240

Asp Phe Tyr Gly Gln Gly Ala Ala Pro Met Ala Thr Pro Leu Asn Asn
                245                 250                 255

Ala Ala Glu Thr Ala Val Thr Gly Thr Glu Thr Glu Val Asp Ile Pro
            260                 265                 270

Pro Ile Glu Asp Ser Val Glu Pro Asp Gly Glu Asp Glu Asp Ser Lys
        275                 280                 285
```

```
Ala Asp Asp Val Glu Ala Glu Ala Glu Val Thr Val Glu Met Glu
    290                 295                 300

Phe Gly Ala Glu Met Asp Thr Glu Ala Asp Asp Val Gln Ser Glu
305                 310                 315                 320

Ser Val Arg Glu Asp Asp Gln Phe Leu Asp Asp Glu Thr Pro Glu Asp
                325                 330                 335

Met Val Gln Cys Leu Val Cys Gly Glu Tyr Tyr Gln Ala Ile Thr Glu
                340                 345                 350

Pro His Leu Gln Thr His Asp Met Thr Ile Lys Lys Tyr Arg Glu Glu
                355                 360                 365

Tyr Gly Glu Asp Val Pro Leu Arg Pro Asp Asp Lys Ala
    370                 375                 380

<210> SEQ ID NO 65
<211> LENGTH: 162
<212> TYPE: PRT
<213> ORGANISM: Microchaete diplosiphon
<220> FEATURE:
<221> NAME/KEY: MISC_FEATURE
<222> LOCATION: (1)..(162)
<223> OTHER INFORMATION: gvpC

<400> SEQUENCE: 65

Met Thr Pro Leu Met Ile Arg Ile Arg Gln Glu His Arg Gly Ile Ala
1               5                   10                  15

Glu Glu Val Thr Gln Leu Phe Lys Asp Thr Gln Glu Phe Leu Ser Val
                20                  25                  30

Thr Thr Ala Gln Arg Gln Ala Gln Ala Lys Glu Gln Ala Glu Asn Leu
            35                  40                  45

His Gln Phe His Lys Asp Leu Glu Lys Asp Thr Glu Glu Phe Leu Thr
    50                  55                  60

Asp Thr Ala Lys Glu Arg Met Ala Lys Ala Lys Gln Ala Glu Asp
65                  70                  75                  80

Leu Phe Gln Phe His Lys Glu Met Ala Glu Asn Thr Gln Glu Phe Leu
                85                  90                  95

Ser Glu Thr Ala Lys Glu Arg Met Ala Gln Ala Gln Gln Ala Arg
            100                 105                 110

Gln Leu Arg Glu Phe His Gln Asn Leu Glu Gln Thr Thr Asn Glu Phe
        115                 120                 125

Leu Ala Asp Thr Ala Lys Glu Arg Met Ala Gln Ala Gln Gln Lys
    130                 135                 140

Gln Gln Leu His Gln Phe Arg Gln Asp Leu Phe Ala Ser Ile Phe Gly
145                 150                 155                 160

Thr Phe

<210> SEQ ID NO 66
<211> LENGTH: 129
<212> TYPE: PRT
<213> ORGANISM: Nostoc sp.
<220> FEATURE:
<221> NAME/KEY: MISC_FEATURE
<222> LOCATION: (1)..(129)
<223> OTHER INFORMATION: gvpC

<400> SEQUENCE: 66

Met Thr Ala Leu Met Val Arg Ile Arg Gln Glu His Arg Ser Ile Ala
1               5                   10                  15

Glu Glu Val Thr Gln Leu Phe Arg Glu Thr His Glu Phe Leu Ser Ala
                20                  25                  30
```

```
Thr Thr Ala His Arg Gln Glu Gln Ala Lys Gln Gln Ala Gln Gln Leu
            35                  40                  45

His Gln Phe His Gln Asn Leu Glu Gln Thr Thr His Glu Phe Leu Thr
 50                  55                  60

Glu Thr Thr Thr Gln Arg Val Ala Gln Ala Glu Ala Gln Ala Asn Phe
 65                  70                  75                  80

Leu His Lys Phe His Gln Asn Leu Glu Gln Thr Thr Gln Glu Phe Leu
                 85                  90                  95

Ala Glu Thr Ala Lys Asn Arg Thr Glu Gln Ala Lys Ala Gln Ser Gln
            100                 105                 110

Tyr Leu Gln Gln Phe Arg Lys Asp Leu Phe Ala Ser Ile Phe Gly Thr
            115                 120                 125

Phe

<210> SEQ ID NO 67
<211> LENGTH: 88
<212> TYPE: PRT
<213> ORGANISM: Bacillus megaterium
<220> FEATURE:
<221> NAME/KEY: MISC_FEATURE
<222> LOCATION: (1)..(88)
<223> OTHER INFORMATION: gvpR

<400> SEQUENCE: 67

Met Glu Ile Lys Lys Ile Met Gln Ala Val Asn Asp Phe Phe Gly Glu
 1               5                  10                  15

His Val Ala Pro Pro His Lys Ile Thr Ser Val Glu Ala Thr Glu Asp
             20                  25                  30

Glu Gly Trp Arg Val Ile Val Glu Val Ile Glu Glu Arg Glu Tyr Met
         35                  40                  45

Lys Lys Tyr Ala Lys Asp Glu Met Leu Gly Thr Tyr Glu Cys Phe Val
     50                  55                  60

Asn Lys Glu Lys Glu Val Ile Ser Phe Lys Arg Leu Asp Val Arg Tyr
 65                  70                  75                  80

Arg Ser Ala Ile Gly Ile Glu Ala
                 85

<210> SEQ ID NO 68
<211> LENGTH: 308
<212> TYPE: PRT
<213> ORGANISM: Bacillus megaterium
<220> FEATURE:
<221> NAME/KEY: MISC_FEATURE
<222> LOCATION: (1)..(308)
<223> OTHER INFORMATION: gvpN

<400> SEQUENCE: 68

Met Thr Val Leu Thr Asp Lys Arg Lys Lys Gly Ser Gly Ala Phe Ile
 1               5                  10                  15

Gln Asp Asp Glu Thr Lys Glu Val Leu Ser Arg Ala Leu Ser Tyr Leu
             20                  25                  30

Lys Ser Gly Tyr Ser Ile His Phe Thr Gly Pro Ala Gly Gly Gly Lys
         35                  40                  45

Thr Ser Leu Ala Arg Ala Leu Ala Lys Lys Arg Lys Arg Pro Val Met
     50                  55                  60

Leu Met His Gly Asn His Glu Leu Asn Lys Asp Leu Ile Gly Asp
 65                  70                  75                  80

Phe Thr Gly Tyr Thr Ser Lys Lys Val Ile Asp Gln Tyr Val Arg Ser
```

```
                        85                  90                  95
Val Tyr Lys Lys Asp Glu Gln Val Ser Glu Asn Trp Gln Asp Gly Arg
                100                 105                 110

Leu Leu Glu Ala Val Lys Asn Gly Tyr Thr Leu Ile Tyr Asp Glu Phe
            115                 120                 125

Thr Arg Ser Lys Pro Ala Thr Asn Asn Ile Phe Leu Ser Ile Leu Glu
        130                 135                 140

Glu Gly Val Leu Pro Leu Tyr Gly Val Lys Met Thr Asp Pro Phe Val
145                 150                 155                 160

Arg Val His Pro Asp Phe Arg Val Ile Phe Thr Ser Asn Pro Ala Glu
                165                 170                 175

Tyr Ala Gly Val Tyr Asp Thr Gln Asp Ala Leu Leu Asp Arg Leu Ile
            180                 185                 190

Thr Met Phe Ile Asp Tyr Lys Asp Ile Asp Arg Glu Thr Ala Ile Leu
        195                 200                 205

Thr Glu Lys Thr Asp Val Glu Glu Asp Glu Ala Arg Thr Ile Val Thr
210                 215                 220

Leu Val Ala Asn Val Arg Asn Arg Ser Gly Asp Glu Asn Ser Ser Gly
225                 230                 235                 240

Leu Ser Leu Arg Ala Ser Leu Met Ile Ala Thr Leu Ala Thr Gln Gln
                245                 250                 255

Asp Ile Pro Ile Asp Gly Ser Asp Glu Asp Phe Gln Thr Leu Cys Ile
            260                 265                 270

Asp Ile Leu His His Pro Leu Thr Lys Cys Leu Asp Glu Glu Asn Ala
        275                 280                 285

Lys Ser Lys Ala Glu Lys Ile Ile Leu Glu Glu Cys Lys Asn Ile Asp
    290                 295                 300

Thr Glu Glu Lys
305

<210> SEQ ID NO 69
<211> LENGTH: 255
<212> TYPE: PRT
<213> ORGANISM: Bacillus megaterium
<220> FEATURE:
<221> NAME/KEY: MISC_FEATURE
<222> LOCATION: (1)..(255)
<223> OTHER INFORMATION: gvpF

<400> SEQUENCE: 69

Met Ser Glu Thr Asn Glu Thr Gly Ile Tyr Ile Phe Ser Ala Ile Gln
1               5                   10                  15

Thr Asp Lys Asp Glu Glu Phe Gly Ala Val Glu Val Glu Gly Thr Lys
            20                  25                  30

Ala Glu Thr Phe Leu Ile Arg Tyr Lys Asp Ala Ala Met Val Ala Ala
        35                  40                  45

Glu Val Pro Met Lys Ile Tyr His Pro Asn Arg Gln Asn Leu Leu Met
    50                  55                  60

His Gln Asn Ala Val Ala Ala Ile Met Asp Lys Asn Asp Thr Val Ile
65                  70                  75                  80

Pro Ile Ser Phe Gly Asn Val Phe Lys Ser Lys Glu Asp Val Lys Val
                85                  90                  95

Leu Leu Glu Asn Leu Tyr Pro Gln Phe Glu Lys Leu Phe Pro Ala Ile
                100                 105                 110

Lys Gly Lys Ile Glu Val Gly Leu Lys Val Ile Gly Lys Lys Glu Trp
            115                 120                 125
```

```
Leu Glu Lys Lys Val Asn Glu Asn Pro Glu Leu Glu Lys Val Ser Ala
            130                 135                 140

Ser Val Lys Gly Lys Ser Glu Ala Ala Gly Tyr Tyr Glu Arg Ile Gln
145                 150                 155                 160

Leu Gly Gly Met Ala Gln Lys Met Phe Thr Ser Leu Gln Lys Glu Val
                165                 170                 175

Lys Thr Asp Val Phe Ser Pro Leu Glu Glu Ala Ala Glu Ala Ala Lys
            180                 185                 190

Ala Asn Glu Pro Thr Gly Glu Thr Met Leu Leu Asn Ala Ser Phe Leu
            195                 200                 205

Ile Asn Arg Glu Asp Glu Ala Lys Phe Asp Glu Lys Val Asn Glu Ala
210                 215                 220

His Glu Asn Trp Lys Asp Lys Ala Asp Phe His Tyr Ser Gly Pro Trp
225                 230                 235                 240

Pro Ala Tyr Asn Phe Val Asn Ile Arg Leu Lys Val Glu Glu Lys
                245                 250                 255

<210> SEQ ID NO 70
<211> LENGTH: 88
<212> TYPE: PRT
<213> ORGANISM: Bacillus megaterium
<220> FEATURE:
<221> NAME/KEY: MISC_FEATURE
<222> LOCATION: (1)..(88)
<223> OTHER INFORMATION: gvpG

<400> SEQUENCE: 70

Met Leu His Lys Leu Val Thr Ala Pro Ile Asn Leu Val Val Lys Ile
1               5                   10                  15

Gly Glu Lys Val Gln Glu Glu Ala Asp Lys Gln Leu Tyr Asp Leu Pro
            20                  25                  30

Thr Ile Gln Gln Lys Leu Ile Gln Leu Gln Met Met Phe Glu Leu Gly
        35                  40                  45

Glu Ile Pro Glu Glu Ala Phe Gln Glu Lys Glu Asp Glu Leu Leu Met
    50                  55                  60

Arg Tyr Glu Ile Ala Lys Arg Glu Ile Glu Gln Trp Glu Glu Leu
65                  70                  75                  80

Thr Gln Lys Arg Asn Glu Glu Ser
                85

<210> SEQ ID NO 71
<211> LENGTH: 269
<212> TYPE: PRT
<213> ORGANISM: Bacillus megaterium
<220> FEATURE:
<221> NAME/KEY: MISC_FEATURE
<222> LOCATION: (1)..(269)
<223> OTHER INFORMATION: gvpL

<400> SEQUENCE: 71

Met Gly Glu Leu Leu Tyr Leu Tyr Gly Leu Ile Pro Thr Lys Glu Ala
1               5                   10                  15

Ala Ala Ile Glu Pro Phe Pro Ser Tyr Lys Gly Phe Asp Gly Glu His
            20                  25                  30

Ser Leu Tyr Pro Ile Ala Phe Asp Gln Val Thr Ala Val Val Ser Lys
        35                  40                  45

Leu Asp Ala Asp Thr Tyr Ser Glu Lys Val Ile Gln Glu Lys Met Glu
    50                  55                  60
```

```
Gln Asp Met Ser Trp Leu Gln Glu Lys Ala Phe His His Glu Thr
 65                  70                  75                  80

Val Ala Ala Leu Tyr Glu Glu Phe Thr Ile Ile Pro Leu Lys Phe Cys
                 85                  90                  95

Thr Ile Tyr Lys Gly Glu Glu Ser Leu Gln Ala Ala Ile Glu Ile Asn
            100                 105                 110

Lys Glu Lys Ile Glu Asn Ser Leu Thr Leu Leu Gln Gly Asn Glu Glu
        115                 120                 125

Trp Asn Val Lys Ile Tyr Cys Asp Asp Thr Glu Leu Lys Lys Gly Ile
130                 135                 140

Ser Glu Thr Asn Glu Ser Val Lys Ala Lys Lys Gln Glu Ile Ser His
145                 150                 155                 160

Leu Ser Pro Gly Arg Gln Phe Phe Glu Lys Lys Ile Asp Gln Leu
                165                 170                 175

Ile Glu Lys Glu Leu Glu Leu His Lys Asn Lys Val Cys Glu Ile
            180                 185                 190

His Asp Lys Leu Lys Glu Leu Ser Leu Tyr Asp Ser Val Lys Lys Asn
                195                 200                 205

Trp Ser Lys Asp Val Thr Gly Ala Ala Glu Gln Met Ala Trp Asn Ser
210                 215                 220

Val Phe Leu Leu Pro Ser Leu Gln Ile Thr Lys Phe Val Asn Glu Ile
225                 230                 235                 240

Glu Glu Leu Gln Gln Arg Leu Glu Asn Lys Gly Trp Lys Phe Glu Val
                245                 250                 255

Thr Gly Pro Trp Pro Pro Tyr His Phe Ser Ser Phe Ala
            260                 265

<210> SEQ ID NO 72
<211> LENGTH: 95
<212> TYPE: PRT
<213> ORGANISM: Bacillus megaterium
<220> FEATURE:
<221> NAME/KEY: MISC_FEATURE
<222> LOCATION: (1)..(95)
<223> OTHER INFORMATION: gvpS

<400> SEQUENCE: 72

Met Ser Leu Lys Gln Ser Met Glu Asn Lys Asp Ile Ala Leu Ile Asp
 1               5                  10                  15

Ile Leu Asp Val Ile Leu Asp Lys Gly Val Ala Ile Lys Gly Asp Leu
                20                  25                  30

Ile Ile Ser Ile Ala Gly Val Asp Leu Val Tyr Leu Asp Leu Arg Val
            35                  40                  45

Leu Ile Ser Ser Val Glu Thr Leu Val Gln Ala Lys Glu Gly Asn His
        50                  55                  60

Lys Pro Ile Thr Ser Glu Gln Phe Asp Lys Gln Lys Glu Leu Met
 65                 70                  75                  80

Asp Ala Thr Gly Gln Pro Ser Lys Trp Thr Asn Pro Leu Gly Ser
                85                  90                  95

<210> SEQ ID NO 73
<211> LENGTH: 94
<212> TYPE: PRT
<213> ORGANISM: Bacillus megaterium
<220> FEATURE:
<221> NAME/KEY: MISC_FEATURE
<222> LOCATION: (1)..(94)
<223> OTHER INFORMATION: gvpK
```

-continued

<400> SEQUENCE: 73

Met Gln Pro Val Ser Gln Ala Asn Gly Arg Ile His Leu Asp Pro Asp
1               5                   10                  15

Gln Ala Glu Gln Gly Leu Ala Gln Leu Val Met Thr Val Ile Glu Leu
            20                  25                  30

Leu Arg Gln Ile Val Glu Arg His Ala Met Arg Arg Val Glu Gly Gly
        35                  40                  45

Thr Leu Thr Asp Glu Gln Ile Glu Asn Leu Gly Ile Ala Leu Met Asn
50                  55                  60

Leu Glu Glu Lys Met Asp Glu Leu Lys Glu Val Phe Gly Leu Asp Ala
65                  70                  75                  80

Glu Asp Leu Asn Ile Asp Leu Gly Pro Leu Gly Ser Leu Leu
                85                  90

<210> SEQ ID NO 74
<211> LENGTH: 100
<212> TYPE: PRT
<213> ORGANISM: Bacillus megaterium
<220> FEATURE:
<221> NAME/KEY: MISC_FEATURE
<222> LOCATION: (1)..(100)
<223> OTHER INFORMATION: gvpJ

<400> SEQUENCE: 74

Met Ala Val Glu His Asn Met Gln Ser Ser Thr Ile Val Asp Val Leu
1               5                   10                  15

Glu Lys Ile Leu Asp Lys Gly Val Val Ile Ala Gly Asp Ile Thr Val
            20                  25                  30

Gly Ile Ala Asp Val Glu Leu Leu Thr Ile Lys Ile Arg Leu Ile Val
        35                  40                  45

Ala Ser Val Asp Lys Ala Lys Glu Ile Gly Met Asp Trp Trp Glu Asn
50                  55                  60

Asp Pro Tyr Leu Ser Ser Lys Gly Ala Asn Asn Lys Ala Leu Glu Glu
65                  70                  75                  80

Glu Asn Lys Met Leu His Glu Arg Leu Lys Thr Leu Glu Glu Lys Ile
                85                  90                  95

Glu Thr Lys Arg
            100

<210> SEQ ID NO 75
<211> LENGTH: 292
<212> TYPE: PRT
<213> ORGANISM: Bacillus megaterium
<220> FEATURE:
<221> NAME/KEY: MISC_FEATURE
<222> LOCATION: (1)..(292)
<223> OTHER INFORMATION: gvpT

<400> SEQUENCE: 75

Met Ala Thr Glu Thr Lys Leu Asp Asn Thr Gln Ala Glu Asn Lys Glu
1               5                   10                  15

Asn Lys Asn Ala Glu Asn Gly Ser Lys Glu Lys Asn Gly Ser Lys Ala
            20                  25                  30

Ser Lys Thr Thr Ser Ser Gly Pro Ile Lys Arg Ala Val Ala Gly Gly
        35                  40                  45

Ile Ile Gly Ala Thr Ile Gly Tyr Val Ser Thr Pro Glu Asn Arg Lys
50                  55                  60

Ser Leu Leu Asp Arg Ile Asp Thr Asp Glu Leu Lys Ser Lys Ala Ser
65                  70                  75                  80

```
Asp Leu Gly Thr Lys Val Lys Glu Lys Ser Lys Ser Ser Val Ala Ser
                85                  90                  95

Leu Lys Thr Ser Ala Gly Ser Leu Phe Lys Lys Asp Lys Asp Lys Ser
            100                 105                 110

Lys Asp Asp Glu Glu Asn Val Asn Ser Ser Ser Glu Thr Glu Asp
        115                 120                 125

Asp Asn Val Gln Glu Tyr Asp Glu Leu Lys Glu Glu Asn Gln Thr Leu
        130                 135                 140

Gln Asp Arg Leu Ser Gln Leu Glu Lys Met Asn Met Leu Val Glu
145                 150                 155                 160

Leu Ser Leu Asn Lys Asn Gln Asp Glu Glu Ala Glu Asp Thr Asp Ser
                165                 170                 175

Asp Glu Glu Asn Asp Glu Asn Asp Glu Asn Asp Glu Asn Glu Gln
            180                 185                 190

Asp Asp Glu Asn Glu Glu Glu Thr Ser Lys Pro Arg Lys Lys Asp Lys
            195                 200                 205

Lys Glu Ala Glu Glu Glu Glu Ser Glu Ser Asp Glu Asp Ser Glu Glu
        210                 215                 220

Glu Glu Glu Asp Ser Arg Ser Asn Lys Lys Asn Lys Lys Val Lys Thr
225                 230                 235                 240

Glu Glu Glu Asp Glu Asp Glu Ser Glu Glu Glu Lys Lys Glu Ala Lys
                245                 250                 255

Pro Lys Lys Ser Thr Ala Lys Lys Ser Lys Asn Thr Lys Ala Lys Lys
                260                 265                 270

Asn Thr Asp Glu Glu Asp Asp Glu Ala Thr Ser Leu Ser Ser Glu Asp
                275                 280                 285

Asp Thr Thr Ala
    290

<210> SEQ ID NO 76
<211> LENGTH: 138
<212> TYPE: PRT
<213> ORGANISM: Bacillus megaterium
<220> FEATURE:
<221> NAME/KEY: MISC_FEATURE
<222> LOCATION: (1)..(138)
<223> OTHER INFORMATION: gvpU

<400> SEQUENCE: 76

Met Ser Thr Gly Pro Ser Phe Ser Thr Lys Asp Asn Thr Leu Glu Tyr
1               5                   10                  15

Phe Val Lys Ala Ser Asn Lys His Gly Phe Ser Leu Asp Ile Ser Leu
                20                  25                  30

Asn Val Asn Gly Ala Val Ile Ser Gly Thr Met Ile Ser Ala Lys Glu
            35                  40                  45

Tyr Phe Asp Tyr Leu Ser Glu Thr Phe Glu Glu Gly Ser Glu Val Ala
    50                  55                  60

Gln Ala Leu Ser Glu Gln Phe Ser Leu Ala Ser Ala Ser Glu Ser
65                  70                  75                  80

Asn Gly Glu Ala Glu Ala His Phe Ile His Leu Lys Asn Thr Lys Ile
                85                  90                  95

Tyr Cys Gly Asp Ser Lys Ser Thr Pro Ser Lys Gly Lys Ile Phe Trp
            100                 105                 110

Arg Gly Lys Ile Ala Glu Val Asp Gly Phe Phe Leu Gly Lys Ile Ser
        115                 120                 125
```

-continued

```
Asp Ala Lys Ser Thr Ser Lys Lys Ser Ser
    130                 135
```

<210> SEQ ID NO 77
<211> LENGTH: 329
<212> TYPE: PRT
<213> ORGANISM: Serratia sp.
<220> FEATURE:
<221> NAME/KEY: MISC_FEATURE
<222> LOCATION: (1)..(329)
<223> OTHER INFORMATION: gvpN

<400> SEQUENCE: 77

```
Met Ile Lys Gln Asn Thr Val Ser Gln Tyr Thr Val Asp Asp Leu
1               5                   10                  15

Val Val Pro Glu Ala Ser Glu His Phe Val Ala Thr Ser Tyr Val Asn
            20                  25                  30

Asp Ile Ile Glu Arg Ala Leu Val Tyr Leu Arg Ala Gly Tyr Pro Val
        35                  40                  45

His Phe Ala Gly Pro Ser Gly Ile Gly Lys Thr Thr Leu Ala Phe His
    50                  55                  60

Leu Ala Ala Leu Trp Gly Arg Pro Val Thr Met Leu Gln Gly Asn Glu
65                  70                  75                  80

Glu Phe Val Ser Ser Asp Leu Thr Gly Lys Asp Ile Gly Tyr Arg Lys
                85                  90                  95

Ser Ser Leu Val Asp Asn Tyr Ile His Ser Val Leu Lys Thr Glu Glu
            100                 105                 110

Gln Met Asn Arg Met Trp Val Asp Asn Arg Leu Thr Thr Ala Cys Arg
        115                 120                 125

Asn Gly Asp Met Leu Ile Tyr Asp Glu Phe Asn Arg Ser Lys Ala Glu
    130                 135                 140

Thr Asn Asn Val Leu Leu Ser Val Leu Ser Glu Gly Ile Leu Asn Leu
145                 150                 155                 160

Pro Gly Leu Arg Gly Val Gly Glu Gly Tyr Leu Asp Val His Pro Glu
                165                 170                 175

Phe Arg Ala Ile Phe Thr Ser Asn Pro Glu Glu Tyr Ala Gly Thr His
            180                 185                 190

Lys Thr Gln Asp Ala Leu Met Asp Arg Met Ile Thr Ile Asn Ile Gly
        195                 200                 205

Leu Val Asp Arg Asp Thr Glu Leu Gln Ile Leu His Ala Arg Ser Glu
    210                 215                 220

Leu Glu Leu Lys Glu Ala Ala Tyr Ile Val Asp Ile Ile Arg Glu Leu
225                 230                 235                 240

Arg Gly Asn Glu His Glu Thr Lys His Gly Leu Arg Ala Gly Ile Ala
                245                 250                 255

Ile Ala His Ile Leu His Gln Gln Gly Ile Lys Pro Arg Tyr Gly Asp
            260                 265                 270

Lys Leu Phe His Ala Ile Cys Tyr Asp Val Leu Ser Met Asp Ala Ala
        275                 280                 285

Lys Ile Gln His Ala Gly Arg Ser Ile Tyr Arg Glu Met Val Asp Gly
    290                 295                 300

Val Ile Arg Lys Ile Cys Pro Pro Ile Gly Ser Asp Thr Val Lys Ala
305                 310                 315                 320

Ser Thr Gln Lys Ile Lys Ala Val Glu
                325
```

-continued

```
<210> SEQ ID NO 78
<211> LENGTH: 105
<212> TYPE: PRT
<213> ORGANISM: Serratia sp.
<220> FEATURE:
<221> NAME/KEY: MISC_FEATURE
<222> LOCATION: (1)..(105)
<223> OTHER INFORMATION: GvpV

<400> SEQUENCE: 78
```

Met Ala Ile Ser Thr Arg Pro Leu Arg Thr Leu Ser Asp Ile Lys Thr
1               5                   10                  15

His Ser Gly Arg Val Ser Gly Glu His Gln Thr Tyr Arg Asp Tyr Phe
            20                  25                  30

Gln Ile Gly Ala Leu Glu Leu Glu Arg Trp Arg Arg Thr Arg Glu Arg
        35                  40                  45

Glu Ala Ala Ser Ser Arg Ile Ala Ser Ile Asp Glu Arg Ile Ala Asp
    50                  55                  60

Ile Asp Lys Glu Lys Ala Ala Leu Leu Ala Asp Ala Thr Ala Ala Ser
65                  70                  75                  80

Ala Val Ala Glu Asn Asn Asp Lys Ser Glu Ala Ala Glu Lys Lys Lys
                85                  90                  95

Lys Ser Ser Gly Leu Arg Ile Lys Tyr
            100                 105

```
<210> SEQ ID NO 79
<211> LENGTH: 273
<212> TYPE: PRT
<213> ORGANISM: Serratia sp.
<220> FEATURE:
<221> NAME/KEY: MISC_FEATURE
<222> LOCATION: (1)..(273)
<223> OTHER INFORMATION: gvpF1

<400> SEQUENCE: 79
```

Met Met Ser Ile Asp Lys Ser Arg Asn His Arg Ala Lys Val Leu Tyr
1               5                   10                  15

Ala Leu Cys Val Ser Asp Asp Ser Thr Pro Asn Tyr Lys Ile Arg Gly
            20                  25                  30

Leu Glu Ala Ala Pro Val Tyr Ser Ile Asp Gln Asp Gly Leu Arg Ala
        35                  40                  45

Val Val Ser Asp Thr Leu Ser Thr Arg Leu Arg Pro Glu Arg Arg Asn
    50                  55                  60

Ile Thr Ala His Gln Ala Val Leu His Lys Leu Thr Glu Glu Gly Thr
65                  70                  75                  80

Val Leu Pro Met Arg Phe Gly Val Ile Ala Arg Asn Ala Glu Ala Val
                85                  90                  95

Lys Asn Leu Leu Val Ala Asn Gln Asp Thr Ile Arg Glu His Phe Glu
            100                 105                 110

Arg Leu Asp Gly Cys Val Glu Met Gly Leu Arg Val Ser Trp Asp Val
        115                 120                 125

Thr Asn Ile Tyr Glu Tyr Phe Val Ala Thr Tyr Pro Val Leu Ser Glu
    130                 135                 140

Thr Arg Asp Glu Ile Trp Asn Gly Asn Ser Asn Ala Asn Asn His Arg
145                 150                 155                 160

Glu Glu Lys Ile Arg Leu Gly Asn Leu Tyr Glu Ser Leu Arg Ser Gly
                165                 170                 175

Asp Arg Lys Glu Ser Thr Glu Lys Val Lys Glu Val Leu Leu Asp Tyr
            180                 185                 190

```
Cys Glu Glu Ile Ile Glu Asn Pro Val Lys Glu Lys Asp Val Met
            195                 200                 205

Asn Leu Ala Cys Leu Val Ala Arg Glu Arg Met Asp Glu Phe Ala Lys
        210                 215                 220

Gly Val Phe Glu Ala Ser Lys Leu Phe Asp Asn Val Tyr Leu Phe Asp
225                 230                 235                 240

Tyr Thr Gly Pro Trp Ala Pro His Asn Phe Val Thr Leu Asp Leu His
                245                 250                 255

Ala Pro Thr Ala Lys Lys Lys Thr Leu Thr Arg Ala Gly Thr Leu Ser
                260                 265                 270

Asp

<210> SEQ ID NO 80
<211> LENGTH: 262
<212> TYPE: PRT
<213> ORGANISM: Serratia sp.
<220> FEATURE:
<221> NAME/KEY: MISC_FEATURE
<222> LOCATION: (1)..(262)
<223> OTHER INFORMATION: GvpF2

<400> SEQUENCE: 80

Met Thr Met Asn Thr Glu Ala Gln Thr Glu Gln Ala Ile Tyr Leu Tyr
1               5                   10                  15

Gly Leu Thr Leu Pro Asp Leu Ala Ala Pro Pro Ile Leu Gly Val Asp
                20                  25                  30

Asn Gln His Pro Ile Asn Thr His Gln Cys Ala Gly Leu Asn Ala Val
                35                  40                  45

Ile Ser Pro Val Ala Leu Ser Asp Phe Thr Gly Glu Lys Gly Glu Asp
        50                  55                  60

Asn Val Gln Asn Val Thr Trp Leu Thr Pro Arg Ile Cys Arg His Ala
65                  70                  75                  80

Gln Ile Ile Asp Ser Leu Met Ala Gln Gly Pro Val Tyr Pro Leu Pro
                85                  90                  95

Phe Gly Thr Leu Phe Ser Ser Gln Asn Ala Leu Glu Gln Glu Met Lys
                100                 105                 110

Ser Arg Ala Thr Asp Val Phe Val Ser Leu Arg Arg Ile Thr Gly Cys
            115                 120                 125

Gln Glu Trp Ala Leu Glu Ala Thr Leu Asp Arg Lys Gln Ala Val Asp
        130                 135                 140

Val Leu Phe Thr Glu Gly Leu Asp Ser Gly Arg Phe Cys Leu Pro Glu
145                 150                 155                 160

Ala Ile Gly Arg Arg His Leu Glu Glu Gln Lys Leu Arg Arg Arg Leu
                165                 170                 175

Thr Thr Glu Leu Ser Asp Trp Leu Ala His Ala Leu Thr Ala Met Gln
                180                 185                 190

Asn Glu Leu His Pro Leu Val Arg Asp Phe Arg Ser Arg Leu Leu
            195                 200                 205

Asp Asp Lys Ile Leu His Trp Ala Tyr Leu Leu Pro Val Glu Asp Val
        210                 215                 220

Ala Ala Phe Gln Gln Val Ala Asp Ile Val Glu Arg Tyr Glu Ala
225                 230                 235                 240

Tyr Gly Phe Ser Phe Arg Val Thr Gly Pro Trp Ala Ala Tyr Ser Phe
                245                 250                 255

Cys Gln Pro Asp Glu Ser
```

<210> SEQ ID NO 81
<211> LENGTH: 222
<212> TYPE: PRT
<213> ORGANISM: Serratia sp.
<220> FEATURE:
<221> NAME/KEY: MISC_FEATURE
<222> LOCATION: (1)..(222)
<223> OTHER INFORMATION: gvpF3

<400> SEQUENCE: 81

Met Ser Leu Leu Leu Tyr Gly Ile Val Ala Glu Asp Thr Gln Leu Ala
1               5                   10                  15

Leu Glu Pro Asp Gly Ser Pro His Ala Gly Glu Pro Met Gln Leu
            20                  25                  30

Val Lys Ala Ala Thr Leu Ala Ala Leu Val Lys Pro Cys Glu Ala Asp
        35                  40                  45

Val Ser Arg Glu Pro Ala Ala Ala Leu Ala Phe Gly Gln Gln Ile Met
    50                  55                  60

His Val His Gln Gln Thr Thr Ile Ile Pro Ile Arg Tyr Gly Cys Val
65                  70                  75                  80

Leu Ala Asp Glu Asp Ala Val Thr Gln His Leu Leu Asn His Glu Ala
                85                  90                  95

His Tyr Gln Thr Gln Leu Val Glu Leu Glu Asn Cys Asp Glu Met Gly
            100                 105                 110

Ile Arg Leu Ser Leu Ala Ser Ala Glu Asp Asn Ala Val Thr Thr Pro
        115                 120                 125

Gln Ala Ser Gly Leu Asp Tyr Leu Arg Ser Arg Lys Leu Ala Tyr Ala
    130                 135                 140

Val Pro Glu His Ala Glu Arg Gln Ala Ala Leu Leu Asn Asn Ala Phe
145                 150                 155                 160

Thr Gly Leu Tyr Arg Arg His Cys Ala Glu Ile Ser Met Phe Asn Gly
                165                 170                 175

Gln Arg Thr Tyr Leu Leu Ser Tyr Leu Val Pro Arg Thr Gly Leu Gln
            180                 185                 190

Ala Phe Arg Asp Gln Phe Asn Thr Leu Ala Asn Asn Met Thr Asp Ile
        195                 200                 205

Gly Val Ile Ser Gly Pro Trp Pro Pro Tyr Asn Phe Ala Ser
    210                 215                 220

<210> SEQ ID NO 82
<211> LENGTH: 138
<212> TYPE: PRT
<213> ORGANISM: Serratia sp.
<220> FEATURE:
<221> NAME/KEY: MISC_FEATURE
<222> LOCATION: (1)..(138)
<223> OTHER INFORMATION: gvpG

<400> SEQUENCE: 82

Met Leu Leu Ile Asp Asp Ile Leu Phe Ser Pro Val Lys Gly Val Met
1               5                   10                  15

Trp Ile Phe Arg Gln Ile His Glu Leu Ala Glu Asp Glu Leu Ala Gly
            20                  25                  30

Glu Ala Asp Arg Ile Arg Glu Ser Leu Thr Asp Leu Tyr Met Leu Leu
        35                  40                  45

Glu Thr Gly Gln Ile Thr Glu Asp Glu Phe Glu Gln Gln Glu Ala Val
    50                  55                  60

```
Leu Leu Asp Arg Leu Asp Ala Leu Asp Glu Glu Asp Met Leu Gly
65                  70                  75                  80

Asp Glu Pro Gly Asp Glu Asp Glu Tyr Glu Glu Asp Asp Asp
                85                  90                  95

Glu Glu Asp Asp Glu Glu Asp Asp Asp Glu Asp Asp Asp
            100                 105                 110

Glu Asp Asp Asp Glu Glu Asp Asp Asp Asp Glu Asp Asp
            115                 120                 125

Asp Glu Asp Glu Pro Glu Gly Thr Thr Lys
130                 135
```

<210> SEQ ID NO 83
<211> LENGTH: 637
<212> TYPE: PRT
<213> ORGANISM: Serratia sp.
<220> FEATURE:
<221> NAME/KEY: MISC_FEATURE
<222> LOCATION: (1)..(637)
<223> OTHER INFORMATION: GvpW

<400> SEQUENCE: 83

```
Met Lys Pro Ala Ile Tyr Pro Lys Phe Leu Glu Ser Pro Leu Lys
1               5                   10                  15

Leu Val Phe Phe Gly Gly Lys Gly Val Gly Lys Ser Thr Cys Ala
                20                  25                  30

Thr Ser Thr Ala Leu Arg Leu Ala Gln Glu Gln Pro Gln His His Phe
            35                  40                  45

Leu Leu Val Ser Thr Asp Pro Ala His Ser Leu Gln Asn Ile Leu Ser
50                  55                  60

Asp Leu Val Leu Pro Lys Asn Leu Asp Val Arg Glu Leu Asn Ala Ala
65                  70                  75                  80

Ala Ser Leu His Glu Phe Lys Ser Gln His Glu Gly Val Leu Lys Glu
            85                  90                  95

Ile Ala Tyr Arg Gly Thr Val Leu Asp Gln Asn Asp Val Gln Gly Leu
            100                 105                 110

Met Asp Thr Ala Leu Pro Gly Met Asp Glu Leu Ala Ala Tyr Leu Glu
            115                 120                 125

Ile Ala Glu Trp Ile Gln Lys Asp Thr Tyr Tyr Arg Ile Ile Ile Asp
130                 135                 140

Thr Ala Pro Thr Gly His Thr Leu Arg Leu Leu Glu Met Pro Asp Leu
145                 150                 155                 160

Ile Tyr Arg Trp Leu Thr Ala Leu Asp Thr Leu Leu Ala Lys Gln Arg
                165                 170                 175

Tyr Ile Arg Lys Arg Phe Ala Gly Asp Asn Arg Leu Asp His Leu Asp
            180                 185                 190

His Phe Leu Leu Asp Met Asn Asp Ser Leu Lys Ala Met His Glu Leu
            195                 200                 205

Val Thr Asp Ser Thr Arg Cys Cys Phe Val Leu Met Leu Ala Glu
            210                 215                 220

Ala Met Ser Val Glu Glu Ser Ile Asp Leu Ala Gly Ala Leu Asn Gln
225                 230                 235                 240

Gln Arg Val Phe Leu Ser Asp Leu Val Val Asn Arg Leu Phe Pro Glu
                245                 250                 255

Asn Asp Cys Pro Thr Cys Cys Val Glu Arg Asn Arg Gln Met Leu Ala
            260                 265                 270
```

```
Leu Gln Asn Gly Tyr Gln Arg Leu Pro Gly His Val Phe Trp Thr Leu
            275                 280                 285

Pro Leu Leu Ala Ile Glu Pro Arg Gly Ala Leu Leu His Glu Phe Trp
        290                 295                 300

Ser Gly Val Arg Leu Leu Asp Glu Asn Glu Val Met Ala Thr Thr Cys
305                 310                 315                 320

His His Gln Leu Pro Leu Arg Val Glu Ser Ile Ser Leu Pro Ala
                325                 330                 335

Ser Thr Phe Arg Leu Leu Ile Phe Ala Gly Lys Gly Val Gly Lys
                340                 345                 350

Thr Thr Leu Ala Cys Ala Thr Ala Leu Arg Leu Asn Ser Glu Tyr Pro
            355                 360                 365

Glu Leu Arg Ile Leu Leu Phe Ser Ala Asp Pro Ala His Ser Leu Ser
        370                 375                 380

Asp Cys Leu Gly Val Thr Leu Gln Gln Gln Pro Ile Ser Val Leu Val
385                 390                 395                 400

Asn Ile Asp Ala Gln Glu Ile Asn Ala Gln Ala Asp Phe Asp Lys Ile
                405                 410                 415

Arg Gln Gly Tyr Arg Ala Glu Leu Glu Ala Phe Leu Leu Asp Thr Leu
                420                 425                 430

Pro Asn Leu Asp Ile Thr Phe Asp Arg Glu Val Leu Glu His Leu Leu
        435                 440                 445

Asp Leu Ala Pro Pro Gly Leu Asp Glu Ile Met Ala Leu Thr Ala Ile
        450                 455                 460

Met Asp His Leu Asp Ser Gly Arg Tyr Asp Met Val Ile Val Asp Gly
465                 470                 475                 480

Ala Pro Ser Gly His Leu Leu Arg Leu Glu Leu Pro Glu Leu Ile
                485                 490                 495

Arg Asp Trp Leu Lys Gln Phe Phe Ser Leu Leu Lys Tyr Arg Lys
                500                 505                 510

Val Met Arg Phe Pro His Leu Ser Glu Arg Leu Val Gln Leu Ser Arg
                515                 520                 525

Glu Leu Lys Asn Leu Arg Ala Leu Leu Gln Asp Thr Lys Gln Thr Gly
        530                 535                 540

Leu Tyr Ala Val Thr Val Pro Thr His Leu Ala Leu Glu Lys Thr Tyr
545                 550                 555                 560

Glu Met Thr Cys Ala Leu Gln Arg Leu Gly Leu Thr Ala Asn Ala Leu
                565                 570                 575

Phe Ile Asn Gln Ile Thr Pro Pro Ser Asp Cys Thr Leu Cys Gln Ala
            580                 585                 590

Ile Thr Ser Arg Glu Ser Leu Glu Leu Lys Cys Ala Asp Glu Met Phe
            595                 600                 605

Pro Ser Gln Pro His Ala Gln Ile Phe Arg Gln Thr Glu Pro Thr Gly
        610                 615                 620

Leu Ser Lys Leu Lys Thr Leu Gly Ser Ala Leu Phe Leu
625                 630                 635

<210> SEQ ID NO 84
<211> LENGTH: 115
<212> TYPE: PRT
<213> ORGANISM: Serratia sp.
<220> FEATURE:
<221> NAME/KEY: MISC_FEATURE
<222> LOCATION: (1)..(115)
<223> OTHER INFORMATION: gvpK
```

<400> SEQUENCE: 84

Met Thr Thr Asn Gln Leu Ser His His Ser Pro Val Phe Gly Pro Thr
1               5                   10                  15

Ser Pro Ala Ile Gln Arg Pro Ile Thr Glu Ala Asn Arg His Lys Ile
            20                  25                  30

Asp Ile Asp Gly Glu Arg Val Arg Asp Gly Leu Ala Gln Leu Val Leu
        35                  40                  45

Thr Leu Val Lys Leu Leu His Glu Leu Leu Arg Gln Ala Ile Arg
    50                  55                  60

Arg Met Asp Ser Gly Ser Leu Ser Asp Glu Glu Val Glu Arg Leu Gly
65                  70                  75                  80

Leu Ala Leu Met Arg Gln Ala Glu Glu Leu Thr His Leu Cys Asp Val
                85                  90                  95

Phe Gly Phe Lys Asp Asp Leu Asn Leu Asp Leu Gly Pro Leu Gly
            100                 105                 110

Arg Leu Leu
        115

<210> SEQ ID NO 85
<211> LENGTH: 87
<212> TYPE: PRT
<213> ORGANISM: Serratia sp.
<220> FEATURE:
<221> NAME/KEY: MISC_FEATURE
<222> LOCATION: (1)..(87)
<223> OTHER INFORMATION: GvpX

<400> SEQUENCE: 85

Met Val Asn Thr Thr Asn Asp Ile Asn Ala Ala Thr Arg Gly Leu Leu
1               5                   10                  15

Leu Arg Met Gly Asn Ala Trp Phe Glu Gln Asp Glu Leu Arg Gln Ala
            20                  25                  30

Val Asp Ile Tyr Leu Lys Ile Ile Glu Gln Tyr Pro Asp Ser Lys Glu
        35                  40                  45

Ser Lys Thr Ala Gln Thr Ala Leu Leu Thr Ile Ser Gln Arg Tyr Glu
    50                  55                  60

Arg Asp Gly Leu Phe Arg Leu Ser Leu Asp Ile Leu Glu Arg Val Gly
65                  70                  75                  80

Glu Ile Thr Pro Thr Ser Ile
                85

<210> SEQ ID NO 86
<211> LENGTH: 192
<212> TYPE: PRT
<213> ORGANISM: Serratia sp.
<220> FEATURE:
<221> NAME/KEY: MISC_FEATURE
<222> LOCATION: (1)..(192)
<223> OTHER INFORMATION: gvpY

<400> SEQUENCE: 86

Met Arg Ala Leu Ile His Phe Pro Ile Ile His Ser Pro Lys Asp Leu
1               5                   10                  15

Gly Thr Leu Ser Glu Ala Ala Ser His Leu Arg Thr Glu Thr Gln Thr
            20                  25                  30

Arg Ala Tyr Leu Ala Ala Val Glu Gly Phe Trp Thr Met Ile Thr Thr
        35                  40                  45

Thr Ile Glu Gly Leu Asp Leu Asp Tyr Thr His Leu Lys Leu Tyr Gln
    50                  55                  60

-continued

Asp Gly Leu Pro Val Cys Gly Lys Glu Asn Glu Ile Val Thr Asp Val
65                  70                  75                  80

Ala Asn Ala Gly Ser Gln Asn Tyr Lys Leu Leu Thr Leu Gln His
                85                  90                  95

Lys Gly Ala Ile Leu Met Gly Thr Glu Ser Pro Glu Leu Leu Leu Gln
                100                 105                 110

Glu Arg Asp Leu Met Thr Gln Leu Leu Gln Ser Thr Glu Gln Thr Glu
            115                 120                 125

Ala Ser Leu Glu Thr Ala Lys Thr Leu Leu Asn Arg Arg Asp Asp Tyr
        130                 135                 140

Ile Ala Gln Arg Ile Asp Glu Thr Leu Gln Asp Gly Glu Met Ala Ile
145                 150                 155                 160

Leu Phe Leu Gly Leu Met His Asn Ile Glu Ala Lys Leu Pro Ala Asp
                165                 170                 175

Ile Val Phe Ile Gln Pro Leu Gly Lys Pro Pro Gly Gly Glu Ser Ile
                180                 185                 190

<210> SEQ ID NO 87
<211> LENGTH: 160
<212> TYPE: PRT
<213> ORGANISM: Serratia sp.
<220> FEATURE:
<221> NAME/KEY: MISC_FEATURE
<222> LOCATION: (1)..(160)
<223> OTHER INFORMATION: gvpH

<400> SEQUENCE: 87

Met Thr Gly Asn Val Glu Gly Ile Leu Arg Gly Leu Gly Asp Leu Val
1               5                   10                  15

Glu Lys Leu Val Glu Thr Gly Glu Gln Ile Lys Arg Ser Gly Ala Phe
                20                  25                  30

Asp Ile Asp Thr Asn Asp Gly Lys Asn Ala Lys Ala Val Tyr Gly Phe
            35                  40                  45

Ser Ile Lys Met Gly Leu Asp Gly Asn Gln Glu Asn Arg Val Glu Pro
50                  55                  60

Phe Gly Asn Ile Arg Arg Asp Glu Gln Thr Gly Glu Ala Thr Val Gln
65                  70                  75                  80

Glu Val Ser Glu Pro Leu Val Asp Val Ile Glu Glu Ser Asp His Val
                85                  90                  95

Leu Val Leu Ala Glu Met Pro Gly Val Ala Asp Glu Asp Val Gln Val
                100                 105                 110

Glu Leu Asn Gly Asp Ile Leu Thr Leu His Ser Glu Arg Gly Ser Lys
            115                 120                 125

Lys Tyr His Lys Glu Ile Val Leu Pro Cys Ser Phe Asp Asp Lys Ala
        130                 135                 140

Met Glu Arg Ser Cys Arg Asn Gly Ile Leu Glu Val Lys Leu Gly Lys
145                 150                 155                 160

<210> SEQ ID NO 88
<211> LENGTH: 720
<212> TYPE: PRT
<213> ORGANISM: Serratia sp.
<220> FEATURE:
<221> NAME/KEY: MISC_FEATURE
<222> LOCATION: (1)..(720)
<223> OTHER INFORMATION: GvpZ

<400> SEQUENCE: 88

```
Met Ser Glu Glu Leu Lys Leu Lys Val Ala Glu Ala Leu Pro Lys Asp
1               5                   10                  15

Ala Gly Arg Gly Tyr Ala Arg Leu Asp Pro Ala Asp Met Ala Arg Leu
            20                  25                  30

Asn Leu Ala Val Gly Asp Ile Val Gln Leu Thr Ser Lys Lys Gly Thr
        35                  40                  45

Gly Ile Ala Lys Leu Met Pro Thr Tyr Pro Asp Met Arg Asn Lys Gly
    50                  55                  60

Ile Val Gln Leu Asp Gly Leu Thr Arg Arg Asn Thr Ser Leu Ser Leu
65                  70                  75                  80

Asp Glu Lys Val Gln Ile Glu Pro Ala Ser Cys Lys His Ala Thr Gln
                85                  90                  95

Ile Val Leu Ile Pro Thr Thr Ile Thr Pro Asn Gln Arg Asp Leu Asp
            100                 105                 110

Tyr Ile Gly Ser Leu Leu Asp Gly Leu Pro Val Gln Lys Gly Asp Leu
        115                 120                 125

Leu Arg Ala His Leu Phe Gly Ser Arg Ser Ala Asp Phe Lys Val Glu
    130                 135                 140

Ser Thr Ile Pro Asp Gly Ala Val Leu Ile Asp Pro Thr Thr Thr Leu
145                 150                 155                 160

Val Ile Gly Lys Ser Asn Ala Val Gly Asn Ser Ser His Ser Thr Gln
                165                 170                 175

Arg Leu Ser Tyr Glu Asp Val Gly Gly Leu Lys Asn Gln Val Arg Arg
            180                 185                 190

Ile Arg Glu Met Ile Glu Leu Pro Leu Arg Tyr Pro Glu Val Phe Glu
        195                 200                 205

Arg Leu Gly Ile Asp Ala Pro Lys Gly Val Leu Leu Ser Gly Pro Pro
    210                 215                 220

Gly Cys Gly Lys Thr Leu Ile Ala Arg Ile Ile Ala Gln Glu Thr Asp
225                 230                 235                 240

Ala Gln Phe Phe Thr Ile Ser Gly Pro Glu Ile Val His Lys Phe Tyr
                245                 250                 255

Gly Glu Ser Glu Ala His Leu Arg Lys Ile Phe Glu Glu Ala Gly Arg
            260                 265                 270

Lys Gly Pro Ser Ile Ile Phe Leu Asp Glu Ile Asp Ser Ile Ala Pro
        275                 280                 285

His Arg Asp Lys Val Val Gly Asp Val Glu Lys Arg Ile Val Ala Gln
    290                 295                 300

Leu Leu Ala Leu Met Asp Gly Leu Lys Asn Arg Gly Lys Val Ile Val
305                 310                 315                 320

Ile Ala Ala Thr Asn Leu Pro Asn Ala Ile Asp Pro Ala Leu Arg Arg
                325                 330                 335

Pro Gly Arg Phe Asp Arg Glu Ile Ser Ile Pro Ile Pro Asp Arg Glu
            340                 345                 350

Gly Arg Arg Glu Ile Ile Glu Ile His Ser Thr Gly Met Pro Leu Asn
        355                 360                 365

Ala Asp Val Asp Leu Asn Val Leu Ala Asp Ile Thr His Gly Phe Val
    370                 375                 380

Gly Ala Asp Leu Glu Ala Leu Cys Arg Glu Ala Met Ser Ala Leu
385                 390                 395                 400

Arg Arg Leu Leu Pro Glu Ile Asp Phe Ser Ser Ala Glu Leu Pro Tyr
                405                 410                 415

Asp Arg Leu Ala Glu Leu Thr Val Met Met Asp Asp Phe Arg Ala Ala
```

420                 425                 430

Leu Cys Glu Val Ser Pro Ser Ala Ile Arg Glu Leu Phe Val Asp Ile
            435                 440                 445

Pro Asp Val Arg Trp Glu Asp Val Gly Gly Leu Asp Asp Val Arg Arg
    450                 455                 460

Arg Leu Ile Glu Ser Val Glu Trp Pro Ile Lys Tyr Pro Glu Leu Tyr
465                 470                 475                 480

Glu Gln Ala Gly Val Lys Pro Pro Lys Gly Leu Leu Ala Gly Pro
                485                 490                 495

Pro Gly Val Gly Lys Thr Leu Ile Ala Lys Ala Val Ala Asn Glu Ser
            500                 505                 510

Gly Val Asn Val Ile Ser Val Lys Gly Pro Ala Leu Met Ser Arg Tyr
            515                 520                 525

Val Gly Asp Ser Glu Lys Gly Val Arg Glu Leu Phe Leu Lys Ala Arg
            530                 535                 540

Gln Ala Ala Pro Cys Ile Ile Phe Leu Asp Glu Val Asp Ser Val Ile
545                 550                 555                 560

Pro Ala Arg Asn Glu Gly Ala Ile Asp Ser His Val Ala Glu Arg Val
                565                 570                 575

Leu Ser Gln Phe Leu Ser Glu Met Asp Gly Leu Glu Glu Leu Lys Gly
            580                 585                 590

Val Phe Val Met Gly Ala Thr Asn Arg Ala Asp Leu Ile Asp Pro Ala
            595                 600                 605

Met Leu Arg Pro Gly Arg Phe Asp Glu Ile Ile Glu Leu Gly Leu Pro
            610                 615                 620

Asp Glu Asp Ala Arg Arg Gln Ile Leu Ala Val His Leu Arg Asn Lys
625                 630                 635                 640

Pro Leu Gly Asp Asn Ile His Ala Asp Leu Ala Glu Arg Cys Asp
                645                 650                 655

Gly Ala Ser Gly Ala Glu Leu Ala Ala Val Cys Asn Arg Ala Ala Leu
                660                 665                 670

Ala Ala Leu Arg Arg Ala Ile Gln Gln Ser Glu Glu Ala Val Leu Ser
            675                 680                 685

Pro Ser Thr Val Gly Glu Thr Pro Val Ala Leu Thr Val Arg Ile Glu
            690                 695                 700

Gln His Asp Phe Ala Glu Val Ile Ala Glu Met Phe Gly Asp Asp Ala
705                 710                 715                 720

<210> SEQ ID NO 89
<211> LENGTH: 60
<212> TYPE: PRT
<213> ORGANISM: Serratia sp. ATCC 39006
<220> FEATURE:
<221> NAME/KEY: MISC_FEATURE
<222> LOCATION: (1)..(60)
<223> OTHER INFORMATION: gvpA2

<400> SEQUENCE: 89

Met Pro Val Asn Lys Gln Tyr Gln Asp Glu Gln Gln Gln Val Ser Leu
1               5                   10                  15

Cys Glu Ala Leu Asp Arg Val Leu Asn Lys Gly Val Val Ile Val Ala
            20                  25                  30

Asp Ile Thr Ile Ser Val Ala Asn Ile Asp Leu Ile Tyr Leu Ser Leu
        35                  40                  45

Gln Ala Leu Val Ser Ser Val Glu Ala Lys Asn Arg
    50                  55                  60

<210> SEQ ID NO 90
<211> LENGTH: 61
<212> TYPE: PRT
<213> ORGANISM: Serratia sp. ATCC 39006
<220> FEATURE:
<221> NAME/KEY: MISC_FEATURE
<222> LOCATION: (1)..(61)
<223> OTHER INFORMATION: gvpA3

<400> SEQUENCE: 90

Met Ser Gly Asn Lys Lys Leu Thr His Ser Thr Asp Ser Thr Thr Val
1               5                   10                  15

Ala Asp Leu Leu Glu Arg Leu Leu Asp Lys Gly Val Val Ile Ser Gly
            20                  25                  30

Asp Ile Arg Ile Arg Leu Val Glu Val Glu Leu Leu Thr Leu Glu Ile
        35                  40                  45

Arg Leu Leu Ile Cys Ser Val Asp Lys Ala Val Glu Met
    50                  55                  60

<210> SEQ ID NO 91
<211> LENGTH: 72
<212> TYPE: PRT
<213> ORGANISM: Streptomyces coelicolor
<220> FEATURE:
<221> NAME/KEY: MISC_FEATURE
<222> LOCATION: (1)..(72)
<223> OTHER INFORMATION: gvpA2

<400> SEQUENCE: 91

Met Thr Val Val Pro Ala Gln Gln Thr Gly Gly Gly Ser Ser Gly
1               5                   10                  15

Leu Tyr Asp Val Leu Glu Leu Val Leu Asp Arg Gly Leu Val Ile Asp
            20                  25                  30

Ala Phe Val Arg Val Ser Leu Val Gly Ile Glu Ile Leu Lys Ile Asp
        35                  40                  45

Val Arg Val Val Val Ala Ser Val Asp Thr Tyr Leu Arg Phe Ala Glu
    50                  55                  60

Ala Cys Asn Arg Leu Asp Leu Glu
65                  70

<210> SEQ ID NO 92
<211> LENGTH: 72
<212> TYPE: PRT
<213> ORGANISM: Streptomyces coelicolor
<220> FEATURE:
<221> NAME/KEY: MISC_FEATURE
<222> LOCATION: (1)..(72)
<223> OTHER INFORMATION: gvpA1

<400> SEQUENCE: 92

Met Ile Thr Tyr Asp Asp Glu Val Val Cys Ala Pro Arg Ala Gly Thr
1               5                   10                  15

Leu Tyr Asp Val Leu Glu Leu Ile Leu Asp Arg Gly Met Val Ile Asp
            20                  25                  30

Val Phe Val Arg Val Ser Leu Val Gly Ile Glu Ile Leu Lys Val Asp
        35                  40                  45

Ala Arg Ile Val Val Ala Ser Val Asp Thr Tyr Leu Arg Phe Ala Glu
    50                  55                  60

Ala Cys Asn Arg Leu Asp Leu Glu
65                  70

<210> SEQ ID NO 93
<211> LENGTH: 72
<212> TYPE: PRT
<213> ORGANISM: Frankia sp.
<220> FEATURE:
<221> NAME/KEY: MISC_FEATURE
<222> LOCATION: (1)..(72)
<223> OTHER INFORMATION: gvpA

<400> SEQUENCE: 93

Met Thr Val Ser Ser Gln Ser Met Asn Arg Ala Pro Lys Pro Ser Ser
1               5                   10                  15

Leu Ala Asp Val Leu Asp Val Val Leu Asp Arg Gly Ile Val Ile Asp
            20                  25                  30

Ala Tyr Ala Arg Val Ala Leu Val Gly Ile Glu Val Leu Thr Ala Asp
        35                  40                  45

Ala Arg Val Val Ile Ala Thr Val Asp Thr Tyr Leu Arg Phe Ala Glu
    50                  55                  60

Ala Val Asn Arg Leu Asp Leu Ala
65                  70

<210> SEQ ID NO 94
<211> LENGTH: 61
<212> TYPE: PRT
<213> ORGANISM: Bacillus megaterium
<220> FEATURE:
<221> NAME/KEY: MISC_FEATURE
<222> LOCATION: (1)..(61)
<223> OTHER INFORMATION: gvpB1

<400> SEQUENCE: 94

Met Thr Ile Asn Lys Ser Asn Asp Cys Ser Ser Leu Ala Glu Val Val
1               5                   10                  15

Asp Arg Ile Leu Asp Lys Gly Val Val Ile Asp Val Phe Ala Arg Ile
            20                  25                  30

Ser Val Ile Gly Ile Glu Leu Ile Thr Ile Glu Ala Arg Ile Val Ile
        35                  40                  45

Ala Ser Val Asp Thr Trp Leu Arg Tyr Ala Glu Ala Val
    50                  55                  60

<210> SEQ ID NO 95
<211> LENGTH: 60
<212> TYPE: PRT
<213> ORGANISM: Methanosarcina barkeri
<220> FEATURE:
<221> NAME/KEY: MISC_FEATURE
<222> LOCATION: (1)..(60)
<223> OTHER INFORMATION: gvpA

<400> SEQUENCE: 95

Met Val Ser Gln Ser Pro Asp Ser Ser Leu Ala Glu Val Leu Asp
1               5                   10                  15

Arg Ile Leu Asp Lys Gly Ile Val Val Asp Thr Trp Ala Arg Val Ser
            20                  25                  30

Leu Val Gly Ile Glu Ile Leu Ala Ile Glu Ala Arg Val Val Val Ala
        35                  40                  45

Ser Val Asp Thr Phe Leu His Tyr Ala Glu Glu Ile
    50                  55                  60

<210> SEQ ID NO 96
<211> LENGTH: 58
<212> TYPE: PRT

<213> ORGANISM: Halorubrum vacuolatum
<220> FEATURE:
<221> NAME/KEY: MISC_FEATURE
<222> LOCATION: (1)..(58)
<223> OTHER INFORMATION: gvpA

<400> SEQUENCE: 96

Met Ala Gln Pro Asp Ser Ser Ser Leu Ala Glu Val Leu Asp Arg Val
1               5                   10                  15

Leu Asp Lys Gly Val Val Val Asp Val Tyr Ala Arg Leu Ser Leu Val
            20                  25                  30

Gly Ile Glu Ile Leu Thr Val Glu Ala Arg Val Val Ala Ala Ser Val
        35                  40                  45

Asp Thr Phe Leu His Tyr Ala Glu Glu Ile
    50                  55

<210> SEQ ID NO 97
<211> LENGTH: 58
<212> TYPE: PRT
<213> ORGANISM: Haloferax mediterranei
<220> FEATURE:
<221> NAME/KEY: MISC_FEATURE
<222> LOCATION: (1)..(58)
<223> OTHER INFORMATION: gvpA

<400> SEQUENCE: 97

Met Val Gln Pro Asp Ser Ser Ser Leu Ala Glu Val Leu Asp Arg Val
1               5                   10                  15

Leu Asp Lys Gly Val Val Val Asp Val Trp Ala Arg Ile Ser Leu Val
            20                  25                  30

Gly Ile Glu Ile Leu Thr Val Glu Ala Arg Val Val Ala Ala Ser Val
        35                  40                  45

Asp Thr Phe Leu His Tyr Ala Glu Glu Ile
    50                  55

<210> SEQ ID NO 98
<211> LENGTH: 58
<212> TYPE: PRT
<213> ORGANISM: Halobacterium sp. NRC-1
<220> FEATURE:
<221> NAME/KEY: MISC_FEATURE
<222> LOCATION: (1)..(58)
<223> OTHER INFORMATION: gvpA1

<400> SEQUENCE: 98

Met Ala Gln Pro Asp Ser Ser Gly Leu Ala Glu Val Leu Asp Arg Val
1               5                   10                  15

Leu Asp Lys Gly Val Val Val Asp Val Trp Ala Arg Val Ser Leu Val
            20                  25                  30

Gly Ile Glu Ile Leu Thr Val Glu Ala Arg Val Val Ala Ala Ser Val
        35                  40                  45

Asp Thr Phe Leu His Tyr Ala Glu Glu Ile
    50                  55

<210> SEQ ID NO 99
<211> LENGTH: 58
<212> TYPE: PRT
<213> ORGANISM: Halobacterium sp. NRC-1
<220> FEATURE:
<221> NAME/KEY: MISC_FEATURE
<222> LOCATION: (1)..(58)
<223> OTHER INFORMATION: gvpA2

<400> SEQUENCE: 99

Met Ala Gln Pro Asp Ser Ser Leu Ala Glu Val Leu Asp Arg Val
1               5                   10                  15

Leu Asp Lys Gly Val Val Asp Val Trp Ala Arg Ile Ser Leu Val
                20                  25                  30

Gly Ile Glu Ile Leu Thr Val Glu Ala Arg Val Ala Ala Ser Val
            35                  40                  45

Asp Thr Phe Leu His Tyr Ala Glu Glu Ile
        50                  55

<210> SEQ ID NO 100
<211> LENGTH: 61
<212> TYPE: PRT
<213> ORGANISM: Bacillus megaterium
<220> FEATURE:
<221> NAME/KEY: MISC_FEATURE
<222> LOCATION: (1)..(61)
<223> OTHER INFORMATION: gvpA

<400> SEQUENCE: 100

Met Ser Ile Gln Lys Ser Thr Asp Ser Ser Leu Ala Glu Val Ile
1               5                   10                  15

Asp Arg Ile Leu Asp Lys Gly Ile Val Ile Asp Ala Phe Ala Arg Val
                20                  25                  30

Ser Leu Val Gly Ile Glu Ile Leu Thr Ile Glu Ala Arg Val Val Ile
            35                  40                  45

Ala Ser Val Asp Thr Trp Leu Arg Tyr Ala Glu Ala Val
        50                  55                  60

<210> SEQ ID NO 101
<211> LENGTH: 61
<212> TYPE: PRT
<213> ORGANISM: Bacillus megaterium
<220> FEATURE:
<221> NAME/KEY: MISC_FEATURE
<222> LOCATION: (1)..(61)
<223> OTHER INFORMATION: gvpB2

<400> SEQUENCE: 101

Met Ser Ile Gln Lys Ser Thr Asn Ser Ser Leu Ala Glu Val Ile
1               5                   10                  15

Asp Arg Ile Leu Asp Lys Gly Ile Val Ile Asp Ala Phe Ala Arg Val
                20                  25                  30

Ser Val Val Gly Ile Glu Ile Leu Thr Ile Glu Ala Arg Val Val Ile
            35                  40                  45

Ala Ser Val Asp Thr Trp Leu Arg Tyr Ala Glu Ala Val
        50                  55                  60

<210> SEQ ID NO 102
<211> LENGTH: 61
<212> TYPE: PRT
<213> ORGANISM: Anabaena flos-aquae
<220> FEATURE:
<221> NAME/KEY: MISC_FEATURE
<222> LOCATION: (1)..(61)
<223> OTHER INFORMATION: gvpA

<400> SEQUENCE: 102

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Val Arg Val
                20                  25                  30

```
Ser Leu Val Gly Ile Glu Leu Leu Ala Ile Glu Ala Arg Ile Val Ile
        35                  40                  45

Ala Ser Val Glu Thr Tyr Leu Lys Tyr Ala Glu Ala Val
    50                  55                  60

<210> SEQ ID NO 103
<211> LENGTH: 61
<212> TYPE: PRT
<213> ORGANISM: Microcystis aeruginosa
<220> FEATURE:
<221> NAME/KEY: MISC_FEATURE
<222> LOCATION: (1)..(61)
<223> OTHER INFORMATION: gvpA

<400> SEQUENCE: 103

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Ala Arg Val
                20                  25                  30

Ser Leu Val Gly Ile Glu Leu Leu Ala Ile Glu Ala Arg Val Val Ile
        35                  40                  45

Ala Ser Val Glu Thr Tyr Leu Lys Tyr Ala Glu Ala Val
    50                  55                  60

<210> SEQ ID NO 104
<211> LENGTH: 62
<212> TYPE: PRT
<213> ORGANISM: Serratia sp. ATCC 39006
<220> FEATURE:
<221> NAME/KEY: MISC_FEATURE
<222> LOCATION: (1)..(62)
<223> OTHER INFORMATION: gvpA1

<400> SEQUENCE: 104

Met Ala Lys Val Gln Lys Ser Thr Asp Ser Ser Leu Ala Glu Val
1               5                   10                  15

Val Asp Arg Ile Leu Asp Lys Gly Ile Val Ile Asp Ala Trp Val Lys
                20                  25                  30

Val Ser Leu Val Gly Ile Glu Leu Leu Ser Ile Glu Ala Arg Val Val
        35                  40                  45

Ile Ala Ser Val Glu Thr Tyr Leu Lys Tyr Ala Glu Ala Ile
    50                  55                  60

<210> SEQ ID NO 105
<211> LENGTH: 6
<212> TYPE: PRT
<213> ORGANISM: Artificial Sequence
<220> FEATURE:
<223> OTHER INFORMATION: sequence forming a portion of an exemplary
      consensus sequence derived from alignment of exemplary gvpA and
      gvpB amino acid sequences

<400> SEQUENCE: 105

Val Val Asn Met Ser Val
1               5

<210> SEQ ID NO 106
<211> LENGTH: 19
<212> TYPE: PRT
<213> ORGANISM: Artificial Sequence
<220> FEATURE:
<223> OTHER INFORMATION: sequence forming a portion of an exemplary
      consensus sequence derived from alignment of exemplary gvpA and
      gvpB amino acid sequences
```

-continued

```
<400> SEQUENCE: 106

Lys Ser Pro Asp Ser Ser Ser Leu Ala Glu Val Leu Asp Arg Ile Leu
1               5                   10                  15

Asp Lys Gly

<210> SEQ ID NO 107
<211> LENGTH: 36
<212> TYPE: PRT
<213> ORGANISM: Artificial Sequence
<220> FEATURE:
<223> OTHER INFORMATION: sequence forming a portion of an exemplary
      consensus sequence derived from alignment of exemplary gvpA and
      gvpB amino acid sequences

<400> SEQUENCE: 107

Val Ile Asp Ala Trp Ala Arg Val Ser Leu Val Gly Ile Glu Ile Leu
1               5                   10                  15

Thr Ile Glu Ala Arg Val Val Ile Ala Ser Val Asp Thr Tyr Leu Arg
            20                  25                  30

Tyr Ala Glu Ala
        35

<210> SEQ ID NO 108
<211> LENGTH: 6
<212> TYPE: PRT
<213> ORGANISM: Artificial Sequence
<220> FEATURE:
<223> OTHER INFORMATION: sequence forming a portion of an exemplary
      consensus sequence derived from alignment of exemplary gvpA and
      gvpB amino acid sequences

<400> SEQUENCE: 108

Asn Arg Leu Asp Leu Glu
1               5
```

GENETICALLY ENGINEERED GAS VESICLE GENE CLUSTERS, GENETIC CIRCUITS, VECTORS, PROKARYOTIC CELLS, COMPOSITIONS, METHODS AND SYSTEMS FOR CONTRAST-ENHANCED IMAGING

CROSS REFERENCE TO RELATED APPLICATIONS

The present application claims priority to U.S. Provisional Application No. 62/413,206, entitled "Acoustic reporter genes for noninvasive imaging of microbes in mammalian hosts" filed on Oct. 26, 2016, which is incorporated herein by reference in its entirety. The present application also claims priority to U.S. Provisional Application No. 62/367,750, entitled "Acoustomagnetic imaging with gas-filled protein nanostructures" filed on Jul. 28, 2016, which is incorporated herein by reference in its entirety. The present application is also related to co-pending U.S. application Ser. No. 15/613,104, entitled "Gas-filled Structures and related Compositions, methods and systems to image a target site" filed on Jun. 2, 2017, and to co-pending U.S. application Ser. No. 15/663,600 entitled "Gas filled structure and related compositions methods and systems for magnetic resonance imaging" filed on Jul. 28, 2017, each of which is also incorporated herein by reference in its entirety.

STATEMENT OF INTEREST

This invention was made with government support under Grant No. EB018975 awarded by the National Institute of Health. The government has certain rights in the invention.

FIELD

The present disclosure relates to gas-filled structures, and in particular genetically engineered gas vesicle gene clusters, related genetic circuits, vectors, prokaryotic cells, compositions, methods and systems to produce gas filled structures and/or to image biological events in a target site, with particular reference to imaging performed by magnetic resonance imaging (MRI) and/or ultrasound.

BACKGROUND

Reporting biological events, such as a gene expression, proteolysis, biochemical reactions as well as cell location and function, is currently primarily based on fluorescent reporter genes.

Challenges remain for identifying, producing and/or developing biocompatible reporters that can be imaged in deep tissues, enable multiplexed imaging of biological events, are genetically modifiable, are capable of enabling detection at nanomolar concentrations and/or produce dynamic contrast in response to local molecular signals.

SUMMARY

Provided herein are gas vesicle gene clusters (GVGC) that are genetically engineered to include gas vesicle genes from at least two different prokaryotic species to form a hybrid GVGC, and related gas vesicles (GVs), genetic circuits, vectors, genetically engineered prokaryotic cells, compositions, methods and systems, which in several embodiments can be used together with contrast-enhanced imaging techniques such as such as magnetic resonance imaging (MRI) and ultrasound, to detect and report biological events in an imaging target site.

According to a first aspect, a hybrid gas vesicle gene cluster (GVGC) configured for expression in a prokaryotic host is described. The hybrid gene cluster comprises gas vesicle assembly (GVA) genes native to a GVA prokaryotic species and capable of being expressed in a functional form in the prokaryotic host. The hybrid gene cluster further comprises one or more gas vesicle structural (GVS) genes native to one or more GVS prokaryotic species, at least one of the one or more GVS prokaryotic species different from the GVA prokaryotic species. In the hybrid gene cluster the one or more gas vesicle structural genes and the gas vesicle assembly genes are in a configuration allowing co-expression of the gas vesicle structural genes and the gas vesicle assembly genes upon operative connection with a regulatory sequence capable of operating in the prokaryotic host. In some embodiments, the host is a prokaryote of a same prokaryotic species of the GVA prokaryotic species. In some embodiments, the host is a prokaryote of a prokaryotic species different from the GVA prokaryotic species. In some embodiments, the GVA prokaryotic species is *Bacillus Megaterium*.

According to a second aspect a method is described to provide a hybrid gas vesicle gene cluster (GVGC) configured for expression in a prokaryotic host and a hybrid gas vesicle gene cluster obtainable thereby. The method comprises: providing a polynucleotide construct comprising gas vesicle assembly (GVA) genes native to a GVA prokaryotic species and capable of forming detectable GVs in the prokaryotic host. In the method, the polynucleotide construct further comprises gas vesicle structural (GVS) genes native to one or more GVS prokaryotic species, at least one of the one or more GVS prokaryotic species different from the GVA prokaryotic species. In the polynucleotide construct, the GVA genes and the GVS genes are in a configuration allowing co-expression of the GVA genes and GVS genes upon operative connection of the GVA genes and GVS genes with a regulatory sequence configured to operate in the prokaryotic host. In the method, the prokaryotic host is of a prokaryotic species different from the GVA prokaryotic species.

In some embodiments, the method further comprises detecting expression in the prokaryotic host of one or more candidate GV gene clusters native to a prokaryotic species other than the prokaryotic host to obtain a GVA prokaryotic cell capable of forming detectable GVs in the prokaryotic host.

According to a third aspect, a method to produce a gas vesicle type in a prokaryotic host is described. The method comprises: introducing into the prokaryotic host a hybrid gas vesicle gene cluster (GVGC) herein described configured for expression in the prokaryotic host, in which the gas vesicle structural gene native to the second prokaryotic species encode for the gas vesicle type and, and expressing the hybrid GVGC in the bacterial host to produce the gas vesicle type.

According to a fourth aspect, a method is described to image a biochemical event in a prokaryotic host comprised in an imaging target site, the method comprising:

introducing into the prokaryotic host a hybrid gas vesicle gene cluster (GVGC) herein described configured for expression in the prokaryotic host, the hybrid gas vesicle gene cluster (GVGC) encoding a gas vesicle (GV) type, wherein the GV type is a reportable molecular component of a gas vesicle reporting (GVR) genetic circuit, in which molecular components are connected one to another in accordance with a circuit design by activating, inhibiting, binding or converting reactions to form a fully connected network of interacting components, wherein in the GVR genetic circuit an expression of the GV type or an intracellular spatial translocation of the GV type occurs when the GVR genetic circuit operates according to the circuit design in response to the biochemical event; and imaging the target site comprising the prokaryotic host by applying a magnetic field and/or ultrasound to obtain an MRI and/or an ultrasound image of the target site.

The system comprises the hybrid GVGC, related GVR genetic circuits, related components and/or prokaryotic host cells in a combination for simultaneous combined or sequential use in the imaging methods herein described.

According to a fifth aspect, a method is described to label a target prokaryotic host, the method comprising:

introducing into the target prokaryotic host a hybrid gas vesicle gene cluster (GVGC) herein described configured for expression in the target prokaryotic host, the hybrid gas vesicle gene cluster (GVGC) encoding a gas vesicle (GV) type, wherein the GV type is a reportable molecular component of a gas vesicle reporting (GVR) genetic circuit, in which molecular components are connected one to another in accordance with a circuit design by activating, inhibiting, binding or converting reactions to form a fully connected network of interacting components, wherein in the GVR genetic circuit an expression of the GV type or an intracellular spatial translocation of the GV type occurs when the GVR genetic circuit operates according to the circuit design in response to a trigger molecular component within the target prokaryotic host;

In the method, the introducing is performed under conditions resulting in presence of the trigger molecular component in the target prokaryotic host.

In some embodiments, the method can further comprise imaging the target site comprising the target prokaryotic host, by applying a magnetic field and/or ultrasound to obtain an MRI and/or a ultrasound image of the target site.

The system comprises the hybrid GVGC, related GVR genetic circuits, related components and/or prokaryotic host cells in a combination for simultaneous combined or sequential use in the imaging methods herein described.

According to a sixth aspect, a gas vesicle reporting (GVR) genetic circuit is described, in which molecular components are connected one to another in accordance with a circuit design by activating, inhibiting, binding or converting reactions to form a fully connected network of interacting components.

In the GVR genetic circuit, at least one reportable molecular component is a hybrid GVGC herein described encoding a gas vesicle (GV) type, in which the gas vesicle (GV) type is expressed by the GVGC when the genetic circuit operates according to the circuit design.

According to a seventh aspect, a vector is described comprising a hybrid GVGC herein described configured for expression in a prokaryotic host and/or one or more genetic molecular components of a Gas Vesicle Reporting (GVR) genetic circuit herein described configured to be operated in the prokaryotic host. The vector is configured to introduce the hybrid GVGC, and/or one or more genetic molecular components of the GVR genetic circuit into the prokaryotic host.

According to an eighth aspect, a genetically engineered prokaryotic host is described comprising one or more hybrid GVGC herein described configured for expression in the genetically engineered prokaryotic host and/or one or more GVR genetic circuits herein described configured for operation in the genetically engineered prokaryotic host.

According to a ninth aspect, a composition is described. The composition comprises one or more genetic molecular components of a GVR genetic circuit, vectors, or genetically engineered prokaryotic cells described herein together with a suitable vehicle.

According to a tenth aspect, a method to provide a genetically engineered prokaryotic cell comprising one or more GVR genetic circuits is described, the method comprising:

genetically engineering a prokaryotic cell by introducing into the prokaryotic cell one or more hybrid GVGC, hybrid GVGC genetic circuits and/or GVGC genetic molecular components herein described.

The hybrid GVGCs, and related GVR genetic circuits, vectors, genetically engineered prokaryotic cells, compositions, methods and systems can be used in several embodiments for reporting biochemical events in a prokaryotic cell in vitro, or in vivo, and in particular can be used for non-invasive reporting of biochemical events in prokaryotic cells using imaging techniques such as MRI and ultrasound, two widely available techniques with high resolution and deep tissue penetration.

In several embodiments described herein, the hybrid GVGCs, and related GVR genetic circuits, vectors, genetically engineered prokaryotic cells, compositions, methods and systems can be used to report the location of prokaryotic cells configured to express one or more GV types within an imaging target site, and/or sense and report one or more biochemical events in prokaryotic cells configured to express one or more GV types within an imaging target site.

The hybrid GVGCs, and related GVR genetic circuits, vectors, genetically engineered prokaryotic cells, compositions, methods and systems herein described can be used in several embodiments to report one or more biochemical events through magnetic resonance imaging with enhanced contrast and molecular sensitivity down to sub-nanomolar concentration.

In particular, in several embodiments, gas vesicles (GVs) expressed in genetically engineered prokaryotic cells comprising hybrid GVGCs and/or GVR genetic circuits described herein can be detected in the imaging target site using contrast-enhanced imaging techniques such as magnetic resonance imaging (MRI) and ultrasound.

The hybrid GVGCs and related GVR genetic circuits, vectors, genetically engineered prokaryotic cells, compositions, methods and systems herein described can be used in several embodiments to allow multiplexed imaging using parametric MRI, and differential acoustic sensitivity and background-free MRI when combined with ultrasound.

The hybrid GVGCs, and related GVR genetic circuits, vectors, genetically engineered prokaryotic cells, compositions, methods and systems herein described can be used in several embodiments to detect events such as multiple gene expression, proteolysis and/or biochemical reactions by clustering-induced changes in MRI contrast also enable the design of dynamic molecular sensors.

The hybrid GVGCs, and related GVR genetic circuits, vectors, genetically engineered prokaryotic cells, compositions, methods and systems herein described can be used in several embodiments to report biochemical events through multiplexing, multimodal MRI and/or ultrasound detection.

The hybrid GVGCs, and related GVR genetic circuits, vectors, genetically engineered prokaryotic cells, compositions, methods and systems herein described can be used in several embodiments to report biochemical events through non-toxic, robust MRI contrast via differential magnetic susceptibility at nanomolar concentrations.

The hybrid GVGCs, and related GVR genetic circuits, vectors, genetically engineered prokaryotic cells, compositions, methods and systems herein described can be used in several embodiments to produce dynamic contrast in response to local molecular signals.

The hybrid GVGCs, and related GVR genetic circuits, vectors, genetically engineered prokaryotic cells, compositions, methods and systems herein described can be used in several embodiments to provide ultrasound imaging with enhanced harmonic responses, multiplexing, multimodal detection and/or molecular targeting to help ultrasound fulfill its potential as a high performance modality for molecular imaging.

The hybrid GVGCs, and related GVR genetic circuits, vectors, genetically engineered prokaryotic cells, compositions, methods and systems as well as GvpC variants herein described can be used in several embodiments to track movement in target sites such as prokaryotic cells within the body of an individual or other environments.

The hybrid GVGCs, and related GVR genetic circuits, vectors, genetically engineered prokaryotic cells, compositions, methods and systems herein described can in some embodiments be used to allow measures of fluid flows within blood and lymphatic circulation systems by detecting the spatial location of the ultrasound contrast produced the by the cells in an image and tracking the spatial changes of that contrast over time.

The hybrid GVGCs, and related GVR genetic circuits, vectors, genetically engineered prokaryotic cells, compositions, methods and systems herein described can be used in connection with various applications wherein reporting of biological events in a target site is desired. For example, the hybrid GVGCs, and related GVR genetic circuits, vectors, genetically engineered prokaryotic cells, compositions, methods and systems herein described can be used for visualization of biological events, such as a gene expression, proteolysis, biochemical reactions as well as prokaryotic cell location on a target site (e.g. bacterial cells inside a host individual, such as mammalian hosts), facilitating for example the study of the mammalian microbiome and the development of diagnostic and therapeutic cellular agents, among other advantages identifiable by a skilled person, in medical applications, as well diagnostics applications. Additional exemplary applications include uses of the hybrid GVGCs, and related GVR genetic circuits, vectors, genetically engineered prokaryotic cells, compositions, methods and systems herein described in several fields including basic biology research, applied biology, bio-engineering, bio-energy, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 14 shows the plasmid sequence of the exemplary ARG1 construct.

FIG. 15 shows the plasmid sequence of the exemplary ARG2 construct.

Panel A shows a schematic diagram of exemplary inducible expression of GVGCs in *E. coli* leading to the intracellular formation of GVs and the generation of susceptibility-based MRI contrast. Panel B shows an exemplary representative acoustomagnetic QSM image of agarose phantom containing *E. coli* expressing GVGCs or a green fluorescent protein (GFP) under the control of an IPTG-inducible promoter, in the presence or absence of the inducer, compared to a well containing buffer. Panel C shows a graph reporting exemplary mean differential susceptibility values relative to buffer. N=6 biological replicates. Error bars represent SEM. All bacterial cells were at culture $OD_{600}$=8.0.

Figure 17:
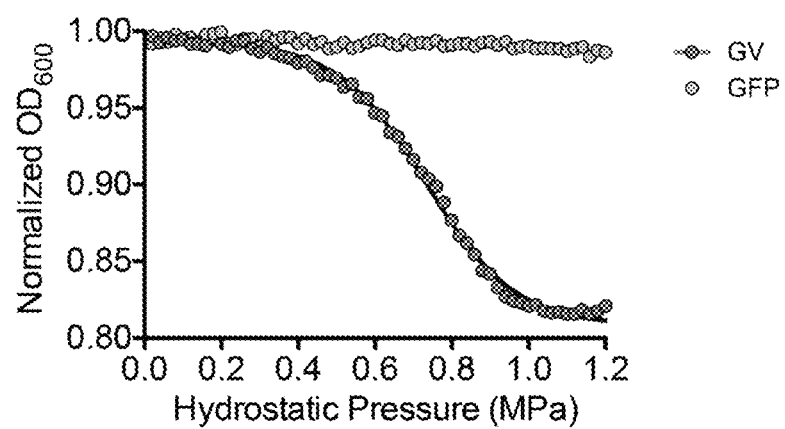

FIG. 17 shows a graph reporting exemplary hydrostatic collapse measurement of *E. coli* cells. *E. coli* cells at optical density at 600 nm (OD600)~1.0 were loaded into a sealed cuvette with path length 1.00 cm. Hydrostatic pressure was ramped stepwise from 0 to 1.2 MPa and OD600 was recorded in each step. Cells expressing exemplary A2C GVs showed a sigmoidal drop in OD600, characteristic of the collapse of intracellular GV. Cells that do not contain GV, such as the control cells expressing the green fluorescent protein (GFP) mNeonGreen5 did not show a drop in OD600. The ratio of post- to pre-collapse optical density was between 0.806 and 0.853 (Min and Max, N=6), and this ratio was used to adjust the OD600 GV-expressing cells to be representative of cell quantity.

Figure 18:
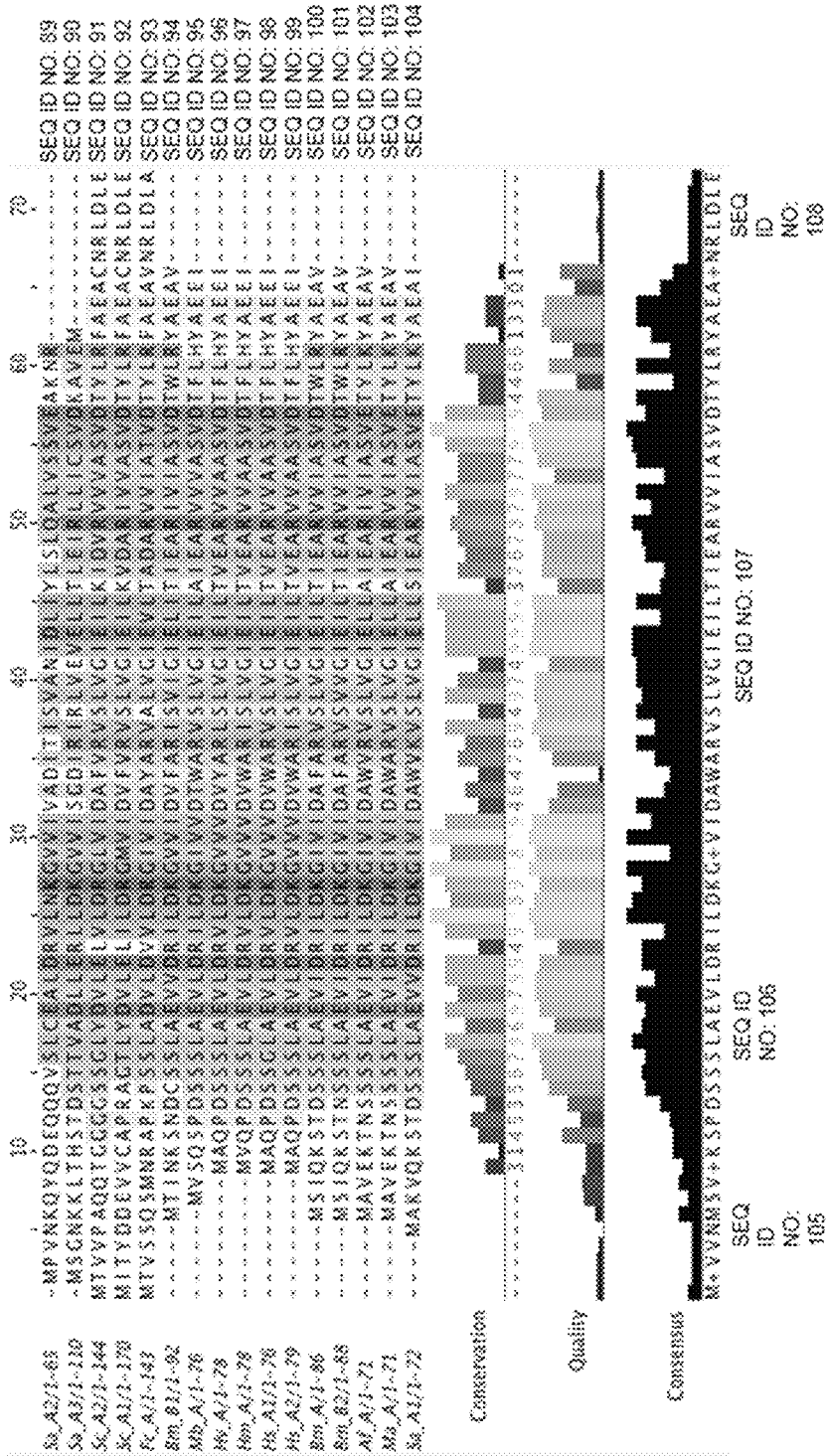

FIG. 18 shows an exemplary Clustal omega alignment of amino acid sequences of selected exemplary gvpA and gvpB proteins. The gvpA and gvpB proteins shown are from the following species: Sa_A2, *Serratia* sp. ATCC 39006 gvpA2; Sa_A3, *Serratia* sp. ATCC 39006 gvpA3; Sc_A2, *Streptomyces coelicolor* gvpA2; Sc_A1, *Streptomyces coelicolor* gvpA1; Fc_A, *Frankia* sp. gvpA; Bm_B1, *B. megaterium* gvpB1; Mb_A, *Methanosarcina barkeri* gvpA; Hv_A, *Halorubrum vacuolatum* gvpA; Hm_A, *Haloferax mediterranei* gvpA; Hs_A1, *Halobacterium* sp. NRC-1 gvpA1; Hs_A2, *Halobacterium* sp. NRC-1 gvpA2; Bm_A, *B. megaterium* gvpA; Bm_B2, *B. megaterium* gvpB2; Af_A, *A. floc-aquae* gvpA; Ma_A, *Microcystis aeruginosa* NIES-843 gvpA; Sa_A1, *Serratia* sp. ATCC 39006 gvpA1. The bottom row of FIG. 18 indicated as "Consensus" shows an exemplary consensus sequence derived from alignment of the gvpA and gvpB amino acid sequences shown.

Figure 19:
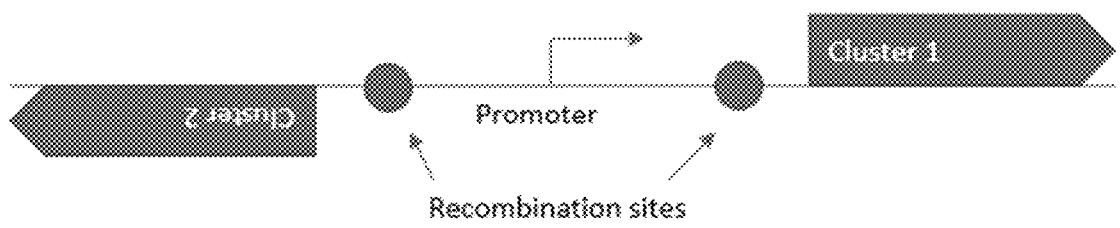

FIG. 19 shows an exemplary configuration of a construct designed to allow expression of two different GV types in one prokaryotic cell. The exemplary construct in FIG. 19 is designed to provide alternating expression of two GV types, the first GV type encoded by Cluster 1, and the second GV type encoded by Cluster 2, shown as block-shaped arrows facing in opposite orientations of a DNA strand (shown as a straight line), with a promoter between the two clusters. The promoter is flanked by recombination sites (e.g. flippase recognition target, FRT sites) shown as circles. For example, initially, the promoter can be oriented in a direction operatively linked to Cluster 1, initiating expression of gyp genes for the formation of GV type 1. In presence of a cognate recombinase (e.g. flippase, Flp), expressed from another genetic construct in the prokaryotic cell, the orientation of the promoter is reversed upon recombination at the FRT sites, and thereafter is oriented in the opposite direction, operatively linked to Cluster 2, initiating expression of gyp genes for the formation of GV type 2.

Figure 20:
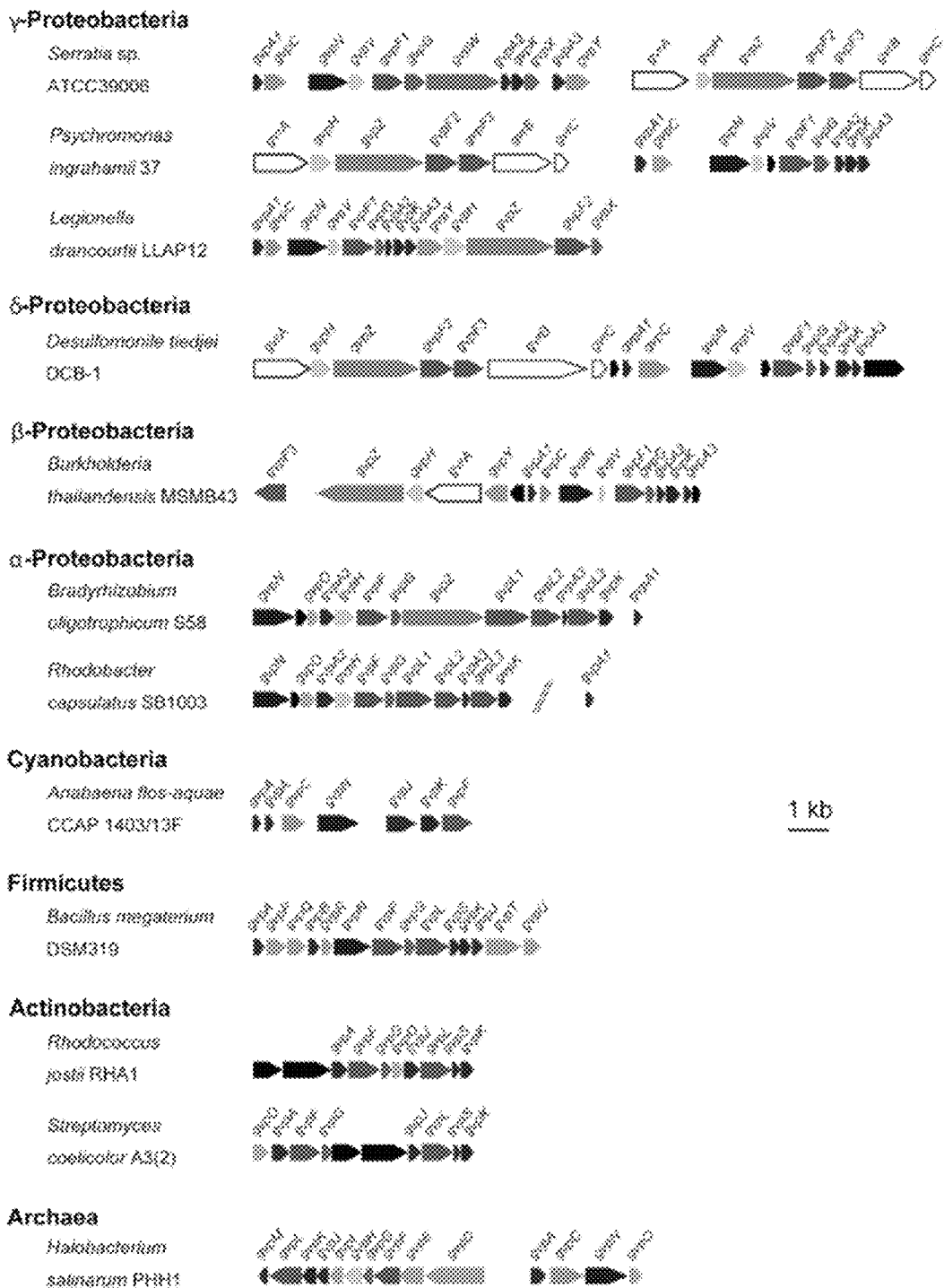

FIG. 20 shows diagrams illustrating the organization of exemplary gas vesicle gene clusters. Gas vesicle gene clusters from the indicated organisms are shown, with genes shown as block-shaped arrows, and genes of predicted similar function indicated in the same shade of grey. The direction of the transcription of genes within a gene cluster is indicated by the direction of the block-shaped arrows, and genes grouped together having block arrows pointed in the same direction are typically organized in the same operon. The scale bar indicates 1 kb. [1]

FIG. 21 shows diagrams illustrating organization of exemplary Gvp gene clusters, wherein each letter indicates a Gvp gene, and an arrow beneath a group of letters indicates an operon, with the direction of the arrow indicating the direction of transcription. [2]

Figure 22:
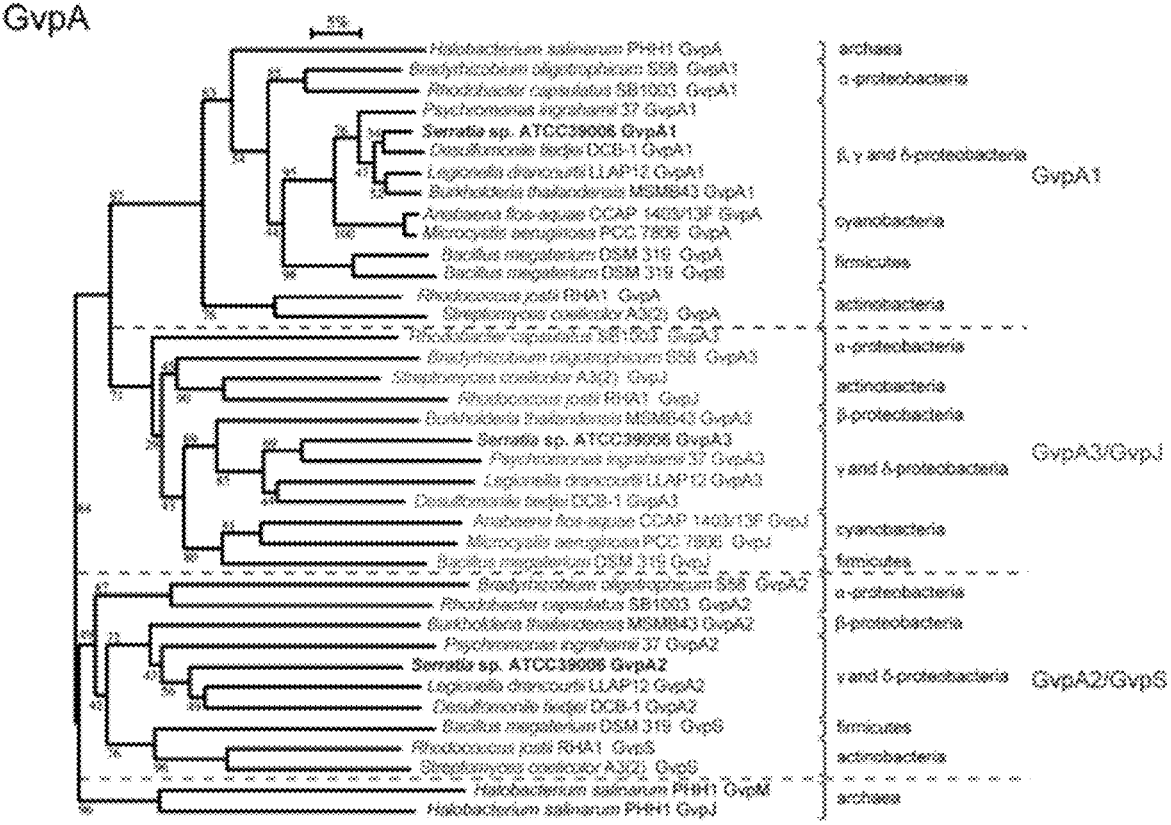

FIG. 22 shows exemplary phylogenetic relationships of the gvpA protein sequences from the indicated prokaryotic species. [1]

Figure 23:
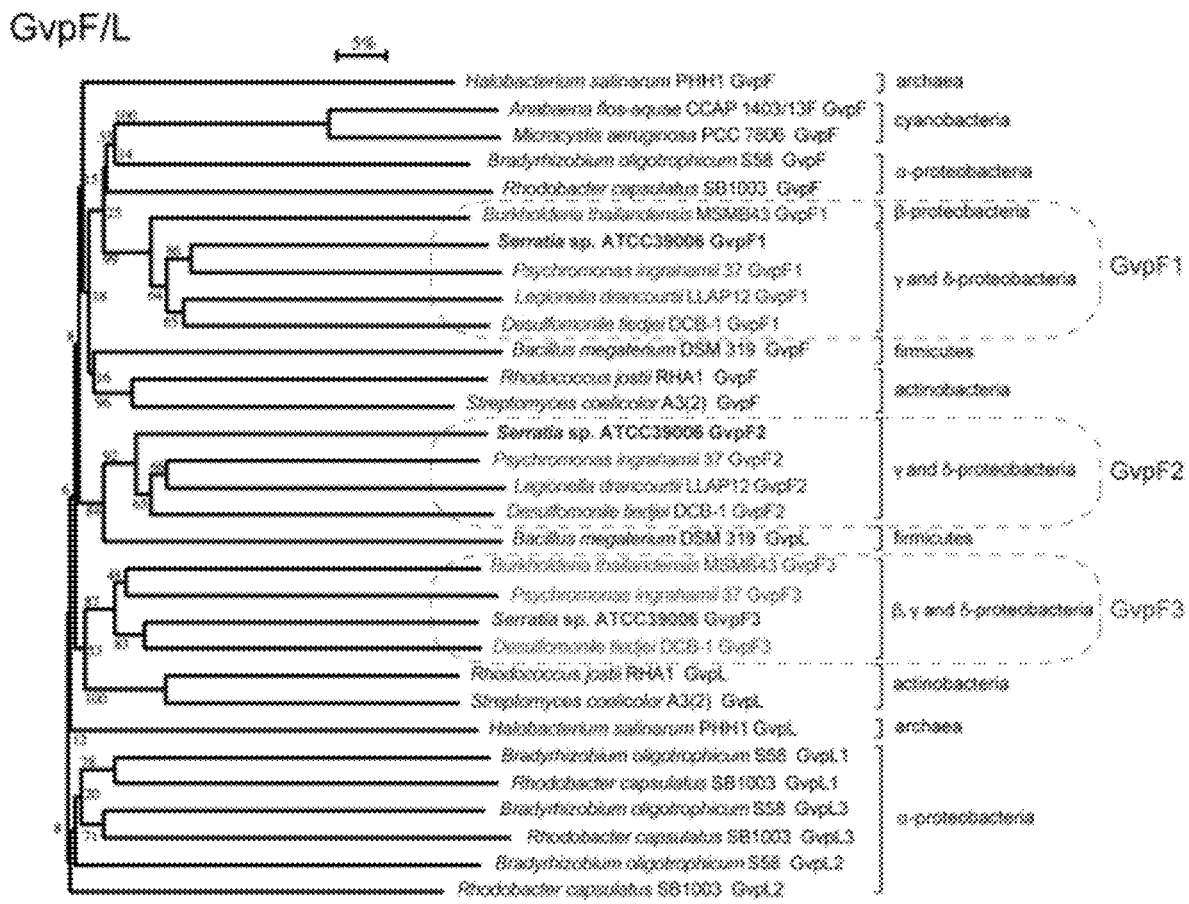

FIG. 23 shows exemplary phylogenetic relationships of the gvpF and gvpL protein sequences from the indicated prokaryotic species. [1]

Figure 24:
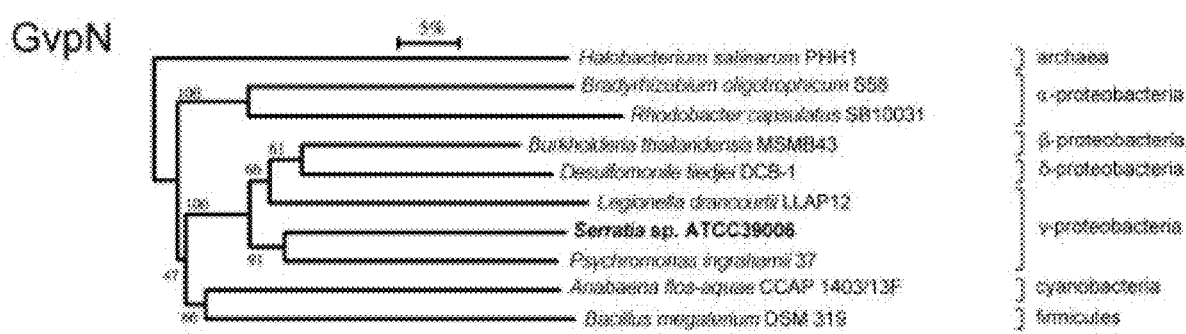

FIG. 24 shows exemplary phylogenetic relationships of the gvpN protein sequences from the indicated prokaryotic species. [1]

DETAILED DESCRIPTION

Provided herein are genetically engineered gas vesicle gene clusters (GVGC), and related gas vesicles (GVs), genetic circuits, vectors, genetically engineered prokaryotic cells, compositions, methods and systems.

The wordings "gas vesicles", GV", "gas vesicles protein structure", or "GVPS", refer to a gas-filled protein structure natively intracellularly expressed by certain bacteria or archea as a mechanism to regulate cellular buoyancy in aqueous environments [3]. In particular, gas vesicles are protein structures natively expressed almost exclusively in microorganisms from aquatic habitats, to provide buoyancy by lowering the density of the cells [3]. GVs have been found in over 150 species of prokaryotes, comprising cyanobacteria and bacteria other than cyanobacteria [4, 5], from at least 5 of the 11 phyla of bacteria and 2 of the phyla of archaea described by Woese (1987) [6]. Exemplary microorganisms expressing or carrying gas vesicle protein structures and/or related genes include cyanobacteria such as *Microcystis aeruginosa, Aphanizomenon flos aquae Oscillatoria agardhii, Anabaena, Microchaete diplosiphon* and *Nostoc*; phototropic bacteria such as *Amoebobacter, Thiodiclyon, Pelodiclyon,* and *Ancalochloris*; non phototropic bacteria such as *Microcyclus aquaticus*; Gram-positive bacteria such as *Bacillus megaterium* Gram-negative bacteria such as *Serratia*; and archaea such as *Haloferax mediterranei*, *Methanosarcina barkeri*, and *Halobacteria salinarium*, as well as additional microorganisms identifiable by a skilled person.

In particular, a GV in the sense of the disclosure is an intracellularly expressed structure forming a hollow structure wherein a gas is enclosed by a protein shell, which is a shell substantially made of protein (at least 95% protein). In gas vesicles in the sense of the disclosure, the protein shell is formed by a plurality of proteins herein also indicated as Gvp proteins or Gvps, which form in the cytoplasm a gas permeable and liquid impermeable protein shell configuration encircling gas. Accordingly, a protein shell of a GV is permeable to gas but not to surrounding liquid such as water. In particular, GV protein shells exclude water but permit gas to freely diffuse in and out from the surrounding media [7] making them physically stable despite their usual nanometer size, unlike microbubbles, which trap pre-loaded gas in an unstable configuration.

Gvp proteins natively expressed by prokaryotes such as bacteria or archea and forming the protein shell of a GV are also indicated as Gas Vesicle Structural (GVS) proteins.

The term Gas Vesicle structural (GVS) proteins as herein indicates proteins forming part of a gas-filled protein structure intracellularly expressed by certain bacteria or archea and can be used as a mechanism to regulate cellular buoyancy in aqueous environments [7]. In particular GVS shell comprises a GVS identified as gvpA or gvpB (herein also referred to as Gvp A/B) and optionally also a GVS identified as GvpC.

In particular, a gyp A/B is a protein of the GV shell that has a higher than 70% identity to the following consensus sequence: SSSLAEVLDRILDKGXVIDAWARVSLVGIEILTIEARVVIASVDTYLR (SEQ ID NO: 3) wherein X can be any amino acid. In particular in a gvpA/B of prokaryotes, the consensus sequence of SEQ ID NO: 3 typically forms a conserved secondary structure having an alpha-beta-beta-alpha structural motif formed by portions of the consensus sequence comprising the amino acids LDRILD (SEQ ID NO:4) having an alpha helical structure, RILDKGXVIDAWARVS (SEQ ID NO:5) wherein X can be any amino acid, having a beta strand, beta strand structure, and DTYLR (SEQ ID NO:6) having an alpha helical structure, as will be understood by a skilled person.

Thus, a gvpA/B protein in a prokaryote of interest can be identified for example by isolating GVs from a prokaryote of interest, isolating the protein from the protein shell of the GV and obtaining the amino acid sequence of the isolated protein. In addition or in the alternative to the isolating the GVs and isolating the protein, the method can include obtaining amino acidic sequences of the shell proteins of the GV of the prokaryote of interest from available database. The method further comprises performing a sequence alignment of the obtained amino acidic sequences against the gvpA/B protein consensus sequence of SEQ ID NO:3.

In particular the isolating GVs from a prokaryote of interest can be performed following methods to isolate gas vesicles as described in U.S. application Ser. No. 15/613,104, filed on Jun. 2, 2017. The isolating the protein for the protein shell of the GV and obtaining the related amino acidic sequence can be performed with tandem liquid chromatography mass-spectrometry alone or in combination with obtaining amino acid sequences of the isolated protein with wet lab techniques or from available databases comprising the sequences of the prokaryote of interest as well as additional techniques and approaches identifiable by a skilled person. Obtaining amino acid sequences of GV shell proteins of the prokaryote of interest can be performed by screening available databases of gene and protein sequences identifiable by a skilled person. Performing a sequence alignment of the sequences of the isolated GV proteins or proteins encoded in the genome of a prokaryote of interest can be performed (using Protein BLAST or other alignment algorithms known in the art) against the gvpA/B protein consensus sequence of SEQ ID NO:3. In particular, a sequence alignment can be performed using gvpA/B protein sequences from the closest phylogenetic relative to the prokaryote of interest. Reference is made to Example 13 and FIG. 22 showing exemplary phylogenetic relationships between gvpA/B proteins of exemplary prokaryotic species.

A GvpC protein is a hydrophilic protein of a GV shell, which includes repetitions of one repeat region flanked by an N-terminal region and a C terminal region. The term "repeat region" or "repeat" as used herein with reference to a protein refers to the minimum sequence that is present within the protein in multiple repetitions along the protein sequence without any gaps. Accordingly, in a GvpC multiple repetitions of a same repeat is flanked by an N-terminal region and a C-terminal region. In a same GvpC, repetitions of a same repeat in the GvpC protein can have different lengths and different sequence identity one with respect to another.

Repeat regions within any given GvpC sequence 'X' from organism 'Y' can be identified by comparing the related sequence with the sequence of a known GvpC (herein e.g. reference GvpC sequence "Z"). In particular, the comparing can be performed by aligning sequence 'X' to the reference GvpC sequence 'Z' using a sequence alignment tools such as BLASTP or other sequence alignment tools identifiable by a skilled person at the date of filing of the application upon reading of the present disclosure. In particular, a reference sequence 'Z' is chosen from a host that is the closest phylogenetic relative of 'Y', from a list of *Anabaena flos-aquae*, *Halobacterium salinarum*, *Haloferax mediditerranei*, *Microchaetae diplosiphon* and *Nostoc* sp. The sequence alignment of 'X' and 'Z' (e.g. a BLASTP) is performed by performing a first alignment of sequence X and sequence Z to identify a beginning and an end of a repeat in 'X as well as a number of repetition of the identified repeat, in accordance with the known repeats in 'Z'. The first alignment results in at least one first aligned portion of X with respect to reference sequence Z. The aligning can also comprises performing a second alignment between the at least one first aligned portion of X identified following the first alignment and additional portions of X to identify at least one repeat 'R1' in X. Other repeats in 'X' (i.e. R2, R3, R4 . . . ) can subsequently be identified with respect to R1.

Figure 16:
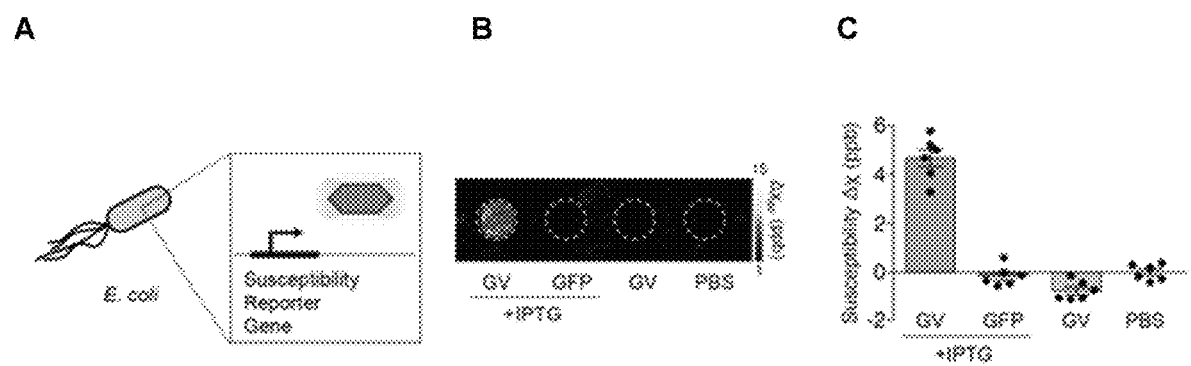
FIG. 16 shows exemplary acoustomagnetic reporter gene imaging in living cells.

In performing alignment steps sequence are identified as repeat when the sequence shows at least 3 or more of the following characteristics:

1) There are no gaps or spacer amino acids between any two adjacent repetition of a repeat (see e.g. FIG. 16 and FIG. 26 of U.S. application Ser. No. 15/613,104 filed on Jun. 2, 2017)
2) Each repetition of a repeat has a sequence length between 18-45 amino acids, e.g. 33 amino acids seen for 100% of the repeats in *Anabaena floc-aquae*, *Microchaetae diplosiphon* and *Nostoc* sp. (e.g. FIG. 26 of U.S. application Ser. No. 15/613,104 filed on Jun. 2, 2017)
3) Upon alignment of all the repeats within a given GvpC sequence, there exists for every position in more than 50% of the total number of repeats, greater than 50% sequence similarity of the amino acid residues in each repeat (e.g. FIG. 26 of U.S. application Ser. No. 15/613,104 filed on Jun. 2, 2017)

4) Sub-sequences of at least 3 or more amino acids at the beginning or end of the that are conserved across 50% or more of the repeats in a given GvpC sequence, also referred to as "consensus sequences". Exemplary embodiments of such consensus sequences are QAQELLAF (SEQ ID NO:7) at the end of repeats in *Anabaena floc-aquae*, LHQF (SEQ ID NO:8) at the end of repeats in *Microchaete diplosiphon*, LSQF (SEQ ID NO:9) at the end of repeats in *Microcystis aeruginosa* and DAF (SEQ ID NO:10) at the beginning of repeats in *Halobacterium salinarum*. (e.g. FIGS. 16 and 26 of U.S. application Ser. No. 15/613,104 filed on Jun. 2, 2017).

5) The consensus sequence of all the repeats within a given GvpC sequence show greater than 60% identity to the consensus sequence of all the repeats within another GvpC from a different microbial host of the same phylogenetic order (e.g. FIG. 26, panels g-h of U.S. application Ser. No. 15/613,104 filed on Jun. 2, 2017).

In some exemplary embodiments, the repeat has at least 90% sequence identity with another repeat within the same GvpC sequence.

In a GvpC the N-terminal region comprises the amino acid residues upstream (towards the N-terminus) of the first repeated sequence of the GvpC's repeat, while the C-terminal region comprises the amino acid residues downstream (towards the C-terminus) of the last repeated sequence of the GvpC's repeat.

GvpC protein is typically rich in glutamine, alanine and glutamic acid residues, which account for >40% of the residues. In the exemplary *Anabaena flos-aqaue*, GvpC comprises five highly conserved 33-amino acid repeats with predicted alpha-helical structure, and is believed to bind across GvpA ribs to provide structural reinforcement [3], which aligns with experimental data. In biochemical studies, removal of GvpC and truncations to its sequence were shown to result in a reduced threshold for Ana GV collapse under hydrostatic pressure. In addition, previous studies in other species have demonstrated that GvpC can tolerate fusions of bacterial and viral polypeptides.

GvpC sequences in different bacteria or archaea producing GVs typically have a greater than 15% sequence identity and are produced by genes found in the gas vesicle gene cluster.

Following purification of GVs from a bacteria or archea naturally expressing the GV, GVS proteins make up over 90% of the bulk GV mass.

In embodiments herein described GVS proteins natively expressed by bacteria or archea assemble in the native bacterial or archeal cell in presence of additional proteins also natively expressed in the native bacterial or archeal cells herein also indicated as Gas Vesicle Assembly (GVA) proteins which putative minor components and chaperones [8-10] as would be understood by a person skilled in the art.

The term Gas Vesicle Assembly (GVA) proteins as used herein indicates proteins enabling assembly of a GV in a prokaryotic cell. GVA proteins comprise proteins with various putative functions such as nucleators and/or chaperons as well as proteins with an unknown specific function related to the assembly of the GV.

Accordingly, in bacterial and archeal cells natively expressing GVS, in presence of natively expressed GVAs, GvpA/B assemble through repeated units to make up the bulk of GVs, while GvpC provides a scaffold protein with repeat units that assemble on the outer shell of GVs.

Figure 1:
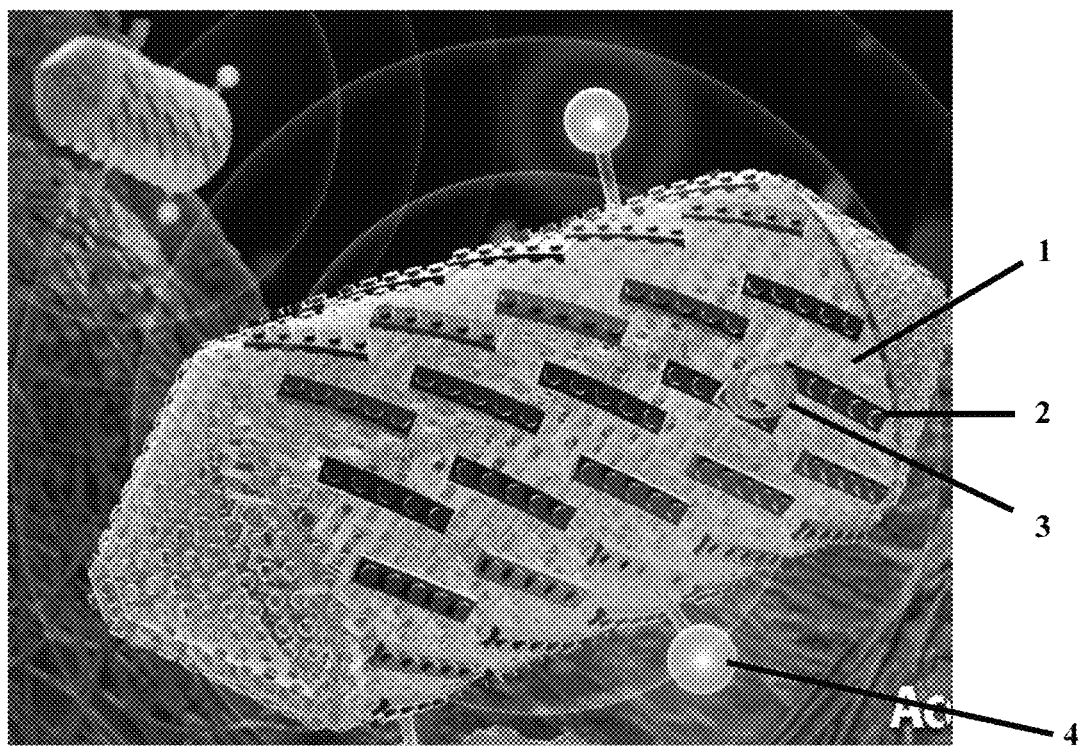
FIG. 1 shows a rendition of GVs showing the related building blocks. GvpA ribs (1) (gray) forming the primary GV shell and the outer scaffold protein GvpC (2) (black dark rectangles (2).

Reference is made to the illustration of FIG. 1 showing a schematic representation of the structure of an exemplary GV. In the illustration of FIG. 1 GvpA and GvpC are indicated as the two major structural constituents of GVs, with GvpA ribs (1) (gray) forming the primary GV shell and the outer scaffold protein GvpC (2) (black) conferring structural integrity. In particular, in the illustration of FIG. 1, the light gray elements represent the proteinaceous gas vesicle shell, comprising multiple copies of GvpA and other minor structural constituents. In the illustration of FIG. 1, the dark rectangles (2) bound to the surface of the gas vesicle shell represent GvpC, a protein that affects mechanical and acoustic properties of the gas vesicle.

GV structures are typically nanostructures with widths and lengths of nanometer dimensions (in particular with widths of 45-250 nm and lengths of 100-800 nm) but can have lengths up to 2 µm as will be understood by a skilled person. In certain embodiments, the gas vesicles protein structure have average dimensions of 1000 nm or less, such as 900 nm or less, including 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 10 nm or less. For example, the average diameter of the gas vesicles may range from 10 nm to 1000 nm, such as 25 nm to 500 nm, including 50 nm to 250 nm, or 100 nm to 250 nm. By "average" is meant the arithmetic mean.

GVs in the sense of the disclosure have different shapes depending on their genetic origins [7]. For example, GVs in the sense of the disclosure can be substantially spherical, ellipsoid, cylindrical, or have other shapes such as football shape or cylindrical with cone shaped end portions depending on the type of bacteria providing the gas vesicles.

Representative examples of endogenously expressed GVs native to bacterial or archaeal species are the gas vesicle protein structure produced by the Cyanobacterium *Anabaena flos-aquae* (Ana GVs) [3], and the *Halobacterium Halobacterium salinarum* (Halo GVs) [10]. In particular, Ana GVs are cone-tipped cylindrical structures with a diameter of approximately 140 nm and length of up to 2 µm and in particular 200-800 nm or longer, encoded by a cluster of nine different genes, including the two primary structural proteins, GvpA and GvpC, and several putative minor components and putative chaperones[11] as would be understood by a person skilled in the art. Halo GVs are typically spindle-like structures with a maximal diameter of approximately 250 nm and length of 250-600 nm, encoded by a cluster of fourteen different genes, including the two primary structural proteins, GvpA and GvpC, and several putative minor components and putative chaperones [11] as would be understood by a person skilled in the art.

In bacteria or archaea expressing GVs, the Gvp structural proteins forming a GV's protein shell and Gvp assembly proteins allowing assembly of the GVS proteins into a shell, are encoded by a gas vesicle gene cluster of 8 to 14 different genes depending on the host bacteria or archaea, as will be understood by a skilled person.

The term "Gas Vesicle Genes Cluster" or "GVGC" as described herein indicates a gene cluster encoding a set of Gvp proteins capable of providing a GV upon expression within a bacterial cell.

The term "gene cluster" as used herein means a group of two or more genes found within an organism's DNA that encode two or more polypeptides or proteins, which collectively share a generalized function or are genetically regulated together to produce a cellular structure and are often located within a few thousand base pairs of each other. The size of gene clusters can vary significantly, from a few genes to several hundred genes [12]. Portions of the DNA sequence of each gene within a gene cluster are sometimes found to be similar or identical; however, the resulting protein of each gene is distinctive from the resulting protein of another gene within the cluster. Genes found in a gene cluster can be observed near one another on the same chromosome or native plasmid DNA, or on different, but homologous chromosomes. An example of a gene cluster is the Hox gene, which is made up of eight genes and is part of the Homeobox gene family. In the sense of the disclosure, gene clusters as described herein also comprise gas vesicle gene clusters, wherein the expressed proteins thereof together are able to form gas vesicles.

In embodiments herein described identification of a gene cluster encoding Gvp proteins naturally expressed in bacteria or archea as described herein can be performed for example by isolating the GVs from the bacteria or archea, isolating the protein for the protein shell of the GV and deriving the related amino acidic sequence with methods and techniques identifiable by a skilled person. The sequence of the genes encoding for the Gvp proteins can then be identified by methods and techniques identifiable by a skilled person. For example, gas vesicle gene clusters can also be identified by persons skilled in the art by performing gene sequencing or partial- or whole-genome sequencing of organisms using wet lab and in silico molecular biology techniques known to those skilled in the art. As understood by those skilled in the art, gas vesicle gene clusters can be located on the chromosomal DNA or native plasmid DNA of microorganisms. After performing DNA or cDNA isolation from a microorganism, the polynucleotide sequences or fragments thereof or PCR-amplified fragments thereof can be sequenced using DNA sequencing methods such as Sanger sequencing, DNASeq, RNASeq, whole genome sequencing, and other methods known in the art using commercially available DNA sequencing reagents and equipment, and then the DNA sequences analyzed using computer programs for DNA sequence analysis known to skilled persons.

In some embodiments, identification of a gene cluster encoding for Gvp proteins [8-10] can also be performed by screening DNA sequence databases such as GenBank, EMBL, DNA Data Bank of Japan, and others. Gas vesicle gene cluster gene sequences in databases such as those above can be searched using tools such as NCBI Nucleotide BLAST and the like, for gas vesicle gene sequences and homologs thereof, using gene sequence query methods known to those skilled in the art. For example, genes of the gene cluster for the exemplary haloarchael GVs (which have the largest number of different gyp genes) and their predicted function and features are illustrated in Example 26 of related U.S. application Ser. No. 15/613,104, filed on Jun. 2, 2017 which is incorporated herein by reference in its entirety.

A GV gene cluster encoding for Gvp proteins typically comprises Gas Vesicle Assembly (GVA) genes and Gas Vesicle Structural (GVS) genes.

The Gas Vesicle Assembly genes are genes encoding for GVA proteins. In a prokaryotic cell GVA genes are all the genes within one or more operons comprising at least one of a GvpN and a GvpF excluding any GvpA/B and GvpC gene possibly present within said one or more operons.

In particular, gvpN gene in the sense of the disclosure is gene encoding for sequence (SEQ ID NO: 11)
MTVLTDKRKKGSGAFIQDDETKEVLSRALSYLKSGYSIHFTGPAGGGKT -continued
SLARALAKKRKRPVMLMHGNHELNNKDLIGDFTGYTSKKVIDQYVRSVY

KKDEQVSENWQDGRLLEAVKNGYTLIYDEFTRSKPATNNIFLSILEEGV

LPLYGVKMTDPFVRVHPDFRVIFTSNPAEYAGVYDTQDALLDRLITMFI

DYKDIDRETAILTEKTDVEEDEARTIVTLVANVRNRSGDENSSGLSLRA

SLMIATLATQQDIPIDGSDEDFQTLCIDILHHPLTKCLDEENAKSKAEK

IILEECKNIDTEEK or a sequence of any length having at least 30% sequence identity with respect to SEQ ID NO:11, preferably at least 50%, and more preferably 60% or higher, and gvpF gene in the sense of the disclosure is gene encoding for sequence (SEQ ID NO: 12)
MSETNETGIYIFSAIQTDKDEEFGAVEVEGTKAETFLIRYKDAAMVAAE

VPMKIYHPNRQNLLMHQNAVAAIMDKNDTVIPISFGNVFKSKEDVKVLL

ENLYPQFEKLFPAIKGKIEVGLKVIGKKEWLEKKVNENPELEKVSASVK

GKSEAAGYYERIQLGGMAQKMFTSLQKEVKTDVFSPLEEAAEAAKANEP

TGETMLLNASFLINREDEAKFDEKVNEAHENWKDKADFHYSGPWPAYNF

VNIRLKVEEK, or a sequence of any length having at least 20% sequence identity with respect to SEQ ID NO:12, preferably at least 50%, more preferably 60%, and at least 70% or higher.

The term "operon" as described herein indicates a group of genes arranged in tandem in a prokaryotic genome as will be understood by a skilled person. Operons typically encode proteins participating in a common pathway are organized together as understood by those skilled in the art. Typically, genes of an operon are transcribed together into a single mRNA molecule referred to as polycistronic mRNA. Polycistronic mRNA comprises several open reading frames (ORFs), each of which is translated into a polypeptide. These polypeptides usually have a related function and their coding sequence is grouped and regulated together in a regulatory region, containing a promoter and an operator. Typically, repressor proteins bound to the operator sequence can physically obstruct the RNA polymerase enzyme from binding the promoter, preventing transcription. An example of a prokaryotic operon is the lac operon, which natively regulates transport and metabolism of lactose in *E. coli* and many other enteric bacteria.

In an operon, each ORF typically has its own ribosome binding site (RBS) so that ribosomes simultaneously translate ORFs on the same mRNA. Some operons also exhibit translational coupling, where the translation rates of multiple ORFs within an operon are linked. This can occur when the ribosome remains attached at the end of an ORF and translocates along to the next ORF without the need for a new RBS. Translational coupling is also observed when translation of an ORF affects the accessibility of the next RBS through changes in RNA secondary structure.

In some embodiments, a GV cluster comprises one of gvpN or gvpF. In several embodiments GV clusters include both gvpN and gvpF as will be understood by a skilled person. In this connection, reference is made to Example 12 and FIGS. 20 and 21 showing exemplary gas vesicle gene clusters operons [1, 2] comprising GVS and GVA genes and related exemplary configuration. In particular, as shown in Example 12, typically a native GV gene cluster has GVA genes comprising both gvpN and gvpF genes, even if native GV gene clusters are known having a gvpN gene or a gvpF gene, as understood by skilled persons.

Accordingly, for a certain prokaryote, GVA genes in the sense of the disclosure indicate all the genes that are comprised in the one or more operons having at least one of a GvpN and/or a GvpF herein described and excluding any Gas Vesicle Structural (GVS) genes of the prokaryotes possibly comprised within the one or more operons. Thus, GVA genes comprised in a gas vesicle gene cluster in a prokaryote can be identified for example by obtaining genome sequence of the prokaryote of interest and performing a sequence alignment of the protein sequences encoded in the genome of the prokaryote of interest against a gvpN protein sequence and/or a gvpF protein sequence.

In particular, obtaining the genome sequence of the prokaryote of interest, can be performed either using wet lab techniques identifiable by a skilled person upon reading of the present disclosure, or obtained from databases of gene and protein sequences also identifiable by a skilled person upon reading of the present disclosure. Performing a sequence alignment of the protein sequences encoded in the genome of the prokaryote of interest can per performed using Protein BLAST or other alignment algorithms identifiable by a skilled person. Exemplary gvpN protein sequence and/or a gvpF protein sequence, that can be used in performing the alignment are sequences SEQ ID NO:11 and/or SEQ ID NO:12. In particular, a sequence alignment can be performed using gvpN and/or gvpF protein sequences from the closest phylogenetic relative to the prokaryote of interest. Reference is made to Example 13 and FIG. 23 and FIG. 24 showing exemplary phylogenetic relationships between gvpF and gvpN proteins of exemplary prokaryotic species. Accordingly, one or more operons that comprise the gvpN and/or gvpF genes can be identified, and any other gyps within the one or more operons can also be identified, wherein the other gyps are comprised in ORFs within the one or more operons, excluding any ORFs encoding gvpA/B or gvpC genes comprised in the one or more operons of the GV gene cluster.

The Gas Vesicle Structural (GVS) genes are genes encoding for GVS proteins of a prokaryote as will be understood by a skilled person. In a prokaryotic cell GVS genes are genes within one or more operons that can be identified as described herein with reference to the consensus amino acid sequence of the encoded gvpA/B protein and gvpC protein sequences. As understood by skilled persons, in different species endogenous GVS genes are natively located at varying positions within the one or more operons of a GV gene cluster (e.g. see FIGS. 20 and 21).

Some prokaryotic cells, such as *Bacillus Megaterium* natively include GVA genes and GVS genes without however natively expressing said genes to provide natively expressed GV.

In embodiments herein described, a GVGC is designed to include GVA genes and GVS genes in a configuration allowing co-expression of these genes in a host prokaryotic cell.

The term "prokaryotic" is used herein interchangeably with the terms "cell" or "host" refers to a microbial species which contains no nucleus or other organelles in the cell, which includes but is not limited to Bacteria and Archaea.

The term "bacteria" as used herein refers to several prokaryotic microbial species which include but are not limited to Gram-positive bacteria, *Proteobacteria*, Cyanobacteria, Spirochetes and related species, Planctomyces, Bacteroides, Flavobacteria, Chlamydia, Green sulfur bacteria, Green non-sulfur bacteria including anaerobic phototrophs, Radioresistant micrococci and related species, Thermotoga and Thermosipho thermophiles. More specifically, the wording "Gram positive bacteria" refers to cocci, non-sporulating rods and sporulating rods, such as, for example, *Actinomyces, Bacillus, Clostridium, Corynebacterium, Erysipelothrix, Lactobacillus, Listeria, Mycobacterium, Myxococcus, Nocardia, Staphylococcus, Streptococcus* and *Streptomyces*. The term "*Proteobacteria*" refers to purple photosynthetic and non-photosynthetic gram-negative bacteria, including cocci, nonenteric rods and enteric rods, such as, for example, *Neisseria, Spirillum, Pasteurella, Brucella, Yersinia, Francisella, Haemophilus, Bordetella, Escherichia, Salmonella, Shigella, Klebsiella, Proteus, Pseudomonas, Bacteroides, Acetobacter, Aerobacter, Agrobacterium, Azotobacter, Spirilla, Serratia, Vibrio, Rhizobium, Chlamydia, Rickettsia, Treponema* and *Fusobacterium*. Cyanobacteria, e.g., oxygenic phototrophs;

The term "Archaea" as used herein refers to prokaryotic microbial species of the division *Mendosicutes*, such as *Crenarchaeota* and *Euryarchaeota*, and include but is not limited to methanogens (prokaryotes that produce methane); extreme halophiles (prokaryotes that live at very high concentrations of salt (NaCl); and extreme (hyper) thermophiles (prokaryotes that live at very high temperatures).

In some embodiments the prokaryotic host is a bacteria and in particular a Gram Negative Bacteria. As understood by those skilled in the art, Gram-negative bacteria are a group of bacteria that do not retain the crystal violet stain used in the Gram staining method of bacterial differentiation. They are characterized by their cell envelopes, which are composed of a thin peptidoglycan cell wall sandwiched between an inner cytoplasmic cell membrane and a bacterial outer membrane.

Exemplary Gram-negative bacteria that can be genetically engineered with GVGC genetic circuits described herein configured to allow heterologous expression of GVs comprise *E. coli, Nissle* 1997, *Salmonella*, and others identifiable by those skilled in the art.

In particular, in embodiments herein described, GVGC herein described comprise GVA genes and GVS genes in a configuration allowing co-expression of the gas vesicle structural genes and the gas vesicle assembly factor genes.

In particular in some embodiments the GVA genes and GVS genes are in one or more polynucleotides at a variable distance one with respect to another with polynucleotides sequences in between GVA and GVS which can vary and are configured to allow co-expression of all the GVA genes and all the GVS genes in one or multiple transcripts upon operative connection with one or more regulatory sequences.

The term "regulatory sequence" or "regulatory regions" as described herein indicate a segment of a nucleic acid molecule which is capable of increasing or decreasing transcription or translation of a gene within an organism either in vitro or in vivo. In particular coding regions of a GVA genes and GVS genes herein described comprise one or more protein coding regions which when transcribed and translated produce a polypeptide. Regulatory regions of a gene herein described comprise promoters, transcription factor binding sites, operators, activator binding sites, repressor binding sites, enhancers, protein-protein binding domains, RNA binding domains, DNA binding domains, silencers, insulators and additional regulatory regions that can alter gene expression in response to developmental and/or external stimuli as will be recognized by a person skilled in the art.

The term "operative connection" as used herein indicate an arrangement of elements in a combination enabling production of an appropriate effect. With respect to genes and regulatory sequences an operative connection indicates a configuration of the genes with respect to the regulatory sequence allowing the regulatory sequences to directly or indirectly increase or decrease transcription or translation of the genes.

In particular, in some embodiments, regulatory sequences directly increasing transcription of the operatively linked gene or gene cluster, comprise promoters typically located on a same strand and upstream on a DNA sequence (towards the 5' region of the sense strand), adjacent to the transcription start site of the genes whose transcription they initiate. In prokaryotic organisms, promoters typically comprise two short DNA sequences located at the −10 (10 bp upstream) and −35 positions from the transcription start site (TSS). Their equivalent to the eukaryotic TATA (SEQ ID NO:13) box, the Pribnow box (TATAAT (SEQ ID NO:14)) is located at the −10 position and is essential for transcription initiation. The −35 position, also referred to as the −35 element, typically consists of the sequence TTGACA (SEQ ID NO:15) and this element controls the rate of transcription. Prokaryotic cells contain sigma factors which assist the RNA polymerase in binding to the promoter region. Each sigma factor recognizes different core promoter sequences identifiable by those skilled in the art. Thus, in several embodiments described herein, promoters comprising binding sites for sigma factors identifiable by those skilled in the art can be used to regulate expression of the GVGC herein described in prokaryotic cells.

In some embodiments regulatory sequences directly increasing transcription of the operatively linked gene or gene cluster comprise enhancers that can be located more distally from the transcription start site compared to promoters, and either upstream or downstream from the regulated genes, as understood by those skilled in the art. Enhancers are typically short (50-1500 bp) regions of DNA that can be bound by transcriptional activators to increase transcription of a particular gene. Typically, enhancers can be located up to 1 Mbp away from the gene, upstream or downstream from the start site.

In some embodiments the GVA genes and GVS genes of the GVGC herein described can be provided in a polynucleotidic construct wherein all the GVA genes and the GVS genes of the GVGC cluster are under control of one or more one or more regulatory sequences.

In other embodiments, the GVA genes and GVS genes of the GVGC herein described can be provided in a plurality of polynucleotide constructs, each comprising subsets of GVA genes and/or GVS genes within operons configured to allow co-expression of the GVA genes and GVS genes in one or more prokaryotes to form a GV type.

In particular in GVGC herein described co-expression of the GVS genes and the GVA genes in connection with regulatory sequence capable of operating in the prokaryotic host are configured to provide a GV type.

Exemplary regulatory regions capable of operating in prokaryotes comprise promoters, enhancers, silencers, terminators, regulators, operators, ribosome binding sites, and riboswitches, among others known in the art. Regulatory regions capable of operating in a prokaryotic host can be selected by a skilled person following selection of the prokaryotic host of interest. Exemplary constitutive and inducible prokaryotic promoters and operators suitable for regulating expression of GVs in a prokaryotic host comprise T7, T7lac, Sp6, araBAD, trp, lac, Ptac, pL, and others identifiable by those skilled in the art and described herein. For example, the lac operator and the araBAD promoter are exemplary regulatory elements that can be used for controlling gene expression in bacteria such as E. coli (see Example 2 and 8).

Riboswitches are another example of a regulatory sequence commonly present in prokaryotic untranslated regions (UTRs) of encoded RNAs. These sequences are configured to switch between alternative secondary structures in the RNA depending on the concentration of key metabolites. The secondary structures then either block or reveal other regulatory sequence regions such as RBSs.

In some embodiments, expression of the GVGC described herein can be regulated by one or more of any native regulatory elements known in the art to control gene expression in the naturally occurring form of prokaryotic cell. In other embodiments, a promoter regulating expression of a GVGC can comprise regulatory elements that are regulated by a factor (e.g. a transcription factor) that is not expressed in the naturally occurring form of the host prokaryotic cell. In some embodiments, GVGC can be regulated by inducible promoters such as those promoters inducible by sugars (e.g., L-arabinose, L-rhamnose, xylose and sucrose), antibiotics (e.g., tetracycline), or CRSPR-dCas9, or regulated by heat shock promoters, pH promoters, oxidation stress promoters, radiation promoters, metal promoters, among others known in the art, or constitutive promoters of varying strengths. In some embodiments, a heterologous factor, e.g. a polynucleotide construct encoding a heterologous transcription factor required for activation of expression of the GVGC in the host prokaryote can be introduced into the host prokaryote. In exemplary embodiments described herein, GVGC constructs are regulated by a bacteriophage T7 promoter and the bacteriophage T7 RNA Polymerase required to activate expression of the T7 promoter is expressed from a polynucleotide introduced into the prokaryotic cell (e.g., Examples 2 and 8).

In particular, GVGCs herein described are provided based on the surprising finding that in a GVGC the GVA genes and proteins and not the GVS genes and proteins determine the prokaryotic host where a GV can be provided. In a prokaryotic host GVA genes can be expressed in a functional or non-functional form depending on the host. Inclusion of GVA genes capable of expression in a functional form in a prokaryotic host enable production in said host of GVs formed by GVS proteins native to one or more prokaryotic species possibly other than the prokaryotic host. Accordingly, it is expected that introduction in a certain prokaryotic host of a GVGC cluster comprising GVA gene that can be expressed in a functional form in the prokaryotic host, allows formation in that host of GVs formed by GVS proteins native to any prokaryotic species including GVs formed by a combination GVS proteins native to more than one prokaryotic species.

Accordingly, described herein are hybrid gene clusters comprising gas vesicle assembly (GVA) genes native to a first bacterial species and capable of being expressed in a functional form in the prokaryotic host, and one or more gas vesicle structural (GVS) genes native to one or more bacterial species, with at least one of the one or more bacterial species different from the first bacterial species.

The term "hybrid gene cluster" or "hybrid cluster" as used herein indicates a cluster comprising at least two genes native to different species and resulting in a cluster not natively in any organisms.

Accordingly in embodiments described herein, GV gene clusters include a combination of GVA and GVS genes which is not native in any naturally occurring prokaryotes.

In some embodiments, in the GVGC of the disclosure the GVA genes are native to a GVA prokaryotic species other than the prokaryotic host and are selected to provide GVA proteins functional in the prokaryotic host. In some embodiments, the GVA prokaryotic species is the same of the host prokaryotic species, the GVA genes are thus native to the prokaryotic host and are included in a hybrid GVGC together with at least one GVS gene native to a prokaryotic species other than the prokaryotic hosts.

A skilled person will be able to select native GVA and GVS genes in view of a specific GV type to be formed in the prokaryotic host according to an experimental design and engineer a hybrid GV gene cluster encoding the GV type in a configuration allowing co-expression in the prokaryotic host In particular, in some embodiments, selecting GVA and GVS genes to form a hybrid GVGC can be performed by first identifying all of the GVA genes in the one or more operons of a GV gene cluster of the GVA prokaryote species, as herein described. Following their identification, all of the GVA genes can then be inserted into one or more expression constructs, in operative connection with suitable regulatory elements (e.g. promoter and other regulatory elements described herein and capable of regulating expression in the prokaryotic host species). In some embodiments, this is performed together initially with the insertion into the one or more expression constructs with GVS genes from the GVA prokaryotic species in order to detect whether the GVA genes are capable of being expressed in a functional form in the prokaryotic host species. In other embodiments, the GVA genes are inserted into one or more expression constructs together with GVS genes from one or more prokaryote species that is different from the GVA prokaryote species in order to detect whether the GVA genes are capable of being expressed in a functional form in the prokaryotic host species.

In general, the selection of GVA genes capable of being expressed in a functional form in a host prokaryote species can be performed by detecting expression in the prokaryotic host of one or more candidate GV gene cluster native to a prokaryotic species other than the prokaryotic host to obtain a GVA prokaryotic cell capable of forming detectable GVs in the prokaryotic host, as would be understood by a skilled person upon reading of the present disclosure.

In general, selection of promoter and other regulatory sequences to be included in expression polynucleotidic constructs can be performed by one or more of the following: detecting functionality of a promoter and/or additional regulatory sequence in the host cells, selecting promoters and/or additional regulatory sequences known to be functional in the host cells; detecting the strength of the promoters and/or additional regulatory sequences in connection with protein production and/or selecting promoter and/or additional regulatory sequences of known strength; and selecting inducible promoters and/or additional regulatory sequence to control GV expression.

In particular some embodiments, identification and selection of GVA capable of being expressed in a functional form in a prokaryotic host can be performed by detecting expression in the prokaryotic host of one or more candidate GV gene cluster native to a prokaryotic species other than the prokaryotic host and repeating the detecting until formation of a GV by at least one candidate GV gene cluster is detected.

Accordingly, the detecting expression is performed to obtain GV gene cluster comprising GVA genes native to prokaryotic cell other than the prokaryotic host and capable of forming detectable GVs in the prokaryotic host.

In some embodiments, the detecting expression is preceded by introducing the prokaryotic host the one or more candidate GV gene cluster native to a prokaryotic species other than the prokaryotic host.

The providing and introducing of the one or more expression constructs can be performed by methods identifiable by a skilled person upon reading of the present disclosure. In particular, vectors suitable for transferring the expression constructs into prokaryotic cells such as bacteria or archaea and methods of transformation of prokaryotic cells such as electroporation, heat-shock transformation and others are known in the art and described herein (e.g., see Examples). Methods of culturing prokaryotic cells to allow analysis of gene expression and for determination of GV formation are known in the art and described herein.

Detection of GVs in the prokaryotic host cells can be performed for example by analysis following a period of time to allow expression of the determining if the cells become buoyant after centrifugation, or by detecting them using transmission electron microscopy and/or additional methods identifiable by a skilled person upon reading of the present disclosure (see also Example 14 and methods described in U.S. application Ser. No. 15/613,104 filed on Jun. 2, 2017 incorporated herein by reference in its entirety).

In some embodiment, GVA genes native capable of forming detectable GVs in the prokaryotic host selected with methods herein described can be used to provide a hybrid GV gene cluster further comprising GVS genes native to one or more prokaryotic species including at least one GVS gene native to a prokaryotic species other than the GVA prokaryotic species.

Following identification and selection of GVA genes capable of being expressed in a functional form, a hybrid GVGC can be constructed, comprised in one or more expression constructs, comprising all of the GVA genes from the GVA prokaryotic species, together with one or more GVS genes from a prokaryotic species different to the GVA prokaryotic species, the GVS proteins genes selected for their structural capability to form GVs with suitable contrast-enhanced imaging properties, as described herein (e.g. see Examples). In particular, all of the gvpA/B genes from one GVS prokaryotic species are inserted into the one or more expression constructs (e.g. both of the two gvpA genes from *Anabaena floc-aquae*, see Examples). Further, optionally a gvpC or a variant thereof from either a same or a different GVS prokaryotic species as the source of the gvpA/B genes can be inserted into the expression constructs (e.g. *Anabaena floc-aquae* gvpC, see Examples).

In some embodiments production of a hybrid gas vesicle gene cluster (GVGC) configured for expression in the prokaryotic host can be performed providing a polynucleotidic construct comprising gas vesicle assembly (GVA) genes native to a GVA prokaryotic species and capable of forming detectable GVs in the prokaryotic host. In the method, the polynucleotidic construct further comprises gas vesicle structural (GVS) genes native to one or more GVS prokaryotic species, at least one of the one or more prokaryotic species different from the GVA prokaryotic species, in a configuration allowing co-expression of the gas vesicle structural genes and the gas vesicle assembly genes upon operative connection of the with regulatory sequence configured to operate in the prokaryotic host.

In some embodiments, the polynucleotidic construct comprises one polynucleotide. For example, all of the GVA genes and GVS genes of a GVGC can be provided in one operon, operatively connected and under regulatory control of the same promoter. In exemplary described herein, a hybrid GVGC comprises GVA genes from *Anabaena flocaquae* comprising two *Anabaena floc-aquae* GvpA genes, optionally with an *Anabaena floc-aquae* gvpC gene together with all of the GVA genes from *B. megaterium*, gvpR, gvpN, gvpF, gvpG, gvpL, gvpS, gvpK, gvpJ, gvpT and gvpU (e.g. see FIG. 2A).

In some embodiments the polynucleotidic construct comprises a plurality of polynucleotides. For example, a subset of all of the GVA genes and GVS genes are comprised in one operon, operatively connected and under regulatory control of a first promoter, whereas another subset of all of the GVA genes and GVS genes are comprised in another operon, operatively connected and under regulatory control of a second promoter. An example of a GV gene cluster comprising two operons is in the native *Halobacterium* genome, wherein one operon comprises a subset of all of the *Halobacterium* GVA genes, and another operon comprises a second subset of all of the *Halobacterium* GVA and GVS genes (e.g. see FIG. 20). Accordingly, it is expected that a hybrid GVGC can be constructed having a similar configuration wherein two or more operons can be provided that together comprise all of the gyp genes of a hybrid GVGC In general, the selection of the regulatory elements to obtain expression of hybrid GV types at a concentration that will allow detection by MRI and/or ultrasound can be determined empirically. Factors to consider in selecting regulatory elements comprise the compatibility of the regulatory elements with the prokaryotic host, the strength of the promoter (strong vs. weak promoters are known in the art), use of alternative RBS, enhancer elements, and alternative codon usage, among others. For hybrid GVGC expression constructs comprising inducible promoters, the concentration of and duration of presence in the prokaryotic host of a drug or other molecule used to activate the promoter and induce expression of the hybrid GVGC can affect the expression level. Further, the fraction of prokaryotic cells expressing hybrid GVGCs within an imaging target site is another consideration relevant to imaging modalities described herein. [Q: please confirm]

Figure 4:
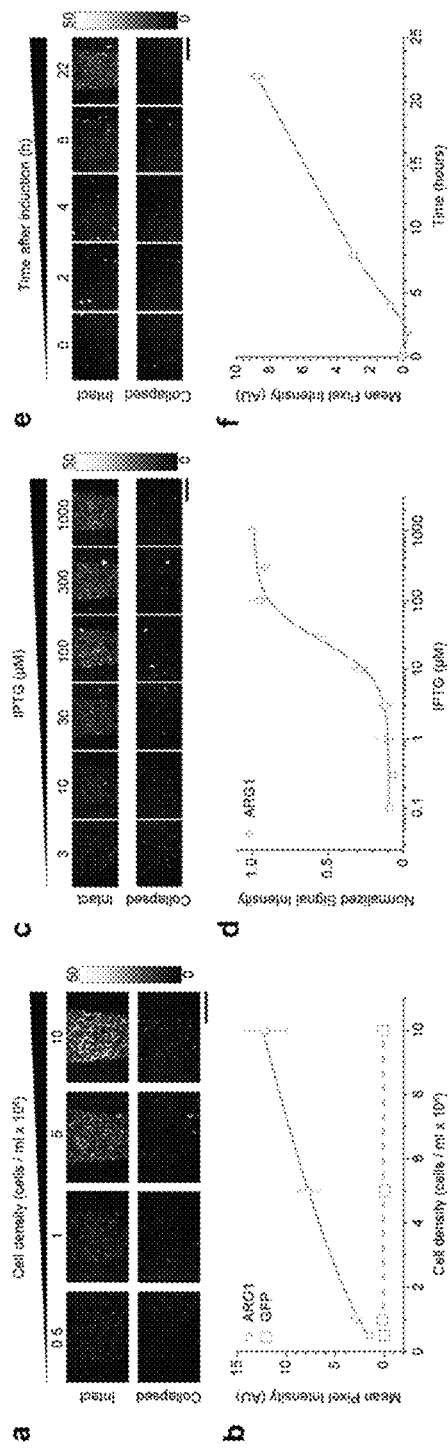
FIG. 4 shows exemplary results of imaging dilute bacterial populations and dynamically regulated gene expression. Panel A shows exemplary ultrasound images of ARG1-expressing *E. coli* at various cellular concentrations, before and after acoustic collapse. Panel B shows a graph reporting exemplary mean ultrasound contrast from *E. coli* expressing ARG1 and GFP at various cell densities (N=4 per sample). Panel C shows exemplary ultrasound images of *E. coli* expressing ARG1 after induction with various IPTG concentrations. Panel D shows a graph reporting exemplary normalized ultrasound contrast as a function of IPTG concentration. Cell concentration was $5\times10^8$ cells/ml. N=3 per sample. Panel E shows exemplary ultrasound images of ARG1-expressing *E. coli* at various times after induction with IPTG. Panel F shows a graph reporting exemplary mean ultrasound contrast at each time point (N=4 per sample). Cell concentration was $5\times10^8$ cells/ml in Panels C-F. The vertical bars on the right of each of Panels A, C and E represent linear signal intensity (0-50). Scale bars represent 2 mm. Error bars represent±S.E.M.; where not seen, they are smaller than the symbol.

In exemplary embodiments described herein, to enable a broad range of in vivo applications, noninvasive imaging can be performed to detect relatively dilute cellular populations. For example, to determine the detection limit of exemplary hybrid GVGC-expressing cells, a concentration series of *E. coli* transformed with exemplary hybrid GVGC (ARG1) was imaged using ultrasound (FIG. 4 Panel A). Cells at concentrations as low as $5\times10^7$ cells/ml produced detectable signal (FIG. 4, Panels A and B), equating to a 0.005% volume fraction, or approximately 100 cells per voxel based on cubic voxel dimensions of 100 µm, providing imaging sensitivity sufficient for many in vivo scenarios (see Example 2).

Similarly, in exemplary embodiments wherein MRI imaging modalities are used, in embodiments wherein the cells occupy 100% of the tissue (e.g. in a tumor or abscess full of bacteria) then it is estimated that ~0.06% of the cell needs to be filled with GVs to become detectable.

In particular, in some embodiments described herein wherein intracellular spatial translocation of an expressed hybrid GV type is a reportable endpoint of a biochemical event in a cell, selection of an expression level of hybrid GVs suitable for imaging modalities such as ultrasound and MRI (e.g. to detect clustering) can be determined empirically.

In the method the prokaryotic host can be of a bacterial species different from the GVA prokaryotic species and the GVA prokaryotic species is different from at least one of the GVS prokaryotic species.

In some embodiments, polynucleotidic constructs comprising hybrid GVGC herein described can be used in methods and systems can be provided to produce a gas vesicle protein structure in a prokaryotic host.

The term "polynucleotide" as used herein indicates an organic polymer composed of two or more monomers including nucleotides, or analogs thereof. The term "nucleotide" refers to any of several compounds that consist of a ribose (ribonucleotide) or deoxyribose (deoxyribonucleotides) sugar joined to a purine or pyrimidine base and to a phosphate group, and that are the basic structural units of nucleic acids. The term "nucleotide analog" refers to a nucleotide in which one or more individual atoms have been replaced with a different atom with a different functional group. Accordingly, the term polynucleotide includes nucleic acids of any length of DNA or RNA analogs and fragments thereof. A polynucleotide of three or more nucleotides is also called nucleotidic oligomers or oligonucleotide.

In those embodiments, methods comprise introducing into the prokaryotic host a hybrid gas vesicle gene cluster (GVGC) herein described configured for expression in the prokaryotic host, in which the gas vesicle structural gene native to the second prokaryotic species encode for the gas vesicle type and, and expressing the hybrid GVGC in the bacterial host to produce the gas vesicle protein structure comprising the GVS proteins encoded by the GVS genes of the hybrid GVGC.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—NH$_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In particular, in embodiments herein described one or more polynucleotidic constructs comprising a hybrid GVGC herein described operatively connected to regulatory sequences can be provided in a configuration designed for heterologous expression of any type of gas vesicle (see also U.S. application Ser. No. 15/613,104 filed on Jun. 2, 2017 incorporated herein by reference in its entirety) in any type of prokaryotic cell.

As used herein, "heterologous expression" refers to expression of GVs in any species that either does not naturally produce gas vesicles, or where its natural production of gas vesicles has been suppressed, for example through genetic knock-out of the genes encoding Gvp proteins, and where foreign DNA encoding gas vesicle genes is introduced into the organism to persist as a plasmid or integrate into the genome.

In some embodiments, heterologously expressed Gvp genes can comprise genes encoding corresponding Gvp proteins which are naturally occurring or have sequences having at least 50% identity with naturally occurring Gvp proteins.

As used herein, "sequence identity" or "identity" in the context of two nucleic acid or polypeptide sequences makes reference to the nucleotide bases or residues in the two sequences that are the same when aligned for maximum correspondence over a specified comparison window. When percentage of sequence identity or similarity is used in reference to proteins, it is recognized that residue positions which are not identical often differ by conservative amino acid substitutions, where amino acid residues are substituted with a functionally equivalent residue of the amino acid residues with similar physiochemical properties and therefore do not change the functional properties of the molecule.

A functionally equivalent residue of an amino acid used herein typically refers to other amino acid residues having physiochemical and stereochemical characteristics substantially similar to the original amino acid. The physiochemical properties include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

A person skilled in the art would understand that similarity between sequences is typically measured by a process that comprises the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

As used herein, "percentage of sequence identity" means the value determined by comparing two optimally aligned sequences over a comparison window, wherein the portion of the polynucleotide sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length protein or protein fragment. A reference sequence can comprise, for example, a sequence identifiable a database such as GenBank and UniProt and others identifiable to those skilled in the art.

As understood by those skilled in the art, determination of percent identity between any two sequences can be accomplished using a mathematical algorithm. Non-limiting examples of such mathematical algorithms are the algorithm of Myers and Miller [13], the local homology algorithm of Smith et al. [14]; the homology alignment algorithm of Needleman and Wunsch [15]; the search-for-similarity-method of Pearson and Lipman [16]; the algorithm of Karlin and Altschul [17], modified as in Karlin and Altschul [18]. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA [16], and TFASTA in the Wisconsin Genetics Software Package, Version 8 (available from Genetics Computer Group (GCG), 575 Science Drive, Madison, Wis., USA). Alignments using these programs can be performed using the default parameters.

In some embodiments, heterologously expressed Gvp proteins to provide a GV type have independently at least 50% sequence identity, preferably at least 80%, more preferably at least 90%, most preferably at least 95% sequence identity compared to a reference sequence of corresponding Gvp protein using one of the alignment programs described using standard parameters.

Heterologous expression of GVs in a prokaryotic cell can be performed by cloning one or more polynucleotides encoding naturally occurring Gvp proteins or homologs thereof that are required for production of GVs (comprising gvpA/B, gvpC, and other proteins known to those skilled in the art and described herein) into one or more suitable constructs configured to express the heterologous GV proteins in the prokaryotic cell. Polynucleotides encoding GV protein genes can be cloned using commercially available reagents from vendors such as Qiagen, Invitrogen, Applied Biosystems, Promega, and others, following standard molecular biology methods known in the art, such as those described herein. As would be understood by those skilled in the art, polynucleotides encoding GV protein genes can be obtained from several different sources. For example, polynucleotides encoding GV proteins can be obtained by isolating genomic DNA or cDNA encoding GV proteins from microorganisms whose genomes encode GV proteins genes, and/or express GV proteins RNA. RNA can be isolated from a cell that expresses GV proteins genes, and cDNA produced by reverse transcription using standard techniques and commercial kits. Genomic DNA can be purified from the cell, and cDNA or genomic DNA encoding one or more GV proteins isolated, following methods known to those in the art. Alternatively, polynucleotides comprising one or more gas vesicle genes can be synthesized using oligonucleotide and polynucleotide synthetic methods known in the art. PCR-based amplification of one or more GV protein genes can be performed using appropriately designed primer pairs (e.g. using PrimerDesign or other programs known to those skilled in the art). PCR-based amplification can be followed by ligation (e.g. using T4 DNA ligase) of a polynucleotide encoding gas vesicle gene amplicon into an appropriate construct in a plasmid suitable for propagation in bacteria or archea, such as transformation-competent E. coli DH5alpha, followed by growth of transformed cell cultures, purification of the plasmid for confirmation of the cloned enzyme by DNA sequence analysis, among other methods known to those skilled in the art. Expression vectors can comprise plasmid DNA, viral vectors, or non-viral vectors, among others known to those skilled in the art, comprising appropriate regulatory elements such as promoters, enhancers, and post-transcriptional and post-translational regulatory sequences that are compatible with the prokaryotic cell intended to heterologously express the GV, as would be understood by a skilled person. In particular, in embodiments described herein, expression vectors suitable for regulating heterologous expression of GVs comprise those having promoters and other regulatory elements known to skilled persons that are compatible with Gram-negative bacteria such as E. coli, and Salmonella. Promoters can be constitutively active or inducible. Exemplary inducible expression systems comprise IPTG-inducible expression as shown in Examples 2 and 8.

In some embodiments, where one or more GVA and GVS proteins are expressed heterologously to form GVs in prokaryotic cells other that the native host, the related sequence can be optimized for expression in the heterologous host microorganism as will be understood by a skilled person.

In particular, in some embodiments described herein, wherein a GV type is produced heterologously in a prokaryotic cell, production of a GV gene sequences can be codon-optimized for expression in the prokaryotic cell type, for example, such as Escherichia coli, according to methods identifiable by a skilled person. As would be understood by those skilled in the art, the term "codon optimization" as used herein refers to the introduction of synonymous mutations into codons of a protein-coding gene in order to improve protein expression in expression systems of a particular organism, such as E. coli in accordance with the codon usage bias of that organism. The term "codon usage bias" refers to differences in the frequency of occurrence of synonymous codons in coding DNA. The genetic codes of different organisms are often biased towards using one of the several codons that encode a same amino acid over others—thus using the one codon with, a greater frequency than expected by chance. Optimized codons in microorganisms, such as Escherichia coli or Salmonella typhimurium, reflect the composition of their respective genomic tRNA pool. The use of optimized codons can help to achieve faster translation rates and high accuracy.

In some embodiments, many statistical methods proposed and used to analyze codon usage bias the field of bioinformatics and computational biology can be used for codon optimization in the sense of the disclosure. Methods such as the 'frequency of optimal codons' (Fop), the Relative Codon Adaptation (RCA) or the 'Codon Adaptation Index' (CAI) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes. There are many computer programs to implement the statistical analyses enumerated above, including CodonW, GCUA, INCA, and others identifiable by those skilled in the art. Several software packages are available online for codon optimization of gene sequences, including those offered by companies such as GenScript, EnCor Biotechnology, Integrated DNA Technologies, ThermoFisher Scientific, among others known those skilled in the art. Those packages can be used in providing Gvp proteins with codon ensuring optimized expression in various prokaryotic cell systems as will be understood by a skilled person.

A representative example of heterologous GVs is the E. coli expressing a heterologous GV gene cluster from Bacillus megaterium (Mega). Mega GVs are typically cone-tipped cylindrical structures with a diameter of approximately 73 nm and length of 100-600 nm, encoded by a cluster of eleven or fourteen different genes, including the primary structural protein, GvpB, and several putative minor components and putative chaperones [11, 19] as would be understood by a person skilled in the art. In some exemplary embodiments described herein (see Example 1), heterologous GV gene clusters comprise B. megaterium regulatory genes GvpR, GvpN, GvpF, GvpG, GvpL, GvpS, GvpK, GvpJ, GvpT and GvpU and structural gene GvpB from B. megaterium.

In embodiments described herein, the GVGC gene cluster is a hybrid GV gene cluster comprising a combination of Gvp genes that are natively encoded in GV gene clusters from two or more different organisms. In exemplary embodiments described herein, a hybrid GV gene cluster comprises a combination of genes from A. floc-aquae and B. megaterium (see Example 1). In particular, in exemplary embodiments, the hybrid GV gene cluster can comprise B. megaterium GVA assembly genes GvpR, GvpN, GvpF, GvpG, GvpL, GvpS, GvpK, GvpJ, GvpT and GvpU and further comprise structural GVS proteins genes from Anabaena floc-aquae such as GvpA and optionally GvpC (see Example 1). In other exemplary embodiments, the hybrid GV gene cluster can comprise *B. megaterium* GVA genes GvpR, GvpN, GvpF, GvpG, GvpL, GvpS, GvpK, GvpJ, GvpT and GvpU and further comprise GVS protein gene GvpA1, and GvpA2 from *Bukholderia thailandensis* or GvpA1, GvpA2, GvpA3 and GvpA4 from *Psychromonas ingrahamii.* (see exemplary GVA and GVS in Example 9).

In other exemplary embodiments, the hybrid GV gene cluster can comprise *B. megaterium* GVA genes GvpR, GvpN, GvpF, GvpG, GvpL, GvpS, GvpK, GvpJ, GvpT and GvpU and further comprise GVS protein genes GvpB from *B. megaterium* and GvpC from *Anabaena floc-aquae.*

Thus, in general, according to embodiments described herein, hybrid GVGC can comprise GVS genes having GvpA/B all from one species, optionally together with GvpC from the same species as GvpA/B or GvpC from a different species. In some embodiments herein described, hybrid GVGC are introduced in a prokaryotic cell to provide a reportable molecular component of a gas vesicle reporting (GVR) genetic circuit in operative connection with other molecular components of the genetic circuit to report occurrence of a biochemical event in the prokaryotic cell.

In the GVR genetic circuits in the sense of the present disclosure, the molecular components forming parts of the GVR genetic circuit can be genetic molecular components or cellular molecular components.

The term "molecular component" as used in connection with the GVR genetic circuits described herein indicates a chemical compound or a structure comprised of a plurality of chemical compounds comprised in a cellular environment. Exemplary molecular components thus comprise polynucleotides, such as ribonucleic acids or deoxyribonucleic acids, polypeptides, polysaccharides, lipids, amino acids, peptides, sugars and/or other small or large molecules and/or polymers that can be found in a cellular environment. In some embodiments described herein, a molecular component of a GVR genetic circuit is a GV type or a cluster thereof.

The term "genetic molecular component" as used herein indicates a molecular unit formed by a gene (possibly comprising or formed by a cluster of genes), an RNA transcribed from the gene or a portion thereof and optionally a polypeptide or a protein translated from the transcribed RNA. In genetic circuits herein described, the biochemical reactions connecting the genetic molecular component to another molecular component of the circuit can involve any one of the gene, the transcribed RNA and/or the polypeptide forming the molecular component.

A gene comprised in a genetic molecular component is a polynucleotide that can be transcribed to provide an RNA and typically comprises coding regions as well as one or more regulatory sequence regions which is a segment of a nucleic acid molecule which is capable of increasing or decreasing transcription or translation of the gene within an organism either in vitro or in vivo. In particular coding regions of a gene herein described can comprise one or more protein coding regions which when transcribed and translated produce a polypeptide, or if an RNA is the final product only a functional RNA sequence that is not meant to be translated. Regulatory regions of a gene herein described comprise promoters, transcription factor binding sites, operators, activator binding sites, repressor binding sites, enhancers, protein-protein binding domains, RNA binding domains, DNA binding domains, silencers, insulators and additional regulatory regions that can alter gene expression in response to stimuli as will be recognized by a person skilled in the art.

An RNA of a genetic molecular component comprises any RNA that can be transcribed from a gene, such as a messenger ribonucleic acid (mRNA), short interfering ribonucleic acid, and ribonucleic acid capable of acting as regulating factors in the cell. mRNA comprised in a genetic molecular component comprise regions coding for the protein as well as regulatory regions e.g. ribosome binding site domains ("RBS"), which is a segment of the upstream (5') part of an mRNA molecule to which the ribosomal machinery of a cell binds to position the message correctly for the initiation of translation. RBSs control the accuracy and efficiency with which the translation of mRNA begins. mRNA can have additional control elements encoded, such as riboregulator sequences or other sequences that form hairpins, thereby blocking the access of the ribosome to the Shine-Delgarno sequence and requiring an external source, such as an activating RNA, to obtain access to the Shine-Delgarno sequence. Other RNAs that serve regulatory roles that can comprise the genetic molecular component include riboswitches, aptamers (e.g. malachite green, Spinach), aptazymes, guide CRISPR RNAs, and other RNAs known to those skilled in the art.

A protein comprised in a molecular component can be proteins with activating, inhibiting, binding, converting, or reporting functions. Proteins that have activating or inhibiting functions typically act on operator sites encoded on DNA, but can also act on other molecular components. Proteins that have binding functions typically act on other proteins, but can also act on other molecular components. Proteins that have converting functions typically act on small molecules, and convert small molecules from one small molecule to another by conducting a chemical or enzymatic reaction. Proteins with converting functions can also act on other molecular components. Proteins with reporting functions have the ability to be easily detectable by commonly used detection methods (absorbance, fluorescence, for example), or otherwise cause a reaction on another molecular component that causes easy detection by a secondary assay (e.g. adjusts the level of a metabolite that can then be assayed for). The activating, inhibiting binding, converting, or reporting functions of a protein typically form the interactions between genetic components of a genetic circuit. Exemplary proteins that can be comprised in a genetic molecular component comprise monomeric proteins and multimeric proteins, proteins with tertiary or quaternary structure, proteins with linkers, proteins with non-natural amino acids, proteins with different binding domains, and other proteins known to those skilled in the art. Specific exemplary proteins include TetR, LacI, LambdaCI, PhlF, SrpR, QacI, BetR, LmrA, AmeR, LitR, met, AraC, LasR, LuxR, IpgC, MxiE, Gal4, GCN4, GR, SP1, CREB, and others known to a skilled person in the art.

The term "cellular molecular component" indicates a molecular component not encoded by a gene, or indicates a molecular component transcribed and/or translated by a gene but comprised in the circuit without the corresponding gene. Exemplary cellular components comprise polynucleotides, polypeptides, polysaccharides, small molecules and additional chemical compounds that are present in a cellular environment and are identifiable by a skilled person. Polysaccharides, small molecules, and additional chemical compounds can include, for example, NAD, FAD, ATP, GTP, CTP, TTP, AMP, GMP, ADP, GDP, Vitamin B1, B12, citric acid, glucose, pyruvate, 3-phosphoglyceric acid, phosphoenolpyruvate, amino acids, PEG-8000, FiColl 400, spermidine, DTT, b-mercaptoethanol maltose, maltodextrin, fructose, HEPES, Tris-Cl, acetic acid, aTc, IPTG, 3OC12HSL, 3OC6HSL, vanillin, malachite green, Spinach, succinate, tryptophan, and others known to those skilled in the art. Polynucleotides can include RNA regulatory factors (small activating RNA, small interfering RNA), or "junk" decoy DNA that either saturates DNA-binding enzymes (such as exonuclease) or contains operator sites to sequester activator or repressor enzymes present in the system. Polypeptides can include those present in the genetic circuit but not produced by genetic components in the circuit, or those added to affect the molecular components of the circuit.

In some embodiments of genetic circuits herein described, one or more molecular components is a recombinant molecular component that can be provided by genetic recombination (such as molecular cloning) and/or chemical synthesis to bring together molecules or related portions from multiple sources, thus creating molecular components that would not otherwise be found in a single source.

In embodiments herein described, a genetic circuit comprises at least one genetic molecular component or at least two genetic molecular components, and possibly one or more cellular molecular components, connected one to another in accordance with a circuit design by activating, inhibiting, binding or converting reactions to form a fully connected network of interacting components.

In embodiments of the GVR genetic circuits described herein, the molecular components are connected one with another according to a circuit design in which a molecular component is an input and another molecular component is an output. In particular, a genetic circuit typically has one or more input or start molecular component which activates, inhibits, binds and/or convert another molecular component, one or more output or end molecular component which are activated, inhibited, bound and/or converted by another molecular component, and intermediary molecular components each inhibiting, binding and/or converting another molecular component and being activated, inhibited, bound and/or converted by another molecular component. In some embodiments of the genetic circuits herein described, the input is the biochemical event and/or a trigger molecular component and the output is activation of expression of a GV gene cluster and assembly of a GV type through binding reactions between Gvps of the GV type. In other embodiments of the genetic circuits herein described, the input is a biochemical event and/or a trigger molecular component and the output is an intracellular spatial translocation of the GV type, the intracellular spatial translocation occurring typically through one or more converting and/or binding reactions as described herein. The output of GVR circuit herein described can be detected with ultrasound contrast, MRI SWI, light scattering and additional techniques to detect GV identifiable by a skilled person upon reading of the present disclosure.

The term "activating" as used herein in connection with a molecular component of a genetic circuit refers to a reaction involving the molecular component which results in an increased presence of the molecular component in the cellular environment. For example, activation of a genetic molecular component indicates one or more reactions involving the gene, RNA and/or protein of the genetic molecular component resulting in an increased presence of the gene, RNA and/or protein of the genetic molecular component (e.g. by increased expression of the gene of the molecular component, and/or an increased translation of the RNA). An example of "activating" described herein comprises the initiation of expression of a GV gene cluster regulated by an IPTG-inducible promoter (e.g., see Examples 2 and 8).

Activation of a molecular component of a genetic circuit by another molecular component of the circuit can be performed by direct or indirect reaction of the molecular components. Examples of a direct activation of a genetic molecular component comprise in a circuit the production of an alternate sigma factor (molecular component of the circuit) that drives the expression of a gene controlled by the alternate sigma factor promoter (other molecular component of the circuit), or the production of a small ribonucleic acid (molecular component of the circuit) that increases expression of a riboregulator-controlled RNA (molecular component of the circuit). Examples of indirect activation of a genetic molecular component comprise the production of a first protein that inhibits an intermediate transcriptional repressor protein, wherein the intermediate transcriptional repressor protein represses the production of a target gene, such that the first protein indirectly activates expression of the target gene.

The term "inhibiting" as used herein in connection with a molecular component of a genetic circuit refers to a reaction involving the molecular component of the genetic circuit and resulting in a decreased presence of the molecular component in the cellular environment. For example, inhibition of a genetic molecular component indicates one or more reactions involving the gene, RNA and/or protein of the genetic molecular component resulting in a decreased presence of the gene, RNA and/or protein (e.g. by decreased expression of the gene of the molecular component, and/or a decreased translation of the RNA). Inhibition of a cellular molecular component indicates one or more reactions resulting in a decreased production or increased conversion, sequestration or degradation of the cellular molecular components (e.g. a polysaccharide or a metabolite) in the cellular environment.

Inhibition can be performed in the genetic circuit by direct reaction of a molecular component of the genetic circuit with another molecular component of the circuit or indirectly by reaction of products of a reaction of the molecular components of the genetic circuit with the another molecular component of the circuit.

The term "binding" as used herein in connection with molecular components of a genetic circuit refers to the connecting or uniting two or more molecular components of the circuit by a bond, link, force or tie in order to keep two or more molecular components together, which encompasses either direct or indirect binding where, for example, a first molecular component is directly bound to a second molecular component, or one or more intermediate molecules are disposed between the first molecular component and the second molecular component another molecular component of the circuit. Exemplary bonds comprise covalent bond, ionic bond, van der Waals interactions and other bonds identifiable by a skilled person.

In some embodiments, the binding can be direct, such as the production of a polypeptide scaffold that directly binds to a scaffold-binding element of a protein. In other embodiments, the binding may be indirect, such as the co-localization of multiple protein elements on one scaffold. In some instances binding of a molecular component with another molecular component can result in sequestering the molecular component, thus providing a type of inhibition of said molecular component. In some instances binding of a molecular component with another molecular component can change the activity or function of the molecular component, as in the case of allosteric interactions between proteins, thus providing a type of activation or inhibition of the bound component.

The term "converting" as used herein in connection with a molecular component of the circuit refers to the direct or indirect conversion of the molecular component into another molecular component. An example of this is the conversion of chemical X by protein A to chemical Y that is then further converted by protein B to chemical Z.

In the GVR genetic circuits in the sense of the present disclosure, the GVGC genes are introduced into a prokaryotic cell to provide a reportable molecular component connected with other genetic or cellular molecular components according to a circuit design, wherein the GV type is expressed or the GV type is intracellularly spatially translocated when the GVGC genetic circuit operates according to the circuit design in response to a biochemical event and/or to a trigger molecular component.

The term "reportable molecular component" as used herein indicates a molecular component capable of detection in one or more systems and/or environments. The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, comprising ability to interact, and in particular bind other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified. In particular, in embodiments herein described detection of the reportable molecular component comprising a GV type is performed through contrast enhanced imaging techniques such as ultrasound and MRI.

The term "biochemical event" as used herein refers to an activating, inhibiting, binding or converting reaction between two or more molecular components within a prokaryotic cell.

Accordingly, in some embodiments, at least one genetic molecular component of the GVR genetic circuit comprises a hybrid gas vesicle (GV) gene cluster operatively connected to a promoter configured to be activated directly or indirectly by the biochemical event, and directly initiate expression of a GV type.

In some embodiments herein described, a genetic molecular component of the GVR genetic circuit comprises a gas vesicle (GV) gene cluster or one or more genes thereof operatively connected to one or more promoters configured to be activated directly or indirectly by the biochemical event, and directly initiate expression of a GV type. In some embodiments, the GVGC is comprised in a genetically engineered polynucleotide construct optionally comprising one or more enhancers and/or other regulatory DNA elements identifiable by those skilled in the art. As would be understood by those skilled in the art, promoters are DNA regulatory elements that are typically located adjacent to the transcription start sites of genes, or a cluster of genes, on the same strand and upstream on a DNA sequence (towards the 5' region of the sense strand), and for transcription to occur, the enzyme that synthesizes RNA, known as RNA polymerase, attaches to the promoter. Promoters contain DNA sequences identifiable by those skilled in the art, such as those that provide binding sites for RNA polymerase and also for proteins that function as transcription regulatory factors that can either activate or repress gene transcription.

The term "transcription regulatory factor" or "transcription factor" as used herein refers to any type of factors that can function by acting on a regulatory DNA element such as a promoter or enhancer sequence. The transcription regulatory factors can be broadly classified into a transcription repression factor (also referred to as "repressor") and a transcription activation factor (also referred to as "activator"). The transcription repression factor acts on a regulatory DNA element to repress the transcription of a gene, thereby reducing the expression level of the gene. The transcription activation factor acts on a regulatory DNA element to promote the transcription of a gene, thereby increasing the expression level of the gene.

In particular, a transcription regulatory factor has typically at least one DNA-binding domain that can bind to a specific sequence of enhancer or promoter sequences. Some transcription factors bind to a DNA promoter sequence near the transcription start site and help form the transcription initiation complex. Other transcription factors bind to other regulatory sequences, such as enhancer sequences, and can either stimulate or repress transcription of the related gene.

Examples of specific transcription repression factors include TetR, LacI, LambdaCI, PhlF, SrpR, QacI, BetR, LmrA, AmeR, LitR, met, and other identifiable by a skilled person, as well as homologues of known repression factors, that function in both prokarayotic and eukarayotic systems. Examples of transcription activation factors include AraC, LasR, LuxR, IpgC, MxiE, Gal4, GCN4, GR, SP1, CREB, etc as well as homologues of known activation factors, that function in prokarayotic systems.

In some embodiments, one or more promoters operatively connected to one or more genes of a GV gene cluster is configured to be activated directly or indirectly by one or more biochemical events. In particular, in some embodiments, activation of expression of a GV gene cluster can be linked to another molecular component in the GVR genetic circuit through activator or repressor transcription factors. In some embodiments, expression of the transcription factors can be regulated by a promoter of interest (see Example 2 and 8). In other embodiments, transcription factors can be regulated post-translationally through degradation or phosphorylation of the transcription factor.

Accordingly, the reportable genetic molecular component of the GVR genetic circuit comprising a gas vesicle (GV) gene cluster operatively connected to a promoter configured to be activated directly or indirectly by the biochemical event, and directly initiate expression of a GV type can in several embodiments comprise promoters and/or other DNA regulatory elements having one or more sequences identifiable to those skilled in the art that are configured to function as binding sites for any known transcription regulatory factor.

For example, in some embodiments GVGC expression can be activated by promoters inducible by sugars (e.g., L-arabinose, L-rhamnose, xylose and sucrose), antibiotics (e.g., tetracycline), CRISPR-dCas9, heat shock promoters, pH-dependent promoters, oxidation stress-dependent promoters, radiation-dependent promoters, metal-inducible promoters, and others identifiable by those skilled in the art. In other embodiments GVGC expression can be induced by activation of constitutive promoters of varying strengths that are suitable for regulating expression in bacterial cells described herein and identifiable by those skilled in the art.

In other embodiments, the hybrid GV gene cluster or one or more of the regulatory elements is surrounded by recombination sites that are recognized by a recombinase, whose expression or activity is connected through the genetic circuit to a biochemical event in the bacterial cell. For example, a GV gene cluster in reverse (3'-5') orientation to its promoter (in 5'-3' orientation) can be flanked by recombination sites surrounding the hybrid GV gene cluster, the recombination sites configured to allow inversion of the hybrid GV gene cluster upon expression or activation of its respective recombinase, wherein upon recombination the hybrid GV gene cluster is flipped into a 5'-3' orientation to allow initiation of expression by the promoter. Suitable recombination systems for use in bacteria are identifiable by those skilled in the art, such as the Flp-FRT recombination system.

In embodiments described herein, a GV gene cluster comprised in one or more genetic molecular components of the GVR genetic circuits described herein is configured to function as a set of reporter genes, which together encode proteins required for the formation of a GV type, such that expression of the GV type functions as a genetically-encoded reporter of the biochemical event in the prokaryotic cell comprising a GVR genetic circuit. As described herein, the reportable characteristics of the GV are such that the genetically-encoded GV can be used as a contrast agent, which, when used together with one or more contrast-enhanced imaging techniques described herein, functions as a genetically-encoded reporter in prokaryotic cells that have been genetically engineered to comprise one or more of the GVR genetic circuits described herein.

In particular, in exemplary embodiments described herein, all the GVA genes GvpF, GvpG, GvpJ, GvpL, GvpK, GvpS, and GvpU and GVS gene GvpA enable GV formation. Therefore, if expression any one of these genes is regulated according to the design of a GVR genetic circuit as described herein then the expression of the GV type will be regulated accordingly.

In some embodiments, the GVR genetic circuits described herein can comprise a plurality of genetic molecular components that function as Boolean logical operators in genetic circuit designs known to those skilled in the art, such as those described in [20, 21]. As would be understood by persons skilled in the art, Boolean logic is a branch of algebra in which the values of the variables are the truth values 'true' and 'false', usually denoted by the digital logic terms '1' and '0' respectively. In contrast with elementary algebra where the values of the variables are numbers, and the main operations are addition and multiplication, the main operations of Boolean logic are the conjunction 'AND', the disjunction 'OR', and the negation 'NOT'. As understood by those skilled in the art, it is thus a formalism for describing logical relations in the same way that ordinary algebra describes numeric relations.

Accordingly, the term "AND gate" refers to a digital logic gate that behaves according to the truth table shown in Table 1. A 'true' output (1) results only if both the inputs to the AND gate are 'true' (1). If neither or only one input to the AND gate is 'true' (1), a 'false' (0) output results. Therefore, the output is always 0 except when all the inputs are 1.

TABLE 1

'AND gate' truth table:

| Input | | Output |
|---|---|---|
| A | B | A AND B |
| 0 | 0 | 0 |
| 0 | 1 | 0 |
| 1 | 0 | 0 |
| 1 | 1 | 1 |

In particular, the term "AND gate" as used herein refers to the logical relation between two genetic molecular components in a GVR genetic circuit, wherein inputs 'A' and 'B' in Table 1 are two biochemical events, and the output 'A AND B' in Table 1 is the GV type.

For example, in some embodiments of an "AND gate" comprised in a GVR genetic circuit described herein, the GVR genetic circuit comprises a plurality of genetic molecular components wherein at least a first genetic molecular component comprises a first subset of genes from the GV gene cluster, and at least a second genetic molecular component comprises a second subset of genes from the GV gene cluster, wherein together the GV proteins expressed from the first and second genetic molecular components are configured to form a GV type. In these embodiments, activation of both the first AND second genetic molecular component is required for the output of the GV type in the genetic circuit when the genetic circuit operates according to the design of the genetic circuit. For example, the first and second genetic molecular components can comprise promoters that are activated by two or more biochemical events in the porkaryotic cell comprising the GVR genetic circuit.

In exemplary embodiments, any of GVA genes GvpF, GvpG, GvpJ, GvpL, GvpK, GvpS, and GvpU and GVS gene GvpA of a GV gene cluster can be split into at least a first and second genetic molecular component comprising at least a first and a second subset of these genes to form an AND gate.

In other embodiments of an "AND gate" comprised in a GVGC genetic circuit, two or more regulatory elements operatively connected to a GV gene cluster comprised in a genetic molecular component of a GVGC genetic circuit that is activated by biochemical events A AND B would result in the output of the GV type in the GVGC genetic circuit. For example, the promoter requires binding of two transcriptional activators for activation of the promoter. In Examples described herein (see the Methods section of the Examples), GV gene clusters of exemplary ARG1 and ARG2 and A2C constructs is driven by the T7 promoter that has a lac operator downstream the promoter. The T7 RNA Polymerase is regulated by the araBAD promoter (inducible by L-arabinose). Lad is controlled by the Lad promoter (IPTG inducible). Therefore only under conditions wherein both IPTG AND L-ara are present are GVs expressed.

The term "OR gate" refers to a digital logic gate that behaves according to the truth table shown in Table 2. A 'true' output (1) results if either of the inputs to the OR gate are 'true' (1).

TABLE 2

'OR gate' truth table:

| Input | | Output |
|---|---|---|
| A | B | A OR B |
| 0 | 0 | 0 |
| 0 | 1 | 1 |
| 1 | 0 | 1 |
| 1 | 1 | 1 |

In particular, the term "OR gate" as used herein refers to the logical relation between two genetic molecular components in a GVGC genetic circuit, wherein inputs 'A' and '13' in Table 2 are two biochemical events, and the output 'A OR B' in Table 2 is the GV type.

For example, in some embodiments of an "OR gate" comprised in a GVGC genetic circuit described herein, a promoter operatively connected to a GV gene cluster comprised in a genetic molecular component of a GVGC genetic circuit that is activated by biochemical events A OR B would result in the output of the GV type in the GVGC genetic circuit. For example, the promoter is activated by binding of either of two different transcriptional activators.

In other embodiments, an OR gate can be achieved through the use of two consecutive promoters. In exemplary embodiments, both these promoters can be located directly upstream of the GV gene cluster or they can be independently located directly upstream of any one or more of GVA genes GvpF, GvpG, GvpJ, GvpL, GvpK, GvpS, or GvpU and GVS gene GvpA.

In other embodiments, the GVR gene cluster or one or more of the GV gene cluster regulatory elements can be flanked by recombination sites that are recognized by a recombinase, whose expression or activity is, in turn, activated in response to a biochemical event in the bacterial cell. For example, in these embodiments, one input signal can activate the GV gene cluster while a constitutive promoter is positioned in the opposite direction of the gene cluster. The second input would drive a recombinase that flips the promoter so that GV genes can be expressed. Exemplary recombinase systems comprise Flp-FRT recombination system systems and others known to those skilled in the art The term "Negated AND gate" or "NOT gate" refers to a digital logic gate that behaves according to the truth table shown in Table 3. A 'true' output (1) results if either of the inputs to the OR gate are 'true' (1).

TABLE 3

'Negated AND gate' or "NOT gate" truth table:

| Input | | Output |
|---|---|---|
| A | B | A NOT B |
| 0 | 0 | 0 |
| 0 | 1 | 0 |
| 1 | 0 | 1 |
| 1 | 1 | 0 |

In particular, the term "Negated AND gate" or "NOT gate" as used herein refers to the logical relation between two genetic molecular components in a GVGC genetic circuit, wherein inputs 'A' and 'B' in Table 3 are two biochemical events, and the output 'A OR B' in Table 3 is the GV type.

For example, in some embodiments of an "Negated AND gate" or a "NOT gate" comprised in a GVGC genetic circuit described herein, the GVGC genetic circuit comprises a plurality of genetic molecular components wherein at least a first genetic molecular component comprises a GV gene cluster, and at least a second genetic molecular component comprises an CRISPR/Cas9 complex configured to inhibit expression of a gyp gene comprised in the GV gene cluster, e.g. a gvpA. In these embodiments, activation of expression and the first genetic molecular component and absence of activation (or repression) of the second genetic molecular component are both required for the output of a GV type in the genetic circuit when the genetic circuit operates according to the design of the genetic circuit. For example, the first and second genetic molecular components can comprise promoters that are activated or repressed by one or more biochemical events in the prokaryotic cell comprising the GVGC genetic circuit.

In embodiments of the genetic circuits herein described wherein the input is a biochemical event and the output is an intracellular spatial translocation of the GV type, the GV type is a molecular component of the genetic circuit and intracellular spatial translocation of the GV type can occur through one or more converting and/or binding reactions involving the GV type as described herein.

Exemplary binding or converting reactions that can result in an intracellular spatial translocation of the GV type comprise the use of a functionalized, tagged hybrid GV type that is configured to bind to an intracellular compartment, or to allow clustering of the GV type.

For example, in some embodiments, hybrid GVs comprising variants of GvpC that are fused with the kinase inducible domain of CREB will cluster upon phosphorylation of this domain by Protein Kinase A, when the cell also contains a multimeric protein (such as ferritin) that is fused to the KIX domain of the CREB binding protein. In another example, GvpC can be fused with a calmodulin-binding domain such as the M13 peptide, and will cluster upon an elevation of calcium concentration when the cell also contains a multimeric protein such as ferritin that is fused to calmodulin.

In those embodiments, the intracellular spatial translocation of the GV type in the bacterial cell is a reportable output of the GVR genetic circuit. In particular embodiments, the spatial translocation of the GV type in the bacterial cell can be detected as a change in the contrast-enhanced image of the target site comprising the genetically engineered bacterial cell expressing the GV type.

Thus, heterologously expressed GVs can also be used as dynamic sensors for imaging specific biochemical events in bacteria. In response to molecular signals of interest, GVs can be designed to aggregate or form clusters in bacteria, thus leading to an increase or decrease in T2 or T2* contrast, as described herein. Differential MRI contrast based on clustering can then be produced.

In particular, the GV type expressed in the bacterial cell can include a specific functional tag attached to a surface of the gas vesicles, for example through genetically engineering a gvpC protein to comprise a tag, as described herein. In some embodiments, the tag can be configured to specifically bind to a corresponding tag on another GV or to a target molecule or sub-cellular compartment in a bacterial cell. The bonds formed between gas vesicles or between gas vesicles and the target in the bacterial cell can include covalent bonds and non-covalent interactions, such as ionic bonds, hydrophobic interactions, hydrogen bonds, van der Walls forces, dipole-dipole interactions and others known to a person skilled in the art.

In some embodiments, the affinity between one binding moiety and its corresponding moiety to which the binding moiety specifically binds can be characterized by a dissociation constant $K_d$. In some instances, $K_d$ has a value less than $10^{-5}$ mol/L, or less than $10^{-7}$ mol/L. In some cases, Kd of a pair of binding moiety can be on the order of about $10^{-14}$ mol/L. "Affinity" refers to the strength of binding, increased binding affinity being correlated with a lower $K_d$.

In some embodiments, in the GVR genetic circuit herein described, an expression of the GV type or an intracellular spatial translocation of the GV type occurs when the hybrid GVR genetic circuit operates according to the circuit design in response to a trigger molecular component within the target prokaryotic host;

In some embodiments, the trigger molecular component is a molecular component that is capable of being natively produced in the target prokaryotic host in its naturally occurring form. In particular, the natively produced molecular component can be a genetic molecular component or a cellular molecular component.

Examples of natively produced genetic molecular component can be one or more RNA or protein natively encoded in the genome of the naturally occurring form of the prokaryote host and natively expressed by the target prokaryotic host. Examples of cellular molecular components natively produced by the target prokaryotic host comprise metabolites of enzymatic reactions produced by enzymes that are natively expressed by the target prokaryotic host in its naturally occurring form.

In these embodiments, the GVR genetic circuit comprises a hybrid GV type when the GVR genetic circuit operates according to a circuit design in response to the presence of the natively produced molecular component in the target prokaryotic cell.

In particular, in these embodiments, expression of the GVR in the prokaryotic host does not require the introduction into the host of any genetic molecular components in addition to the genetic molecular components comprising the GVGC. In these embodiments, the promoter operatively connected to a hybrid GV gene cluster in the GVGC genetic molecular component is configured to be activated in response to molecular components capable of being natively produced by the prokaryotic host in its naturally occurring form, such as natively expressed transcription factors. Natively produced proteins or RNAs natively encoded in the genome of a particular host prokaryote, e.g. *E. coli* are identifiable by those skilled in the art, as are metabolites produced in biochemical reactions produced in the naturally occurring form of the prokaryotic host.

Thus, in these embodiments, the target prokaryotic host is labeled with expression of a GV type, wherein expression of the GV type occurs in presence of the trigger molecular component that is capable of being natively produced in the target prokaryotic host in its naturally occurring form. In several embodiments described herein, one or more GVR genetic circuits can be introduced into a prokaryotic cell or one or more prokaryotic cell types according to genetic engineering methods described herein and known to those skilled in the art.

In other embodiments, the trigger molecular component is a heterologous molecular component that is not capable of being natively produced in the target prokaryotic host in its naturally occurring form. In these embodiments, the GVGC genetic molecular component is not configured to express the GV type in presence of a molecular component that is capable of being natively produced in the target prokaryotic host in its naturally occurring form, but is instead configured to express the GV type in presence of one or more heterologous (non-natively produced) trigger molecular components.

In these embodiments, the trigger molecular component can be one or more heterologous molecular components comprising a heterologous genetic molecular component and/or a heterologous cellular molecular component.

In some embodiments, the heterologous genetic molecular component can comprise one or more protein- and/or RNA-encoding genes and/or regulatory elements such as promoters and/or enhancer elements that are not native to the target prokaryotic genome. In some embodiments, the heterologous genetic molecular component can be introduced into the target prokaryotic host in addition to the one or more genetic molecular components comprising the hybrid GVGC. The additional heterologous genetic molecular component can be a constitutively expressed or an inducible genetic molecular component.

In some embodiments, the heterologous cellular molecular component can comprise a molecular component that is naturally present in the environment comprising the target prokaryotic cell, such as a metabolite produced by a mammalian host comprising the target prokaryotic host cell, or it can be a molecular component that is not naturally present in the environment comprising the target prokaryotic host cell, and introduced into the prokaryotic host cell, such as a drug configured to activate expression of the heterologous genetic component.

In some embodiments, the hybrid GVGC genetic molecular component comprises promoter and/or enhancer elements that are configured to be activated in response to the presence of a heterologous molecular component. In exemplary embodiments, the promoter is drug-inducible promoter, such as an IPTG-inducible promoter, and activation of the promoter and initiation of expression of the GV type occurs in presence of the drug e.g. IPTG (e.g., see Example 2 and 8). In other exemplary embodiments, the promoter is activated by a heterologous transcription factor that is encoded in a heterologous genetic molecular component introduced into the target prokaryotic host in addition to the GVGC genetic molecular component; in exemplary embodiments described herein, the GVGC genetic molecular component comprises a T7 promoter and an additional genetic molecular component introduced into the target prokaryotic host comprises a T7 RNA polymerase (e.g., see Example 2 and 8).

In some embodiments, the GVGC genetic molecular component comprises recombination sites (e.g. Flp-FRT recombination sites) surrounding one or more Gvp genes comprised in the hybrid GV gene cluster or one or more regulatory elements (e.g. promoter) wherein the one or more Gvp genes or regulatory elements are introduced into a prokaryotic host cell in an orientation that prevents expression of the encoded GV type, e.g., the promoter is in reverse orientation relative to the GV gene cluster; in these embodiments a heterologous genetic molecular component comprising the recombinase enzymes required for flipping the orientation of the elements flanked by the recombinase sites in the GVGC genetic molecular component is also introduced into the prokaryotic host cell and expression of the GV type occurs upon recombinase-mediated flipping of the flanked elements in the GVGC genetic molecular component into an orientation allowing initiation of expression of the GV type.

In these embodiments, the GVR genetic circuit comprises a hybrid GV type is when the GVR genetic circuit operates according to a circuit design in response to the presence of the one or more heterologous molecular components in the target prokaryotic cell.

Thus, in these embodiments, the target prokaryotic host is labeled with expression of a GV type, wherein expression of the GV type occurs in presence of the heterologous trigger molecular component introduced into the target prokaryotic host.

Accordingly, in some embodiments, a method to provide a genetically engineered prokaryotic cell comprising one or more GVR genetic circuits is described. The method comprises genetically engineering a prokaryotic cell by introducing into the cell one or more GVR genetic circuits described herein.

The prokaryotic cells described herein can be genetically engineered using methods known to those skilled in the art. For example, one or more genetic molecular components of a GVR genetic circuit comprised in vectors described herein can be introduced into bacterial cells using bacterial transformation techniques such as electroporation, heat shock, and others known to those skilled in the art and described herein. In some embodiments, the genetic molecular components of a GVR genetic circuit are introduced into the prokaryotic cell to persist as a plasmid or integrate into the genome, following methods known in the art and described herein.

In some embodiments the prokaryotic cells are gram negative bacteria and in particular *E. coli*, Nissle 1997, and *Salmonella*. In some embodiments the prokaryotic cell can be a cyanobacteria such as *Anabaena*. In some embodiments, the prokaryotic cells are archea and in particular *Halobacterium*

In embodiments herein described, the gas vesicle reporter genes (GVGC), and related genetic circuits, vectors, genetically engineered prokaryotic cells, compositions, methods and systems, which in several embodiments can be used together with contrast-enhanced imaging techniques to detect and report a biological event the location of and/or biochemical events in genetically engineered prokaryotic cells in an imaging target site.

The term "contrast enhanced imaging" or "imaging", as used herein indicates a visualization of a target site performed with the aid of a contrast agent present in the target site, wherein the contrast agent is configured to improve the visibility of structures or fluids by devices process and techniques suitable to provide a visual representation of a target site. Accordingly a contrast agent is a substance that enhances the contrast of structures or fluids within the target site, producing a higher contrast image for evaluation. In particular, as used herein, the term "contrast agent" refers to GVs expressed in prokaryotic cells comprised in the target site, the GVs comprised in GVGC genetic circuits in the prokaryotic cells when the GVGC genetic circuit operates according to a circuit design in response to a biochemical event, as described herein.

The term "target site" as used herein indicates an environment comprising one or more targets intended as a combination of structures and fluids to be contrasted, such as cells. In particular the term "target site" refers to biological environments such as cells, tissues, organs in vitro in vivo or ex vivo that contain at least one target. A target is a portion of the target site to be contrasted against the background (e.g. surrounding matter) of the target site. Accordingly, as used herein a target comprises one or more prokaryotic cells genetically engineered to comprise one or more GVGC genetic circuits as described herein within any suitable environment in vitro, in vivo or ex vivo as will be understood by a skilled person. Exemplary target sites include collections of microorganisms, including, bacteria or archaea in a solution or other medium in vitro, as well as cells grown in an in vitro culture, including, primary mammalian, cells, immortalized cell lines, tumor cells, stem cells, and the like. Additional exemplary target sites include tissues and organs in an ex vivo culture and tissue, organs, or organ systems in a subject, for example, lungs, brain, kidney, liver, heart, the central nervous system, the peripheral nervous system, the gastrointestinal system, the circulatory system, the immune system, the skeletal system, the sensory system, within a body of an individual and additional environments identifiable by a skilled person. The term "individual" or "subject" or "patient" as used herein in the context of imaging includes a single plant, fungus or animal and in particular higher plants or animals and in particular vertebrates such as mammals and more particularly human beings.

In some embodiments herein described, the contrast enhanced imaging of a target site is performed by imaging the target site with magnetic resonance imaging (MRI).

The term "magnetic resonance imaging" or "MRI" as used herein indicates an imaging technique performed by applying a magnetic field to a target site and detecting the resulting magnetic resonance. In MRI, a target site is positioned within a magnet provided by an MRI scanner where the magnetic field is used to align the magnetization of some atomic nuclei in the target site, and radio frequency magnetic fields are applied to systematically alter the alignment of this magnetization. This causes the nuclei to produce a rotating magnetic field detectable by the scanner, and this information is recorded to construct an image of the scanned area of the target site. The magnetic resonance of the target site is then detected, and the resulting data is analyzed to produce an image. MRI is thus performed based on nuclear magnetic resonance (NMR) property of nuclei of atoms inside the target site. For example, MRI is commonly used in radiology to visualize a target site formed by internal structures of the body of an individual. In this example, MRI makes use of the property of nuclear magnetic resonance (NMR) to image nuclei of atoms inside the body.

Exemplary MRI systems comprise systems operating at around 1.5 Tesla (T), as well as commercial system which can run between 0.2 and 7 T and other systems identifiable by a skilled person.

In contrast enhanced imaging performed by MRI, an image contrast can be further enhanced by weighting. Two forms of weighting are T1 and T2. T1, also known as spin-lattice weighting, allow magnetization to recover before the magnetic resonance signal is measured by changing the repetition time. The repetition time is the time, measured in milliseconds, from the application of an excitation pulse to the application of the next pulse, which shows how much of the longitudinal magnetization recovers between each pulse. T2, or spin-spin weighting, allows magnetization to decay before the magnetic resonance signal is measured by changing the echo time. The echo time refers to time, measured in milliseconds, between the application of radiofrequency excitation pulse and the peak of the signal induced in the coil. The spin-spin weighting rate can also be denoted T2*. T2* can be considered an "observed" or "effective" T2 (which includes effects from the magnetic field inhomogeneity), whereas the first T2 can be considered the "natural" or "true" T2 of the tissue being imaged (i.e. purely spin-spin interaction). T2* is less than or equal to T2.

In contrast enhanced imaging performed by MRI, an image contrast can be further enhanced by quantitative susceptibility mapping (QSM) which utilizes phase images to generate a 3D susceptibility distribution. The mapping can be performed by various techniques (COSMOS, MEDI, TKD, etc.), but ultimately the result is a calculated determination of the underlying susceptibility value at each pixel/voxel of the image. The susceptibility is theoretically linearly proportional to the concentration of the contrast material (in this case, air). Different contrast agent with different volumes would, therefore, produce different delta susceptibility per contrast agent.

Another MRI technique is Chemical Exchange Saturation Transfer (CEST). CEST works by having exchangeable solute protons that resonate at a frequency different from the bulk water protons when selectively saturated using RF irradiation. "Hyper-CEST" refers to a CEST technique that utilizes hyperpolarized agents, such as 129Xe. Using Hyper-CEST with Xe based contrast allows imaging at much lower concentrations (i.e. increased sensitivity) compared to usual susceptibility-based MRI techniques (e.g. T1, T2/T2*, QSM). However, unlike T2/T2* and QSM, multiparametric GV multiplexing is not available in Hyper-CEST, since the Hyper-CEST cannot measure T2/T2* and QSM of the surrounding nuclear spin. Since Hyper-CEST requires xenon as the contrast agent gas, GVs need to be exposed to xenon gas before acting as a Hyper-CEST contrast agent.

In contrast enhanced imaging performed by MRI, various contrast agent can be used as it will be understood by a skilled person. In particular, existing contrast agents for MRI are primarily based on heavy metal chelates [22], superparamagnetic iron oxides and in particular superparamagnetic iron oxide nanoparticles (SPIONs) [23, 24], metalloproteins [25-28], molecules with chemically exchangeable nuclei [29-32] and fluorinated compounds [33]. More particularly, commonly used contrast agents for MRI are chelates of gadolinium, and iodinated agents, as well as SPIONs used as conventional T2 and T2* contrast agents used in MRI applications such as in vivo cell tracking [34] [35]. [36-39]. Further contrast agents are CEST agents with distinct chemical shifts for exchanging nuclei [40, 41], and contrast agents to be used as dynamic sensors capable of imaging specific biological activities such as neurotransmission or enzymatic function [27, 42-45], e.g. superparamagnetic structures designed to cluster in response molecular signals of interest leading to an increase or decrease in T2 or T2* contrast [42, 44, 46].

In certain embodiments, imaging the target site comprises applying an external magnetic field to the target site in the subject, transmitting a radio frequency (RF) signal from a transmitter to the target site, and receiving MRI data at a receiver. The MRI data can be analyzed using a processor, such as a processor configured to analyze the MRI data and produce an MRI image from the MRI data. In certain embodiments, the MRI data detected by the receiver includes an MRI signal (e.g., a radio frequency MRI signal of the target site of the subject). In certain embodiments, the method includes obtaining a MRI data (e.g., signal) of the target site, and analyzing the MRI data (e.g., signal) to produce an MRI image of the target site. The MRI data (e.g., signal) can be obtained using a standard MRI device, or can be obtained using an MRI device configured to specifically detect the contrast agent used. Obtaining the MRI data (e.g., signal) can include detecting the MRI data (e.g., signal) with an MRI detector.

In certain embodiments, MRI data is obtained by applying to a subject a strong static magnetic field, a rapidly switching gradient field for spatial coding, and RF pulses with frequency matched such that the RF pulses trigger magnetic resonance signals from excited atomic nuclei at the target site. For example, an atomic nucleus can produce magnetic resonance signals when the RF pulse has a frequency that matches the resonance frequency (measured in chemical shifts (δ) in parts per million (ppm)) of the atomic nucleus. In such cases, the nucleus absorbs the RF pulse energy to become excited, and releases a magnetic resonance signal when the excited nucleus subsequently relaxes to an unexcited state after characteristic time periods. The magnetic resonance signals are detected by RF receiving antennas and digitized to generate the MRI data. The MRI data is analyzed using any known method of analyzing MRI data. In certain instances, the MRI data is analyzed to reconstruct the MRI image. For example, the MRI image is reconstructed from the MRI data by decoding the spatial information encoded in the MRI data using a linear reconstruction algorithm, such as Fourier transformation.

Additional methods to perform imaging of one or more GV types through MRI detection alone or in combination with ultrasound which are applicable in the present disclosure, such as described in U.S. patent application Ser. No. 15/663,600, entitled "Gas-Filled Structures and Related Compositions, Methods and Systems for Magnetic Resonance Imaging" and filed on Jul. 28, 2017, incorporated herein by reference in its entirety. The MRI can be, for example, T2 type, T2* type, T2 type weighted, T2* type weighted, QSM type, or Hyper-CEST (Xe). The MRI can be enhanced by background erasure through ultrasound collapse of the GVPS, can be multiplexed by selected collapse of certain GVPS types, and/or multiplexed by multiparametric unmixing of two or more MRI types (not including Hyper-CEST) where the different GVPS types have different parametric fingerprints (the ratio of values—susceptibility or relaxivity—measured by the different MRI types are unique for each GVPS type used). The MRI can be combined with ultrasound imaging to produce an enhanced image.

In some embodiments, a hybrid GV gene cluster comprising a combination of the structural GvpA and GvpC genes from *A. floc-aquae* with the expression-enabling GVA secondary genes GvpR-U from *B. megaterium* results in the formation of gas vesicles with characteristics favorable for MRI. For example, in Example 8 an exemplary GVGC construct is referred to herein as A2C showing robust, acoustically erasable QSM contrast that was absent from prokaryotic cells that were not induced or prokaryotic cells induced to express a control fluorescent protein.

In particular, in exemplary embodiments where imaging is performed by MRI, the hybrid GV gene cluster can comprise *B. megaterium* GVA genes GvpR, GvpN, GvpF, GvpG, GvpL, GvpS, GvpK, GvpJ, GvpT and GvpU and further comprise structural GV proteins genes from *Anabaena floc-aquae* such as GvpA and optionally GvpC (see Example 8). In other embodiments, the hybrid GV gene cluster can comprise *B. megaterium* GV regulatory genes GvpR, GvpN, GvpF, GvpG, GvpL, GvpS, GvpK, GvpJ, GvpT and GvpU and further comprise structural GV protein gene GvpA from *Bukholderia thailandensis* or *Psychromonas ingrahamii*.

In some embodiments, imaging the target site comprising the prokaryotic host can be performed by applying ultrasound to obtain an ultrasound image of the target site.

The term "ultrasound imaging" or "ultrasound scanning" or "sonography" as used herein indicate imaging performed with techniques based on the application of ultrasound.

Ultrasound refers to sound with frequencies higher than the audible limits of human beings, typically over 20 kHz. Ultrasound devices typically can range up to the gigahertz range of frequencies, with most medical ultrasound devices operating in the 1 to 18 MHz range. The amplitude of the waves relates to the intensity of the ultrasound, which in turn relates to the pressure created by the ultrasound waves. Applying ultrasound can be accomplished, for example, by sending strong, short electrical pulses to a piezoelectric transducer directed at the target. Ultrasound can be applied as a continuous wave, or as wave pulses as will be understood by a skilled person.

Accordingly, the wording "ultrasound imaging" as used herein refers in particular to the use of high frequency sound waves, typically broadband waves in the megahertz range, to image structures in the body. The image can be up to 3D with ultrasound. In particular, ultrasound imaging typically involves the use of a small transducer (probe) transmitting high-frequency sound waves to a target site and collecting the sounds that bounce back from the target site to provide the collected sound to a computer using sound waves to create an image of the target site. Ultrasound imaging allows detection of the function of moving structures in real-time. Ultrasound imaging works on the principle that different structures/fluids in the target site will attenuate and return sound differently depending on their composition. A contrast agent sometimes used with ultrasound imaging are microbubbles created by an agitated saline solution, which works due to the drop in density at the interface between the gas in the bubbles and the surrounding fluid, which creates a strong ultrasound reflection. Ultrasound imaging can be performed with conventional ultrasound techniques and devices displaying 2D images as well as three-dimensional (3-D) ultrasound that formats the sound wave data into 3-D images. In addition to 3D ultrasound imaging, ultrasound imaging also encompasses Doppler ultrasound imaging, which uses the Doppler Effect to measure and visualize movement, such as blood flow rates. Types of Doppler imaging includes continuous wave Doppler, where a continuous sinusoidal wave is used; pulsed wave Doppler, which uses pulsed waves transmitted at a constant repetition frequency, and color flow imaging, which uses the phase shift between pulses to determine velocity information which is given a false color (such as red=flow towards viewer and blue=flow away from viewer) superimposed on a grey-scale anatomical image. Ultrasound imaging can use linear or non-linear propagation depending on the signal level. Harmonic and harmonic transient ultrasound response imaging can be used for increased axial resolution, as harmonic waves are generated from non-linear distortions of the acoustic signal as the ultrasound waves insonate tissues in the body. Other ultrasound techniques and devices suitable to image a target site using ultrasound would be understood by a skilled person.

Types of ultrasound imaging of biological target sites include abdominal ultrasound, vascular ultrasound, obstetrical ultrasound, hysterosonography, pelvic ultrasound, renal ultrasound, thyroid ultrasound, testicular ultrasound, and pediatric ultrasound as well as additional ultrasound imaging as would be understood by a skilled person.

Applying ultrasound refers to sending ultrasound-range acoustic energy to a target. The sound energy produced by the piezoelectric transducer can be focused by beamforming, through transducer shape, lensing, or use of control pulses. The soundwave formed is transmitted to the body, then partially reflected or scattered by structures within a body; larger structures typically reflecting, and smaller structures typically scattering. The return sound energy reflected/scattered to the transducer vibrates the transducer and turns the return sound energy into electrical signals to be analyzed for imaging. The frequency and pressure of the input sound energy can be controlled and are selected based on the needs of the particular imaging task and, in some methods described herein, collapsing GVs. To create images, particularly 2D and 3D imaging, scanning techniques can be used where the ultrasound energy is applied in lines or slices which are composited into an image.

In some embodiments, the ultrasound imaging herein described can comprising collapsing a GV type expressed in the genetically engineered bacteria by applying collapsing ultrasound to the target site and/or imaging a GV type in the contrast agent by applying imaging ultrasound to the target site.

In some embodiments, imaging the target site can be performed by scanning an ultrasound image of the target site in a subject. In some cases, imaging the target site includes transmitting an imaging ultrasound signal from an ultrasound transmitter to the target site, and receiving a set of ultrasound data at a receiver. The visible image is formed by ultrasound signals backscattered from the target site. The ultrasound data can be analyzed using a processor, such as a processor configured to analyze the ultrasound data and produce an ultrasound image from the ultrasound data. In certain embodiments, the ultrasound data detected by the receiver includes an ultrasound signal, an ultrasound signal reflected by the target site of the subject.

In certain embodiments, the method includes applying a set of imaging pulses from an ultrasound transmitter to the target site, and receiving ultrasound signal at a receiver. In certain instances, the ultrasound signal detected by the receiver includes an ultrasound echo signal. Additional information of ultrasound systems and methods can be found in related publications as will be understood by a person skilled in the art.

Methods for performing ultrasound imaging are known in the art and can be employed in methods of the current disclosure. In certain aspects, an ultrasound transducer, which comprises piezoelectric elements, transmits an ultrasound imaging signal (or pulse) in the direction of the target site. Variations in the acoustic impedance (or echogenicity) along the path of the ultrasound imaging signal causes backscatter (or echo) of the imaging signal, which is received by the piezoelectric elements. The received echo signal is digitized into ultrasound data and displayed as an ultrasound image. Conventional ultrasound imaging systems comprise an array of ultrasonic transducer elements that are used to transmit an ultrasound beam, or a composite of ultrasonic imaging signals that form a scan line. The ultrasound beam is focused onto a target site by adjusting the relative phase and amplitudes of the imaging signals. The imaging signals are reflected back from the target site and received at the transducer elements. The voltages produced at the receiving transducer elements are summed so that the net signal is indicative of the ultrasound energy reflected from a single focal point in the subject. An ultrasound image is then composed of multiple image scan lines.

In some embodiments, imaging the target site is performed by applying or transmitting an imaging ultrasound signal from an ultrasound transmitter to the target site and receiving a set of ultrasound data at a receiver. The ultrasound data can be obtained using a standard ultrasound device, or can be obtained using an ultrasound device configured to specifically detect the contrast agent used. Obtaining the ultrasound data can include detecting the ultrasound signal with an ultrasound detector. In some embodiments, the imaging step further comprises analyzing the set of ultrasound data to produce an ultrasound image.

In certain embodiments, the ultrasound signal has a transmit frequency of at least 1 MHz, 5 MHz, 10 MHz, 20 MHz, 30 MHz, 40 MHz or 50 MHz. For example, an ultrasound data is obtained by applying to the target site an ultrasound signal at a transmit frequency from 4 to 11 MHz, or at a transmit frequency from 14 to 22 MHz.

In the embodiments herein described, the collapsing ultrasound and imaging ultrasound are selected to have a collapsing pressure and an imaging pressure amplitude based on the acoustic collapse pressure profile of the GV type expressed in the prokaryotic cells comprising a GVR genetic circuit. The collapsing ultrasound is typically provided at a high ultrasound pressure amplitude in order to collapse the GVs, while the imaging ultrasound is typically provided at a low ultrasound pressure amplitude to avoid collapsing of the GVs.

In some embodiments herein described, when collapsing ultrasound is used in combination with ultrasound imaging, acoustically collapsing a GV type expressed in a prokaryotic cell can remotely in situ erase the GV type to enable a background-free ultrasound imaging. The background-free ultrasound imaging removes background noise posed by background contrast from endogenous sources [35, 36] by subtracting the background image from the GV contrasted image, thus providing higher structure contrast in a final image and increased sensitivity of visualization of the GVs.

In some embodiments, a method is described to provide imaging of one or more biochemical events in a prokaryotic cell comprised in an imaging target site, the method comprising:

introducing into the prokaryotic cell a hybrid gas vesicle reporter gene cluster (GVGC) encoding a gas vesicle (GV) type, the GVGC introduced to provide a reportable genetic molecular components of a GVR genetic circuit, in which molecular components are connected one to another in accordance with a circuit design by activating, inhibiting, binding or converting reactions to form a fully connected network of interacting components, wherein in the reportable genetic molecular component the gas vesicle (GV) type when the genetic circuit operates according to the circuit design in response to the one or more biochemical events, wherein the GV type has a selectable acoustic collapse pressure value derived from an acoustic collapse pressure profile of the GV type and a hydrostatic collapse pressure profile, and a midpoint of the acoustic collapse pressure profile higher than a midpoint of the hydrostatic collapse pressure profile, and collapsing the GV type by applying collapsing ultrasound to a target site comprising the prokaryotic cell, the collapsing ultrasound applied at a collapsing ultrasound pressure greater than the selectable acoustic collapse pressure value.

The method further comprises imaging the target site comprising the prokaryotic cell by MRI and/or by applying imaging ultrasound to the target site.

In embodiments where imaging is performed by ultrasound, the imaging ultrasound is typically a low-pressure ultrasound, applied at an imaging ultrasound pressure lower than a selectable acoustic collapse pressure value. The selectable acoustic collapse pressure value is selected from the acoustic collapsing profile of the GV type expressed by the prokaryotic cells in the target site.

In some of those embodiments, the imaging ultrasound transmit pulses are selected to have an imaging ultrasound pressure equal to or lower than an initial collapse pressure in the acoustic collapse profile of the GV type expressed by the prokaryotic cells in the target site.

In some of those embodiments, the imaging ultrasound transmit pulses are selected to an imaging ultrasound pressure equal to or lower than a midpoint collapse pressure in the acoustic collapse profile of the GV type expressed by the prokaryotic cells in the target site.

In some of those embodiments, the imaging ultrasound transmit pulses are selected to have an imaging ultrasound pressure equal to or lower than a complete collapse pressure in the acoustic collapse profile of the GV type expressed by the prokaryotic cells in the target site.

In some of those embodiments, the target site can be treated with collapsing ultrasound to collapse the GV type expressed by the prokaryotic cells in the target site prior to or after the imaging.

Additional methods to perform imaging of one or more GV types through ultrasound detection alone which are applicable in the present disclosure, such as ultrasound imaging with GVs as contrast agents, background erasure of ultrasound imaging by GV ultrasound collapse, and multiplexing ultrasound imaging of multiple GV types by selective ultrasound collapse, all of which are described in U.S. patent application Ser. No. 15/613,104 filed on Jun. 2, 2017 and incorporated herein by reference in its entirety.

Accordingly, in the present disclosure, a GV type or types herein can be used as a contrast agent in MRI and/or ultrasound imaging which allows non-toxic, highly sensitive and robust contrast at sub-nanomolar concentrations, with the optional ability of background erasure and/or multiplexing as would be understood by a skilled person upon reading of the present disclosure.

In some embodiments, a method is described to image a biochemical event in a prokaryotic host comprised in an imaging target site, the method comprising:

introducing into the bacterial host a hybrid gas vesicle gene cluster (GVGC) herein described configured for expression in the prokaryotic host, the hybrid gas vesicle gene cluster (GVGC) encoding a gas vesicle (GV) type, wherein the GV type is a reportable molecular component of a gas vesicle reporting (GVR) genetic circuit, in which molecular components are connected one to another in accordance with a circuit design by activating, inhibiting, binding or converting reactions to form a fully connected network of interacting components, wherein in the GVR genetic circuit an expression of the GV type or an intracellular spatial translocation of the GV type occurs when the GVR genetic circuit operates according to the circuit design in response to the biochemical event; and imaging the target site comprising the prokaryotic host by applying a magnetic field and/or ultrasound to obtain an MRI and/or an ultrasound image of the target site.

In some embodiments, a GVGC can be introduced into a bacterial cell to provide the bacterial cell with an expressed reportable molecular component comprising a GV type, rendering the cell detectable using contrast-enhanced imaging techniques described herein. In these embodiments, expression of the GV type in the genetically engineered bacterial cell allows labeling of a target prokaryotic host through a GVR genetic circuit operating according to the circuit design in response to a trigger molecular component within the target prokaryotic host.

Accordingly, in some embodiments, a method is described to provide a magnetic resonance and/or ultrasound imaging of a target prokaryotic cell comprised in an imaging target site, to label a target prokaryotic host, the method comprising:

introducing into the target prokaryotic host a hybrid gas vesicle gene cluster (GVGC) herein described configured for expression in the bacteria host, the hybrid gas vesicle gene cluster (GVGC) encoding a gas vesicle (GV) type, wherein the GV type is a reportable molecular component of a gas vesicle reporting (GVR) genetic circuit, in which molecular components are connected one to another in accordance with a circuit design by activating, inhibiting, binding or converting reactions to form a fully connected network of interacting components, wherein in the GVR genetic circuit an expression of the GV type or an intracellular spatial translocation of the GV type occurs when the GVR genetic circuit operates according to the circuit design in response to a trigger molecular component within the target prokaryotic host;

the introducing performed under conditions resulting in presence of the trigger molecular component in the prokaryotic host.

In some embodiments, the method can further comprise imaging the target site comprising the prokaryotic host, by applying a magnetic field and/or ultrasound to obtain an MRI and/or an ultrasound image of the target site. In particular, in some embodiments the imaging can be performed at same or different time intervals and/or in different target sites (e.g. target sites contiguous in space) to detect a spatial location of a labeled prokaryotic host.

In embodiments methods to label a target prokaryotic host, expression of the GV type occurs when the GVGC genetic circuit operates according to the circuit design in response to a trigger molecular component in the target bacterial cell. The trigger molecular components in the target bacterial cell that allow activation of the promoter comprised in the GVGC genetic molecular component that regulates initiation of expression of the GV type comprises transcription factors and other molecular components native to the prokaryotic cell. In some embodiments, heterologous molecular components can also be introduced into the cell to allow activation of expression of the GV type. In some embodiments, the GVGC genetic molecular component comprises a constitutively active promoter comprising binding sites for transcription factors native to the target prokaryotic cell. In other embodiments, the GVGC genetic molecular component comprises an inducible promoter. Exemplary constitutive and inducible bacterial promoters suitable for regulating expression of GVs in a bacterial cell comprise T7, T7lac, Sp6, araBAD, trp, lac, Ptac, pL, and others identifiable by those skilled in the art and described herein.

In some embodiments, the expression of the GV type in the prokaryotic host when the GVR genetic circuit operates according to the circuit design in response to the biochemical event and/or the trigger molecular component in the prokaryotic host allows the selective labeling of a selected prokaryotic host cell type.

In these embodiments, the GVGC genetic circuit is designed to specifically regulate expression of the GV type in a specific type of prokaryotic cell. In some embodiments, the GVR genetic circuit is designed to comprise genetic molecular components having promoters that are selectively activated by prokaryote species-specific transcription factors. For example, in embodiments wherein the labeling of E. coli cells is specifically required, the GVR genetic circuit can be designed to comprise promoters having E. coli-specific promoters that will not be activated in prokaryotic cells of another species. Species-specific promoters are identifiable by those skilled in the art. In other embodiments, a selected prokaryotic species can be specifically engineered to control regulation of a GVGC genetic circuit by introducing additional heterologous genetic molecular components into the selected prokaryotic host cell, as described herein. Thus, in these embodiments, specific labeling of the selected prokaryotic species allows selective imaging of the specific prokaryotic host using contrast-enhanced imaging techniques described herein.

In some embodiments, the expression of the GV type in the prokaryotic host when the GVR genetic circuit operates according to the circuit design in response to the biochemical event and/or the trigger molecular component in the prokaryotic host allows the detection of movement and tracking of the location of the prokaryotic host cell within an imaging target site. In these embodiments, the tracking of movement of a labeled prokaryotic cell comprises performing serial imaging of one or more imaging target sites comprising the labeled prokaryotic cell, wherein the changes in location of the labeled prokaryotic cell in the serially collected images of the labeled prokaryotic cell in the one or more imaging target sites relative to the structures comprised in the environment surrounding the labeled prokaryotic cell in the one or more imaging target sites indicate the movement of the labeled prokaryotic cell within the imaging target site. Exemplary tracking of movement comprises movement of labeled bacteria within the colon (e.g., Nissle) of a mammalian host or tracking the location of a labeled prokaryotic cell in relation to a tumor in a mammalian host or within blood (e.g. *Salmonella*) or lymph. In some exemplary embodiments described herein, imaging of engineered bacterial cells expressing GV types in vivo allows imaging of the location of engineered bacteria in target sites such as gastrointestinal tract and tumors (see Examples 6-7). In several embodiments, acoustic erasing of one or more GV types can be used to confirm the specificity of the imaging of the labeled prokaryotic cell within the one or more imaging target sites.

The ability of GVs to act as a contrast agent for both ultrasound and magnetic imaging allows them to act as an acoustomagnetic reporter, thus creating possibilities for multimodal imaging. In some embodiments herein described, when collapsing ultrasound is used in combination with MRI imaging, acoustically collapsing a GV type expressed in a prokaryotic cell can remotely in situ erase the GV type to enable a background-free magnetic resonance imaging of a target site. The background-free magnetic resonance imaging removes background noise posed by background contrast from endogenous sources [35, 36] by allowing GV types to be identified specifically based on their acoustic responses.

In some embodiments, the ability of GVs to act as a contrast agent with a distinguishable parametric fingerprint for susceptibility-based MRI and/or to allow MRI imaging in combination with ultrasound collapsing allows for the detection of multiple GV types intracellularly as will be understood. A parametric fingerprint is a GV types relative (ratio) of response strength for a given concentration for two or more of the parameters: susceptibility, r2 relaxivity, and r2* relaxivity.

Accordingly, in various embodiments herein described imaging of a biochemical event and/or labeling of a prokaryotic cell can be performed by multiplex imaging as will be understood by a skilled person upon reading of the present disclosure.

The term "multiplex" refers to the presence of two or more GV types, each of which exhibits an acoustic collapse pressure profile substantially distinct from one another and/or MRI parametric fingerprint substantially distinct one from the other.

In particular, in some embodiments, methods for acoustomagnetic multiplexed imaging of a target site herein described comprise a MRI imaging method to be used in combination with ultrasound collapsing on a target site contrasted with a contrast agent comprising at least a first GV type and a second GV type are described in U.S. patent application Ser. No. 15/613,104 and US patent application Ser. No. 15/663,600, entitled "Gas-Filled Structures and Related Compositions, Methods and Systems for Magnetic Resonance Imaging" and filed on Jul. 28, 2017, both incorporated herein by reference in their entirety.

In some embodiments of the multiplexed imaging methods herein described, a magnetic resonance imaging of two or more biochemical events in one prokaryotic cell type comprised in an imaging target site is described. In some of these embodiments, the one prokaryotic cell type comprises a GVR genetic circuit, wherein in the GVR genetic circuit at least two molecular components are a first GV type and a second GV type when the GVR genetic circuit operates according to the circuit design in response to the two or more biochemical events. In other embodiments, the one prokaryotic cell type comprises at least a first GVR genetic circuit and a second GVR genetic circuit, wherein in the first GVR genetic circuit at least one molecular component comprises a first GV type and wherein in the second GVGC genetic circuit at least one molecular component comprises a first GV type, when the first and second GVR genetic circuits operate according to the circuit designs in response to the two or more biochemical events.

In some embodiments wherein two different GV types are expressed in one prokaryotic cell, a GVR genetic circuit can be introduced into the prokaryotic cell that is configured to provide alternating expression of the two different GV types in the cell, wherein the alternation of expression between a first GV gene cluster and a second GV gene cluster is in response to one or more biochemical events in the prokaryotic cell. For example, in some embodiments, a first GV gene cluster can be operatively linked to a promoter and expression of the first GV type occurs in response to a biochemical event that directly or indirectly activates the promoter operatively linked to the first GV type; in addition, in response to a second biochemical event, the expression of the first GV type is inactivated and the expression of the second GV type is activated. An exemplary configuration of a construct comprising two GV gene clusters encoding two different GV types configured for alternating expression of the two GV types is shown in Example 11, wherein a promoter is placed in between a first GV gene cluster and a second gene cluster, the two GV gene clusters oriented in opposite directions, and the promoter is flanked by recombination sites that mediate the reversal of orientation of the promoter to alternate from operative connection with the first GV gene cluster and the second GV gene cluster. Thus, for example, upon the occurrence of the second biochemical event, the recombinase is expressed and mediates re-orientation of the promoter to be in operative connection with the second GV gene cluster.

In other embodiments of the multiplexed imaging methods herein described, a magnetic resonance imaging of one or more biochemical events in each of two or more prokaryotic cell types comprised in an imaging target site is described. In some of these embodiments, the two or more prokaryotic cell types each comprises a GVR genetic circuit, wherein in a first GVR genetic circuit comprised in a first prokaryotic cell type at least one molecular component is a first GV type and wherein in a second GVR genetic circuit comprised in a second prokaryotic cell type at least one molecular component is a second GV type when the first and second GVR genetic circuits operate according to the circuit designs in response to the two or more biochemical events.

Thus, in several embodiments, the multiplexed imaging methods described herein can be used to independently detect expression of two or more different types of GVs having distinct acoustic collapse profiles. In exemplary embodiments described herein (see Example 4), multiplexed imaging allows the imaging of more than one population of GV-expressing bacterial cells in a target site. Further, in these embodiments, a spectral unmixing method as described herein and U.S. application Ser. No. 15/613,104, filed on Jun. 2, 2017 can be used to detect different prokaryotic cell type populations expressing distinct GVs in a target site. In those embodiments, imaging the target site further comprises processing the produced images using spectral unmixing to obtain spectrally unmixed images. The term "spectral unmixing", "acoustic spectral unmixing" or "pressure spectral unmixing" as used herein refers to a mathematical image processing method for obtaining spectrally unmixed images by subtracting each sub-population of signals from a sum of signal contributed by each sub-population present in any given pixel (e.g., see Example 4).

In exemplary embodiments described herein (see Example 4), multiplexed imaging allows the imaging of more than one population of GV-expressing bacterial cells in a target site.

GVs from distinct genetic origins can have different shapes and sizes and therefore can be distinguished on the basis of their differential effects on T2, T2*, T2-weighted, T2*-weighed, and QSM contrast. Differences in GV morphology result in different nanoscale magnetic field patterns for a given quantity of gas, which can in turn alter the efficiency of aqueous T2 and T2* relaxation. The magnetic susceptibility calculated from QSM reports a value primarily dependent on the total amount of air in the sample, independent of its nanoscale arrangement. Therefore, each type of GV has its own parametric fingerprint.

Accordingly, in some embodiments, a MRI and/or ultrasound multiplexing method and system are described to image of two or more biochemical events in one or more one prokaryotic cell types comprised in an imaging target site, the method comprising:

introducing into the one or more prokaryotic cell types a first hybrid gas vesicle reporter gene cluster (GVGC) encoding a first gas vesicle (GV) type to provide a first reportable genetic molecular component of one or more GVR genetic circuits in which molecular components are connected one to another in accordance with a circuit design by activating, inhibiting, binding or converting reactions to form a fully connected network of interacting components wherein in the first reportable genetic molecular component the first gas vesicle (GV) type is expressed from the first GVGC when the one or more GVR genetic circuits operate according to the respective circuit design in response to the first biochemical event;

introducing into the one or more prokaryotic cell types a second hybrid gas vesicle reporter gene cluster (GVGC) encoding a second gas vesicle (GV) type, to provide a second reporting genetic molecular component of the one or more GVR genetic circuits, wherein in the second reportable molecular component the second gas vesicle type is expressed from the second GVGC when the one or more GVR genetic circuits operate according to the respective circuit design in response to the second biochemical event, and imaging the target site comprising the one or more prokaryotic cell types.

Exemplary methods to perform imaging the target site comprising the one or more prokaryotic cell types are described in U.S. patent application Ser. No. 15/613,104 and U.S. patent application Ser. No. 15/663,600, entitled "Gas-Filled Structures and Related Compositions, Methods and Systems for Magnetic Resonance Imaging" and filed on Jul. 28, 2017, both incorporated by reference herein in their entirety.

In some embodiments, a method and system is described to provide an ultrasound imaging of two or more biochemical events in one or more one prokatyotic cell types comprised in an imaging target site, the method comprising:

introducing into the one or more prokaryotic cell types a first hybrid gas vesicle reporter gene cluster (GVGC) encoding a first gas vesicle (GV) type to provide a first reportable genetic molecular component of one or more GVR genetic circuits in which molecular components are connected one to another in accordance with a circuit design by activating, inhibiting, binding or converting reactions to form a fully connected network of interacting components wherein in the first reportable genetic molecular component the first gas vesicle (GV) type is expressed from the first GVGC when the one or more GVR genetic circuits operate according to the respective circuit design in response to the first biochemical event;

introducing into the one or more prokaryotic cell types a second hybrid gas vesicle reporter gene cluster (GVGC) encoding a second gas vesicle (GV) type, to provide a second reporting genetic molecular component of the one or more GVR genetic circuits, wherein in the second reportable molecular component the second gas vesicle type is expressed from the second GVGC when the one or more GVR genetic circuits operate according to the respective circuit design in response to the second biochemical event, wherein the first GV type exhibits a first acoustic collapse pressure profile and a first selectable acoustic collapse pressure value and the second GV type exhibits a second acoustic collapse pressure profile and a second selectable acoustic collapse pressure value, and selectively collapsing the first GV type by applying collapsing ultrasound to the target site comprising the one or more prokaryotic cell types, the collapsing ultrasound applied at a first acoustic collapse pressure value equal to or higher than the first selectable acoustic collapse pressure value and lower than the second selectable acoustic collapse pressure value, imaging the target site containing the second, uncollapsed, GV type by applying MRI and/or ultrasound imaging to the target site, the imaging ultrasound applied at a pressure value lower than the acoustic collapse pressure value of the second GV type.

In some embodiments, a method and system is described to provide an MRI and/or ultrasound imaging of two or more biochemical events in one or more one prokaryotic cell types comprised in an imaging target site, the method comprising:

introducing into the one or more prokaryotic cell types a plurality of hybrid gas vesicle reporter genes (GVGCs) encoding a plurality of gas vesicle (GV) types, the plurality of GVGCs introduced to provide a plurality of reportable genetic molecular components of one or more GVR genetic circuits, in which molecular components are connected one to another in accordance with a circuit design by activating, inhibiting, binding or converting reactions to form a fully connected network of interacting components, wherein in each reportable genetic molecular component the gas vesicle (GV) type is expressed from the plurality of GVGCs when the one or more GVR genetic circuits operate according to the circuit design in response to a biochemical event, wherein each GV type exhibits i) an acoustic collapse pressure profile defined as a collapse function from which a collapse amount can be determined, and ii) a selectable acoustic collapse pressure value, selectable acoustic collapse pressure values going from a lowest acoustic collapse pressure value to a highest acoustic collapse pressure value, selectively collapsing each GV type to a collapse amount higher than a collapse amount of each remaining GV type by applying collapsing ultrasound to the target site comprising the one or more prokaryotic cell types, the collapsing ultrasound applied at a pressure value equal to or higher than the selectable acoustic collapse pressure value of the GV type being collapsed and lower than an acoustic collapse pressure value of said each remaining GV type or types.

The method further comprises imaging the target site containing the remaining GV type or types by applying imaging ultrasound to the target site, the imaging ultrasound applied at a pressure value lower than a lowest acoustic collapse pressure value of said each remaining GV type or types. The method also comprises repeating the collapsing and the imaging until all GV types are collapsed, thus providing a sequence of visible images of the target site, the sequence being indicative of image-by-image decreasing remaining GV types.

Figure 2:
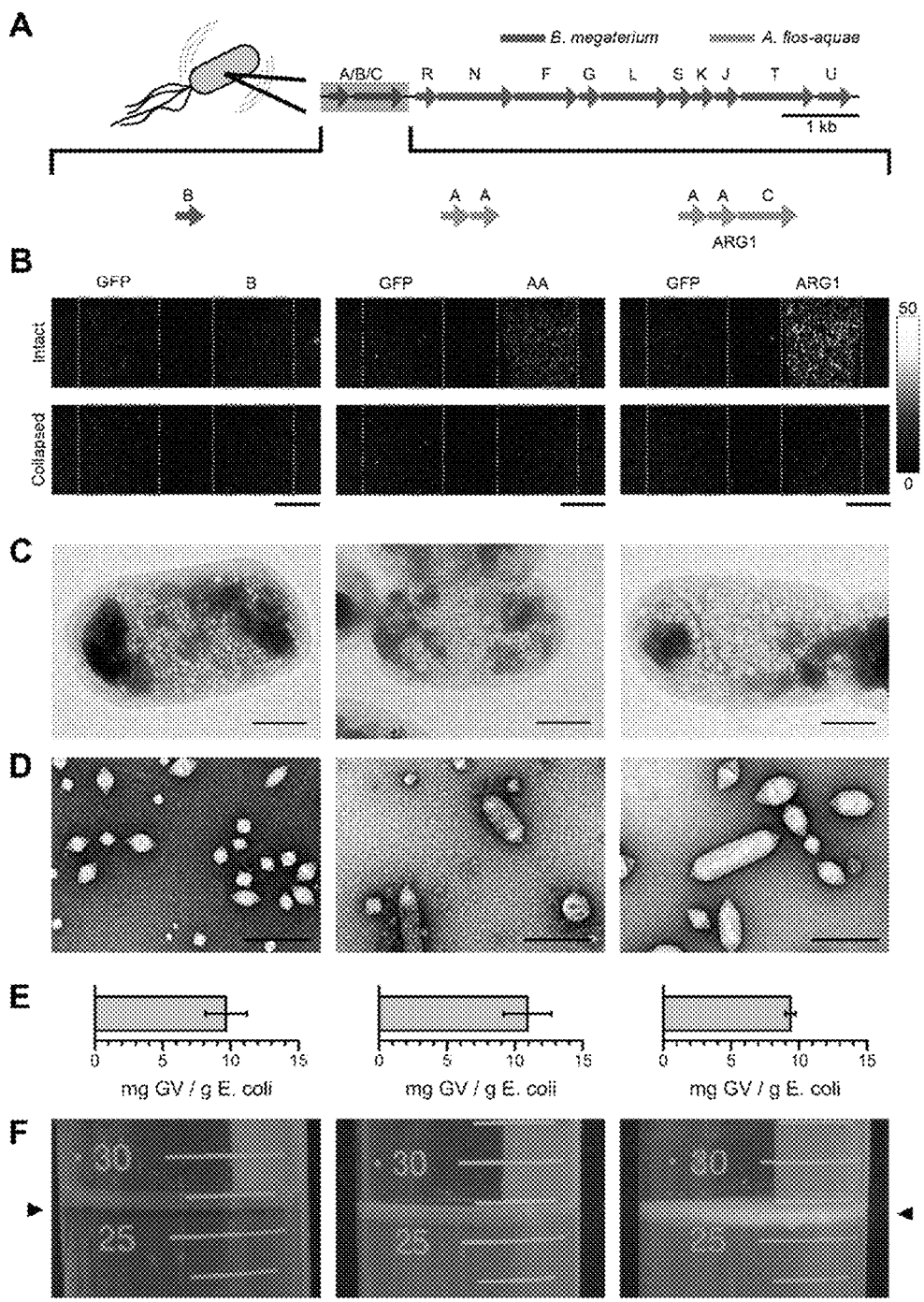
FIG. 2 shows schematics and images showing exemplary genetic engineering of GVGCs. Panel A shows a schematic of exemplary architecture of GVGC gene clusters. All clusters shown contain the *B. megaterium* genes GvpR-U, and vary in their composition of the structural genes GvpB (*B. megaterium*), GvpA and GvpC (*A. floc-aquae*). Three different constructs are shown, wherein each comprises a different set of GV structural genes, shown in the 'zoomed-in' view of the portion of the construct labeled 'A/B/C'. The construct on the left comprises GvpB (*B. megaterium*); the construct in the middle comprises GvpA (*A. floc-aquae*); the construct on the right comprises GvpA and GvpC (*A. floc-aquae*). The structural genes comprised in an exemplary GVGC referred to herein as Acoustic Reporter Gene 1 (ARG1) shown on the right, in which ARG1 comprises *A. floc-aquae* structural genes GvpA and GvpC. Panels B-F are organized in columns (left, middle, right) corresponding to each of the constructs shown in Panel A. Panel B shows exemplary ultrasound images of agarose phantoms containing *E. coli* expressing each construct or GFP. The cell concentration is $10^9$ cells/ml. Images in bottom images of Panel B were acquired after acoustic collapse. Dotted outlines indicate the location of each specimen. The vertical bar on the right represents linear signal intensity of the images in Panel B (0-50). Panel C shows exemplary TEM images of representative *E. coli* cells expressing each construct. Panel D shows exemplary TEM images of gas vesicles isolated from *E. coli* expressing each construct. Panel E shows graphs reporting mass of GV proteins obtained from *E. coli* cultures expressing each construct (N=3 per sample). Panel F shows exemplary images of *E. coli* expressing each construct in liquid culture. Arrow points to the meniscus layer, where the ARG1 construct contains buoyant cells. Scale bars represent 2 mm in Panel B, 500 nm in Panel C and 250 nm in Panel D. Error bars represent±S.E.M.

In some embodiments where imaging is performed by ultrasound, a hybrid GV gene cluster comprising a combination of the structural GvpA gene from *A. floc-aquae* with the expression-enabling secondary GVA genes GvpR-U from *B. megaterium* (FIG. 2 Panel A, middle) results in the formation of gas vesicles with characteristics favorable for ultrasound. Indeed, in exemplary embodiments described herein, expression of this hybrid gene cluster results in *E. coli* with robust ultrasound contrast compared to green fluorescent protein (GFP) controls (FIG. 2 Panel B, middle). This exemplary GV gene cluster produces gas vesicles with significantly larger dimensions compared to the *B. megaterium* operon and appear to occupy a greater fraction of intracellular volume (FIG. 2 Panels C-D, middle). In other exemplary embodiments described herein, the addition of a gene encoding the *A. floc-aquae* scaffolding protein GvpC (FIG. 2 Panel A, right) can further enhance the production of larger gas vesicles (FIG. 2, Panels C-D, right), resulting in wider and more elongated nanostructures resembling those native to *A. floc-aquae* [47], and producing stronger ultrasound contrast (FIG. 2 Panel B, right). This exemplary GVGC construct is referred to herein as ARG1 or acoustic reporter gene 1, used herein in exemplary ultrasound imaging methods (see e.g., Examples 1-7).

In particular, in exemplary embodiments where imaging is performed by ultrasound, the hybrid GV gene cluster can comprise *B. megaterium* GVA genes GvpR, GvpN, GvpF, GvpG, GvpL, GvpS, GvpK, GvpJ, GvpT and GvpU and further comprise structural GV proteins genes from *Anabaena floc-aquae* such as GvpA and optionally GvpC (see Example 1). In other embodiments, the hybrid GV gene cluster can comprise *B. megaterium* GVA genes GvpR, GvpN, GvpF, GvpG, GvpL, GvpS, GvpK, GvpJ, GvpT and GvpU and further comprise structural GV protein gene GvpA from *Bukholderia thailandensis* or *Psychromonas ingrahamii*.

Figure 14:
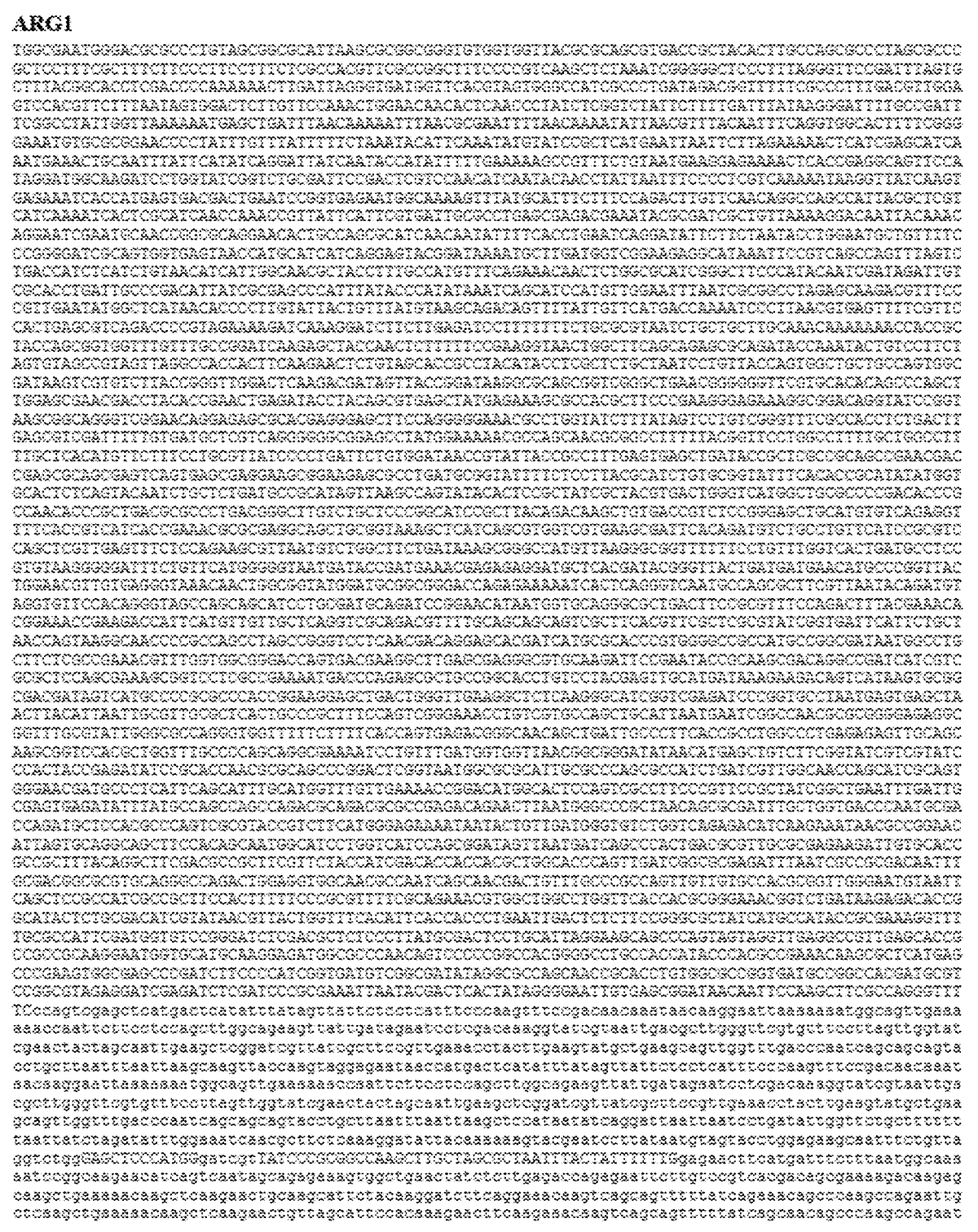
Figure 15:
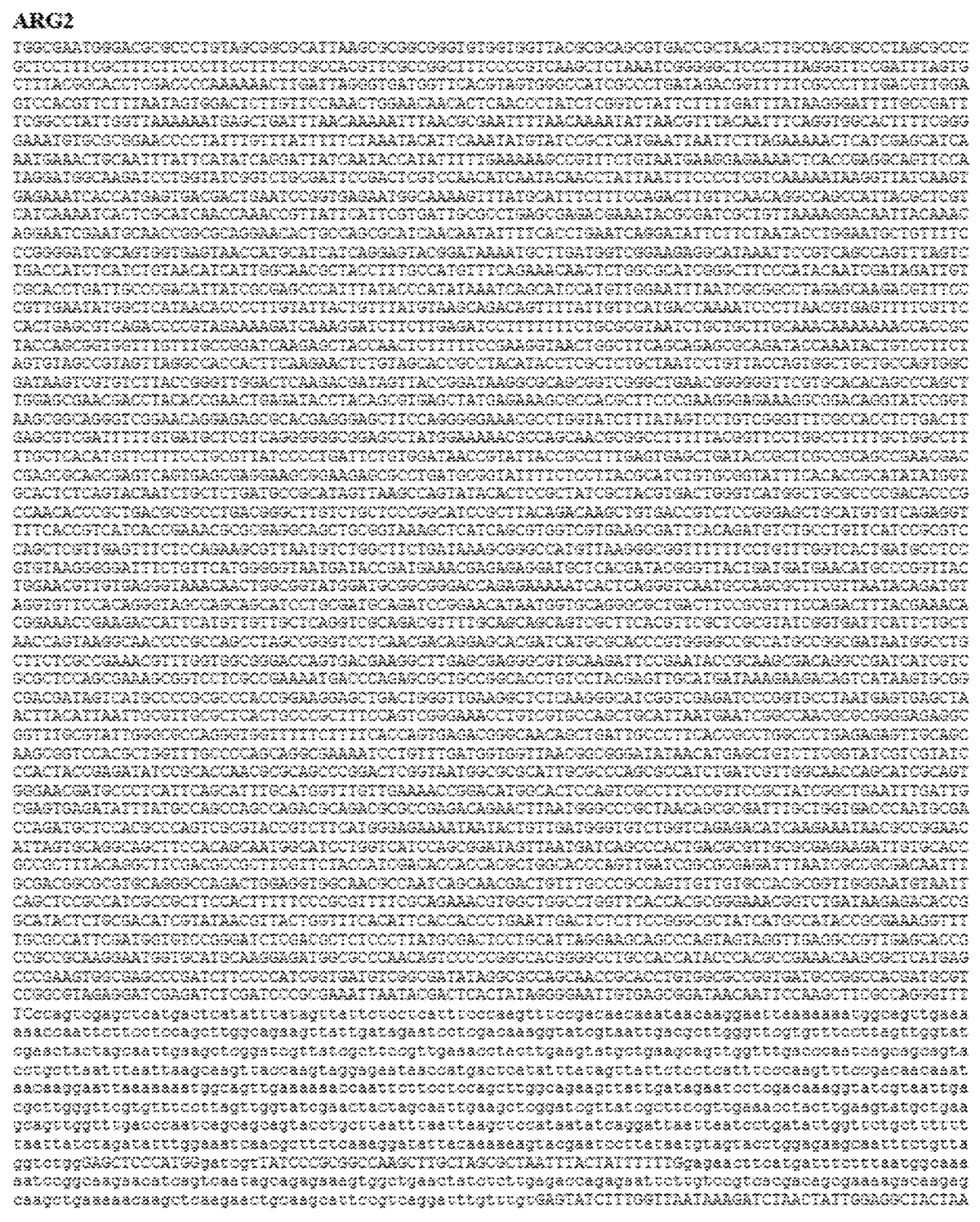

The DNA sequences of the exemplary constructs of hybrid GV clusters encoding acoustic reporter gene 1 (ARG1; SEQ ID NO: 16) and an exemplary variant of ARG1 referred to herein as acoustic reporter gene 2 (ARG2; SEQ ID NO:17) are shown in FIG. 14 and FIG. 15.

In some embodiments, a method is described to provide a magnetic resonance imaging and an ultrasound imaging of one or more biochemical events in a prokaryotic cell comprised in an imaging target site, the method comprising:

introducing into the prokaryotic cell a hybrid gas vesicle reporter gene cluster (GVGC) encoding a gas vesicle (GV) type to provide a reportable genetic molecular component of a GVR genetic circuit, in which molecular components are connected one to another in accordance with a circuit design by activating, inhibiting, binding or converting reactions to form a fully connected network of interacting components, wherein in the reportable genetic molecular component the GV type is expressed by the GVR when the GVR genetic circuit operates according to the circuit design in response to the one or more biochemical events, wherein the GV type has a selectable acoustic collapse pressure value derived from an acoustic collapse pressure profile of the GV type, imaging the target site comprising the prokaryotic cell, wherein the target site comprises water having a water susceptibility and the GV type has an associated susceptibility and relaxivity property distinct from water and a selectable acoustic collapse pressure value derived from an acoustic collapse pressure profile of the GV type, the imaging performed by applying an external magnetic field to the target site to obtain a MRI image by detecting relaxivity of the water in the target site, and imaging the target site by applying imaging ultrasound to the target site to obtain an ultrasound image of the target site, the imaging ultrasound applied an imaging ultrasound pressure lower than a selectable acoustic collapse pressure value of the GV type.

In methods herein described, administration of one or more genetically engineered bacterial cell types comprising one or more GVR genetic circuits to a target site to be imaged, can be performed in any way suitable to deliver the one or more bacterial cells comprising a GVR genetic circuit to the target site to be imaged.

In some embodiments, in which the target site is the body of an individual or a part thereof, the one or more genetically engineered bacterial cell types comprising a GVR genetic circuit can be administered to the target site locally or systemically.

The wording "local administration" or "topic administration" as used herein indicates any route of administration by which the one or more genetically engineered bacterial cell types comprising a GVR genetic circuit is brought in contact with the body of the individual, so that the resulting location of the one or more genetically engineered bacterial cell types comprising a GVR genetic circuit in the body is topic (limited to a specific tissue, organ or other body part where the imaging is desired). Exemplary local administration routes include injection into a particular tissue by a needle, gavage into the gastrointestinal tract, and spreading a solution containing the one or more genetically engineered bacterial cell types comprising a GVR genetic circuit on a skin surface.

The wording "systemic administration" as used herein indicates any route of administration by which the one or more genetically engineered bacterial cell types comprising a GVR genetic circuit is brought in contact with the body of the individual, so that the resulting location of the one or more genetically engineered bacterial cell types comprising a GVR genetic circuit in the body is systemic (not limited to a specific tissue, organ or other body part where the imaging is desired). Systemic administration includes enteral and parenteral administration. Enteral administration is a systemic route of administration where the substance is given via the digestive tract, and includes but is not limited to oral administration, administration by gastric feeding tube, administration by duodenal feeding tube, gastrostomy, enteral nutrition, and rectal administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion.

Accordingly, in some embodiments of methods herein described, administering the one or more genetically engineered bacterial cell types comprising a GVR genetic circuit can be performed topically or systemically by intradermal, intramuscular, intraperitoneal, intravenous, subcutaneous, intranasal, rectal, vaginal, and oral routes. In particular, the one or more genetically engineered bacterial cell types comprising a GVR genetic circuit can be administered by infusion or bolus injection, and can optionally be administered together with other biologically active agents. In some embodiments of methods herein described, administering the one or more genetically engineered bacterial cell types comprising a GVR genetic circuit can be performed by injecting the one or more genetically engineered bacterial cell types comprising a GVR genetic circuit such as in a body cavity or lumen. Upon expression of one or more GV types in one or more genetically engineered bacterial cell types comprised in the target site, the target site can be contrast imaged.

Accordingly, in some embodiments, a vector comprising one or more genetic molecular components of a GVR genetic circuit is described, wherein the vector is configured to introduce the one or more genetic molecular components comprised in a GVR genetic circuit into a prokaryotic cell.

The term "vector" indicates a molecule configured to be used as a vehicle to artificially carry foreign genetic material into a cell, where it can be replicated and/or expressed. An expression vector is configured to carry and express the material in a cell under appropriate conditions. In some embodiments, a suitable vector can comprise a recombinant plasmid, a recombinant non-viral vector, or a recombinant viral vector. Vectors described herein can comprise suitable promoters, enhancers, post-transcriptional and post-translational elements for expression in bacteria that are identifiable by those skilled in the art. Vectors suitable for transduction of prokaryotic cells, and in particular various Gram negative bacterial cell types are known to those skilled in the art. In exemplary embodiments herein described, bacterial expression plasmids contain all the necessary components to allow cloning methods using *E. coli*, and comprise elements such as a bacterial origin of replication (ORI) and elements for plasmid maintenance such as antibiotic selection markers and toxin-antitoxin systems, and also optionally to allow incorporating the genes into the bacterial genome using recombinases such as Lambda Red, and others identifiable by those skilled in the art.

Exemplary vectors for bacterial transformation of *E. coli* and *S. typhimurium* with genetic molecular components comprising GV gene clusters are described herein in the Examples.

Accordingly, in some embodiments herein described, a genetically engineered prokaryotic cell and in particular a genetically engineered prokaryotic cell comprising one or more GVR genetic circuits is described. In embodiments described herein, any type of Gram negative bacterial cell can be genetically engineered to comprise one or more GVR genetic circuits herein described.

In particular, as described above, prokaryotic cells that do not natively express GVs, or bacterial or archaeal cells in which native expression of GVs has been suppressed, for example through genetic knockout techniques known to those skilled in the art, can be used for heterologous expression of the GVR genetic circuits described herein. In embodiments herein described, exemplary species of bacteria engineered to express GV types comprised in GVR genetic circuits described herein are *E. coli* and *S. typhimurium* (see Examples). In some embodiments, bacteria that can be engineered to express GV types comprised in GVR genetic circuits described herein comprise any type of Gram negative bacteria, such as *E. coli*, Nissle 1997, and *Salmonella*. Additional species of bacteria that can be used for heterologous expression of GVs described herein are identifiable by those skilled in the art.

In embodiments herein described, a composition is provided. The composition comprises one or more genetic molecular components of a GVR genetic circuit, vectors, or genetically engineered prokaryotic cells described herein together with a suitable vehicle.

The term "vehicle" as used herein indicates any of various media acting usually as solvents, carriers, binders or diluents for the one or more genetic molecular components, vectors, or prokaryotic cells herein described that are comprised in the composition as an active ingredient. In particular, the composition including the one or more genetic molecular components, vectors, or prokaryotic cells herein described can be used in one of the methods or systems herein described.

In some embodiments, one or more Gvp genes in the GV gene cluster comprised in a genetic molecular component of a GVR genetic circuit can be engineered to produce GVs with altered mechanical, acoustic, surface and targeting properties in order to achieve enhanced harmonic responses and multiplexed imaging to be better distinguished from background tissues. In particular in those embodiments, a GvpC gene encoded in a GVGC gene cluster can be engineered to provide a variant GvpC protein and corresponding variant GV type, as described in U.S. application Ser. No. 15/613,104, filed on Jun. 2, 2017. In exemplary embodiments described herein, GvpC genes in GVGC gene clusters herein described are engineered to produce genetically encoded GVs in exemplary GVGC constructs ARG1 and ARG2 having different acoustic collapse pressure values (see Example 4).

In some embodiments, a GV can be engineered to tune the related acoustic properties. In particular the engineering can be performed by genetically engineering a GV having an acoustic collapse pressure $aP_0$ performed to obtain a variant GV with a critical collapse pressure $aP_1$ lower than the $aP_0$.

In some embodiments of methods to tune the acoustic properties of a GV, the genetically modified GvpC protein can be modified by at least one of a) a deletion of the N-terminal region, C-terminal region or both b) a deletion of 3 or more repeats, in particular starting from the repeat adjacent to the C-terminus and moving towards the N-terminus c) a deletion of at least one repeat immediately after the N-terminus, and d) addition of amino acids such as functional tags e) substitution of a sub-sequence comprising at least nine amino acids within the GvpC sequence, wherein the substitution refers to replacement of amino acids in the original GvpC sequence with any other amino acid sequence, particularly with other amino acid sequence having sequence similarity lower than 50% with respect to the sub-sequence within the GvpC sequence, to obtain a gas vesicle variant with a critical collapse pressure $aP_1$ lower than the $aP_0$.

In some embodiments, a deletion can comprise a deletion of up to all of the amino acids of an N-terminal region, one or more repeat regions, or a C-terminal region. In some embodiments, a deletion can comprise a deletion of part of one or more of an N-terminal region, a C-terminal region, or a repeat region. For example, a deletion can comprise part of region 2 and part of repeat region 3, as shown in the Examples (exemplary variant N-rep2to3-C). In some embodiments, a deletion can comprise a deletion of more than one repeat region.

In some embodiments, a deletion of a gvpC N-terminal region or a C-terminal region can produce a gvpC variant comprised in a GV having a lower $aP_1$ than a deletion of a gvpC repeat region.

In some embodiments, a deletion of a gvpC N-terminal deletion can produce a gvpC variant comprised in a GV having a lower $aP_1$ than a deletion of a gvpC C-terminal deletion.

In some embodiments, a deletion of both a gvpC N-terminal region and a gvpC C-terminal region can produce a gvpC variant comprised in a GV having a lower $aP_1$ than a deletion of a gvpC N-terminal region or a C-terminal region performed individually.

In some embodiments, a deletion of one or more repeats regions that are in a position further towards the gvpC N-terminus can produce a gvpC variant comprised in a GV having a lower $aP_1$ than a deletion of one or more repeats regions that are in a position further towards the gvpC C-terminus.

In some embodiments herein described, GV variants without GvpC proteins or with truncated or mutated GvpC proteins exhibit lower collapse pressure compared to the native GVs under both hydrostatic pressure and ultrasound (Example 2 of U.S. application Ser. No. 15/613,104 filed on Jun. 2, 2017).

For example, the native Ana GVs have a hydrostatic collapse pressure about 569.85 kPa, while the Ana GV variants free of GvpC proteins and the Ana GV variants with truncated GvpC proteins have a hydrostatic collapse pressure about 195.30 kPa and 374.30 kPa, respectively (see Table 5 of U.S. application Ser. No. 15/613,104 filed on Jun. 2, 2017). The native Ana GVs have an acoustic collapse pressure about 868.81 kPa, while the Ana GV variants free of GvpC proteins and the Ana GV variants with truncated GvpC proteins have a hydrostatic collapse pressure about 571.00 kPa and 657.04 kPa, respectively (see Table 7 of U.S. application Ser. No. 15/613,104 filed on Jun. 2, 2017).

In some embodiments described herein, a variant GV can be obtained using a method of directed evolution, and the resulting GV selected using a method of high-throughput screening. The term "directed evolution" means a process wherein random mutagenesis is applied to a protein (e.g. gvpA and gvpC), and a selection regime is used to pick out variants that have the desired qualities, such as selecting for an altered collapse pressure value. In addition, for example, screening of directed evolution gvpA variants can be performed to select GVs having different (e.g. higher) T2/T2* signal for MRI imaging modalities. Accordingly, polynucleotides encoding gvP proteins as described herein can be genetically mutated using recombinant techniques known to those of ordinary skill in the art, including by site-directed mutagenesis, or by random mutagenesis such as by exposure to chemical mutagens or to radiation, as known in the art. The advantage of directed evolution is that it requires no prior structural knowledge of a protein, nor is it necessary to be able to predict what effect a given mutation will have. In particular, directed evolution can be performed to detect gene mutations resulting in increased harmonic signal (reduced mechanical stiffness of GVs) for ultrasound, and/or for producing a higher T2/T2* signal in MRI imaging.

An example of high-throughput screening of variant GV types expressed in genetically engineered bacteria is shown in Example 5.

In some embodiments, GV variants without GvpC proteins or with truncated or mutated GvpC proteins show harmonic signals several-fold higher than the native GVs both in vitro and in vivo.

Figure 9:
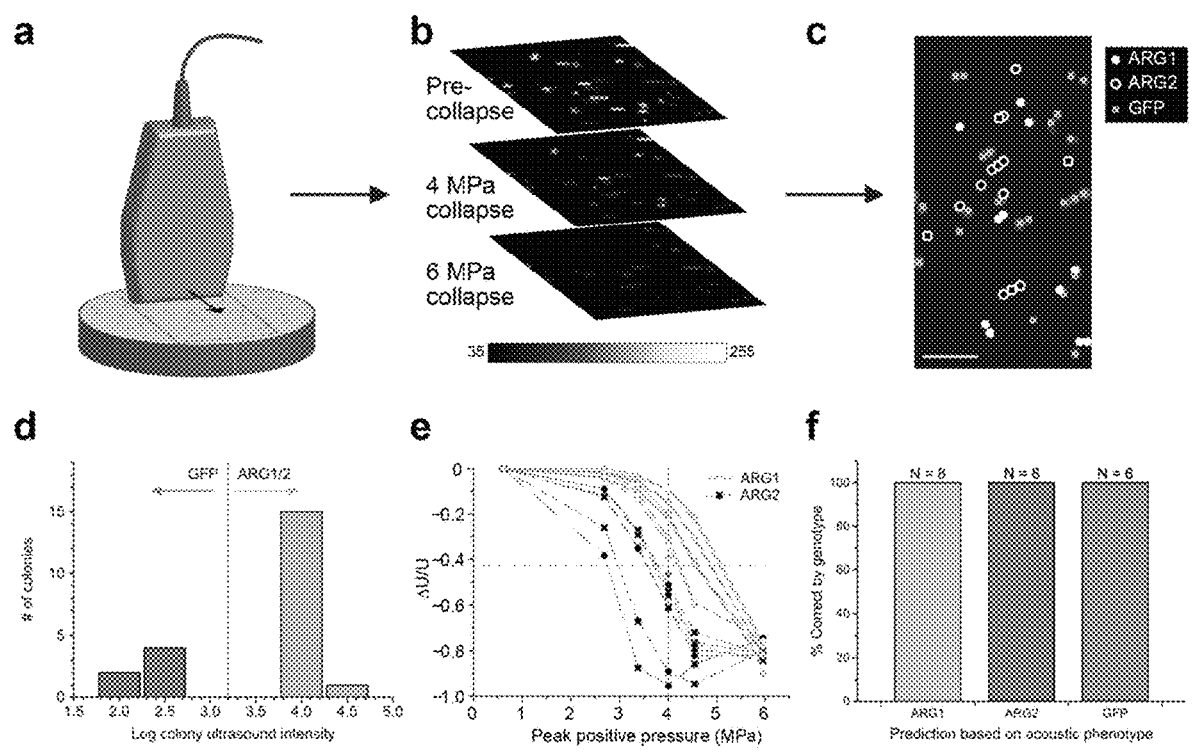
FIG. 9 shows an exemplary illustration and exemplary data of high throughput screening of acoustic phenotypes. Panel A shows an exemplary illustration of acoustic colony screening. In the illustration, bacteria plated on agar are scanned with an ultrasound transducer that collects images and applies various peak pressures for acoustic collapse. An image of the 2D colony surface perpendicular to the transducer is computed from a series of contiguous images acquired in the transducer's imaging plane. Panel B shows exemplary colony ultrasound images of a mixed population of ARG1, ARG2, and GFP expressing *E. coli* colonies. Images were acquired before collapse and after collapse at 4.0 and 6.0 MPa peak acoustic pressures. Panel C shows an exemplary image of predicted genotypes of each colony based on the acoustic phenotype seen in the images in Panel B. Panel D shows an exemplary ultrasound intensity histogram of 22 randomly picked colonies. Colonies with low contrast were predicted to be GFP and those with high contrast to be ARG1 or ARG2. Panel E shows a graph reporting normalized change in ultrasound intensity for each of the randomly picked colonies after insonation at increasing pressures. At 4 MPa, colonies with signal above the indicated threshold were predicted to be ARG1 and below to be ARG2. Panel F shows an exemplary graph reporting confirmation by sequencing of predicted genotypes indicated in Panels D and E. Scale bar represents 10 mm.
Figure 11:
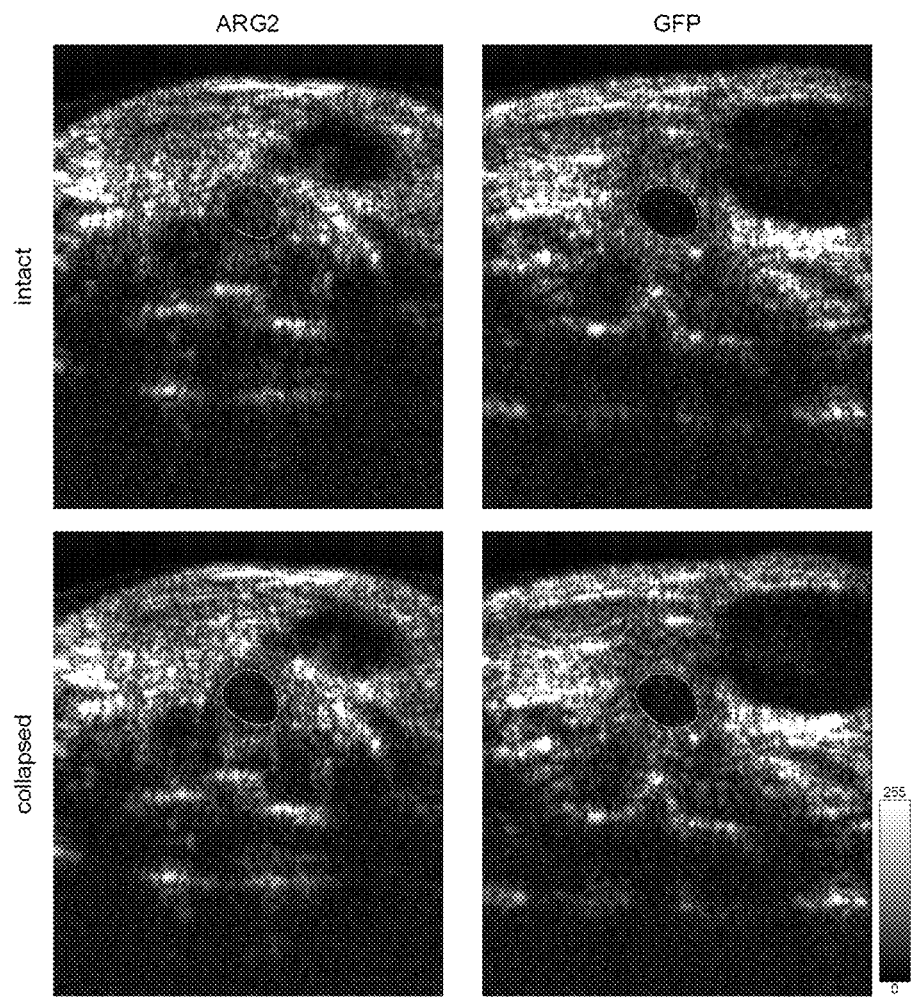
FIG. 11 shows exemplary anatomical ultrasound images of bacteria expressing GVGC in the gastrointestinal tract. Shown are raw images underlying the difference map shown in FIG. 10. The circle outline identifies the colon region of interest for difference processing.

As used herein, the term "harmonic signal" or "harmonic frequency" refers to a frequency in a periodic waveform that is an integer multiple of the frequency of the fundamental signal. In addition, this term encompasses sub-harmonic signals, which are signals with a frequency equal to an integral submultiple of the frequency of the fundamental signal. In ultrasound imaging, the transmitted pulse is typically centered around a fundamental frequency, and received signals may be processed to isolate signals centered around the fundamental frequency or one or more harmonic frequencies. In relation to the imaging of GVs, for those natural or modified GVs that are capable of producing harmonic scattering at a particular acoustic pressure, isolating received harmonic signals during imaging can improve the fraction of the image signal that is due to the GVs rather than background scattering and reflection. Exemplary GV variants showing show harmonic signals several fold higher than the native GVs comprise GV variants such as ΔGvpC, ΔN&C-term, ΔN-term, ΔC-term, SR1, SR3, ST-GvpC, GvpC-R8, GvpC-RGD, GvpC-LRP, GvpC-mCD7, SR1CERY1, SR3CERY1, ΔN&C-CERY1, WTCERY1, GvpC-ACPP, GvpC-hPRM, N-term-rep1to2-C-term, Nterm-rep1to3-C-term, N-term-rep2to3-C-term and N-term-rep1to4-C-term in U.S. application Ser. No. 15/613,104. FIG. 9 of U.S. application Ser. No. 15/613,104 shows exemplary images and graphed results showing that GV engineering enables modulation of harmonic signals in vivo. FIG. 11 of U.S. application Ser. No. 15/613,104 filed on Jun. 2, 2017 shows an exemplary Clustal Omega sequence alignment of exemplary genetically engineered GvpC proteins described therein.

The term "fundamental signal" or "fundamental wave" refers to the primary frequency of the transmitted ultrasound pulse.

The term "non-linear signal" refers to a signal that does not obey superposition and scaling properties, with regards to the input. The term "linear signal" refers to a signal that does obey those properties. One example of non-linearity is the production of harmonic signals in response to ultrasound excitation at a certain fundamental frequency. Another example is a non-linear response to acoustic pressure. One embodiment of such a non-linearity is the acoustic collapse profile of GVs, in which there is a non-linear relationship between the applied pressure and the disappearance of subsequent ultrasound contrast from the GVs as they collapse. Another example of a non-linear signal that does not involve the destruction of GVs, is the increase in both fundamental and harmonic signals with increasing pressure of the transmitted imaging pulse, wherein certain GVs exhibit a super-linear relationship between these signals and the pulse pressure. [48]

In some embodiments, the engineered GvpC variants are obtained by further linking the native GvpC protein to one or more other proteins, polypeptides, or domains to form a recombinant fusion protein.

Recombinant fusion proteins can be created artificially using recombinant DNA technology identifiable by a person skilled in the art of molecular biology. In general, the methods for producing recombinant fusion proteins comprise removing the stop codon from a cDNA or genomic sequence, such as a polynucleotide coding for a GvpC protein or a derivative thereof, then appending the cDNA or genomic sequence of the second protein in frame through ligation or overlap extension PCR. Optionally, PCR primers can further encode a linker of one or more amino acids residues and/or a PCR primer-encoded protease cleavage site placed between two proteins, polypeptides, or domains or parts thereof. The resulting DNA sequence will then be expressed by a prokaryotic cell as a single protein. A fusion protein can also comprise a linker of one or more amino acids residues, which can enable the proteins to fold independently and retain functions of the original separate proteins or polypeptides or domains or parts thereof. Linkers in protein or peptide fusions can be engineered with protease cleavage sites that can enable the separation of one or more proteins, polypeptides, domains or parts thereof from the rest of the fusion protein. Other methods for genetically engineering these recombinant fusion proteins include Site Directed Mutagenesis (e.g. using Q5 Site-Directed Mutagenesis Kit from NEB or the QuickChange Lightning Kit from Agilent), Gibson Assembly (e.g. using the NEB Hi-Fi DNA Assembly Kit), Error-prone PCR (e.g. Mutazyme from Agilent) and Golden-Gate assembly (e.g. using the NEB Golden Gate Assembly Mix).

In some embodiments, a gvpC variant can be produced by engineering a gvpC protein from any species that encodes a gvpC protein in its genome, or a synthetically designed gvpC protein. In some embodiments, a gvpC protein is a gvpC protein from *Anabaena floc-aquae, Halobacterium salinarum, Halobacterium mediterranei, Microchaete diplosiphon* or *Nostoc* sp., or homologs thereof, and others identifiable by a skilled person.

In some embodiments herein described one or more GVs (including variants GVs) can be engineered to include one or more protein tags to provide the GV with additional functionalities. In particular, in some embodiments GVs can be functionalized through genetic modification of a Gvp protein (including variants GvpC protein herein described).

In particular, in some embodiments herein described, one or more protein tags can be added through genetic modification of a GvpC protein or a variant thereof in accordance with the present disclosure of a set type of GV.

The term "tag" as used herein means protein tags comprising peptide sequences introduced onto a recombinant protein. Tags can be removable by chemical agents or by enzymatic means, such as proteolysis or splicing. Tags can be attached to proteins for various purposes: Affinity tags are appended to proteins so that they can be purified from their crude biological source using an affinity technique. These include chitin binding protein (CBP), and the poly(His) tag. The poly(His) tag is a widely-used protein tag; it binds to metal matrices. Chromatography tags can be used to alter chromatographic properties of the protein to afford different resolution across a particular separation technique. Often, these consist of polyanionic amino acids, such as FLAG-tag.

Epitope tags are short peptide sequences which are chosen because high-affinity antibodies can be reliably produced in many different species. These are usually derived from viral genes, which explain their high immunoreactivity. Epitope tags include V5-tag, Myc-tag, HA-tag and NE-tag. These tags are particularly useful for western blotting, immunofluorescence and immunoprecipitation experiments, although they also find use in antibody purification. Protein tags can allow specific enzymatic modification (such as biotinylation by biotin ligase) or chemical modification (such as reaction with FlAsH-EDT2 for fluorescence imaging). Tags can be combined, in order to connect proteins to multiple other components. However, with the addition of each tag comes the risk that the native function of the protein may be abolished or compromised by interactions with the tag. Therefore, after purification, tags are sometimes removed by specific proteolysis (e.g. by TEV protease, Thrombin, Factor Xa or Enteropeptidase).

Exemplary tags comprise the following, among others known to persons skilled in the art: Peptide tags, such as: AviTag, a peptide allowing biotinylation by the enzyme BirA and so the protein can be isolated by streptavidin (GLNDIFEAQKIEWHE (SEQ ID NO:18)); Calmodulin-tag, a peptide that can be bound by the protein calmodulin (KRRWKKNFIAVSAANRFKKISSSGAL (SEQ ID NO:19)); polyglutamate tag, a peptide binding efficiently to anion-exchange resin such as Mono-Q (EEEEEE (SEQ ID NO:20)); E-tag, a peptide recognized by an antibody (GAPVPYPDPLEPR (SEQ ID NO:21)); FLAG-tag, a peptide recognized by an antibody (DYKDDDDK (SEQ ID NO:22)); HA-tag, a peptide from hemagglutinin recognized by an antibody (YPYDVPDYA (SEQ ID NO:23)); His-tag, typically 5-10 histidines that can be bound by a nickel or cobalt chelate (HHHHHH (SEQ ID NO:24)); Myc-tag, a peptide derived from c-myc recognized by an antibody (EQKLISEEDL (SEQ ID NO:25)); NE-tag, a novel 18-amino-acid synthetic peptide (TKENPRSNQEESYDD-NES (SEQ ID NO:26)) recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, a peptide derived from Ribonuclease A (KETAAAKFERQHMDS (SEQ ID NO:27)); SBP-tag, a peptide which binds to streptavidin (MDEKTTGWRGGHVVEGLAGELEQLRAR-LEHHPQGQREP (SEQ ID NO:28)); Softag 1, for mammalian expression (SLAELLNAGLGGS (SEQ ID NO:29)); Softag 3, for prokaryotic expression (TQDPSRVG (SEQ ID NO:30)); Strep-tag, a peptide which binds to streptavidin or the modified streptavidin called streptactin (Strep-tag II: WSHPQFEK (SEQ ID NO:31)); TC tag, a tetracysteine tag that is recognized by FlAsH and ReAsH biarsenical compounds (CCPGCC (SEQ ID NO:32)); V5 tag, a peptide recognized by an antibody (GKPIPNPLLGLDST (SEQ ID NO:33)); VSV-tag, a peptide recognized by an antibody (YTDIEMNRLGK (SEQ ID NO:34)); Xpress tag (DLYDD-DDK (SEQ ID NO:35)); Covalent peptide tags such as: Isopeptag, a peptide which binds covalently to pilin-C protein (TDKDMTITFTNKKDAE (SEQ ID NO:36)); Spy-Tag, a peptide which binds covalently to SpyCatcher protein (AHIVMVDAYKPTK (SEQ ID NO:37)); SnoopTag, a peptide which binds covalently to SnoopCatcher protein (KLGDIEFIKVNK (SEQ ID NO:38)).

In some embodiments, GvpC can be tagged to alter sub-cellular localization of intracellularly expressed GVs to specific bacterial cell compartments, such as the cell membrane (e.g. with myristoylation tags or palmitoylation tags). An exemplary myristoylation tag from Src Kinase has the sequence GSSKSKPKDPSQR (SEQ ID NO:39). An exemplary palmitoylation tag from GAP43 has the sequence MLCCMRRTKQVEKNDEDQKI (SEQ ID NO:40)

In some embodiments, GvpC proteins can be tagged to allow clustering of expressed GV types in genetically engineered bacterial cells. Exemplary tags allowing clustering comprise homodimerizing proteins such as coiled coils or dimeric fluorescent proteins.

In embodiments described herein, any of the tags of SEQ ID NO:18-40, and other tags described herein and identifiable by those skilled in the art, can comprise one or more amino acid substitutions, insertions, or deletions that do not alter the function of the tag, and can further comprise one or more additional amino acids, up to a maximum tag length of 100 amino acids.

In embodiments described herein a GvpC or a variant gvpC can be engineered to attach a tag fused to or inserted into an N-terminal region, a C-terminal region of a gvpC or a variant gvpC.

In some embodiments, engineering of a GvpC to attach one or more tags can be performed with or without substantially alter the critical collapse pressure of the base GvpC.

For example in some embodiments described herein, a GvpC protein of a GV can be engineered to attach one or more protein tags or polypeptide tags while optionally substantially altering the acoustic collapse pressure of a GV shell comprising the engineered GvpC as compared to a GV shell of a same non-engineered GvpC.

The term "substantially alter" or "substantially decrease" as used herein means a decrease of more than 10% in acoustic collapse pressure, preferably more than 20% in acoustic collapse pressure.

In some embodiments described herein, an engineered GvpC protein can comprise one or more protein tags or polypeptide tags. In embodiments described herein, appending functional residues comprising one or more polypeptide tags or protein tags to the N-terminus or the C-terminus of GvpCWT can reduce collapse pressure depending on the length and exact properties of the amino acid sequence.

In particular, in some embodiments, engineering of a GvpC can be further engineered to attach one or more tags up to the C-terminus without substantially alter the critical collapse pressure as compared to deleting the N- and/or C-terminal regions. In some embodiments, small tags such as RGD and RDG do not substantially alter the collapse pressure value. In some embodiments, tags comprising longer sequences such as LRP (100 residues) decrease acoustic collapse pressure to a greater extent. In some embodiments, tags such as those comprising mCD47 cause a substantial decrease in acoustic collapse pressure value. In some embodiments, appending a His-Tag (e.g. 6 His amino acids) to the N-terminus of the wild-type GvpC sequence does not substantially alter the acoustic collapse pressure value. In some embodiments, appending a gvpC with a Spytag (FIG. 12 of U.S. application Ser. No. 15/613,104 filed on Jun. 2, 2017) is an effective method to functionalize GVs with large molecules (greater than 100 amino acids in length) such as fluorescent proteins, without substantially altering their collapse pressure value.

In some embodiments, an in-frame insertion or C- or N-terminal fusion of a protein tag to a gvpC or a variant gvpC can be performed in an N- or C-terminal region of a gvpC or a variant gvpC. An in-frame insertion can be performed in several steps, by first providing the gvpC- or variant gvpC-coding and the protein tag-coding polynucleotides and performing the insertion by breaking a bond (typically a phosphodiester bond) between two adjacent nucleotide bases of the first polynucleotide and then forming new bonds between the gvpC-coding polynucleotide and the protein tag-coding polynucleotide. For example, the gvpC coding polynucleotide can be digested with one or more restriction endonucleases and then the protein tag-coding polynucleotide inserted by ligation (e.g., using T7 DNA ligase) into compatible site(s) allowing formation of phosphodiester bonds between the first and second polynucleotide bases. Compatible DNA ligation sites can be "sticky" ends, digested with restriction endonuclease producing an overhang (e.g. EcoRI), or can be "blunt ends" with no overhang, as would be understood by those skilled in the art. A fusion of a polynucleotide encoding a tag can also be ligated to an N- or C-terminus of a gvpC or a variant gvpC polynucleotide by ligation (e.g., using T7 DNA ligase) into compatible site(s).

In some embodiments, the gvpC- or variant gvpC-coding and the protein tag-coding polynucleotides can be provided within a single polynucleotide by design. For example, a tag can be added by inserting the polynucleotide encoding a protein of interest in a plasmid or vector that has the tag ready to fuse at the N-terminus or C-terminus. The tag can be added using PCR primers encoding the tag; using PCR the tag can be fused to the N-terminus or C-terminus of the protein-coding polynucleotide, or can be inserted at an internal location, using internal epitope tagging [49], among other methods known to those skilled in the art. Other methods such as overlap extension PCR and infusion HD cloning can be used to insert a tag at a site between the N-terminus and C-terminus of a protein-coding polynucleotide (see Examples of U.S. application Ser. No. 15/613,104). Optionally, a polynucleotide encoding a 'linker' (such as a sequence encoding a short polypeptide or protein sequence, e.g., gly-gly-gly or gly-ser-gly can be placed between the protein of interest and the tag; this can be useful to prevent the tag from affecting the activity of the protein being tagged.

The choice of the location where a tag is added to a protein sequence depends mainly on the structural and functional features of a protein and the intended downstream methods employing the use of the tag.

In embodiments herein described, the insertion location of a protein tag in a genetically engineered gvpC or variant gvpC is performed at insertion position selected to have the tag presented on the external surface-exposed position of the gvpC or variant gvpC.

Accordingly, in embodiments described herein, GVR genetic circuits comprising genetically-encoded GV types can be used together with contrast-enhanced imaging techniques such as ultrasound imaging and/or MRI to detect the location of and/or dynamic biochemical events in prokaryotic cells in an imaging target site, wherein the prokaryotic cells have been genetically engineered to comprise one or more GVR genetic circuits described herein.

In some exemplary embodiments, this allows monitoring the activity of various natural and engineered signaling circuits in prokaryotic cells, such as bacterial cells. Furthermore, the ability to distinguish different prokaryotic cell type populations, such as bacterial populations through acoustic multiplexing of distinct expressed GV types in some embodiments allows the study of complex bacterial population dynamics or the monitoring of multiple engineered therapeutic or diagnostic agents.

In some exemplary embodiments described herein, imaging of engineered bacterial cells expressing GV types in vivo allows imaging of engineered bacteria in target sites such as gastrointestinal tract and tumors (see Examples 6-7). As understood by those skilled in the art, studies of the mammalian microbiome are uncovering an increasing number of critical roles for bacteria in health and disease, ranging from infection and immunity to nervous system function [50-53]. Additionally, advances in synthetic biology and genome engineering have led to the development of microbial therapeutics and diagnostics for diseases such as gastrointestinal inflammation and cancer [54-63]. The function of both natural and engineered microbes depends strongly on their anatomical location within the host organism, making it important to monitor their spatial distribution, viability, proliferation and function inside the body [64-66]. Such monitoring requires reporter genes that can be produced by proliferating prokaryotic cells and connected to specific genetic circuits. However, conventional reporters based on fluorescent and luminescent proteins or radionuclide capture suffer from the poor penetration of light into tissue or the need to administer radioactive tracers [67-69]. In contrast to these techniques, ultrasound and MRI are widely available, inexpensive, radiation-free technologies capable of noninvasively imaging deep tissues [70]. For example, the spatial resolution of ultrasound is routinely on the order of 100 µm [71, 72] and can approach the single-micron level with recently developed super-resolution techniques [73]. With these performance characteristics and the ability to place signals within an anatomical context, ultrasound is an ideal technique for imaging microbes in vivo.

As described herein, hybrid GVGCs and related GVR genetic circuits, vectors, genetically engineered bacterial cells, compositions, methods and systems can be used in several embodiments to detect biochemical events in prokaryotic cells using ultrasound imaging or MRI. In particular embodiments, the hybrid GVGCs and related genetic circuits, vectors, genetically engineered bacterial cells, compositions, methods and systems described herein enable ultrasound imaging or MRI of microbes inside mammalian hosts (see e.g., Example 6-7).

In exemplary embodiments described herein, hybrid GVGCs are provided by engineering gas vesicle operons for efficient expression in *Escherichia coli* and *Salmonella typhimurium*—two exemplary commensal and pathogenic species that are also chasses for the development of microbial therapeutics. In some embodiments described herein, GV type-expressing prokaryotic cells can be visualized in vivo in settings relevant to gastrointestinal (GI) colonization and antitumor therapy. In exemplary embodiments described herein, expression of GV types can make prokaryotic cells visible to ultrasound at volumetric concentrations below 0.01%, allowing dynamic imaging of gene expression and other biochemical events, and allows the visualization of bacteria in vivo, such as in mouse colons and tumor xenografts as shown in the Examples.

In some embodiments described herein, engineered gas vesicle gene clusters are used as reporter genes for ultrasound, giving this widely used noninvasive imaging modality the ability to visualize bacteria inside living animals with sub-100 µm resolution. In several embodiments described herein, hybrid GVGCs allow prokaryotic cells to be detected at concentrations below 0.005% v/v or 100 prokaryotic cells per ultrasound voxel, making this technology relevant to a broad range of studies involving commensal, disease-causing and engineered microbes. In exemplary embodiments described herein, bacteria are imaged in the murine GI tract and tumor xenografts, demonstrating the ability of GVGC-expressing prokaryotic cells to be detected within living animals at relevant concentrations.

In some embodiments, the GVs and variants thereof comprised in GVR genetic circuits described herein can be used as a contrast agent in the multiplexed contrast-enhanced imaging methods herein described (see e.g., Example 4).

In particular, a combination of different GV types and/or variants thereof comprised in GVR genetic circuits, can be used as contrast agents, each expressed GV exhibiting a different acoustic collapse profile with progressively decreased midpoint collapse pressure values. In some cases, the percentage difference between the midpoint collapse pressure values of any given two expressed GVs types is at least twenty percent.

As mentioned above, the hybrid GV gene cluster and related GVR circuit, molecular component, polynucleotidic constructs, vectors, cells and compositions herein described can be provided as a part of systems to perform any of the above mentioned methods. The systems can be provided in the form of kits of parts. In a kit of parts, one or more the hybrid GV gene cluster and related GVR circuit, molecular component, polynucleotidic constructs, vectors, cells and other reagents to perform the methods herein described are comprised in the kit independently. The hybrid GV gene cluster and related GVR circuit, molecular component, polynucleotidic constructs, vectors, cells can be included in one or more compositions, and each the hybrid GV gene cluster and related GVR circuit, molecular component, polynucleotidic construct, vector and cell is in a composition together with a suitable vehicle.

In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (such as. wash buffers and the like).

The hybrid GVGCs, and related genetic circuits, vectors, genetically engineered prokaryotic cells, compositions, methods and systems herein described can be used in several embodiments to provide magnetic resonance imaging with enhanced contrast and molecular sensitivity at sub-nanomolar concentration.

The hybrid GVGCs, and related genetic circuits, vectors, genetically engineered prokaryotic cells, compositions, methods and systems herein described can be used in several embodiments to allow multiplexed imaging using parametric MRI, and differential acoustic sensitivity and background-free MRI when combined with ultrasound.

The hybrid GVGCs, and related genetic circuits, vectors, genetically engineered prokaryotic cells, compositions, methods and systems herein described can be used in several embodiments to detect clustering-induced changes in MRI contrast also enable the design of dynamic molecular sensors.

The hybrid GVGCs, and related genetic circuits, vectors, genetically engineered prokaryotic cells, compositions, methods and systems herein described can be used in several embodiments to allow multiplexing, multimodal detection and/or molecular targeting to help MRI fulfill its potential as a high-performance modality for molecular imaging.

The hybrid GVGCs, and related genetic circuits, vectors, genetically engineered prokaryotic cells, compositions, methods and systems herein described can be used in several embodiments to produce non-toxic, robust MRI contrast via differential magnetic susceptibility at nanomolar concentrations.

The hybrid GVGCs, and related genetic circuits, vectors, genetically engineered prokaryotic cells, compositions, methods and systems herein described can be used in several embodiments to produce dynamic contrast in response to local molecular signals.

The hybrid GVGCs, and related genetic circuits, vectors, genetically engineered prokaryotic cells, compositions, methods and systems herein described can be used in several embodiments to provide ultrasound imaging with enhanced harmonic responses, cellular targeting, multiplexing, multimodal detection and/or molecular targeting to help ultrasound fulfill its potential as a high performance modality for molecular imaging.

The hybrid GVGCs, and related genetic circuits, vectors, genetically engineered prokaryotic cells, compositions, methods and systems as well as GvpC variants herein described can be used in several embodiments to track moving target sites such as bacterial cells within the body of an individual or other environments.

The hybrid GVGCs, and related genetic circuits, vectors, genetically engineered prokaryotic cells, compositions, methods and systems herein described can be used in connection with various applications wherein contrast-enhanced imaging of a target site is desired. For example, the hybrid GVGCs, and related genetic circuits, vectors, genetically engineered prokaryotic cells, compositions, methods and systems herein described can be used for visualization of prokaryotic cells inside a host individual, such as mammalian hosts, facilitating for example the study of the mammalian microbiome and the development of diagnostic and therapeutic prokaryotic cellular agents, among other advantages identifiable by a skilled person, in medical applications, as well diagnostics applications. Additional exemplary applications include uses of the hybrid GVGCs, and related genetic circuits, vectors, genetically engineered prokaryotic cells, compositions, methods and systems herein described in several fields including basic biology research, applied biology, bio-engineering, bio-energy, medical research, medical diagnostics, therapeutics, and in additional fields identifiable by a skilled person upon reading of the present disclosure.

Further details concerning the hybrid GVGCs, and related genetic circuits, engineered bacterial cells and methods of the present disclosure will become more apparent hereinafter from the following detailed disclosure of examples by way of illustration only with reference to an experimental section.

EXAMPLES

The hybrid GVGCs, and related genetic circuits, vectors, genetically engineered prokaryotic cells, compositions, methods and systems herein disclosed are further illustrated in the following examples, which are provided by way of illustration and are not intended to be limiting.

In particular, the following examples illustrate exemplary methods and protocols for providing and using hybrid GVGCs, and related genetic circuits, vectors, genetically engineered prokaryotic cells, compositions, methods and systems. A person skilled in the art will appreciate the applicability and the necessary modifications to adapt the features described in detail in the present section, to additional GVGCs, and related genetic circuits, vectors, genetically engineered prokaryotic cells, compositions, methods and systems according to embodiments of the present disclosure.

The following materials and methods were used:

Chemicals.

All chemicals were purchased from Sigma Aldrich (St. Louis, Mo.) unless otherwise noted.

Molecular Cloning.

To construct the plasmid for E. coli expression of ARGs, the gene cluster encoding B. megaterium gas vesicle (GV) proteins B, R, N, F, G, L, S, K, J, T and U was amplified from pNL29 [19] (gift of Maura Cannon) and cloned into pET28a using Gibson assembly to give pET28-RNFGL-SKJTU. The amplicon included an additional 46 bp upstream of the GvpB start codon and 180 bp downstream of the GvpU stop codon. To generate hybrid gene clusters, the genes encoding GvpA and GvpC were amplified from A. floc-aquae and cloned into pET28-RNFGLSKJTU using Gibson assembly. A control gene encoding the green fluorescent protein (GFP) mNeonGreen [74] was similarly constructed in the pET28 vector. For S. typhimurium expression, the ARG gene cluster was cloned into pTD103 (gift of Jeff Hasty). A control plasmid encoding the luxCDABE gene cluster from Photorhabdus luminescens on the pTD103 backbone was also a gift of Jeff Hasty.

Bacterial Expression.

Plasmids expressing ARGs or GFP were transformed into chemically competent E. coli BL21(A1) cells (Thermo Fisher Scientific, Carlsbad, Calif.) and grown in 5 ml starter cultures in LB media with 50 µg/ml kanamycin, 1% glucose for 16 h at 37° C. Large-scale cultures in LB media containing 50 µg/ml kanamycin and 0.2% glucose were inoculated 1:100 with the starter culture. Cells were grown at 37° C. to OD600=0.5, then induced with 0.5% L-arabinose and 0.4 mM IPTG for 22 h at 30° C. For Salmonella typhimurium expression, the same protocol was followed except constructs were electroporated into S. typhimurium ELH1301 (gift of Jeff Hasty) and induction was with 3 nM N-(β-ketocaproyl)-L-homoserine lactone (AHL).

Gas Vesicle Purification and Quantification.

Harvested cells were centrifugated at 350 g in 50 ml conical tubes for 4 h with a liquid height <10 cm to prevent collapse of GVs by hydrostatic pressure. For ARG variants that produce a buoyant band of cells, the midnatant was removed and discarded. For ARG variants that do not produce a buoyant band, the supernatant was discarded. The remaining cells were resuspended in 8 ml Solulyse-Tris #L200500 (Genlantis, San Diego, Calif.) per 100 ml culture and 250 µl/ml lysozyme, and incubated for 1 h at 4° C. with rotation. Subsequently, 10 µl/ml DNAseI was added to the lysate and incubated for 10 min at 25° C. The lysate was transferred to 2 ml tubes and centrifuged for 2 h at 400 g at 8° C. The subnatant was removed with a 21.5 G needle, and the supernatant containing the GVs was transferred to a clean tube. PBS was added to the GVs in a 3-fold volume excess and centrifugation, removal of subnatant and PBS dilution was repeated 3 times. Purified GVs were quantified using the Micro BCA Protein Assay Kit (Thermo Fisher Scientific, Carlsbad, Calif.). GVs were collapsed with hydrostatic pressure prior to quantification. Bovine serum albumin was used to generate the standard curve. Absorbance measurements were taken on a Spectramax M5 spectrophotometer (Molecular Devices, Sunnyvale, Calif.).

TEM Sample Preparation and Imaging.

Cells expressing ARGs, or purified GVs, were exchanged into water or 10 mM HEPES pH8.0 with 150 mM NaCl, respectively, via 3 rounds of buoyancy purification and buffer exchange as described above. Samples were deposited on Formvar/carbon 200 mesh grids (Ted Pella) that were rendered hydrophilic by glow discharging (Emitek K100X). For purified GVs, 2% uranyl acetate was added for staining. The samples were then imaged on a FEI Tecnai T12 transmission electron microscope equipped with a Gatan Ultrascan CCD. Images were processed with FIJI [75].

Hydrostatic Collapse Pressure Measurements.

Cells expressing ARGs, or purified GVs, were diluted to OD600=1.0 in PBS and 0.4 ml was loaded into an absorption cell (176.700-QS, Hellma GmbH & Co. KG, Müllheim, Germany). A single valve pressure controller (PC series, Alicat Scientific, Tucson, Ariz., USA) supplied by a 1.5 MPa nitrogen gas source applied hydrostatic pressure in the cell, while a microspectrometer (STS-VIS, Ocean Optics, Dunedin Fla., USA) measured the optical density of the sample at 500 nm. OD500 was measured from 0 to 1.2 MPa gauge pressure with a 10 kPa step size and a 7 second equilibration period at each pressure.

In Vitro Ultrasound Imaging.

Phantoms for imaging were prepared by melting 1% w/v agarose in PBS and casting wells using a custom 3D-printed template. Cells at 2× the final concentration were mixed 1:1 with molten agarose (at 50° C.) and immediately loaded into the phantom. The concentration of cells was determined prior to loading by measuring their OD600 after exposure to 1.2 MPa hydrostatic pressure to eliminate any contribution to light scattering from GVs. The optical density was then converted into cells/ml using the relationship 1 OD=8×10$^8$ cells/ml (http://www.genomics.agilent.com/biocalculators/calcODBacterial.j sp). Ultrasound imaging was performed using a Verasonics Vantage programmable ultrasound scanning system and L22-14v 128-element linear array transducer (Verasonics, Kirkland, Wash.). The transducer was mounted a computer-controlled 3D translatable stage (Velmex, Inc., Bloomfield, N.Y.). Image acquisition was performed using conventional B-mode imaging using a 128 ray lines protocol with a synthetic aperture to form a focused excitation beam. The transmit waveform was set to a frequency of 19 MHz, 67% intra-pulse duty cycle, and a one cycle pulse. Samples were positioned 6 mm from the transducer face, which is the elevation focus of the L22-14v transducer, coupled through a layer of PBS. The transmit beam was also digitally focused at 6 mm. For imaging, the transmit voltage was 2 V and the f-number was 3, resulting in a peak positive pressure of 0.4 MPa. Backscattered ultrasound signals were filtered with a 7 MHz bandpass filter centered at 19 Mhz. Signals backscattered from four transmit events were summed prior to image processing. Pixel gain was set to 3 and persistence to 90. For GV collapse, the transmit power was 25 V and the f-number was 0.2. This increased the peak positive pressure to >5 MPa. To ensure complete collapse of the volume, the transmit focus was scanned from 3 mm to 9 mm. Transducer output pressures were measured using a fiber-optic hydrophone (Precision Acoustics, Dorset, UK).

Plate-Based Induction and Optical Imaging.

ARG and GFP constructs were transformed as described above, and the transformation mix after recovery was plated on two-layer LB-Agar plates. The underlayer contained 50 µg/ml kanamycin, 1.0% L-arabinose, and 0.8 mM IPTG. The overlayer contained 50 µg/ml kanamycin and 0.4% glucose. The overlayer was poured 30 min prior to plating, and each layer was 4 mm thick. Plates with transformants were incubated at 30° C. for 20 h and then imaged for white light scattering and green fluorescence using a Chemidoc MP instrument (Bio-Rad, Hercules, Calif.).

Colony Ultrasound.

ARG and GFP constructs were transformed into BL21 (A1) one-shot competent cells (Thermo Fisher Scientific, Carlsbad, Calif.) and plated onto LB-Agar two-layer inducer plates as described above. Plates were grown at 37° C. for 14 h. The colonies were immobilized by depositing a 4 mm layer of 0.5% Agarose-PBS gently onto the plate surface. Ultrasound imaging was performed using a L11-4v128-element linear array transducer (Verasonics, Kirkland, Wash.). The transducer was mounted on a computer-controlled 3D translatable stage (Velmex, Inc., Bloomfield, N.Y.). Image acquisition was performed using conventional B-mode imaging using a 128 ray lines protocol with a synthetic aperture to form a focused excitation beam. The transmit waveform was set to a frequency of 6.25 MHz, 67% intra-pulse duty cycle, and a four-cycle pulse. Colonies were positioned 20 mm from the transducer face, which is the elevation focus of the L11-4v transducer, coupled through a layer of PBS. The transmit beam was also digitally focused at 20 mm. For imaging, the transmit power was 2 V and the f-number was 3, resulting in a peak positive pressure of 0.61 MPa. For collapse, the voltage was increased stepwise to 40V to obtain a maximal peak positive pressure of 5.95 MPa. Pixel gain was set to 0.1 and persistence to 20. Cross-sectional images of the plate (perpendicular to the plate surface) were acquired at spatial intervals of 250 μm using computer-controlled steps. The cross-sectional images were processed in MATLAB to form 2D images of the plate surface. First, the cross-sectional images were stacked to produce a 3D-volumetric reconstruction of the plate. The signals in a 2 mm slice of the volume parallel to and centered on the bacterial growth surface after thresholding to eliminate background were then summed, forming a 2D projection image of the plate. After ultrasound imaging, image processing, and acoustic phenotype prediction, the colonies were picked using 10 μl sterile pipet tips. Each colony was used to inoculate a 5 ml LB+50 μg/ml kanamycin culture. The cultures were mini-prepped and sequenced to determine whether the plasmid contained GFP, ARG1, or ARG2.

In Vivo Ultrasound Imaging.

All in vivo experiments were performed on BALB/c or SCID nude female mice under a protocol approved by the Institutional Animal Care and Use Committee of the California Institute of Technology. Ultrasound imaging was performed. Mice were anesthetized with 1-2% isoflurane, maintained at 37° C. on a heating pad, depilated over the imaged region, and imaged using an L22-14v transducer with the pulse sequence described above. For imaging of *E. coli* in the gastrointestinal tract (GI), BALB/c mice were placed in a supine position, with the ultrasound transducer positioned on the lower abdomen, transverse to the colon. Anatomical landmarks including the bladder were used to identify the colon's position. Prior to imaging, buoyancy-enriched *E. coli* expressing ARG2 or GFP were mixed 1:1 with 42° C. 2% agarose-PBS for a final bacterial concentration of $10^9$ cells/ml. The agarose was used to help the live bacteria stay in place within the GI tract. 150 μL of the mixture was introduced rectally. For imaging of *S. typhimurium* in tumors, hindlimb ovarian tumor xenografts were formed in SCID nude mice via subcutaneous injection of $5 \times 10^7$ OVCAR8 cells with matrigel. After tumors grew to dimensions larger than approximately 6 mm (14 weeks), they were injected with ARG1-expressing *S. typhimurium*. (50 μL, $3.2 \times 10^9$ cells/ml). The tumors were then imaged with ultrasound, with mice in a prone position with anesthesia, homeostasis and imaging parameters as described above.

Image Processing.

MATLAB was used to process ultrasound and optical images. Regions-of-interest (ROIs) were defined to capture all the ultrasound signal from the phantom well, colon, or tumor region. All in vitro phantom experiments had the same ROI dimensions. For in vivo experiments ROIs were selected consistently to exclude edge effects from the colon wall or skin. Mean pixel intensity was calculated from each ROI, and pressure-sensitive ultrasound intensity was calculated by subtracting the mean pixel intensity of the collapsed image from the mean pixel intensity of the intact image. For the multiplexed imaging of ARG1 and ARG2, acoustic spectral unmixing was performed according to [76] after a spatial averaging filter (kernel size 30×30 pixels or 750×750 μm) was applied to reduce noise. Images were pseudo-colored, with maximum and minimum levels adjusted for maximal contrast as indicated in accompanying color bars.

Reporter Gene Expression—MRI Experiments.

For reporter gene experiments for MRI imaging, a hybrid GV variant was heterologously expressed in *E. coli*. In this variant, the major Mega GV coat protein, GvpB, is replaced by two copies of GvpA and one copy of GvpC from *Anabaena floc-aquae* and is therefore named A2C[77]. A2C, instead of Mega, was chosen for the reporter gene experiment because it results in stronger per-cell expression of GVs[77]. The A2C GV gene cluster was expressed from a pET28a plasmid (Novagen, Temecula, Calif.) in BL21(A1) cells (Thermo Fisher Scientific, Waltham, Mass.). 400 μM IPTG and 0.5% arabinose were added at $OD_{600}$ between 0.4 and 0.6 to induce expression. The control green fluorescent protein mNeonGreen[74] was inserted into the same plasmid and followed the identical culturing protocol. Cell density was measured after collapsing any intracellular GVs to eliminate their contribution to optical scattering. (FIG. 17). A sample of each *E. coli* specimen at $OD_{600}$~1.0 was loaded onto a flow-through, 1 cm path-length quartz cuvette (Hellma Analytics, Plainview, N.Y.), which was pressurized by an $N_2$ cylinder and a digital pressure controller (Alicat Scientific, Tucson, Ariz.). The pressure was incremented in 20 kPa steps from 0 to 1.2 MPa and $OD_{600}$ was recorded using a spectrophotometer (EcoVis, OceanOptics, Winter Park, Fla.). $OD_{600}$ at 1.2 MPa was used to measure cell density. Prior to the preparation of MRI phantoms, the cells were concentrated by centrifugation to the indicated density.

In Vitro MRI and Relaxometry.

*E. coli* cells were embedded in agarose phantoms. 1% agarose stock solution was prepared in PBS and maintained at 60° C. until use. The size of the phantom was ~18×6×4 cm (length×width×height). Using a custom 3D-printed caster, the bottom half was first cast with cylindrical wells of the size 3×5 mm (diameter×depth) separated by 3 mm. The cylindrical geometry perpendicular to $B_0$ was chosen to ensure a homogeneous field in the sample wells to facilitate susceptibility-based imaging. The gel was allowed to solidify and exposed to air for 1 h for gas equilibration. *E. coli* cells in PBS were mixed 1:1 with the melted agarose stock solution and immediately loaded into the wells. Subsequently, the top half of the phantom was cast so that all the wells were surrounded by agarose. Care was taken to avoid bubbles. MRI was performed on a 7T horizontal bore Bruker-Biospin scanner, using a 7.2 cm diameter volume coil for transmit and receive. T2* relaxivity was measured with 3D Multi Gradient Echo (MGE) experiments with the following parameters: repetition time (TR)=500 ms, 32 echos, echo spacing (TE)=9.0 ms, field of view (FOV)=12× 6×0.8 $cm^3$, spatial resolution=0.25×0.25×0.25 $mm^3$ and 1 average. T2 relaxometry was performed by 2D Multi Slice Multi Echo (MSME) spin echo experiments with the following parameters: TR=2500 ms, 16 echos, TE=16.0 ms, FOV=8×6 cm$^2$, and spatial resolution=0.25×0.25 mm$^2$. Slice thickness=1 mm and 16 averages were used for multiparametric multiplexing experiments and 0.5 mm and 4 averages for all other experiments. T1 relaxometry was performed by 2D Rapid Acquisition with Relaxation Enhancement with Variable TR (RAREVTR) with the following parameters: Effective TE=9.683 ms, RARE factor=12, FOV=8×6 cm$^2$, spatial resolution=0.25×0.25 mm$^2$, slice thickness=0.5 mm, 2 average and 8 variable TR times including: 126.43, 738.40, 1461.21, 2344.09, 3478.70, 5068.54, 7746.55, 20000.00 ms. For data analysis, a circular region of interest (ROI) was drawn for each well using Fiji[75]. The average intensity of the ROI was imported into Matlab for exponential fitting to derive the T2*, T2 and T1 values. Voxel-wise T2* and T2 maps were generated by ImageJ plugin, MRI Processor, using Simplex fitting. For T2* relaxometry, the ROI excluded the rim of the wells.

Quantitative Susceptibility Mapping.

Magnitude and phase images of 3D MGE or 3D fast low angle shot (FLASH) experiments were obtained in ParaVision 5.1 (Bruker), and the images from a single echo served as the input to the Susceptibility Mapping and Phase artifacts Removal Toolbox (SMART) (MRI Institute for Biomedical Research, Detroit, Mich.). This software performed phase unwrapping using the 3D-SRNCP algorithm[78], background field removal by the SHARP algorithm[79] and susceptibility map generation using the SWIM algorithm [80]. The resulting QSM images were analyzed in Fiji[75]. Unless specified otherwise, all QSM images were processed from the 5$^{th}$ echo (TE=45.0 ms) of a 3D MGE experiment.

In Vitro Acoustic Collapse—MRI Experiments.

Figure 3:
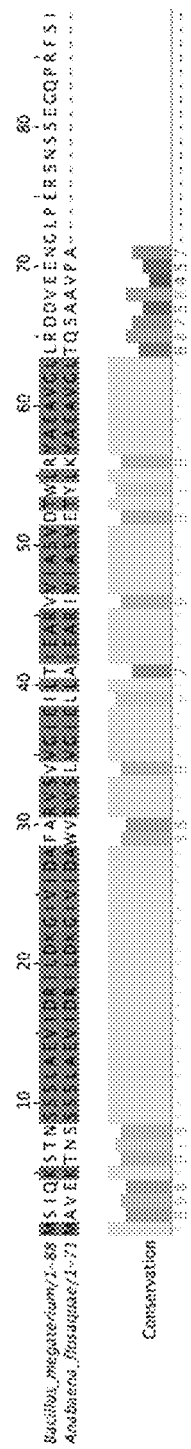
FIG. 3 shows a schematic of exemplary sequence homology of GvpA/B. The schematic shows amino acid sequence alignment of the primary gas vesicle structural protein, GvpB from *B. megaterium*, showing the sequence MSIQK-STNSSSLAEVIDRILDKGIVIDAFARVSVVGIEILT-IEARVVIASVDTWLRYAEAVG LLRDDVEENGLPER-SNSSEGQPRFSI (SEQ ID NO:1) and GvpA from *A. floc-aquae*, showing the sequence MAVEKTNSSSSLAEVIDRILDK-GIVIDAWVRVSLVGIELLAIEARIVIASVETYLKY-AEAV GLTQSAAVPA (SEQ ID NO:2).

For collapsing the intracellular GVs in *E. coli*, a Verasonics Vantage programmable ultrasound scanning system using the L11-4v 128-element linear array transducer (Verasonics, Kirkland, Mass.) was used with the following parameters: transmit frequency=6.25 MHz, transmit voltage=15 V. Panels C-D, left) have poor acoustic properties. At the same time, transforming *E. coli* with a gas vesicle gene cluster derived from the cyanobacterium *Anabaena floc-aquae*, whose gas vesicles are highly echogenic [47, 76], did not yield gas vesicle expression. Given the high sequence homology of GvpA between organisms (FIG. 3), it was hypothesized that a combination of the structural GvpA genes from *A. flos-aquae* with the expression-enabling secondary genes GvpR-U from *B. megaterium* (FIG. 2 Panel A, middle) would result in the formation of gas vesicles with characteristics favorable for ultrasound imaging. Indeed, expression of this hybrid gene cluster resulted in *E. coli* with robust ultrasound contrast compared to green fluorescent protein (GFP) controls (FIG. 2 Panel B, middle). These cells produced gas vesicles with significantly larger dimensions compared to the *B. megaterium* operon and appeared to occupy a greater fraction of intracellular volume (FIG. 2 Panels C-D, middle). The addition of a gene encoding the *A. floc-aquae* scaffolding protein GvpC (FIG. 2 Panel A, right) further enhanced the production of larger gas vesicles (FIG. 2, Panels C-D, right), resulting in wider and more elongated nanostructures resembling those native to *A. floc-aquae* [47], and producing stronger ultrasound contrast (FIG. 2 Panel B, right); this construct is referred to herein as ARG1 or acoustic reporter gene 1.

To confirm that the ultrasound signal from ARG1-expressing cells is due to the presence of gas vesicles, acoustic pulses were applied with amplitudes above the gas vesicles' critical collapse pressure. In purified form, this results in the immediate collapse of these protein nanostructures and dissolution of their gas contents, eliminating ultrasound contrast [47]. As expected, the application of high-pressure pulses made cells expressing ARG1 invisible to ultrasound (FIG. 2 Panel B). The ability of ARG-based contrast to be erased in situ is used throughout this study to confirm the source of acoustic signals and subtract background.

ARG1 expression resulted in average gas vesicle contents of 9.4±0.4 mg/g *E. coli* (FIG. 2 Panel E), corresponding to

TABLE 4

MRI measurements of *E. coli* in agarose phantom. All the values were zeroed by the PBS sample. Errors represent SEM and N = 6.

|  | ΔΧ (ppb) | | ΔR2* (sec$^{-1}$) | | ΔR2 (sec$^{-1}$) | |
| --- | --- | --- | --- | --- | --- | --- |
|  | Before US | After US | Before US | After US | Before US | After US |
| GV + IPTG | 1.93 ± 0.31 | −2.73 ± 0.26 | 0.97 ± 0.13 | 0.45 ± 0.08 | 0.65 ± 0.03 | 0.34 ± 0.04 |
| GFP + IPTG | −1.97 ± 0.36 | −1.82 ± 0.39 | 0.32 ± 0.10 | 0.50 ± 0.09 | 0.28 ± 0.04 | 0.26 ± 0.04 |
| GV | −2.75 ± 0.17 | −2.00 ± 0.19 | 0.34 ± 0.10 | 0.29 ± 0.03 | 0.35 ± 0.05 | 0.33 ± 0.05 |
| PBS | 0 ± 0.14 | 0 ± 0.16 | 0 ± 0.09 | 0 ± 0.04 | 0 ± 0.02 | 0 ± 0.03 |

Example 1. Genetic Engineering of Acoustic Reporter Genes

Gas vesicles are encoded in their native bacterial or archaeal hosts by operons of 8-14 genes, which include the primary structural protein GvpA, the optional external scaffolding protein GvpC, and several secondary proteins that function as essential minor constituents or chaperones [11] (FIG. 2 Panel A). It was previously shown that *E. coli* transformed with a gas vesicle gene cluster from *B. megaterium* are capable of producing small bicone-shaped gas vesicles [19]. However, it was found that expression of this gene cluster in *E. coli* does not result in bacteria detectable by ultrasound (FIG. 2 Panel B, left), most likely because the small gas vesicles produced from this construct (FIG. 2, approximately 100 gas vesicles per cell. These nanostructures occupy roughly 10 percent of the intracellular space, which is sufficient to make a subset of ARG1-expressing cells buoyant (FIG. 2 Panel F). Cells expressing the other operons produced a similar quantity of proteins but were not buoyant, presumably due to the smaller volume-to-surface ratio of their gas vesicles. These results show that genetic engineering enables the creation and optimization of ARGs for ultrasound imaging of bacteria.

Figure 5:
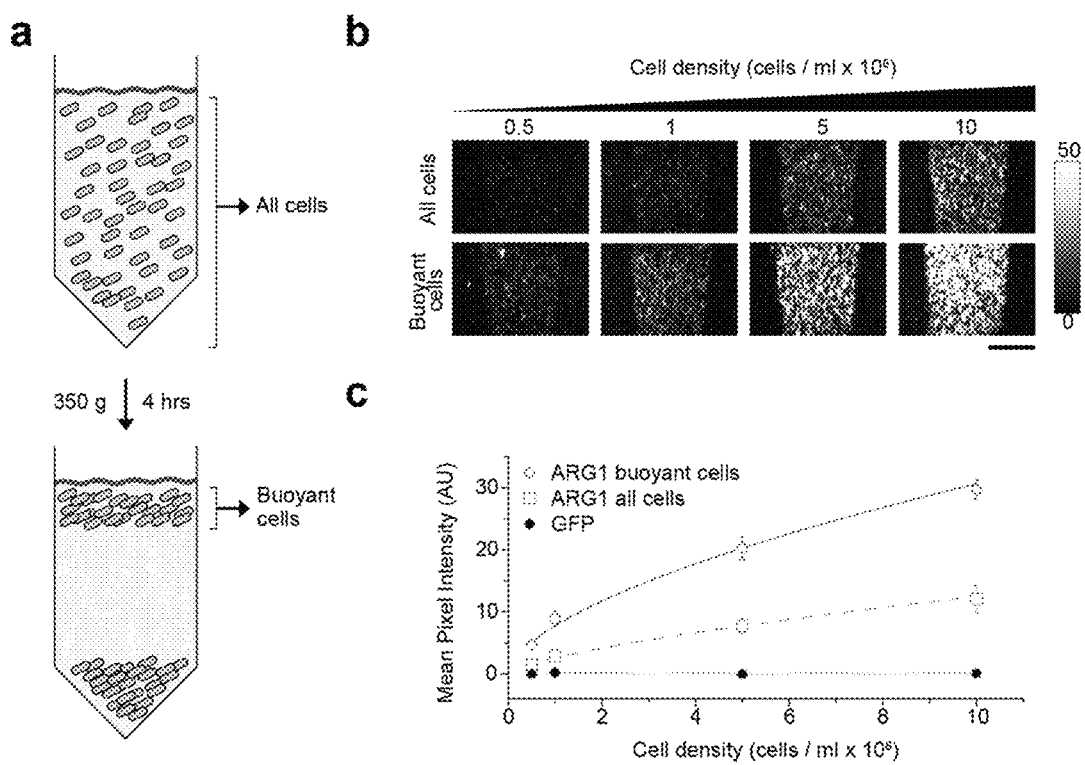
FIG. 5 shows a schematic diagram and exemplary data of ultrasound contrast from buoyancy-enriched cells. Panel A shows a diagram of centrifugation-assisted enrichment of buoyant cells. Panel B shows exemplary ultrasound images of *E. coli* expressing ARG1 at various cellular concentrations, with and without buoyancy enrichment. Panel C shows a graph reporting exemplary mean ultrasound contrast from *E. coli* expressing ARG1, with and without buoyant enrichment, and GFP at various cell densities (N=4 per sample).

Example 2. ARGs Enable the Imaging of Dilute Cell Populations and Conditional Gene Expression To enable a broad range of in vivo applications, noninvasive imaging is designed be able to detect relatively dilute cellular populations. For example, the large intestine, a key target of microbiome research and engineered microbial therapeutics, hosts a bacterial population of approximately $10^{10}$ cells/ml [81], representing a volume fraction of about 1%. To determine the detection limit of ARG-expressing cells, a concentration series of *E. coli* transformed with ARG1 was imaged (FIG. 4 Panel A). Cells at concentrations as low as $5 \times 10^7$ cells/ml produced detectable signal (FIG. 4, Panels A and B). This equates to a roughly 0.005% volume fraction, or approximately 100 cells per voxel based on cubic voxel dimensions of 100 µm. This sensitivity should be sufficient for many in vivo scenarios. Furthermore, bacteria enriched for buoyancy prior to imaging provide 2.4-fold higher signal (FIG. 5), suggesting that sensitivity could be improved further by optimizing ARG expression.

In addition to observing the spatial distribution of cells, it is desirable to monitor dynamic cellular signals. Many biological states, signaling pathways and environmental stimuli can be connected to gene expression, as often done with gene circuits wired to fluorescent indicators [82]. To test whether ARGs could provide a similar readout of state-dependent genetic pathways, ARGs were placed under the control of a promoter regulated by the chemical inducer isopropyl β-D-1-thiogalactopyranoside (IPTG). Ultrasound signals from *E. coli* expressing ARG1 in this configuration followed the expected dose-response curve of IPTG-controlled expression (FIG. 4, Panels C and D), confirming their ability to serve as the output signal for engineered genetic circuits.

Example 3. ARG Expression and Ultrasound Imaging do not Affect Cell Viability

Figure 6:
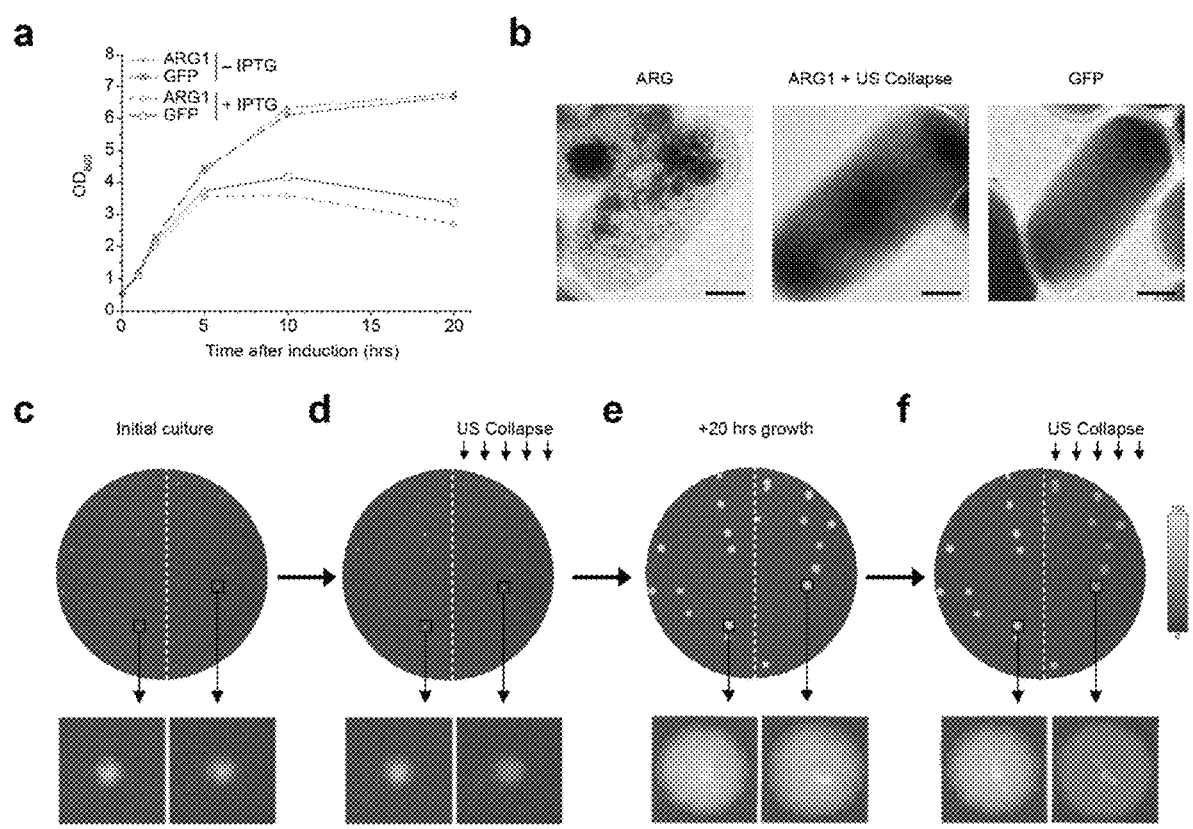
FIG. 6 shows exemplary data showing that GVGC expression and ultrasound imaging does not affect cell viability. Panel A shows a graph reporting exemplary growth curves of *E. coli* containing the ARG1 or GFP expression plasmid, with or without induction using 0.4 mM IPTG (N=3 per sample). Panel B shows exemplary representative TEM images of whole *E. coli* cells expressing ARG1 with and without exposure to acoustic collapse pulses, and *E. coli* cells expressing GFP. Panel C shows an exemplary dark field optical image of agar plate containing colonies of *E. coli* expressing ARG1 14 hours after seeding. Panel D shows an exemplary image of the plate shown in Panel C after the right half of the plate was insonated with high-pressure ultrasound. Panel E shows an exemplary image of the plate shown in Panels C and D 20 h after insonation. Panel F shows an exemplary image after the right half of the plate in Panel E was insonated with high-pressure ultrasound. Zoomed in images of representative colonies are shown below each plate image. Scale bars represent 500 nm. Error bars represent±S.E.M; where not seen, they are smaller than the symbols.

To determine whether the expression of ARGs has any deleterious effect on host cells, the growth curves of *E. coli* expressing ARG1 or GFP were measured. After induction, cells expressing both constructs continued to divide and reached similar saturation densities (FIG. 6 Panel A). For both ARG1 and GFP the final density was somewhat lower than in uninduced controls, as expected from the metabolic demand of protein expression [83]. This has not been a major limitation for the use of GFP-based reporters.

Next, the viability of ARG-expressing cells was assessed after ultrasound imaging and acoustic collapse. TEM images of cells acquired before and after exposure to collapsing acoustic pulses show that gas vesicles can be eliminated without obvious cellular damage (FIG. 6 Panel B). To examine the impact of ultrasound exposure on cell growth, *E. coli* expressing ARG1 were cultured as colonies on solid media and acoustic collapse pulses were applied to half the plate. Gas vesicle collapse in insonated cells was confirmed by a decrease in optical scattering, as seen on dark-field images of the plates (FIG. 6, Panels C-D). After incubation for an additional 20 h, no significant difference was observed in the diameter of the insonated colonies compared to un-insonated controls, indicating that ultrasound exposure does not affect cell viability (FIG. 6 Panel E). Strikingly, insonated colonies re-expressed gas vesicles during this period, as indicated by the restoration of pressure-sensitive light scattering (FIG. 6, Panels E-F). This result suggests that ultrasound could be used for pulse-chase studies analogous to fluorescence photobleaching recovery assays [84].

Example 4. Engineered Variants of ARGs Enable Multiplexed Cellular Imaging

It is often informative to simultaneously image more than one population of cells, for example to monitor the dynamics of competing microbial species or the interaction of multiple therapeutic or diagnostic constructs. Optical multiplexing typically makes use of spectrally distinct fluorescent proteins, and analogous acoustic multiplexing can be performed using genetic variants of gas vesicles that collapse at different pressures [76]. Such gas vesicles can be distinguished from each other by applying acoustic pulses of gradually increasing amplitude and monitoring the disappearance of backscattered signal: one subset of gas vesicles collapses first, followed by another, and so on. A signal processing paradigm similar to spectral unmixing then determines the contribution of each population to the total signal [76]. It was hypothesized that if ARGs could be engineered to produce intracellular gas vesicles collapsing at different pressures, this would enable multiplexed imaging of distinct cellular populations.

Figure 7:
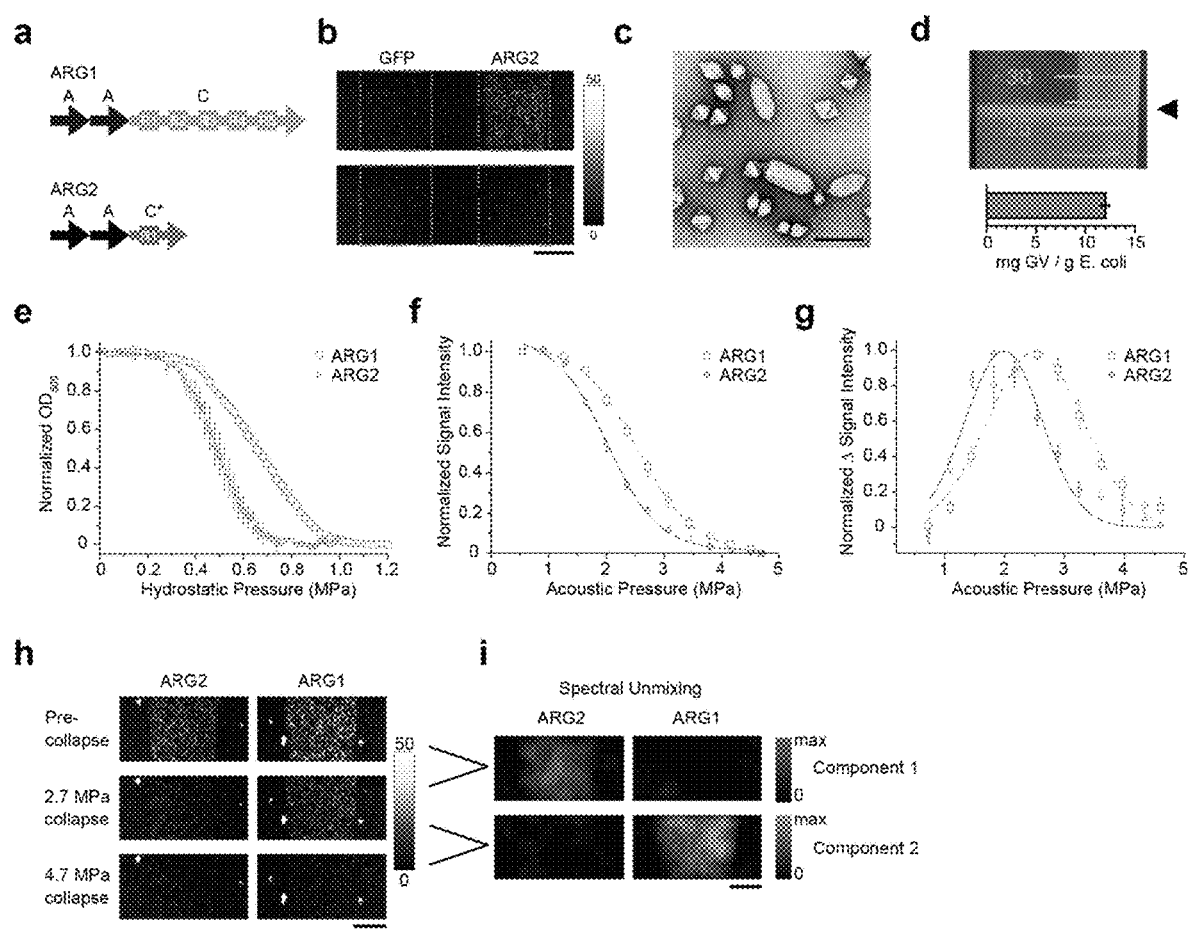
FIG. 7 shows exemplary schematic diagrams and data of multiplexed imaging of genetically engineered reporter variants. Panel A shows a diagram of the exemplary GvpA and GvpC sequences included in the ARG1 and ARG2 gene clusters. ARG2 was created by deleting 4 of the 5 repeat domains in wild-type GvpC. Panel B shows exemplary ultrasound images of a gel phantom containing *E. coli* expressing ARG2 or GFP ($10^9$ cells/ml). Dotted outlines indicate the location of each specimen. Panel C shows exemplary transmission electron micrographs of isolated ARG2 gas vesicles. Panel D shows an exemplary image of ARG2 *E. coli* culture 22 hours after induction showing the presence of buoyant cells and a graph reporting exemplary mass fraction of gas vesicles produced 22 hours after induction. (N=3). Panel E shows a graph reporting exemplary normalized optical density (representing the intact fraction) of gas vesicles isolated from ARG1- or ARG2-expressing *E. coli* as a function of applied hydrostatic pressure (N=3 per sample). Panel F shows a graph reporting exemplary normalized ultrasound intensity as a function of peak positive pressure from 0.6 to 4.7 MPa for *E. coli* expressing ARG1 or ARG2 (N=3 per sample). Panel G shows a graph reporting exemplary acoustic collapse spectra derived by differentiating the data and curves in Panel F with respect to applied pressure (N=3 per sample). Panel H shows exemplary ultrasound images of gel phantoms containing ARG1 or ARG2 before collapse, after collapse at 2.7 MPa and after collapse at 4.5 MPa ($10^9$ cells/mL). Panel I shows exemplary spectrally unmixed maps of ARG2 and ARG1 obtained from the set of images in Panel H. Scale bars represent 2 mm in Panel B and Panels H-I and 250 nm in Panel C. Error bars represent +/−S.E.M.
Figure 8:
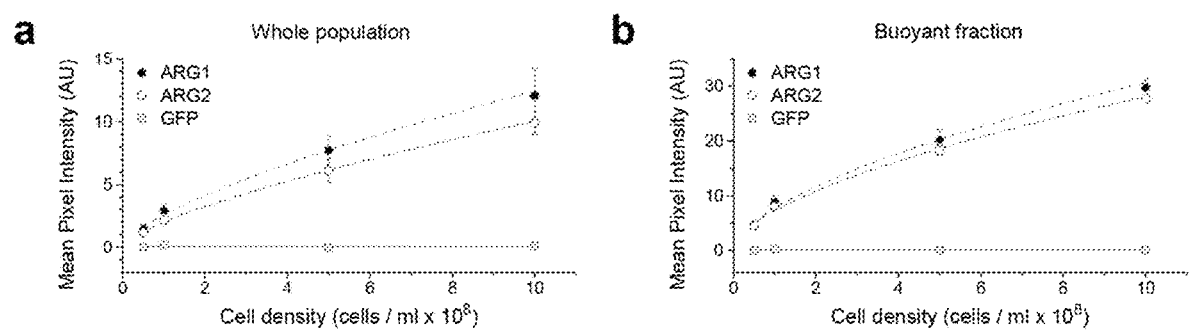
FIG. 8 shows graphs reporting exemplary ultrasound contrast from cells expressing ARG1 and ARG2. Panel A shows a graph reporting exemplary ultrasound contrast from the whole population of cells expressing ARG1, ARG2 or GFP (N=4 per sample). Panel B shows a graph reporting exemplary ultrasound contrast from the buoyancy-enriched population of cells expressing ARG1, ARG2 or GFP (N=3 per sample). Error bars represent ±SEM.

To explore this possibility, a new version of the ARG gene cluster containing a modified version of *A. floc-aquae* GvpC was constructed. Previous work has shown that deletion or truncation of this outer scaffolding protein results in gas vesicles with lower collapse pressures [85, 86], allowing the production of nanostructures distinguishable from each other under ultrasound [76]. Following this approach, the gene cluster was modified by truncating GvpC to retain only one of its five repeating alpha-helical domains (FIG. 7 Panel A). *E. coli* expressing the resulting gene cluster, referred to herein as ARG2, showed robust gas vesicle production and ultrasound contrast, similar to ARG1 (FIG. 7, Panels B to D, FIG. 8). Consistent with the design, gas vesicles purified from ARG2-expressing *E. coli* had a lower critical collapse pressure than nanostructures formed by cells expressing ARG1 (FIG. 7 Panel E), and cellular ARG2 contrast was erasable at lower acoustic pressures (FIG. 7 Panel F). The two variants' distinct collapse spectra (FIG. 7 Panel G) allowed *E. coli* expressing ARG1 and ARG2 to be imaged in multiplex using pressure spectrum unmixing (FIG. 7, Panels H-I).

Example 5. High-Throughput Screening of Acoustic Reporter Genes

Directed evolution has served as an effective approach to fluorescent protein engineering to identify variants with new spectral and biochemical properties [87-89]. This approach typically requires a high-throughput screen, which is commonly implemented by plating a bacterial library of genetic variants on agar and imaging the resulting colonies to identify mutants with desired optical properties [88, 89]. To determine whether a similar approach could be used with ARGs, a method was developed to scan bacterial colonies with ultrasound (FIG. 9 Panels A-C). In this method, colonies are immobilized on agar plates with an over-layer of agarose, then scanned with an ultrasound transducer translated by a computer-controlled robot. This results in a series of transverse images that can be reconstructed to form an in-plane image of the plate. To assess the ability of this screening platform to discriminate acoustic phenotypes, a mixed plate of *E. coli* transformed with ARG1, ARG2 or GFP was imaged. Serial acoustic collapse imaging (FIG. 9 Panel B) revealed three distinct colony populations: one lacking ultrasound signal (FIG. 9 Panel D), one collapsing at a lower pressure, and one collapsing at a higher pressure (FIG. 9 Panel E). Based on these acoustic properties, the ARG1, ARG2 and GFP genotypes could be distinguished from each other with 100% accuracy, as determined by DNA sequencing (FIG. 9 Panel F). This result confirms that colony screening can discriminate acoustic phenotypes with sufficient accuracy to serve as a high-throughput assay for acoustic protein engineering.

Example 6. In Vivo Gastrointestinal Imaging of Engineered Microbes

Figure 10:
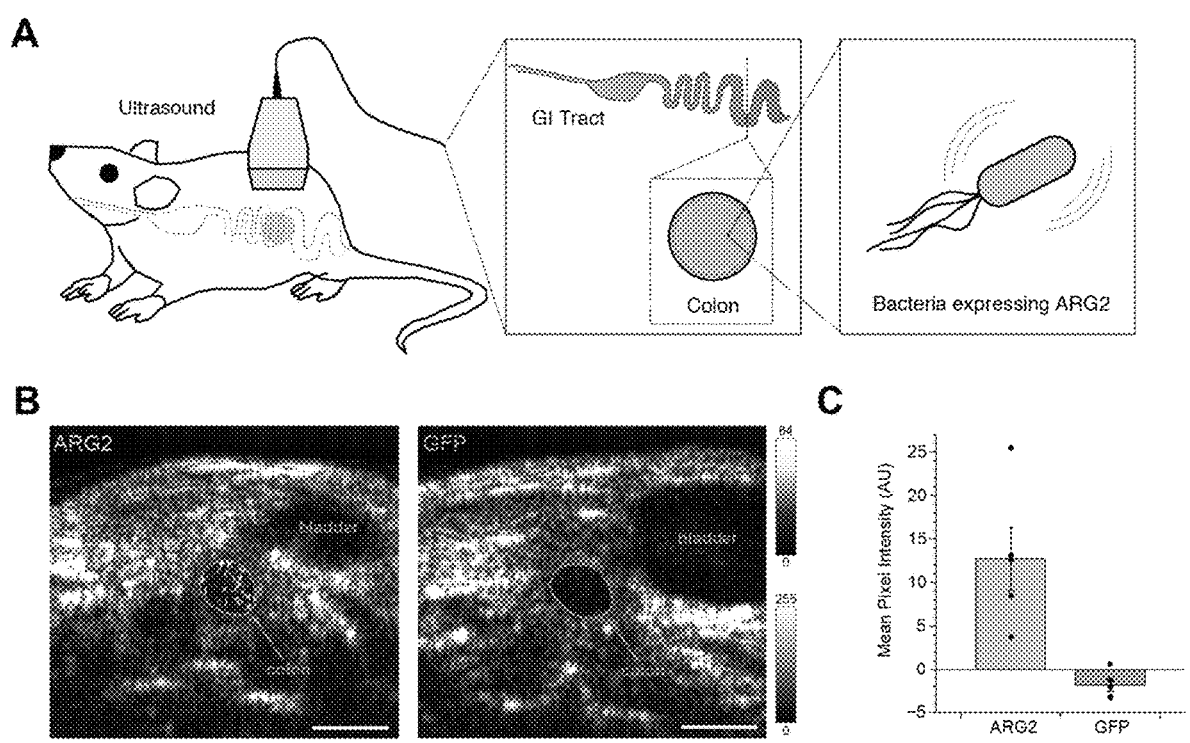
FIG. 10 shows exemplary diagrams and data of ultrasound imaging of bacteria in the gastrointestinal tract. Panel A shows an exemplary diagram of GI imaging experiment. *E. coli* expressing ARG2 were introduced into the colon of mice and imaged with ultrasound. Panel B shows exemplary transverse ultrasound images of mice whose colon contains *E. coli* expressing either ARG2 or GFP at a final concentration of $10^9$ cells/ml. A difference heat map of ultrasound contrast within the colon ROI (circled region of interest indicated with arrow) before and after acoustic collapse is overlaid on an anatomical image. Panel C shows a graph reporting exemplary average signal intensity of ultrasound contrast within the colon ROI in mice with *E. coli* expressing either ARG2 or GFP. N=5 mice per sample. Scale bar represents 2.5 mm in Panel B. Error bars represent ±SEM.

After establishing the core capabilities of ARGs in vitro, their basic functionality in vivo was demonstrated by imaging ARG-expressing cells in biologically relevant anatomical contexts. One particularly important target for in vivo microbial imaging is the mammalian GI tract, given recent findings concerning the impact of the gut microbiome on human health [50, 64-66] and the development of GI-targeted microbial therapeutics [57, 58, 60, 90, 91]. Due to its location deep inside the body, the GI tract is difficult to image using optical techniques, and therefore represents a major opportunity for ultrasound. To establish a proof of concept for the imaging of ARG-expressing E. coli within the gut, cells expressing ARG2 were introduced into the colons of live mice and imaged their abdomens with ultrasound (FIG. 10 Panel A). Background subtraction after acoustic collapse allowed us to obtain signals from the colon that were specific to ARG-labeled cells and absent in GFP controls (FIG. 10, Panels B and C, FIG. 11). These signals are overlaid on anatomical images showing the location of the bacteria within the context of other internal organs. These results establish the ability of ARGs to make microbial gene expression visible noninvasively in deep tissue.

Example 7. ARG Expression in *Salmonella typhimurium* and Imaging Inside Tumors

Figure 12:
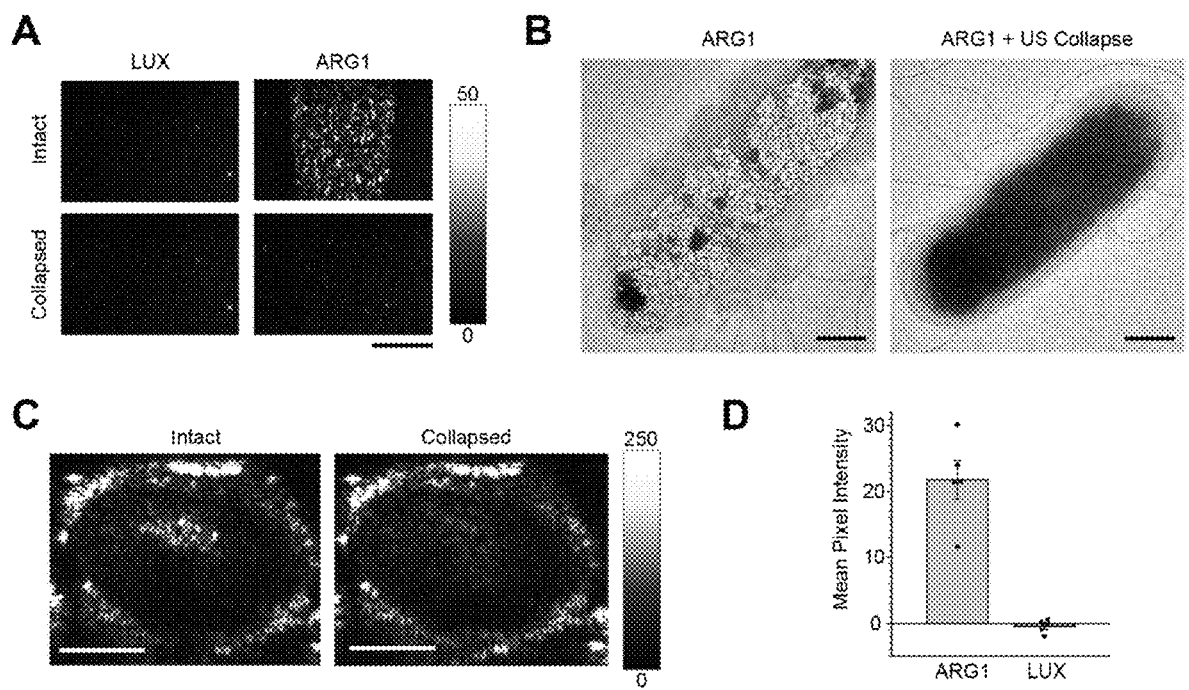
FIG. 12 shows exemplary ultrasound imaging of *S. typhimurium* in tumor xenografts. Panel A shows exemplary ultrasound images of a gel phantom containing *S. typhimurium* expressing ARG1 or the LuxABCDE operon. Cell concentration is $10^9$ cells/ml. Panel B shows exemplary representative TEM images of whole *S. typhimurium* cells expressing ARG1 with and without exposure to acoustic collapse pulses. Panel C shows exemplary representative ultrasound images of mouse OVCAR8 tumors injected with 50 µL of $3.2 \times 10^9$ cells/ml ARG1-expressing *S. typhimurium*, before and after acoustic collapse. Panel D shows a graph reporting exemplary mean collapse-sensitive ultrasound contrast in N=5 tumors injected with ARG1-expressing or LuxABCDE-expressing cells. Scale bars 500 nm in Panel B and 2.5 mm in Panel C. Error bars represent ±SEM.
Figure 13:
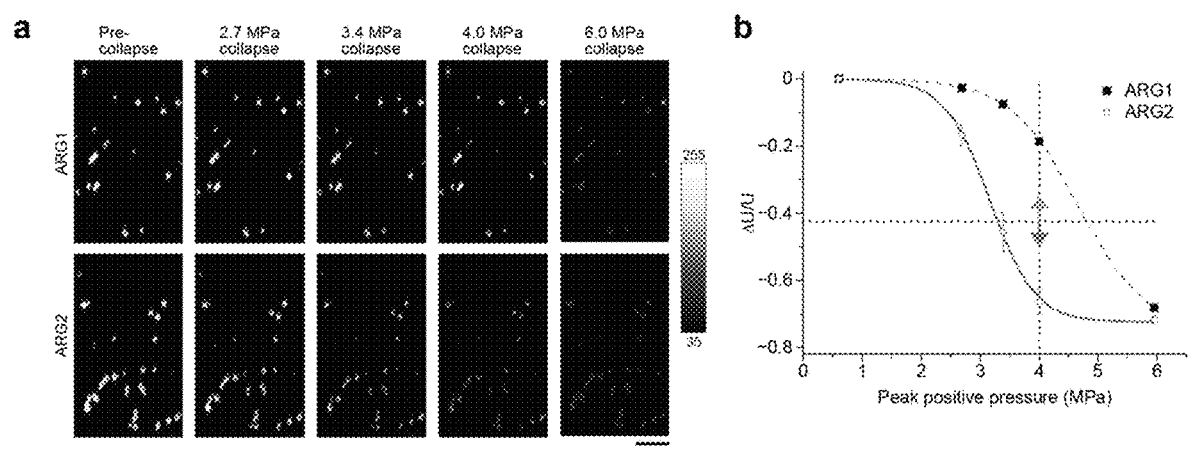
FIG. 13 shows exemplary data of colony ultrasound of *E. coli* expressing ARG1 or ARG2. Panel A shows exemplary ultrasound images of plates containing either ARG1 or ARG2 expressing *E. coli* colonies. Images were acquired before collapse and after collapse at the indicated peak acoustic pressures. Panel B shows a graph reporting exemplary normalized average colony change in ultrasound intensity after insonation at increasing pressures (N=15 per sample). All error bars represent +/−SEM. The crosshairs indicate determined thresholds for distinguishing ARG1 vs ARG2 based on acoustic phenotype. Scale bar 10 mm. Error bars represent ±S.E.M.

Another emerging application of engineered microbes is as antitumor therapies and diagnostics [61, 63, 92]. For example, Salmonella typhimurium has been engineered to colonize tumors and secrete proteins causing cancer cell lysis and immune system stimulation [61, 92]. Being able to image such therapies in the body could facilitate their development and clinical translation. To enable this possibility, the genetic construct encoding ARG1 was adapted for expression in attenuated *S. typhimurium* strain ELH1301, which has been used in tumor-homing studies [61, 92]. Upon induction with N-(β-ketocaproyl)-L-homoserine lactone (AHL), ARG-expressing *S. typhimurium* cells produced abundant intracellular gas vesicles and were readily observable using ultrasound compared to controls expressing the bacterial luciferase operon LuxABCDE (FIG. 12, Panels A-B). The level of ultrasound contrast was similar to ARG-expressing E. coli, with mean intensities per pixel of 9.5±0.7 and 12.1±2.1, respectively, at a density of $10^9$ cells/ml. Following pressure-induced collapse, these cells are indistinguishable from luciferase-expressing controls (FIG. 12 Panel A).

Next, it was tested whether ARG-expressing *S. typhimurium* could be imaged in vivo in a murine tumor, where these bacteria can proliferate to densities of $10^{10}$ cells per gram tissue [92]. Live ARG-expressing cells were injected into OVCAR8 ovarian adenocarcinoma xenografts in nude mice and imaged with ultrasound. Contrast was readily apparent in tumors containing engineered *S. typhimurium*, and disappeared after acoustic collapse (FIG. 12 Panels C, D). Cells expressing the luciferase operon had no discernable ultrasound contrast (FIG. 12 Panel D). These results demonstrate that ARGs can be employed in more than one bacterial species and that tumor-homing bacteria are detectable inside tumors at concentrations relevant to therapeutic and diagnostic applications.

Example 8. Acoustomagnetic Imaging of Gene Expression

Heterologous expression of a GVGC gene cluster comprising a combination of genes from *A. floc-aquae* and *B. megaterium*[77] was placed under the control of a promoter inducible by isopropyl b-D-1-thiogalactopyranoside (IPTG, FIG. 16, Panel A). Overnight induction resulted in GV expression and robust, acoustically erasable QSM contrast that was absent from cells that were not induced or cells induced to express a control fluorescent protein (FIG. 16, Panels B-C). Notably, the *E. coli* concentration in the phantom, estimated from $OD_{600}$ to be ~14 g/L wet cellular weight [93], indicates that the GV-containing cells can be detected while comprising less than 1.4% of the imaged volume.

Example 9: Amino Acid Sequences of Exemplary GVS and GVA Proteins

Table NF1, NF2 and NF3 show amino acid sequences of exemplary GVS (GvpA/B or GvpC) and GVA proteins from several exemplary prokaryotic species. In particular, these exemplary amino acid sequences can be used as reference amino acid sequences in some embodiments for homology-based searches for related GVS and GVA proteins.

TABLE 5

Amino acid sequences of exemplary gvpA and gvpB proteins

| Species, protein; GenBank accession | Amino acid sequence | SEQ ID NO.: |
|---|---|---|
| Anabaena flos-aquae, gvpA; gi\|121860\|sp\|P10397.3 | MAVEKTNSSSSLAEVIDRILDKGIVIDAWVRVS LVGIELLAIEARIVIASVETYLKYAEAVGLTQSA AVPA | 41 |
| B. megaterium, gvpA; gi\|294500059\|ref\|YP_003563759.1 | MSIQKSTDSSSLAEVIDRILDKGIVIDAFARVSL VGIEILTIEARVVIASVDTWLRYAEAVGLLTDK VEEEGLPGRTEERGAGLSF | 42 |
| B. megaterium, gvpB1; gi\|294500056\|ref\|YP_003563756.1\| | MSIQKSTNSSSLAEVIDRILDKGIVIDAFARVSV VGIEILTIEARVVIASVDTWLRYAEAVGLLRDD VEENGLPERSNSSEGQPRFSI | 43 |
| Frankia sp, gvpA; gi\|86739718\|ref\|YP_480118.1 | MTVSSQSMNRAPKPSSLADVLDVVLDRGIVID AYARVALVGIEVLTADARVVIATVDTYLRFAE AVNRLDLAPKEQVPGLPGLMHEVTDGTARQK | 44 |

TABLE 5-continued

Amino acid sequences of exemplary gvpA and gvpB proteins

| Species, protein; GenBank accession | Amino acid sequence | SEQ ID NO.: |
|---|---|---|
| | SKGALEGLKDTAEEAVGSLRGGSSEEHARRDL PAGRSAPGDRRSGREG | |
| *Haloferax mediterranei*, gvpA; gi\|389847150\|ref\|YP_006349389.1 | MVQPDSSSLAEVLDRVLDKGVVVDVWARISL VGIEILTVEARVVAASVDTFLHYAEEIAKIEQAE LTAGAEAAPTEA | 45 |
| *Halobacterium sp NRC-1*, gvpA1; gi\|16120003\|ref\|NP_395591.1 | MAQPDSSGLAEVLDRVLDKGVVVDVWARVSL VGIEILTVEARVVAASVDTFLHYAEEIAKIEQAE LTAGAEAAPEA | 46 |
| *Halobacterium sp NRC-1*, gvpA2; gi\|16120172\|ref\|NP_395760.1 | MAQPDSSSLAEVLDRVLDKGVVVDVWARISL VGIEILTVEARVVAASVDTFLHYAEEIAKIEQAE LTAGAEAPEPAPEA | 47 |
| *Halorubrum vacuolatum*, gvpA; gi\|22095734\|sp\|O33397.1 | MAQPDSSSLAEVLDRVLDKGVVVDVYARLSL VGIEILTVEARVVAASVDTFLHYAEEIAKIEQAE LTAGAEAAPTEA | 48 |
| *Microcystis aeruginosa NIES-843*, gvpA; gi\|166366499\|ref\|YP_001658772.1 | MAVEKTNSSSLAEVIDRILDKGIVIDAWARVS LVGIELLAIEARVVIASVETYLKYAEAVGLTQS AAVPA | 49 |
| *Methanosarcina barkeri*, gvpA; gi\|73667875\|ref\|YP_303890.1 | MVSQSPDSSSLAEVLDRILDKGIVVDTWARVSL VGIEILAIEARVVVASVDTFLHYAEEITKIEIAAR EEKPAIAA | 50 |
| *Serratia sp. ATCC 39006*, gvpA1; gi\|555225836\|gb\|ESN63289.1 | MAKVQKSTDSSSLAEVVDRILDKGIVIDAWVK VSLVGIELLSIEARVVIASVETYLKYAEAIGLTA SAATPA | 51 |
| *Serratia sp. ATCC 39006*, gvpA2; gi\|555225844\|gb\|ESN63297.1 | MPVNKQYQDEQQQVSLCEALDRVLNKGVVIV ADITISVANIDLIYLSLQALVSSVEAKNRLPGRE | 52 |
| *Serratia sp. ATCC 39006*, gvpA3; gi\|555225847\|gb\|ESN63300.1 | MSGNKKLTHSTDSTTVADLLERLLDKGVVISG DIRIRLVEVELLTLEIRLLICSVDKAVEMGLDW WSGNPAFDSRARVSSSAPAPELEERLQRLEARL EAAPSVIEETHL | 53 |
| *Streptomyces coelicolor*, gvpA1; gi\|21219180\|ref\|NP_624959.1 | MITYDDEVVCAPRAGTLYDVLELILDRGMVID VFVRVSLVGIEILKVDARIVVASVDTYLRFAEA CNRLDLEHDVRSKTVPEMFGSPMAKTVGRAG ARRTARSLTDKVRDVLTPEHEHEEEPEEAEDRP RAGAERGRSTQRPRSRPAARPRDEDDRPRSPR RRTEEEDR | 54 |
| *Streptomyces coelicolor*, gvpA2; gi\|21224803\|ref\|NP_630582.1 | MTVVPAQQTGGGGSSGLYDVLELVLDRGLVID AFVRVSLVGIEILKIDVRVVVASVDTYLRFAEA CNRLDLEAGPRKDPGLPDLVGEMTESGARGKS KGALSGAAETISDAFKQARDDGGSERETSSRPR ARKAAPSRRKEEQE | 55 |
| *Bukholderia*, gvpA1 | MAKVQKSTDSSSLAEVVDRILDKGIVIDVWAK VSLVGIELLSIEARVVIASVETYLKYAEAIGLTA TAAAPTA | 56 |
| *Bukholderia*, gvpA2 | MADLLERVLDKGVVITGDIRINLVDVELLTIRIR LLVCSVDKAKELGIDWWNADTFFLGPDRGQSA LPGRASAVDVAAGSAVHADAAHR | 57 |
| *Psychromonas* gvpA1 | MANVQKSTDSSGLAEVVDRILEKGIVIDAFVKV SLVGIELLSIEARVVIASVETYLKYAEAIGLTAS AATPA | 58 |
| *Psychromonas* gvpA2 | MANVQKTTDSSGLAEVIDRILDKGIVIDAFVKV SLVGIELLSIEARVVIASVETYLKYAEAIGLIAS AATPA | 59 |
| *Psychromonas* gvpA3 | MATGKPQSMTHSVKSTTVADLLERILDKGIVV TGDIKIKLVDVELLTVELRLVICSVDKAVEMG MDWWNNNPAFAPQAPAQEGELSSIEKRLEKIE KALVK | 60 |

TABLE 5-continued

Amino acid sequences of exemplary gvpA and gvpB proteins

| Species, protein; GenBank accession | Amino acid sequence | SEQ ID NO.: |
|---|---|---|
| *Psychromonas* gvpA4 | MPMANVSINPELTAQECEKISLCDALDRIINKG VVIHGEITISVANVDLISLGVRLILSNVETREQSN TPKEEV | 61 |

TABLE 6

Protein sequences of gvpC from exemplary species:

| Species | UniProt ID No. | Amino acid Sequence | SEQ ID NO: |
|---|---|---|---|
| *Anabaena flos-aquae* | P09413 | MISLMAKIRQEHQSIAEKVAELSLETREFLSVTTAK RQEQAEKQAQELQAFYKDLQETSQQFLSETAQARI AQAEKQAQELLAFHKELQETSQQFLSATAQARIAQ AEKQAQELLAFYQEVRETSQQFLSATAQARIAQAE KQAQELLAFHKELQETSQQFLSATADARTAQAKE QKESLLKFRQDLFVSIFG | 62 |
| *Halobacterium salinarum* | P24574 | MSVTDKRDEMSTARDKFAESQQEFESYADEFAADI TAKQDDVSDLVDAITDFQAEMTNTTDAFHTYGDE FAAEVDHLRADIDAQRDVIREMQDAFEAYADIFAT DIADKQDIGNLLAAIEALRTEMNSTHGAFEAYADD FAADVAALRDISDLVAAIDDFQEEFIAVQDAFDNY AGDFDAEIDQLHAAIADQHDSFDATADAFAEYRD EFYRIEVEALLEAINDFQQDIGDFRAEFETTEDAFV AFARDFYGHEITAEEGAAEAEAEPVEADADVEAE AEVSPDEAGGESAGTEEEETEPAEVETAAPEVEGSP ADTADEAEDTEAEEETEEEAPEDMVQCRVCGEYY QAITEPHLQTHDMTIQEYRDEYGEDVPLRPDDKT | 63 |
| *Halobacterium mediterranei* | Q02228 | MSVKDKREKMTATREEFAEVQQAFAAYADEFAA DVDDKRDVSELVDGIDTLRTEMNSTNDAFRAYSE EFAADVEHFHTSVADRRDAFDAYADIFATDVAEM QDVSDLLAAIDDLRAEMDETHEAFDAYADAFVTD VATLRDVSDLLTAISELQSEFVSVQGEFNGYASEFG ADIDQFHAVVAEKRDGHKDVADAFLQYREEFHGV EVQSLLDNIAAFQREMGDYRKAFETTEEAFASFAR DFYGQGAAPMATPLNNAAETAVTGTETEVDIPPIE DSVEPDGEDEDSKADDVEAEAEVETVEMEFGAEM DTEADEDVQSESVREDDQFLDDETPEDMVQCLVC GEYYQAITEPHLQTHDMTIKKYREEYGEDVPLRPD DKA | 64 |
| *Microchaete diplosiphon* | P08041 | MTPLMIRIRQEHRGIAEEVTQLFKDTQEFLSVTTAQ RQAQAKEQAENLHQFHKDLEKDTEEFLTDTAKER MAKAKQQAEDLFQFHKEMAENTQEFLSETAKER MAQAQEQARQLREFHQNLEQTTNEFLADTAKERM AQAEQKQQLHQFRQDLFASIFGTF | 65 |
| *Nostoc* sp. | Q8YUS9 | MTALMVRIRQEHRSIAEEVTQLFRETHEFLSATTA HRQEQAKQQAQQLHQFHQNLEQTTHEFLTETTTQ RVAQAEAQANFLHKFHQNLEQTTQEFLAETAKNR TEQAKAQSQYLQQFRKDLFASIFGTF | 66 |

TABLE 7

Amino acid sequences of exemplary GVA proteins from *B. megaterium*.

| GVA Protein | Amino acid sequence | SEQ ID NO.: |
|---|---|---|
| gvpR | MEIKKIMQAVNDFFGEHVAPPHKITSVEATEDEGWRVIVEVIEERE YMKKYAKDEMLGTYECFVNKEKEVISFKRLDVRYRSAIGIEA | 67 |
| gvpN | MTVLTDKRKKGSGAFIQDDETKEVLSRALSYLKSGYSIHFTGPAG GGKTSLARALAKKRKRPVMLMHGNHELNNKDLIGDFTGYTSKK VIDQYVRSVYKKDEQVSENWQDGRLLEAVKNGYTLIYDEFTRSK | 68 |

TABLE 7-continued

Amino acid sequences of exemplary GVA proteins from *B. megaterium*.

| GVA Protein | Amino acid sequence | SEQ ID NO.: |
|---|---|---|
| | PATNNIFLSILEEGVLPLYGVKMTDPFVRVHPDFRVIFTSNPAEYA GVYDTQDALLDRLITMFIDYKDIDRETAILTEKTDVEEDEARTIVT LVANVRNRSGDENSSGLSLRASLMIATLATQQDIPIDGSDEDFQTL CIDILHHPLTKCLDEENAKSKAEKIILEECKNIDTEEK | |
| gvpF | MSETNETGIYIFSAIQTDKDEEFGAVEVEGTKAETFLIRYKDAAMV AAEVPMKIYHPNRQNLLMHQNAVAAIMDKNDTVIPISFGNVFKSK EDVKVLLENLYPQFEKLFPAIKGKIEVGLKVIGKKEWLEKKVNEN PELEKVSASVKGKSEAAGYYERIQLGGMAQKMFTSLQKEVKTDV FSPLEEAAEAAKANEPTGETMLLNASFLINREDEAKFDEKVNEAH ENWKDKADFHYSGPWPAYNFVNIRLKVEEK | 69 |
| gvpG | MLHKLVTAPINLVVKIGEKVQEEADKQLYDLPTIQQKLIQLQMMF ELGEIPEEAFQEKEDELLMRYEIAKRREIEQWEELTQKRNEES | 70 |
| gvpL | MGELLYLYGLIPTKEAAAIEPFPSYKGFDGEHSLYPIAFDQVTAVV SKLDADTYSEKVIQEKMEQDMSWLQEKAFHHHETVAALYEEFTII PLKFCTIYKGEESLQAAIEINKEKIENSLTLLQGNEEWNVKIYCDDT ELKKGISETNESVKAKKQEISHLSPGRQFFEKKKIDQLIEKELELHK NKVCEEIHDKLKELSLYDSVKKNWSKDVTGAAEQMAWNSVFLLP SLQITKFVNEIEELQQRLENKGWKFEVTGPWPPYHFSSFA | 71 |
| gvpS | MSLKQSMENKDIALIDILDVILDKGVAIKGDLIISIAGVDLVYLDLR VLISSVETLVQAKEGNHKPITSEQFDKQKEELMDATGQPSKWTNP LGS | 72 |
| gvpK | MQPVSQANGRIHLDPDQAEQGLAQLVMTVIELLRQIVERHAMRR VEGGTLTDEQIENLGIALMNLEEKMDELKEVFGLDAEDLNIDLGP LGSLL | 73 |
| gvpJ | MAVEHNMQSSTIVDVLEKILDKGVVIAGDITVGIADVELLTIKIRLI VASVDKAKEIGMDWWENDPYLSSKGANNKALEEENKMLHERLK TLEEKIETKR | 74 |
| gypT | MATETKLDNTQAENKENKNAENGSKEKNGSKASKTTSSGPIKRA VAGGIIGATIGYVSTPENRKSLLDRIDTDELKSKASDLGTKVKEKS KSSVASLKTSAGSLFKKDKDKSKDDEENVNSSSSETEDDNVQEYD ELKEENQTLQDRLSQLEEKMNMLVELSLNKNQDEEAEDTDSDEE ENDENDENDENEQDDENEEETSKPRKKDKKEAEEEESESDEDSEE EEEDSRSNKKNKKVKTEEEDEDESEEEKKEAKPKKSTAKKSKNTK AKKNTDEEDDEATSLSSEDDTTA | 75 |
| gvpU | MSTGPSFSTKDNTLEYFVKASNKHGFSLDISLNVNGAVISGTMISA KEYFDYLSETFEEGSEVAQALSEQFSLASEASESNGEAEAHFIHLK NTKIYCGDSKSTPSKGKIFWRGKIAEVDGFFLGKISDAKSTSKKSS | 76 |

TABLE 8

Amino acid sequences of exemplary GVA proteins from *Serratia* sp.

| GVA Protein | Amino acid sequence | SEQ ID NO.: |
|---|---|---|
| gvpN | MIKQNTVSQYTVDDDLVVPEASEHFVATSYVNDIIERALVYLRAG YPVHFAGPSGIGKTTLAFHLAALWGRPVTMLQGNEEFVSSDLTGK DIGYRKSSLVDNYIHSVLKTEEQMNRMWVDNRLTTACRNGDMLI YDEFNRSKAETNNVLLSVLSEGILNLPGLRGVGEGYLDVHPEFRAI FTSNPEEYAGTHKTQDALMDRMITINIGLVDRDTELQILHARSELE LKEAAYIVDIIRELRGNEHETKHGLRAGIAIAHILHQQGIKPRYGDK LFHAICYDVLSMDAAKIQHAGRSIYREMVDGVIRKICPPIGSDTVK ASTQKIKAVE | 77 |
| GvpV | MAISTRPLRTLSDIKTHSGRVSGEHQTYRDYFQIGALELERWRRTR EREAASSRIASIDERIADIDKEKAALLADATAASAVAENNDKSEAA EKKKKSSGLRIKY | 78 |
| gvpF1 | MMSIDKSRNHRAKVLYALCVSDDSTPNYKIRGLEAAPVYSIDQDG LRAVVSDTLSTRLRPERRNITAHQAVLHKLTEEGTVLPMRFGVIAR NAEAVKNLLVANQDTIREHFERLDGCVEMGLRVSWDVTNIYEYF VATYPVLSETRDEIWNGNSNANNHREEKIRLGNLYESLRSGDRKE STEKVKEVLLDYCEEIIENPVKKEKDVMNLACLVARERMDEFAK | 79 |

TABLE 8-continued

Amino acid sequences of exemplary GVA proteins from *Serratia* sp.

| GVA Protein | Amino acid sequence | SEQ ID NO.: |
|---|---|---|
| | GVFEASKLFDNVYLFDYTGPWAPHNFVTLDLHAPTAKKKTLTRA GTLSD | |
| GvpF2 | MTMNTEAQTEQAIYLYGLTLPDLAAPPILGVDNQHPINTHQCAGL NAVISPVALSDFTGEKGEDNVQNVTWLTPRICRHAQIIDSLMAQGP VYPLPFGTLFSSQNALEQEMKSRATDVFVSLRRITGCQEWALEAT LDRKQAVDVLFTEGLDSGRFCLPEAIGRRHLEEQKLRRRLTTELSD WLAHALTAMQNELHPLVRDFRSRRLLDDKILHWAYLLPVEDVAA FQQQVADIVERYEAYGFSFRVTGPWAAYSFCQPDES | 80 |
| gvpF3 | MSLLLYGIVAEDTQLALEPDGSPHAGEEPMQLVKAATLAALVKPC EADVSREPAAALAFGQQIMHVHQQTTIIPIRYGCVLADEDAVTQH LLNHEAHYQTQLVELENCDEMGIRLSLASAEDNAVTTPQASGLDY LRSRKLAYAVPEHAERQAALLNNAFTGLYRRHCAEISMFNGQRT YLLSYLVPRTGLQAFRDQFNTLANNMTDIGVISGPWPPYNFAS | 81 |
| gvpG | MLLIDDILFSPVKGVMWIFRQIHELAEDELAGEADRIRESLTDLYM LLETGQITEDEFEQQEAVLLDRLDALDEEDDMLGDEPGDDEDDEY EEDDDEEDDDEEDDDDEDDDDEDDDDEEDDDDDEDDDDEDEPE GTTK | 82 |
| GvpW | MKPAIYPKFLLESPLKLVFFGGKGGVGKSTCATSTALRLAQEQPQ HHFLLVSTDPAHSLQNILSDLVLPKNLDVRELNAAASLHEFKSQHE GVLKEIAYRGTVLDQNDVQGLMDTALPGMDELAAYLEIAEWIQK DTYYRIIDTAPTGHTLRLLEMPDLIYRWLTALDTLLAKQRYIRKR FAGDNRLDHLDHFLLDMNDSLKAMHELVTDSTRCCFVLVMLAE AMSVEESIDLAGALNQQRVFLSDLVVNRLFPENDCPTCCVERNRQ MLALQNGYQRLPGHVFWTLPLLAIEPRGALLHEFWSGVRLLDEN EVMATTCHHQLPLRVESSISLPASTFRLLIFAGKGGVGKTTLACAT ALRLNSEYPELRILLFSADPAHSLSDCLGVTLQQQPISVLVNIDAQE INAQADFDKIRQGYRAELEAFLLDTLPNLDITFDREVLEHLLDLAP PGLDEIMALTAIMDHLDSGRYDMVIVDGAPSGHLLRLLELPELIRD WLKQFFSLLLKYRKVMRFPHLSERLVQLSRELKNLRALLQDTKQT GLYAVTVPTHLALEKTYEMTCALQRLGLTANALFINQITPPSDCTL CQAITSRESLELKCADEMFPSQPHAQIFRQTEPTGLSKLKTLGSALF L | 83 |
| gvpK | MTTNQLSHHSPVFGPTSPAIQRPITEANRHKIDIDGERVRDGLAQL VLTLVKLLHELLERQAIRRMDSGSLSDEEVERLGLALMRQAEELT HLCDVFGFKDDDLNLDLGPLGRLL | 84 |
| GvpX | MVNTTNDINAATRGLLLRMGNAWFEQDELRQAVDIYLKIIEQYPD SKESKTAQTALLTISQRYERDGLFRLSLDILERVGEITPTSI | 85 |
| gvpY | MRALIHFPIIHSPKDLGTLSEAASHLRTETQTRAYLAAVEGFWTMI TTTIEGLDLDYTHLKLYQDGLPVCGKENEIVTDVANAGSQNYKLL LTLQHKGAILMGTESPELLLQERDLMTQLLQSTEQTEASLETAKTL LNRRDDYIAQRIDETLQDGEMAILFLGLMHNIEAKLPADIVFIQPL GKPPGGESI | 86 |
| gvpH | MTGNVEGILRGLGDLVEKLVETGEQIKRSGAFDIDTNDGKNAKAV YGFSIKMGLDGNQENRVEPFGNIRRDEQTGEATVQEVSEPLVDVIE ESDHVLVLAEMPGVADEDVQVELNGDILTLHSERGSKKYHKEIVL PCSFDDKAMERSCRNGILEVKLGK | 87 |
| GvpZ | MSEELKLKVAEALPKDAGRGYARLDPADMARLNLAVGDIVQLTS KKGTGIAKLMPTYPDMRNKGIVQLDGLTRRNTSLSLDEKVQIEPA SCKHATQIVLIPTTITPNQRDLDYIGSLLDGLPVQKGDLLRAHLFGS RSADFKVESTIPDGAVLIDPTTTLVIGKSNAVGNSSHSTQRLSYED VGGLKNQVRRIREMIELPLRYPEVFERLGIDAPKGVLLSGPPGCGK TLIARIIAQETDAQFFTISGPEIVHKFYGESEAHLRKIFEEAGRKGPSI IFLDEIDSIAPHRDKVVGDVEKRIVAQLLALMDGLKNRGKVIVIAA TNLPNAIDPALRRPGRFDREISIPIPDREGRREIIEIHSTGMPLNADV DLNVLADITHGFVGADLEALCREAAMSALRRLLPEIDFSSAELPYD RLAELTVMMDDFRAALCEVSPSAIRELFVDIPDVRWEDVGGLDD VRRRLIESVEWPIKYPELYEQAGVKPPKGLLLAGPPGVGKTLIAKA VANESGVNVISVKGPALMSRYVGDSEKGVRELFLKARQAAPCIIF LDEVDSVIPARNEGAIDSHVAERVLSQFLSEMDGLEELKGVFVMG ATNRADLIDPAMLRPGRFDEIIELGLPDEDARRQILAVHLRNKPLG DNIHADDLAERCDGASGAELAAVCNRAALAALRRAIQQSEEAVL SPSTVGETPVALTVRIEQHDFAEVIAEMFGDDA | 88 |

Example 10: Alignment of Exemplary gvpA and gvpB Protein Sequences

FIG. 18 shows an exemplary Clustal omega alignment of amino acid sequences of selected exemplary gvpA and gvpB proteins. The gvpA and gvpB proteins shown are from the following species: Sa_A2, *Serratia* sp. ATCC 39006 gvpA2; Sa_A3, *Serratia* sp. ATCC 39006 gvpA3; Sc_A2, *Streptomyces coelicolor* gvpA2; Sc_A1, *Streptomyces coelicolor* gvpA1; Fc_A, *Frankia* sp. gvpA; Bm_B1, *B. megaterium* gvpB1; Mb_A, *Methanosarcina barkeri* gvpA; Hv_A, *Halorubrum vacuolatum* gvpA; Hm_A, *Haloferax mediterranei* gvpA; Hs_A1, *Halobacterium* sp. NRC-1 gvpA1; Hs_A2, *Halobacterium* sp. NRC-1 gvpA2; Bm_A, *B. megaterium* gvpA; Bm_B2, *B. megaterium* gvpB2; Af_A, *A. floc-aquae* gvpA; Ma_A; Sa_A1, *Serratia* sp. ATCC 39006 gvpA1. The bottom row of FIG. 18 indicated as "Consensus" shows an exemplary consensus sequence derived from alignment of the gvpA and gvpB amino acid sequences shown.

In some embodiments described herein, homology-based searching (e.g., BLAST alignment) of sequences of proteins encoded in the genome of a prokaryotic organism compared to the exemplary consensus sequence shown in FIG. 18 can be used to identify gvpA and/or gvpB protein sequences in the prokaryotic organism.

Example 11: Exemplary GVGC Polynucleotide Construct to Allow Expression of Two Different GV Types in One Cell FIG. 19 shows an exemplary configuration of a construct designed to allow expression of two different GV types in one prokaryotic cell. The exemplary construct in FIG. 19 is designed to provide alternating expression of two GV types, the first GV type encoded by Cluster 1, and the second GV type encoded by Cluster 2, shown as block-shaped arrows facing in opposite orientations of a DNA strand (shown as a straight line), with a promoter between the two clusters. The promoter is flanked by recombination sites (e.g. flippase recognition target, FRT sites) shown as circles. For example, initially, the promoter can be oriented in a direction operatively linked to Cluster 1, initiating expression of gyp genes for the formation of GV type 1. In presence of a cognate recombinase (e.g. flippase, Flp), expressed from another genetic construct in the prokaryotic cell, the orientation of the promoter is reversed upon recombination at the FRT sites, and thereafter is oriented in the opposite direction, operatively linked to Cluster 2, initiating expression of gyp genes for the formation of GV type 2.

Example 12: Exemplary Gas Vesicle Gene Clusters

FIG. 20 shows diagrams illustrating the organization of exemplary gas vesicle gene clusters. Gas vesicle gene clusters from the indicated organisms are shown, with genes shown as block-shaped arrows, and genes of predicted similar function indicated in the same shade of grey. The direction of the transcription of genes within a gene cluster is indicated by the direction of the block-shaped arrows, and genes grouped together having block arrows pointed in the same direction are typically organized in the same operon. The scale bar indicates 1 kb [1]. In addition, FIG. 21 shows diagrams illustrating organization of exemplary gyp gene clusters, wherein each letter indicates a gyp gene, and an arrow beneath a group of letters indicates an operon, with the direction of the arrow indicating the direction of transcription [2].

Example 13: Phylogenetic Relationships Between Exemplary gvpA, gvpF and gvpN Proteins FIG. 22 shows exemplary phylogenetic relationships of the gvpA protein sequences from the indicated prokaryotic species [1]. In some embodiments described herein, the identification of a GvpA/B protein can be performed by comparing the sequence of an unknown protein in a prokaryotic cell with that of a known gvpA sequence from the closest phylogenetic relative of the prokaryotic species, such as those indicated in the exemplary phylogenetic tree diagram in FIG. 22.

FIG. 23 shows exemplary phylogenetic relationships of the gvpF and gvpL protein sequences from the indicated prokaryotic species [1]. In some embodiments described herein, the identification of a GvpF protein can be performed by comparing the sequence of an unknown protein in a prokaryotic cell with that of a known gvpF sequence from the closest phylogenetic relative of the prokaryotic species, such as those indicated in the exemplary phylogenetic tree diagram in FIG. 23.

FIG. 24 shows exemplary phylogenetic relationships of the gvpN protein sequences from the indicated prokaryotic species [1]. In some embodiments described herein, the identification of a GvpN protein can be performed by comparing the sequence of an unknown protein in a prokaryotic cell with that of a known gvpN sequence from the closest phylogenetic relative of the prokaryotic species, such as those indicated in the exemplary phylogenetic tree diagram in FIG. 24.

Example 14: Detection of GVs Production in Prokaryotic Cell

Detection of GVs in cells can be through determining if 1) the cells become buoyant after centrifugation or 2) through detecting them using transmission electron microscopy. 3) cells can be lysed, the lysate can be centrifuged for 4-16 hours at 300×g and the top 60 µl of solution can be analyzed using Transmission electron microscopy.

After the cells have been expressing GV proteins, after 16-24 hours of expression, cells in a liquid culture can be put in 1-50 mL tubes and centrifuged for 1-2 hours at 300×g.

After the cells have been expression GV proteins, after 16-24 hours of expression, cells from a liquid culture can be placed on TEM grids. Skilled person can look for hollow vesicles with the right size and shape indicating that GVs have been expressed and formed as per FIG. 2C.

Cells can be lysed using detergents provided in our manuscript. The lysate can be centrifuged for 4-16 hours at 300×g. The top 60 µl of the solution can be analyzed using TEM.

The examples set forth above are provided to give those of ordinary skill in the art a complete disclosure and description of how to make and use the embodiments of the hybrid GVGCs, and related GVR genetic circuits, vectors, genetically engineered prokatyoric cells, compositions, methods and systems of the disclosure, and are not intended to limit the scope of what the inventors regard as their disclosure. Those skilled in the art will recognize how to adapt the features of the exemplified hybrid GVGCs, and related genetic circuits, vectors, genetically engineered prokaryotic cells, compositions, methods and systems herein disclosed to additional hybrid GVGCs, and related genetic circuits, vectors, genetically engineered prokaryotic cells, compositions, methods and systems according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P2075-US-Seq-List-ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, system elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the genetic circuits, genetic molecular components, and methods steps set forth in the present description. As will be obvious to one of skill in the art, methods and systems useful for the present methods and systems may include a large number of optional composition and processing elements and steps.

In particular, it will be understood that various modifications may be made without departing from the spirit and scope of the present disclosure. Accordingly, other embodiments are within the scope of the following claims.

REFERENCES

1. Tashiro, Y., et al., *Molecular Genetic and Physical Analysis of Gas Vesicles in Buoyant Enterobacteria*. Environmental microbiology, 2016. 18(4): p. 1264-1276.
2. Van Keulen, G., et al., *Gas vesicles in actinomycetes: old buoys in novel habitats?* Trends in microbiology, 2005. 13(8): p. 350-354.
3. Walsby, A. E., *Gas vesicles*. Microbiol. Rev., 1994. 58(1): p. 94-144.
4. Walsby, A. E., *Gas-vacuolate bacteria (apart from cyanobacteria)*, in *The Prokaryotes*. 1981, Springer. p. 441-447.
5. Walsby, A. E., *Cyanobacteria: planktonic gas-vacuolate forms*. The Prokaryotes, a Handbook on Habitats, Isolation, and Identification of Bacteria, 2013. 1: p. 224-235.
6. Woese, C. R., *Bacterial evolution*. Microbiological reviews, 1987. 51(2): p. 221.
7. Walsby, A. E., *Gas vesicles*. Microbiol Rev, 1994. 58(1): p. 94-144.
8. Hayes, P. and R. Powell, *The gvpA/C cluster of Anabaena flos-aquae has multiple copies of a gene encoding GvpA*. Archives of microbiology, 1995. 164(1): p. 50-57.
9. Kinsman, R. and P. Hayes, *Genes encoding proteins homologous to halobacterial Gvps N, J, K, F & L are located downstream of gvpC in the cyanobacterium Anabaena flos-aquae*. DNA Sequence, 1997. 7(2): p. 97-106.
10. Pfeifer, F., *Distribution, formation and regulation of gas vesicles*. Nat. Rev. Microbiol., 2012. 10(10): p. 705-15.
11. Pfeifer, F., *Distribution, formation and regulation of gas vesicles*. Nat Rev Microbiol, 2012. 10(10): p. 705-15.
12. Yi, G., S.-H. Sze, and M. R. Thon, *Identifying clusters of functionally related genes in genomes*. Bioinformatics, 2007. 23(9): p. 1053-1060.
13. Myers, E. W. and W. Miller, *Optimal alignments in linear space*. Computer applications in the biosciences: CABIOS, 1988. 4(1): p. 11-17.
14. Smith, T. F. and M. S. Waterman, *Comparison of biosequences*. Advances in applied mathematics, 1981. 2(4): p. 482-489.
15. Needleman, S. B. and C. D. Wunsch, *A general method applicable to the search for similarities in the amino acid sequence of two proteins*. Journal of molecular biology, 1970. 48(3): p. 443-453.
16. Pearson, W. R. and D. J. Lipman, *Improved tools for biological sequence comparison*. Proceedings of the National Academy of Sciences, 1988. 85(8): p. 2444-2448.
17. Karlin, S. and S. F. Altschul, *Methods for assessing the statistical significance of molecular sequence features by using general scoring schemes*. Proceedings of the National Academy of Sciences, 1990. 87(6): p. 2264-2268.

18. Karlin, S. and S. F. Altschul, *Applications and statistics for multiple high-scoring segments in molecular sequences*. Proceedings of the National Academy of Sciences, 1993. 90(12): p. 5873-5877.
19. Li, N. and M. C. Cannon, *Gas vesicle genes identified in Bacillus megaterium and functional expression in Escherichia coli*. J Bacteriol, 1998. 180(9): p. 2450-8.
20. Buchler, N. E., U. Gerland, and T. Hwa, *On schemes of combinatorial transcription logic*. Proceedings of the National Academy of Sciences, 2003. 100(9): p. 5136-5141.
21. Silva-Rocha, R. and V. de Lorenzo, *Mining logic gates in prokaryotic transcriptional regulation networks*. FEBS letters, 2008. 582(8): p. 1237-1244.
22. Caravan, P., et al., *Gadolinium(III)Chelates as MRI Contrast Agents: Structure, Dynamics, and Applications*. Chemical Reviews, 1999. 99(9): p. 2293-2352.
23. Lee, J.-H., et al., *Artificially engineered magnetic nanoparticles for ultra-sensitive molecular imaging*. Nat Med, 2007. 13(1): p. 95-99.
24. Weissleder, R., et al., *Ultrasmall superparamagnetic iron oxide: characterization of a new class of contrast agents for MR imaging*. Radiology, 1990. 175(2): p. 489-493.
25. Genove, G., et al., *A new transgene reporter for in vivo magnetic resonance imaging*. Nat Med, 2005. 11(43): p. 450-454.
26. Cohen, B., et al., *Ferritin as an Endogenous MRI Reporter for Noninvasive Imaging of Gene Expression in C6 Glioma Tumors*. Neoplasia, 2005. 7(2): p. 109-117.
27. Shapiro, M. G., et al., *Directed evolution of a magnetic resonance imaging contrast agent for noninvasive imaging of dopamine*. Nat Biotech, 2010. 28(3): p. 264-270.
28. Cohen, B., et al., *MRI detection of transcriptional regulation of gene expression in transgenic mice*. Nat Med, 2007. 13(4): p. 498-503.
29. Gilad, A. A., et al., *Artificial reporter gene providing MRI contrast based on proton exchange*. Nat Biotech, 2007. 25(2): p. 217-219.
30. Zhang, S., et al., *PARACEST Agents: Modulating MRI Contrast via Water Proton Exchange*. Accounts of Chemical Research, 2003. 36(10): p. 783-790.
31. Taratula, O. and I. J. Dmochowski, *Functionalized 129Xe contrast agents for magnetic resonance imaging*. Current Opinion in Chemical Biology, 2010. 14(1): p. 97-104.
32. Evbuomwan, O. M., et al., *CEST and PARACEST Agents for Molecular Imaging*, in *The Chemistry of Molecular Imaging*. 2014, John Wiley & Sons, Inc. p. 225-243.
33. Kislukhin, A. A., et al., *Paramagnetic fluorinated nanoemulsions for sensitive cellular fluorine-19 magnetic resonance imaging*. Nat Mater, 2016. advance online publication.
34. Ahrens, E. T. and J. W. M. Bulte, *Tracking immune cells in vivo using magnetic resonance imaging*. Nature Reviews: Immunology, 2013. 13(10): p. 755-763.
35. Terreno, E., et al., *Challenges for Molecular Magnetic Resonance Imaging*. Chemical Reviews, 2010. 110(5): p. 3019-3042.
36. Cunningham, C. H., et al., *Positive contrast magnetic resonance imaging of cells labeled with magnetic nanoparticles*. Magnetic Resonance in Medicine, 2005. 53(5): p. 999-1005.
37. Stuber, M., et al., *Positive contrast visualization of iron oxide-labeled stem cells using inversion-recovery with ON-resonant water suppression (IRON)*. Magnetic Resonance in Medicine, 2007. 58(5): p. 1072-1077.
38. Mani, V., et al., *Gradient echo acquisition for superparamagnetic particles with positive contrast (GRASP): Sequence characterization in membrane and glass superparamagnetic iron oxide phantoms at 1.5T and 3T*. Magnetic Resonance in Medicine, 2006. 55(1): p. 126-135.
39. Zurkiya, O. and X. Hu, *Off-resonance saturation as a means of generating contrast with superparamagnetic nanoparticles*. Magnetic Resonance in Medicine, 2006. 56(4): p. 726-732.
40. McMahon, M. T., et al., *New "multicolor" polypeptide diamagnetic chemical exchange saturation transfer (DIACEST) contrast agents for MRI*. Magnetic Resonance in Medicine, 2008. 60(4): p. 803-812.
41. Shapiro, M. G., et al., *Genetically encoded reporters for hyperpolarized xenon magnetic resonance imaging*. Nat Chem, 2014. 6(7): p. 629-34.
42. Perez, J. M., et al., *Magnetic relaxation switches capable of sensing molecular interactions*. Nat Biotech, 2002. 20(8): p. 816-820.
43. Zabow, G., S. J. Dodd, and A. P. Koretsky, *Shape-changing magnetic assemblies as high-sensitivity NMR-readable nanoprobes*. Nature, 2015. 520(7545): p. 73-U157.
44. Atanasijevic, T., et al., *Calcium-sensitive MRI contrast agents based on superparamagnetic iron oxide nanoparticles and calmodulin*. Proceedings of the National Academy of Sciences, 2006. 103(40): p. 14707-14712.
45. Srivastava, A. K., et al., *Advances in using MRI probes and sensors for in vivo cell tracking as applied to regenerative medicine*. Disease Models and Mechanisms, 2015. 8(4): p. 323-336.
46. Shapiro, M. G., et al., *Protein Nanoparticles Engineered to Sense Kinase Activity in MRI*. Journal of the American Chemical Society, 2009. 131(7): p. 2484-2486.
47. Shapiro, M. G., et al., *Biogenic gas nanostructures as ultrasonic molecular reporters*. Nature nanotechnology, 2014. 9(4): p. 311-316.
48. Maresca, D., et al., *Nonlinear Ultrasound Imaging of Nanoscale Acoustic Biomolecules*. Applied Physics Letters, 2017. 110(7).
49. Zordan, R. E., et al., *Avoiding the ends: internal epitope tagging of proteins using transposon Tn7*. Genetics, 2015. 200(1): p. 47-58.
50. Round, J. L. and S. K. Mazmanian, *The gut microbiota shapes intestinal immune responses during health and disease*. Nature Reviews Immunology, 2009. 9(5): p. 313-323.
51. Yurist-Doutsch, S., et al., *Gastrointestinal microbiota-mediated control of enteric pathogens*. Annual review of genetics, 2014. 48: p. 361-382.
52. Belkaid, Y. and T. W. Hand, *Role of the microbiota in immunity and inflammation*. Cell, 2014. 157(1): p. 121-141.
53. Wang, Y. and L. H. Kasper, *The role of microbiome in central nervous system disorders*. Brain, behavior, and immunity, 2014. 38: p. 1-12.
54. Courbet, A., et al., *Detection of pathological biomarkers in human clinical samples via amplifying genetic switches and logic gates*. Science translational medicine, 2015. 7(289): p. 289ra83-289ra83.
55. Danino, T., et al., *Programmable probiotics for detection of cancer in urine*. Science translational medicine, 2015. 7(289): p. 289ra84-289ra84.
56. Kotula, J. W., et al., *Programmable bacteria detect and record an environmental signal in the mammalian gut*. Proceedings of the National Academy of Sciences, 2014. 111(13): p. 4838-4843.

57. Archer, E. J., A. B. Robinson, and G. r. M. Süel, *Engineered E. coli that detect and respond to gut inflammation through nitric oxide sensing.* ACS synthetic biology, 2012. 1(10): p. 451-457.
58. Steidler, L., et al., *Treatment of murine colitis by Lactococcus lactis secreting interleukin-10.* Science, 2000. 289(5483): p. 1352-1355.
59. Claesen, J. and M. A. Fischbach, *Synthetic microbes as drug delivery systems.* ACS synthetic biology, 2014. 4(4): p. 358-364.
60. Wells, J. M. and A. Mercenier, *Mucosal delivery of therapeutic and prophylactic molecules using lactic acid bacteria.* Nature Reviews Microbiology, 2008. 6(5): p. 349-362.
61. Din, M. O., et al., *Synchronized cycles of bacterial lysis for in vivo delivery.* Nature, 2016. 536(7614): p. 81-85.
62. Fischbach, M. A., J. A. Bluestone, and W. A. Lim, *Cell-based therapeutics: the next pillar of medicine.* Science translational medicine, 2013. 5(179): p. 179ps7-179ps7.
63. Danino, T., et al., *Programmable probiotics for detection of cancer in urine.* Science Translational Medicine, 2015. 7(289): p. 289ra84.
64. Mowat, A. M. and W. W. Agace, *Regional specialization within the intestinal immune system.* Nature Reviews Immunology, 2014.
65. Donaldson, G. P., S. M. Lee, and S. K. Mazmanian, *Gut biogeography of the bacterial microbiota.* Nature Reviews Microbiology, 2015.
66. Derrien, M. and J. E. van Hylckama Vlieg, *Fate, activity, and impact of ingested bacteria within the human gut microbiota.* Trends in microbiology, 2015.
67. Foucault, M.-L., et al., *In vivo bioluminescence imaging for the study of intestinal colonization by Escherichia coli in mice.* Applied and environmental microbiology, 2010. 76(1): p. 264-274.
68. Daniel, C., et al., *Bioluminescence imaging study of spatial and temporal persistence of Lactobacillus plantarum and Lactococcus lactis in living mice.* Applied and environmental microbiology, 2013. 79(4): p. 1086-1094.
69. Chu, J., et al., *A bright cyan-excitable orange fluorescent protein facilitates dual-emission microscopy and enhances bioluminescence imaging in vivo.* Nat Biotech, 2016. 34(7): p. 760-767.
70. Smith-Bindman, R., et al., *Use of diagnostic imaging studies and associated radiation exposure for patients enrolled in large integrated health care systems, 1996-2010.* JAMA, 2012. 307(22): p. 2400-9.
71. Foster, F. S., et al., *Advances in ultrasound biomicroscopy.* Ultrasound in medicine & biology, 2000. 26(1): p. 1-27.
72. Foster, F. S., et al., *Principles and applications of ultrasound backscatter microscopy.* Ultrasonics, Ferroelectrics and Frequency Control, IEEE Transactions on, 1993. 40(5): p. 608-617.
73. Errico, C., et al., *Ultrafast ultrasound localization microscopy for deep super-resolution vascular imaging.* Nature, 2015. 527(7579): p. 499-502.
74. Shaner, N.C., et al., *A bright monomeric green fluorescent protein derived from Branchiostoma lanceolatum.* Nat Meth, 2013. 10(5): p. 407-409.
75. Schindelin, J., et al., *Fiji: an open-source platform for biological-image analysis.* Nat Meth, 2012. 9(7): p. 676-682.
76. Lakshmanan, A., et al., *Molecular Engineering of Acoustic Protein Nanostructures.* ACS Nano, 2016. 10(8): p. 7314-7322.
77. Bourdeau, R. W., et al., *Acoustic reporter genes for non-invasive imaging of microbial populations in mammalian hosts.* In preparation.
78. Abdul-Rahman, H. S., et al., *Fast and robust three-dimensional best path phase unwrapping algorithm.* Applied Optics, 2007. 46(26): p. 6623-6635.
79. Schweser, F., et al., *Quantitative imaging of intrinsic magnetic tissue properties using MRI signal phase: An approach to in vivo brain iron metabolism?* NeuroImage, 2011. 54(4): p. 2789-2807.
80. Tang, J., et al., *SWIM: Susceptibility Mapping as a Means to Visualize Veins and Quantify Oxygen Saturation*, in *Susceptibility Weighted Imaging in MRI.* 2011, John Wiley & Sons, Inc. p. 461-485.
81. Gorbach, S. L., *Microbiology of the gastrointestinal tract.* 1996.
82. Sprinzak, D. and M. B. Elowitz, *Reconstruction of genetic circuits.* Nature, 2005. 438(7067): p. 443-448.
83. Klumpp, S. and T. Hwa, *Bacterial growth: global effects on gene expression, growth feedback and proteome partition.* Current opinion in biotechnology, 2014. 28: p. 96-102.
84. Reits, E. A. and J. J. Neefjes, *From fixed to FRAP: measuring protein mobility and activity in living cells.* Nature cell biology, 2001. 3(6): p. E145-E147.
85. Hayes, P., B. Buchholz, and A. Walsby, *Gas vesicles are strengthened by the outer-surface protein, GvpC.* Archives of microbiology, 1992. 157(3): p. 229-234.
86. Kinsman, R., A. Walsby, and P. Hayes, *GvpCs with reduced numbers of repeating sequence elements bind to and strengthen cyanobacterial gas vesicles.* Molecular microbiology, 1995. 17(1): p. 147-154.
87. Romero, P. A. and F. H. Arnold, *Exploring protein fitness landscapes by directed evolution.* Nature Reviews Molecular Cell Biology, 2009. 10(12): p. 866-876.
88. Shaner, N. C., et al., *Improving the photostability of bright monomeric orange and red fluorescent proteins.* Nature methods, 2008. 5(6): p. 545-551.
89. Shaner, N. C., et al., *Improved monomeric red, orange and yellow fluorescent proteins derived from Discosoma sp. red fluorescent protein.* Nature biotechnology, 2004. 22(12): p. 1567-1572.
90. Braat, H., et al., *A phase I trial with transgenic bacteria expressing interleukin-10 in Crohn's disease.* Clinical gastroenterology and hepatology, 2006. 4(6): p. 754-759.
91. Daniel, C., et al., *Recombinant lactic acid bacteria as mucosal biotherapeutic agents.* Trends in biotechnology, 2011. 29(10): p. 499-508.
92. Danino, T., et al., *In vivo gene expression dynamics of tumor-targeted bacteria.* ACS synthetic biology, 2012. 1(10): p. 465-470.
93. Milo, R., et al., *BioNumbers—the database of key numbers in molecular and cell biology.* Nucleic Acids Research, 2010. 38(suppl 1): p. D750-D753.

The invention claimed is:

1. A hybrid gas vesicle gene cluster (GVGC) encoding a hybrid gas vesicle (GV) type, the hybrid gas vesicle gene cluster configured for expression in a prokaryotic host and comprising
   gas vesicle assembly (GVA) genes comprising GvpR, GvpN, GvpF, GvpG, GvpL, GvpS, GvpK, GvpJ, GvpT and GvpU native to *Bacillus Megaterium*, and
   one or more gas vesicle structural (GVS) genes comprising GvpA native to *Anabaena flos-aquae*,
   wherein the one or more gas vesicle structural genes and the gas vesicle assembly genes are in operative connection to allow co-expression in the prokaryotic host of the gas vesicle structural genes and the gas vesicle assembly genes to provide the hybrid gas vesicle (GV) type in the prokaryotic host.

2. The hybrid gas vesicle gene cluster (GVGC) of claim 1, wherein the prokaryotic host is *Bacillus Megaterium*.

3. The hybrid gas vesicle gene cluster (GVGC) of claim 1, wherein the prokaryotic host is a prokaryote of a prokaryotic species different from *Bacillus Megaterium*.

4. The hybrid gas vesicle gene cluster (GVGC) of claim 1, wherein the prokaryotic host is *E. coli*, or *Salmonella*.

5. The hybrid gas vesicle gene cluster (GVGC) of claim 1, wherein the GVS genes from *Anabaena flos-aquae* further comprises GvpC.

6. The hybrid gas vesicle gene cluster (GVGC) of claim 1, wherein the GVS genes comprise a GVS gene encoding at least one GVS variant engineered to present a tag allowing clustering of expressed corresponding GV types in the prokaryotic host.

7. A vector comprising the hybrid GVGC of claim 1, configured for expression in a prokaryotic host, wherein the vector is configured to introduce the hybrid GVGC into the prokaryotic host.

8. A genetically engineered prokaryotic host comprising one or more hybrid GVGC of claim 1 configured for expression in the genetically engineered prokaryotic host.

9. The genetically engineered prokaryotic host of claim 8, wherein the prokaryotic host is *E. Coli*.

10. The hybrid gas vesicle gene cluster (GVGC) of claim 1, wherein GVGC is ARG1 gene cluster having SEQ ID NO: 16.

11. The hybrid gas vesicle gene cluster (GVGC) of claim 1, wherein GVGC is ARG2 gene cluster having SEQ ID NO: 17.

12. A method to provide a hybrid gas vesicle gene cluster (GVGC) configured for expression in a prokaryotic host, the hybrid gas vesicle gene cluster encoding a gas vesicle (GV) type, the method comprising:
   providing a polynucleotidic construct comprising gas vesicle assembly (GVA) genes and gas vesicle structural (GVS) genes forming a candidate GV gene cluster,
   the gas vesicle assembly (GVA) genes native to a GVA prokaryotic species and capable of forming detectable GVs in the prokaryotic host, and the gas vesicle structural (GVS) genes native to one or more GVS prokaryotic species, with at least one of the one or more GVS prokaryotic species different from the GVA prokaryotic species, providing a prokaryotic host of a prokaryotic species different from the GVA prokaryotic species;

transforming the candidate GV gene cluster into the prokaryotic host;

detecting expression in the prokaryotic host of one or more candidate GV gene cluster and repeating the detecting until formation of a GV by at least one candidate GV gene cluster is detected, identifying the detected at least one candidate GV gene cluster as the hybrid gas vesicle gene cluster (GVGC) configured for expression in the prokaryotic host.

13. The method of claim 12, wherein the prokaryotic host is a Gram-negative bacteria.

14. The method of claim 13, wherein the prokaryotic host is *E. coli*, or *Salmonella*.

15. The method of claim 12, wherein the prokaryotic host is *Halobacterium*.

16. The method of claim 12, wherein the gas vesicle assembly (GVA) genes forming the candidate GV gene cluster comprise GVA genes from *Bacillus Megaterium Anabaena flos-aquae Serratia* sp., *Bukholderia thailandensis, B. megaterium, Frankia* sp, *Haloferax mediaterranei, Halobacterium* sp, *Halorubrum vacuolatum, Microcystis aeruginosa, Methanosarcina barkeri, Streptomyces coelicolor*, and/or *Psychromonas ingrahamii*.

17. The method of claim 12, wherein the gas vesicle structural (GVS) genes forming the candidate GV gene cluster comprise GVS genes from *Bacillus Megaterium Anabaena flos-aquae Serratia* sp., *Bukholderia thailandensis, B. megaterium, Frankia* sp, *Haloferax mediaterranei, Halobacterium* sp, *Halorubrum vacuolatum, Microcystis aeruginosa, Methanosarcina barkeri, Streptomyces coelicolor*, and/or *Psychromonas ingrahamii*.

18. The method of claim 12, wherein the gas vesicle assembly (GVA) genes comprise GVA genes from *Bacillus Megaterium, Anabaena flos-aquae*, and/or *Serratia* sp., and the gas vesicle structural (GVS) genes forming the candidate GV gene cluster comprise GVS genes from *Bacillus Megaterium Anabaena flos-aquae Bukholderia thailandensis, B. megaterium, Frankia* sp, *Haloferax mediaterranei, Halobacterium* sp, *Halorubrum vacuolatum, Microcystis aeruginosa, Methanosarcina barkeri, Streptomyces coelicolor*, and/or *Psychromonas ingrahamii*.

19. The method of claim 12, wherein the gas vesicle assembly (GVA) genes forming the candidate GV gene cluster comprise GVA genes from *Bacillus Megaterium, Anabaena flos-aquae*, and/or *Serratia* sp., and the gas vesicle structural (GVS) genes forming the candidate GV gene cluster comprise GVA genes from *Bacillus Megaterium* and/or *Anabaena flos-aquae*.

20. The method of claim 12, wherein the gas vesicle assembly (GVA) genes comprise *B. megaterium* GVA genes GvpR, GvpN, GvpF, GvpG, GvpL, GvpS, GvpK, GvpJ, GvpT and/or GvpU.

21. The method of claim 12, wherein the gas vesicle assembly (GVA) genes comprise *B. megaterium* GVA genes GvpA, GvpF, GvpG, GvpJ, GvpL, GvpK, GvpS, GvpU.

22. A method to produce a hybrid gas vesicle type in a prokaryotic host, the method comprising:

introducing into the prokaryotic host a hybrid gas vesicle gene cluster (GVGC), encoding a hybrid gas vesicle (GV) type, the hybrid gas vesicle gene cluster configured for expression in a prokaryotic host and comprising gas vesicle assembly (GVA) genes comprising GvpR, GvpN, GvpF, GvpG, GvpL, GvpS, GvpK, GvpJ, GvpT and GvpU native to *Bacillus Megaterium*, and one or more gas vesicle structural (GVS) genes comprising GvpA native to *Anabaena flos-aquae*, wherein the one or more gas vesicle structural genes and the gas vesicle assembly genes are in operative connection, the introducing performed under condition allowing co-expression of the hybrid GVGC in the prokaryotic host of the gas vesicle structural genes and the gas vesicle assembly genes to produce the gas vesicle type in the prokaryotic host.

23. The method of claim 22, wherein the prokaryotic host is a Gram-negative bacteria.

24. The method of claim 23, wherein the prokaryotic host is *E. coli*, or *Salmonella*.

25. The method of claim 22, wherein the prokaryotic host is *Halobacterium*.

26. A hybrid gas vesicle obtained by the method of claim 22.

27. A method to image a target site comprising a prokaryotic host, the method comprising:

introducing into the prokaryotic host a hybrid gas vesicle gene cluster (GVGC) encoding a hybrid gas vesicle (GV) type, the hybrid gas vesicle gene cluster configured for expression in a prokaryotic host and comprising gas vesicle assembly (GVA) genes comprising GvpR, GvpN, GvpF, GvpG, GvpL, GvpS, GvpK, GvpJ, GvpT and GvpU native to *Bacillus Megaterium,and* one or more gas vesicle structural (GVS) genes comprising GvpA native to *Anabaena flos-aquae*, wherein the one or more gas vesicle structural genes and the gas vesicle assembly genes are in operative connection to allow co-expression in the prokaryotic host of the gas vesicle structural genes and the gas vesicle assembly genes to produce the hybrid gas vesicle type in the prokaryotic host, and imaging the target site comprising the prokaryotic host by applying a magnetic field and/or ultrasound to obtain an MRI and/or an ultrasound image of the target site.

28. The method of claim 27, wherein the prokaryotic host is a Gram-negative bacteria.

29. The method of claim 28, wherein the prokaryotic host is *E. coli*, or *Salmonella*.

30. The method of claim 27, wherein the prokaryotic host is *Halobacterium*.

\* \* \* \* \*